(12) United States Patent
Do et al.

(10) Patent No.: US 9,260,425 B2
(45) Date of Patent: Feb. 16, 2016

(54) PYRAZOLO[3,4-C]PYRIDINE COMPOUNDS AND METHODS OF USE

(75) Inventors: Steven Do, San Jose, CA (US); Huiyong Hu, San Mateo, CA (US); Aleksandr Kolesnikov, San Francisco, CA (US); Wendy Lee, San Ramon, CA (US); Vickie H. Tsui, San Francisco, CA (US); Xiaojing Wang, Foster City, CA (US); Zhaoyang Wen, San Francisco, CA (US)

(73) Assignee: Genetech, Inc., South San Francisco, CA (US)

(*) Notice: Subject to any disclaimer, the term of this patent is extended or adjusted under 35 U.S.C. 154(b) by 0 days.

(21) Appl. No.: 13/571,595

(22) Filed: Aug. 10, 2012

(65) Prior Publication Data

US 2013/0039906 A1    Feb. 14, 2013

Related U.S. Application Data

(60) Provisional application No. 61/522,857, filed on Aug. 12, 2011.

(51) Int. Cl.
  *C07D 471/04* (2006.01)
  *C07D 231/00* (2006.01)

(52) U.S. Cl.
  CPC ............ *C07D 471/04* (2013.01); *C07D 231/00* (2013.01)

(58) Field of Classification Search
  CPC .............................. C07D 471/04; C07D 231/00
  See application file for complete search history.

(56) References Cited

U.S. PATENT DOCUMENTS

| 5,604,240 | A | 2/1997 | Chambers et al. |
| 7,429,609 | B2 | 9/2008 | Ohi et al. |
| 2005/0208582 | A1* | 9/2005 | Ohi et al. ................ 435/7.1 |

FOREIGN PATENT DOCUMENTS

| EP | 1510516 A1 | 3/2005 |
| WO | 02/14317 A2 | 2/2002 |
| WO | 02/20013 A2 | 3/2002 |
| WO | 2006/042102 A2 | 4/2006 |
| WO | 2010/022081 A1 | 2/2010 |
| WO | 2012/078777 A1 | 6/2012 |

OTHER PUBLICATIONS

Dong et al., "QSAR study of Akt/protein kinase B (PKB) inhibitors using support vector machine" Eur J Med Chem. 44(10):4090-7 (2009).
Muddassar et al., "Elucidation of binding mode and three dimensional quantitative structure-activity relationship studies of a novel series of protein kinase B/Akt inhibitors" J Mol Model. 15(2):183-92 (Feb. 2009).
Ohi et al., CAS Registry, Database Accession No. 2003:972059, "Preparation of pyrazole derivatives as JNK inhibitors".
PCT ISR and Written Opinion of the ISA for PCT/EP2012/065643.
Wang et al., "Discovery of novel pyrazolo[1,5-a]pyrimidines as potent pan-Pim inhibitors by structure- and property-based drug design" Bioorg Med Chem Lett. 23(11):3149-53 (Jun. 2013).
Zhu et al., "Design and synthesis of pyridine-pyrazolopyridine-based inhibitors of protein kinase B/Akt" Bioorg Med Chem. 15(6):2441-52 (2007).

* cited by examiner

*Primary Examiner* — Samira Jean-Louis
(74) *Attorney, Agent, or Firm* — Tony W. Peng

(57) ABSTRACT

Pyrazolo[3,4-c]pyridine compounds of Formula I, including stereoisomers, geometric isomers, tautomers, and pharmaceutically acceptable salts thereof, wherein $R^1$ and $R^2$ are as defined herein, are useful for inhibiting Pim kinase, and for treating disorders such as cancer mediated by Pim kinase. Methods of using compounds of Formula I for in vitro, in situ, and in vivo diagnosis, prevention or treatment of such disorders in mammalian cells, or associated pathological conditions, are disclosed.

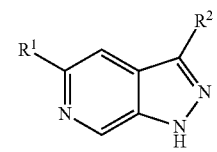

14 Claims, No Drawings

PYRAZOLO[3,4-C]PYRIDINE COMPOUNDS AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 61/522,857 filed on 12 Aug. 2011, which is incorporated by reference in its entirety.

FIELD OF THE INVENTION

The invention relates generally to pyrazolo[3,4-c]pyridine compounds for treating disorders mediated by Pim kinase (Pim-1, Pim-2, and/or Pim-3) inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ, and in vivo diagnosis or treatment of mammalian cells, or associated pathological conditions.

BACKGROUND OF THE INVENTION

Pim kinases are family of three highly-related serine and threonine protein kinases encoded by the genes Pim-1, Pim-2, and Pim-3. The gene names are derived from the phrase Proviral Insertion, Moloney, frequent integration sites for murine moloney virus wherein the insertions lead to overexpression of Pim kinases and either de novo T-cell lymphomas, or dramatic acceleration of tumorigenesis in a transgenic Myc-driven lymphoma model (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52). These experiments reveal synergy with the oncogene c-Myc, and suggest that inhibition of the Pim kinases may have therapeutic benefit.

Mouse genetics suggests that antagonizing Pim kinases may have an acceptable safety profile; a Pim 1−/−; Pim-2−/−, Pim-3−/− mouse knockout is viable although slightly smaller than wild type littermates (Mikkers et al. (2004) Mol Cell Biol vol. 24 (13) pp. 6104-154). The three genes give rise to six protein isoforms including a protein kinase domain, and apparently without recognizable regulatory domains. All six isoforms are constitutively active protein kinases that do not require post-translational modification for activity, thus Pim kinases are regulated primarily at the transcriptional level (Qian et al. (2005) J Biol Chem, vol. 280 (7) pp. 6130-7). Pim kinase expression is highly inducible by cytokines and growth factors receptors and Pims are direct transcriptional targets of the Stat proteins, including Stat3 and Stat5. Pim-1, for example, is required for the 130-mediated Stat3 proliferation signal (Aksoy et al. (2007) Stem Cells, vol. 25 (12) pp. 2996-3004; Hirano et al. (2000) Oncogene vol. 19 (21) pp. 2548-56; Shirogane et al. (1999) Immunity vol. 11 (6) pp. 709-19).

Pim kinases function in cellular proliferation and survival pathways parallel to the PI3k/Akt/mTOR signaling axis (Hammerman et al. (2005) Blood vol. 105 (11) pp. 4477-83). Indeed, several of the phosphorylation targets of the PI3k axis including Bad and eIF4E-BP1 are cell growth and apoptosis regulators and are also phosphorylation targets of the Pim kinases (Fox et al. (2003) Genes Dev vol. 17 (15) pp. 1841-54; Macdonald et al. (2006) Cell Biol vol. 7 pp. 1; Aho et al. (2004) FEBS Letters vol. 571 (1-3) pp. 43-9; Tamburini et al. (2009) Blood vol. 114 (8) pp. 1618-27). Pim kinase may affect cell survival since phosphorylation of Bad increases Bcl-2 activity and therefore promotes cell survival. Likewise, phosphorylation of eIF4E-BP1 by mTOR or Pim kinases causes depression of eIF4E, promoting mRNA translation and cellular growth. In addition, Pim-1 has been recognized to promote cell cycle progression through phosphorylation of CDC25A, p21, and Cdc25C (Mochizuki et al. (1999) J Biol Chem vol. 274 (26) pp. 18659-66; Bachmann et al. (2006) Int J Biochem Cell Biol vol. 38 (3) pp. 430-43; Wang et al. (2002) Biochim Biophys Acta vol. 1593 (1) pp. 45-55.

Pim kinases show synergy in transgenic mouse models with c-Myc-driven and Akt-driven tumors (Verbeek et al. (1991) Mol Cell Biol vol. 11 (2) pp. 1176-9; Allen et al. Oncogene (1997) vol. 15 (10) pp. 1133-41; Hammerman et al. (2005) Blood vol. 105 (11) pp. 4477-83). Pim Kinases are involved in transforming activity of oncogenes identified in acute myeloid leukemia (AML) including Flt3-ITD, BCR-abl, and Tel-Jak2. Expression of these oncogenes in BaF3 cells results in upregulation of Pim-1 and Pim-2 expression, resulting in IL-3 independent growth, and subsequent Pim inhibition results in apoptosis and cell growth arrest (Adam et al. (2006) Cancer Research vol. 66 (7) pp. 3828-35). Pim overexpression and dysregulation has also been noted as a frequent event in many hematopoietic cancers, including leukemias and lymphoma (Amson et al. (1989) Proc Natl Acad Sci USA vol. 86 (22) pp. 8857-61); Cohen et al. (2004) Leuk Lymphoma vol. 45 (5) pp. 951-5; Hüttmann et al. (2006) Leukemia vol. 20 (10) pp. 1774-82) as well as multiple myeloma (Claudio et al. (2002) Blood vol. 100 (6) pp. 2175-86. Pim 1 has been shown to be overexpressed and correlated to prostate cancer progression (Cibull et al. (2006) J Clin Pathol vol. 59 (3) pp. 285-8; Dhanasekaran et al. (2001) Nature vol. 412 (6849) pp. 822-6). Pim 1 expression increases in mouse models with disease progression (Kim et al. (2002) Proc Natl Acad Sci USA vol. 99 (5) pp. 2884-9). Pim-1 has been reported to be the most highly overexpressed mRNA in the subset of human prostate tumor samples which have a c-Myc-driven gene signature (Ellwood-Yen et al. (2003) Cancer Cell vol. 4 (3) pp. 223-38). Pim-3 has been also been shown to be overexpressed and to have a functional role in pancreatic cancer and hepatocellular carcinoma (Li et al. (2006) Cancer Research vol. 66 (13) pp. 6741-7; Fujii et al. (2005) Int J. Cancer, vol. 114 (2) pp. 209-18).

Beyond oncology therapeutic and diagnostic applications, Pim kinases could play an important role in normal immune system function and Pim inhibition could be therapeutic for a number of different immunologic pathologies including inflammation, autoimmune conditions, allergy, and immune suppression for organ transplantation (Aho et al. Expression of human Pim family genes is selectively up-regulated by cytokines promoting T helper type 1, but not T helper type 2, cell differentiation. Immunology (2005) vol. 116 (1) pp. 82-8).

SUMMARY OF THE INVENTION

The invention relates to pyrazolo[3,4-c]pyridine compounds for treating disorders mediated by Pim kinase (Pim-1, Pim-2, and/or Pim-3) inhibitors Formula I compounds.

Formula I compounds have the structure:

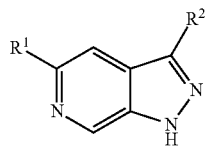

and stereoisomers, geometric isomers, tautomers, and pharmaceutically acceptable salts thereof. The various substituents, including $R^1$ and $R^2$ are as defined herein.

One aspect of the invention is a pharmaceutical composition comprised of a Formula I compound and a pharmaceutically acceptable carrier, glidant, diluent, or excipient. The pharmaceutical composition may further comprise a second chemotherapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from cancer, immune disorders, cardiovascular disease, viral infection, inflammation, metabolism/endocrine function disorders and neurological disorders, and mediated by Pim kinase. The method includes further administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The invention includes a kit for treating a condition mediated by Pim kinase, comprising: a) a first pharmaceutical composition comprising a Formula I compound; and b) instructions for use.

The invention includes a Formula I compound for use as a medicament, and for use in treating a disease or disorder selected from cancer, immune disorders, cardiovascular disease, viral infection, inflammation, metabolism/endocrine function disorders and neurological disorders, and mediated by Pim kinase.

The invention includes use of a Formula I compound in the manufacture of a medicament for the treatment of cancer, immune disorders, cardiovascular disease, viral infection, inflammation, metabolism/endocrine function disorders and neurological disorders, and where the medicament mediates Pim kinase.

The invention includes methods of making a Formula I compound.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)$ $CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH$ $(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH$ $(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally and independently substituted with one or more substituents described herein, and includes radicals having "cis" and "trans" orientations, or alternatively, "E" and "Z" orientations. Examples include, but are not limited to, ethylenylene or vinylene (—CH═CH—), allyl (—CH₂CH═CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH₂C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —CH₂C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), everolimus (AFINITOR®, Novartis), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), abiraterone (ZYTIGA®, Johnson & Johnson), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard;

nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Examples of chemotherapeutic agents also include: dexamethasone, thioTEPA, doxorubicin, vincristine, rituximab, cyclophosphamide, prednisone, melphalan, lenalidomide, bortezomib, rapamycin, and cytarabine.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion.

The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Pyrazolo[3,4-c]Pyridine Compounds

The present invention provides pyrazolo[3,4-c]pyridine compounds of Formula I, and pharmaceutical formulations thereof, which are potentially useful in the treatment of diseases, conditions and/or disorders modulated by Pim kinases.

Formula I compounds have the structure:

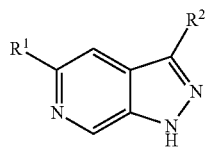

I and stereoisomers, geometric isomers, tautomers, or pharmaceutically acceptable salts thereof, wherein:

$R^1$ is selected from —CN, —CH$_2$CN, —CH$_2$CONH$_2$, —CONH$_2$, —CONHCH$_3$, —CON(CH$_3$)$_2$, —NHCONH$_2$, $C_3$-$C_{12}$ carbocyclyl, $C_2$-$C_{20}$ heterocyclyl, $C_1$-$C_{20}$ heteroaryl, —($C_1$-$C_{20}$ heteroaryl)-($C_1$-$C_{20}$ heteroaryl), —($C_1$-$C_{20}$ heteroaryl)-($C_2$-$C_{20}$ heterocyclyl), —($C_1$-$C_{20}$ heteroaryl)-O—($C_2$-$C_{20}$ heterocyclyl), —($C_1$-$C_{20}$ heteroaryl)-O—($C_1$-$C_{12}$ alkylene)-($C_2$-$C_{20}$ heterocyclyl), —($C_1$-$C_{20}$ heteroaryl)-NR$^3$—($C_2$-$C_{20}$ heterocyclyl), and —($C_1$-$C_{20}$ heteroaryl)-NR$^3$—($C_1$-$C_{12}$ alkylene)-($C_2$-$C_{20}$ heterocyclyl);

$R^2$ is selected from $C_1$-$C_{12}$ alkyl, $C_3$-$C_{12}$ carbocyclyl, $C_2$-$C_{20}$ heterocyclyl, $C_1$-$C_{20}$ heteroaryl, $C_6$-$C_{20}$ aryl, —($C_6$-$C_{20}$ aryl)-($C_2$-$C_{20}$ heterocyclyl), —($C_1$-$C_{12}$ alkylene)-($C_2$-$C_{20}$ heterocyclyl), —($C_1$-$C_{12}$ alkylene)-NR$^3$($C_2$-$C_{20}$ heterocyclyl), —($C_1$-$C_{12}$ alkylene)-NR$^3$—($C_1$-$C_{12}$ alkylene)-($C_2$-$C_{20}$ heterocyclyl), —($C_1$-$C_{20}$ heteroaryl)-($C_1$-$C_{20}$ heteroaryl), —($C_1$-$C_{20}$ heteroaryl)-($C_2$-$C_{20}$ heterocyclyl), —($C_1$-$C_{20}$ heteroaryl)-($C_2$-$C_{20}$ heterocyclyl)-($C_2$-$C_{20}$ heterocyclyl), —($C_1$-$C_{20}$ heteroaryl)-NR$^3$—($C_2$-$C_{20}$ heterocyclyl), —($C_1$-$C_{20}$ heteroaryl)-($C_1$-$C_{12}$ alkylene)-($C_2$-$C_{20}$ heterocyclyl), —($C_1$-$C_{20}$ heteroaryl)-NR$^3$—($C_1$-$C_{12}$ alkylene)-($C_2$-$C_{20}$ heterocyclyl), and —($C_1$-$C_{20}$ heteroaryl)-NR$^3$—($C_1$-$C_{12}$ alkylene)-($C_1$-$C_{20}$ heteroaryl);

$R^3$ is independently selected from H and $C_1$-$C_{12}$ alkyl optionally substituted with F, Cl, CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$OCH$_3$, —OCH$_2$CH$_2$NH$_2$, —S(O)$_2$N(CH$_3$)$_2$, —SCH$_3$, and —S(O)$_2$CH$_3$;

where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$NHCH$_3$, —CH$_2$N(CH$_3$)$_2$, —CH$_2$CH$_2$NH$_2$, —CH$_2$CHCH$_2$NH$_2$, —CH$_2$CHCH$_2$CH$_2$NH$_2$, —CH$_2$CH(CH$_3$)NH$_2$, —CH$_2$CONH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$C(CH$_3$)$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino.

Exemplary embodiments of Formula I compounds include wherein $R^1$ is $C_1$-$C_{20}$ heteroaryl.

Exemplary embodiments of Formula I compounds include wherein $R^1$ is selected from the structures:

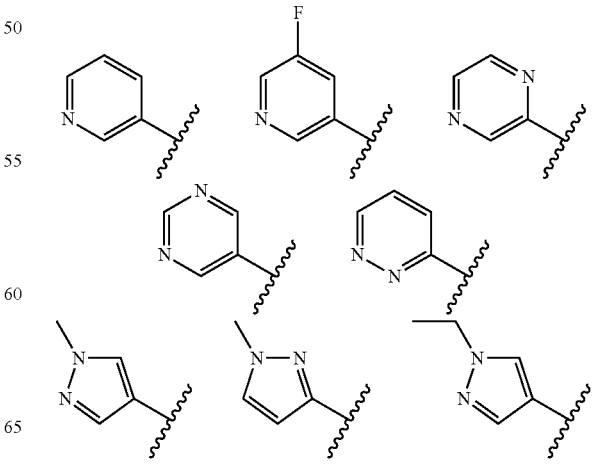

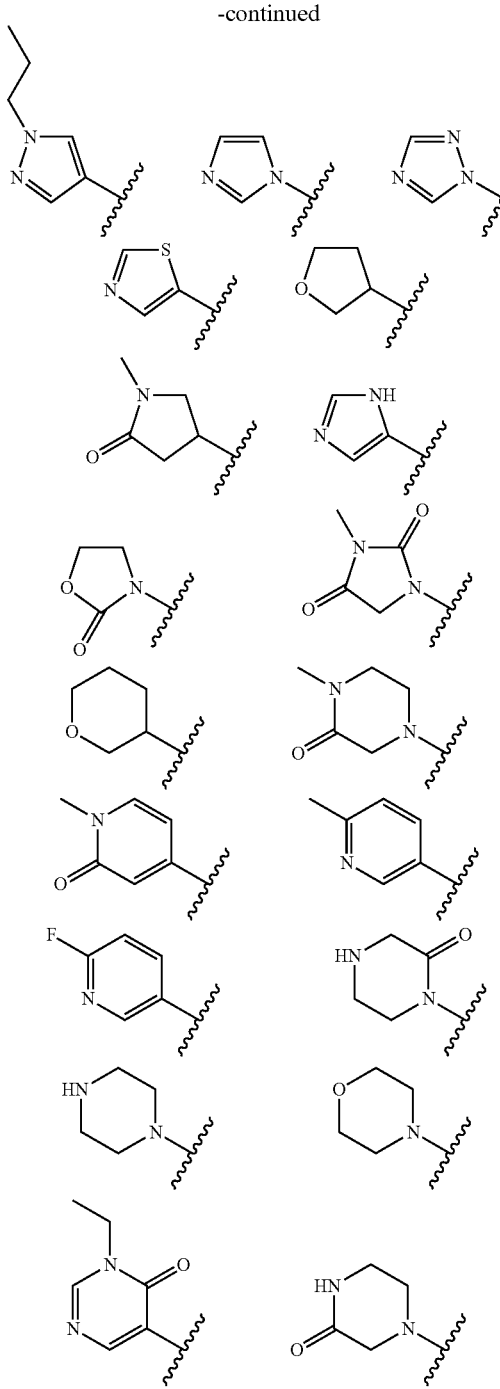
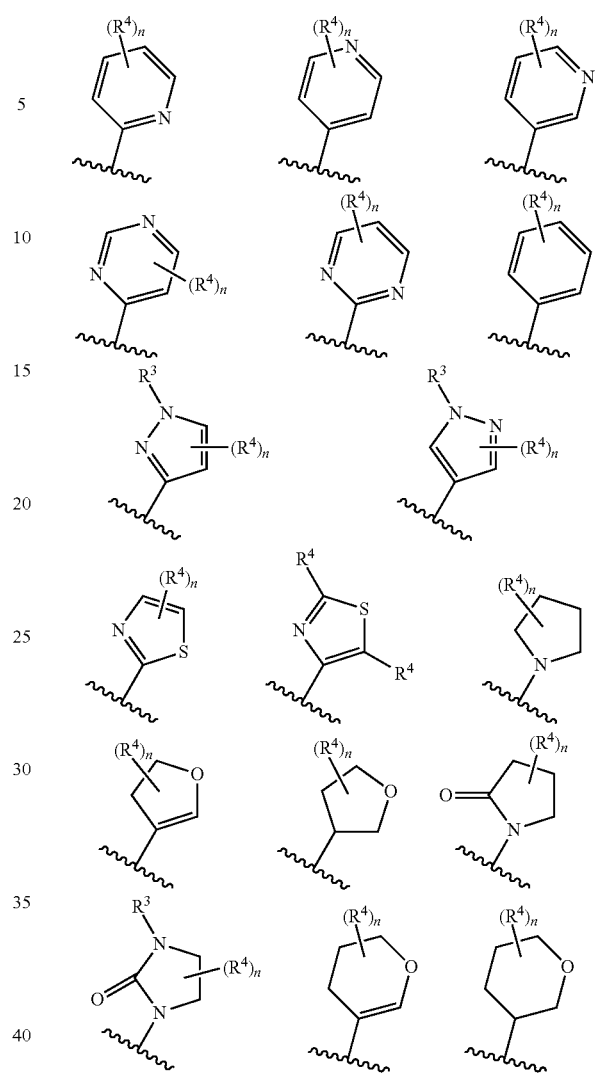

where the wavy line indicates the site of attachment.

Exemplary embodiments of Formula I compounds include wherein $R^1$ is selected from —CN, —CH$_2$CN, —CH$_2$CONH$_2$, —CONH$_2$, —CONHCH$_3$, —CON(CH$_3$)$_2$, and —NHCONH$_2$.

Exemplary embodiments of Formula I compounds include wherein $R^2$ is $C_1$-$C_{20}$ heteroaryl.

Exemplary embodiments of Formula I compounds include wherein $R^2$ is —($C_1$-$C_{20}$ heteroaryl)-($C_2$-$C_{20}$ heterocyclyl).

Exemplary embodiments of Formula I compounds include wherein $R^2$ is selected from the structures:

where the wavy line indicates the site of attachment; and $R^4$ is selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$NHCH$_3$, —CH$_2$N(CH$_3$)$_2$, —CH$_2$CH$_2$NH$_2$, —CH$_2$CHCH$_2$NH$_2$, —CH$_2$CHCH$_2$CH$_2$NH$_2$, —CH$_2$CH(CH$_3$)NH$_2$, —CH$_2$CONH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$C(CH$_3$)$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, or 2.

Exemplary embodiments of Formula I compounds include compounds having the structure of Formula Ia:

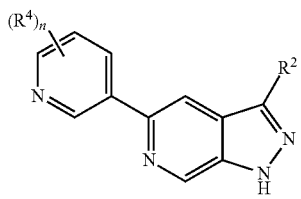

Ia where R⁴ is selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$NHCH$_3$, —CH$_2$N(CH$_3$)$_2$, —CH$_2$CH$_2$NH$_2$, —CH$_2$CHCH$_2$NH$_2$, —CH$_2$CHCH$_2$CH$_2$NH$_2$, —CH$_2$CH(CH$_3$)NH$_2$, —CH$_2$CONH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$C(CH$_3$)$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, or 2.

Exemplary embodiments of Formula I compounds include compounds having the structure of Formula Ib:

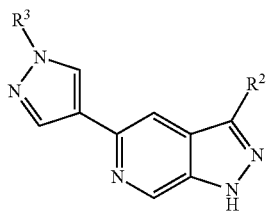

Ib where R³ is selected from H, C$_3$-C$_{12}$ carbocyclyl, and C$_1$-C$_{12}$ alkyl where carbocyclyl and alkyl are optionally substituted with F, Cl, CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, and —S(O)$_2$CH$_3$; and n is 0, 1, or 2.

Exemplary embodiments of Formula I compounds include compounds having the structure of Formula Ic:

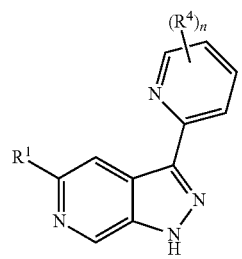

Ic where R⁴ is selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$NHCH$_3$, —CH$_2$N(CH$_3$)$_2$, —CH$_2$CH$_2$NH$_2$, —CH$_2$CHCH$_2$NH$_2$, —CH$_2$CHCH$_2$CH$_2$NH$_2$, —CH$_2$CH(CH$_3$)NH$_2$, —CH$_2$CONH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$C(CH$_3$)$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, or 2.

Biological Evaluation

Determination of the Pim kinase activity of a Formula I compound is possible by a number of direct and indirect detection methods. Certain exemplary compounds described herein were assayed for their Pim kinase binding activity, including isoforms Pim-1, Pim-2, and Pim-3, (Example 901) and in vitro activity against tumor cells (Example 902). Certain exemplary compounds of the invention had Pim binding activity IC$_{50}$ values less than about 1 micromolar (μM). Certain compounds of the invention had tumor cell-based activity EC$_{50}$ values less than about 1 micromolar (μM).

Exemplary Formula I compounds in Table 1 were made, characterized, and tested for inhibition of Pim kinase according to the methods of this invention, and have the following structures and corresponding names (ChemBioDraw Ultra, Version 11.0, CambridgeSoft Corp., Cambridge Mass.).

TABLE 1

| No. | Structure | Name | Pim-1 Ki (μm) |
|---|---|---|---|
| 101 | 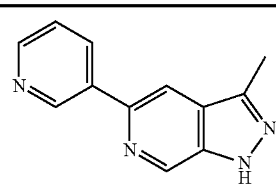 | 3-methyl-5-(pyridin-3-yl)-1H-pyrazolo[3,4-c]pyridine | 0.19 |

TABLE 1-continued

| No. | Structure | Name | Pim-1 Ki (μm) |
|---|---|---|---|
| 102 | 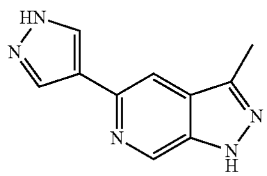 | 3-methyl-5-(1H-pyrazol-4-yl)-1H-pyrazolo[3,4-c]pyridine | 0.302 |
| 103 | 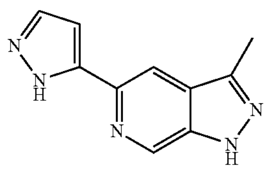 | 3-methyl-5-(1H-pyrazol-5-yl)-1H-pyrazolo[3,4-c]pyridine | 1.3 |
| 104 | 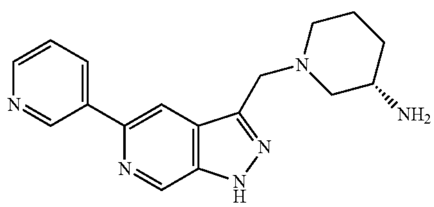 [SMILES: N[C@H]1CCCN(Cc2n[nH]c3cnc(-c4cccnc4)cc23)C1] | (S)-1-((5-(pyridin-3-yl)-1H-pyrazolo[3,4-c]pyridin-3-yl)methyl)piperidin-3-amine | 3.0 |
| 105 | 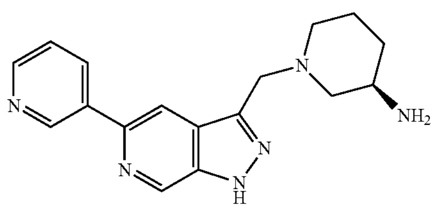 [SMILES: N[C@@H]1CCCN(Cc2n[nH]c3cnc(-c4cccnc4)cc23)C1] | (R)-1-((5-(pyridin-3-yl)-1H-pyrazolo[3,4-c]pyridin-3-yl)methyl)piperidin-3-amine | 3.4 |
| 106 | 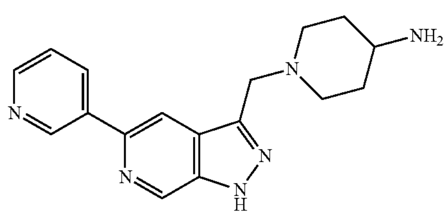 [SMILES: NC1CCN(Cc2n[nH]c3cnc(-c4cccnc4)cc23)CC1] | 1-((5-(pyridin-3-yl)-1H-pyrazolo[3,4-c]pyridin-3-yl)methyl)piperidin-4-amine | 1.4 |
| 107 | 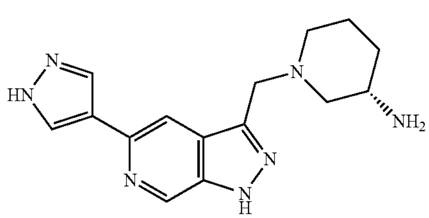 [SMILES: N[C@H]1CCCN(Cc2n[nH]c3cnc(-c4cn[nH]c4)cc23)C1] | (S)-1-((5-(1H-pyrazol-4-yl)-1H-pyrazolo[3,4-c]pyridin-3-yl)methyl)piperidin-3-amine | 3.0 |
| 108 | 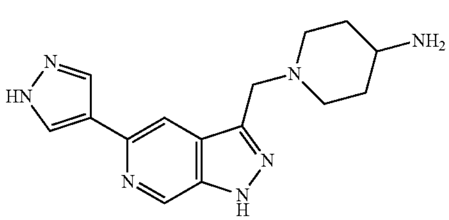 [SMILES: NC1CCN(Cc2n[nH]c3cnc(-c4cn[nH]c4)cc23)CC1] | 1-((5-(1H-pyrazol-4-yl)-1H-pyrazolo[3,4-c]pyridin-3-yl)methyl)piperidin-4-amine | 1.1 |

TABLE 1-continued
| No. | Structure | Name | Pim-1 Ki (μm) |
|---|---|---|---|
| 109 | 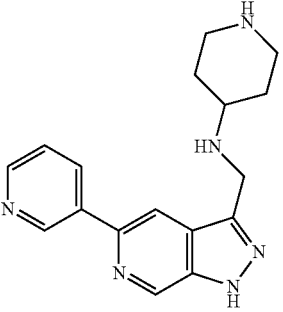 [SMILES: c1cncc(-c2cc3c(CNC4CCNCC4)n[nH]c3cn2)c1] | N-((5-(pyridin-3-yl)-1H-pyrazolo[3,4-c]pyridin-3-yl)methyl)piperidin-4-amine | 3.8 |
| 110 | 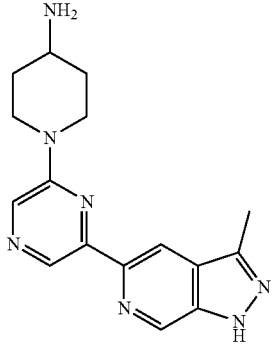 [SMILES: Cc1n[nH]c2cnc(-c3cncc(N4CCC(N)CC4)n3)cc12] | 1-(6-(3-methyl-1H-pyrazolo[3,4-c]pyridin-5-yl)pyrazin-2-yl)piperidin-4-amine | 0.0058 |
| 111 | 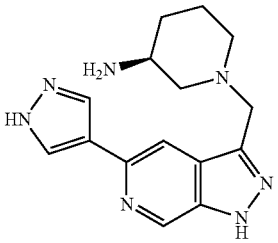 [SMILES: N[C@H]1CCCN(Cc2n[nH]c3cnc(-c4cn[nH]c4)cc23)C1] | (S)-1-((5-(1H-pyrazol-4-yl)-1H-pyrazolo[3,4-c]pyridin-3-yl)methyl)piperidin-3-amine | 4.0 |
| 112 | 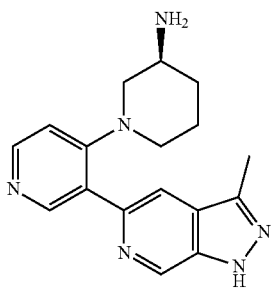 [SMILES: Cc1n[nH]c2cnc(-c3cnccc3N3CCC[C@H](N)C3)cc12] | (S)-1-(3-(3-methyl-1H-pyrazolo[3,4-c]pyridin-5-yl)pyridin-4-yl)piperidin-3-amine | 3.5 |
| 113 | 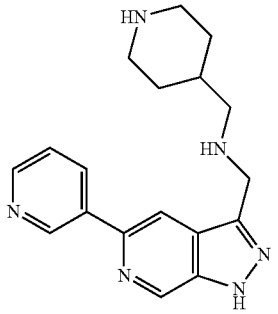 [SMILES: c1cncc(-c2cc3c(CNCC4CCNCC4)n[nH]c3cn2)c1] | 1-(piperidin-4-yl)-N-((5-(pyridin-3-yl)-1H-pyrazolo[3,4-c]pyridin-3-yl)methyl)methanamine | 3.2 |

TABLE 1-continued

| No. | Name | Pim-1 Ki (μm) |
|---|---|---|
| 114 | 3-methyl-5-(1-(oxetan-3-yl)-1H-pyrazol-4-yl)-1H-pyrazolo[3,4-c]pyridine | 0.844 |
| 115 | 3-methyl-5-(pyrimidin-5-yl)-1H-pyrazolo[3,4-c]pyridine | 3.5 |
| 116 | 3-phenyl-5-(pyridin-3-yl)-1H-pyrazolo[3,4-c]pyridine | 0.00965 |
| 117 | 3-(2-fluorophenyl)-5-(pyridin-3-yl)-1H-pyrazolo[3,4-c]pyridine | 0.122 |
| 118 | 3-methyl-5-(pyrazin-2-yl)-1H-pyrazolo[3,4-c]pyridine | 0.62 |
| 119 | (R)-1-(3-(3-methyl-1H-pyrazolo[3,4-c]pyridin-5-yl)pyridin-4-yl)piperidin-3-amine | 1.1 |

TABLE 1-continued

| No. | Structure | Name | Pim-1 Ki (μm) |
|---|---|---|---|
| 120 | 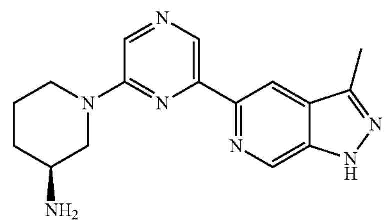 [SMILES: Cc1n[nH]c2cnc(-c3cncc(N4CCC[C@H](N)C4)n3)cc12] | (S)-1-(6-(3-methyl-1H-pyrazolo[3,4-c]pyridin-5-yl)pyrazin-2-yl)piperidin-3-amine | 0.00478 |
| 121 | 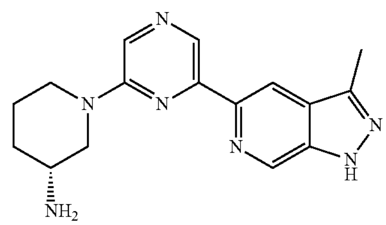 [SMILES: Cc1n[nH]c2cnc(-c3cncc(N4CCC[C@@H](N)C4)n3)cc12] | (R)-1-(6-(3-methyl-1H-pyrazolo[3,4-c]pyridin-5-yl)pyrazin-2-yl)piperidin-3-amine | 0.00691 |
| 122 | 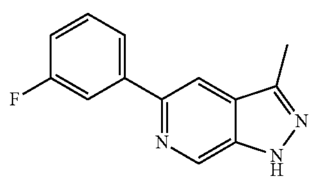 [SMILES: Cc1n[nH]c2cnc(-c3cccc(F)c3)cc12] | 5-(3-fluorophenyl)-3-methyl-1H-pyrazolo[3,4-c]pyridine | 2.2 |
| 123 | 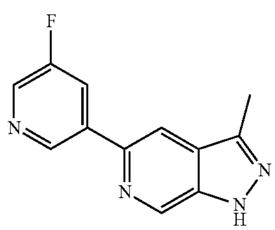 [SMILES: Cc1n[nH]c2cnc(-c3cncc(F)c3)cc12] | 5-(5-fluoropyridin-3-yl)-3-methyl-1H-pyrazolo[3,4-c]pyridine | 0.737 |
| 124 | 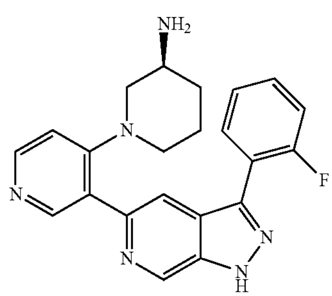 [SMILES: N[C@H]1CCCN(c2ccncc2-c2cc3c(-c4ccccc4F)n[nH]c3cn2)C1] | (S)-1-(3-(3-(2-fluorophenyl)-1H-pyrazolo[3,4-c]pyridin-5-yl)pyridin-4-yl)piperidin-3-amine | 0.0142 |
| 125 | 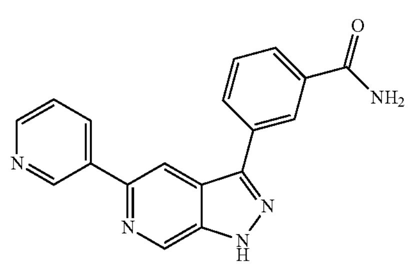 [SMILES: NC(=O)c1cccc(-c2n[nH]c3cnc(-c4cccnc4)cc23)c1] | 3-(5-(pyridin-3-yl)-1H-pyrazolo[3,4-c]pyridin-3-yl)benzamide | 0.307 |

TABLE 1-continued

| No. | Name | Pim-1 Ki (μm) |
|---|---|---|
| 126 | 5-(pyridin-3-yl)-3-(3-(trifluoromethyl)phenyl)-1H-pyrazolo[3,4-c]pyridine | 0.0159 |
| 127 | 3-methyl-5-(1-methyl-1H-pyrazol-4-yl)-1H-pyrazolo[3,4-c]pyridine | 0.261 |
| 128 | 1-(3-(3-(2-fluorophenyl)-1H-pyrazolo[3,4-c]pyridin-5-yl)pyridin-4-yl)piperidin-4-amine | 1.5 |
| 129 | 3-(2-fluorophenyl)-5-(1-methyl-1H-pyrazol-4-yl)-1H-pyrazolo[3,4-c]pyridine | 0.00785 |
| 130 | (S)-(1-(3-(3-(2-fluorophenyl)-1H-pyrazolo[3,4-c]pyridin-5-yl)pyridin-4-yl)pyrrolidin-3-yl)methanamine | 1.5 |
| 131 | 3-(6-fluoropyridin-2-yl)-5-(pyridin-3-yl)-1H-pyrazolo[3,4-c]pyridine | 0.0131 |

TABLE 1-continued

| No. | Structure | Name | Pim-1 Ki (μm) |
|---|---|---|---|
| 132 | 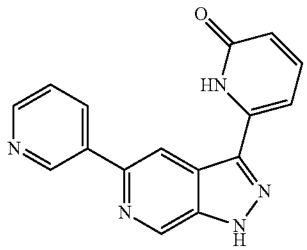 [SMILES: O=c1cccc(-c2n[nH]c3cnc(-c4cccnc4)cc23)[nH]1] | 6-(5-(pyridin-3-yl)-1H-pyrazolo[3,4-c]pyridin-3-yl)pyridin-2(1H)-one | 0.13 |
| 133 | 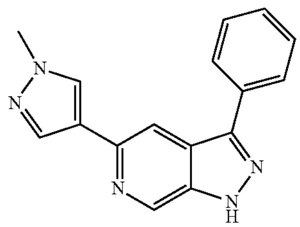 [SMILES: Cn1cc(-c2cc3c(-c4ccccc4)n[nH]c3cn2)cn1] | 5-(1-methyl-1H-pyrazol-4-yl)-3-phenyl-1H-pyrazolo[3,4-c]pyridine | 0.00557 |
| 134 | 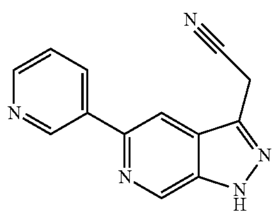 [SMILES: N#CCc1n[nH]c2cnc(-c3cccnc3)cc12] | 2-(5-(pyridin-3-yl)-1H-pyrazolo[3,4-c]pyridin-3-yl)acetonitrile | 0.826 |
| 135 | 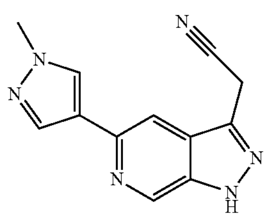 [SMILES: Cn1cc(-c2cc3c(CC#N)n[nH]c3cn2)cn1] | 2-(5-(1-methyl-1H-pyrazol-4-yl)1H-pyrazolo[3,4-c]pyridin-3-yl)acetonitrile | 0.387 |
| 136 | 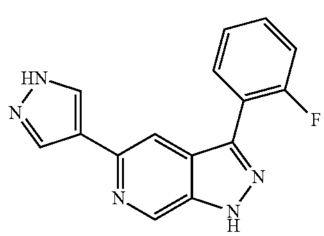 [SMILES: Fc1ccccc1-c1n[nH]c2cnc(-c3cn[nH]c3)cc12] | 3-(2-fluorophenyl)-5-(1H-pyrazol-4-yl)-1H-pyrazolo[3,4-c]pyridine | 0.00869 |
| 137 | 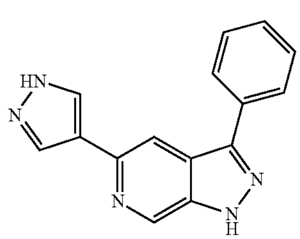 [SMILES: c1ccc(-c2n[nH]c3cnc(-c4cn[nH]c4)cc23)cc1] | 3-phenyl-5-(1H-pyrazol-4-yl)-1H-pyrazolo[3,4-c]pyridine | 0.00461 |

TABLE 1-continued

| No. | Name | Pim-1 Ki (μm) |
|---|---|---|
| 138 | 3-(2-fluorophenyl)-5-(pyrimidin-5-yl)-1H-pyrazolo[3,4-c]pyridine | 0.577 |
| 139 | 1-(3-(3-(2-fluorophenyl)-1H-pyrazolo[3,4-c]pyridin-5-yl)pyridin-4-yl)azepan-4-amine | 0.255 |
| 140 | (S)-(1-(3-(3-(2-fluorophenyl)-1H-pyrazolo[3,4-c]pyridin-5-yl)pyridin-4-yl)piperidin-3-yl)methanamine | 0.412 |
| 141 | (R)1-(3-(3-(2-fluorophenyl)-1H-pyrazolo[3,4-c]pyridin-5-yl)pyridin-4-yl)piperidin-3-amine | 0.142 |
| 142 | 3-phenyl-5-(1H-1,2,4-triazol-1-yl)-1H-pyrazolo[3,4-c]pyridine | 0.306 |

TABLE 1-continued

| No. | Structure | Name | Pim-1 Ki (μm) |
|---|---|---|---|
| 143 | 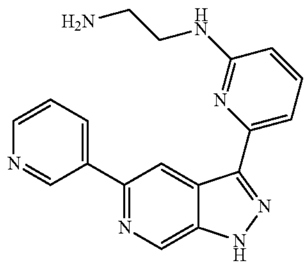 [SMILES: NCCNc1cccc(-c2n[nH]c3cnc(-c4cccnc4)cc23)n1] | N1-(6-(5-(pyridin-3-yl)-1H-pyrazolo[3,4-c]pyridin-3-yl)pyridin-2-yl)ethane-1,2-diamine | 0.000312 |
| 144 | 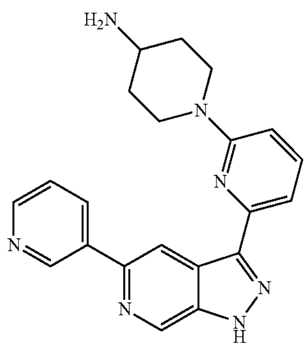 [SMILES: NC1CCN(c2cccc(-c3n[nH]c4cnc(-c5cccnc5)cc34)n2)CC1] | 1-(6-(5-(pyridin-3-yl)-1H-pyrazolo[3,4-c]pyridin-3-yl)pyridin-2-yl)piperidin-4-amine | 0.0000839 |
| 145 | 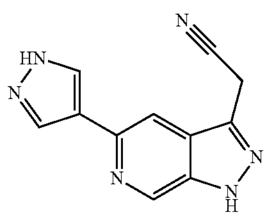 [SMILES: N#CCc1n[nH]c2cnc(-c3cn[nH]c3)cc12] | 2-(5-(1H-pyrazol-4-yl)-1H-pyrazolo[3,4-c]pyridin-3-yl)acetonitrile | 0.324 |
| 146 | 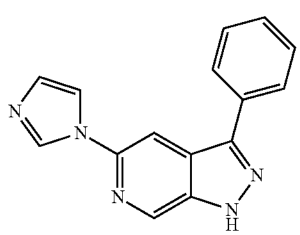 [SMILES: c1ccc(-c2n[nH]c3cnc(-n4ccnc4)cc23)cc1] | 5-(1H-imidazol-1-yl)-3-phenyl-1H-pyrazolo[3,4-c]pyridine | 0.0267 |
| 147 | 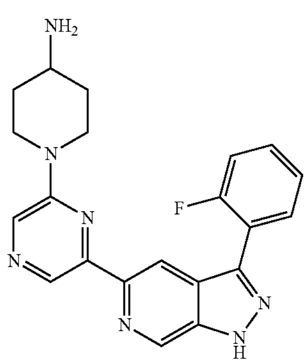 [SMILES: NC1CCN(c2cncc(-c3cc4c(-c5ccccc5F)n[nH]c4cn3)n2)CC1] | 1-(6-(3-(2-fluorophenyl)-1H-pyrazolo[3,4-c]pyridin-5-yl)pyrazin-2-yl)piperidin-4-amine | 0.000121 |

TABLE 1-continued

| No. | Structure | Name | Pim-1 Ki (μm) |
|---|---|---|---|
| 148 | 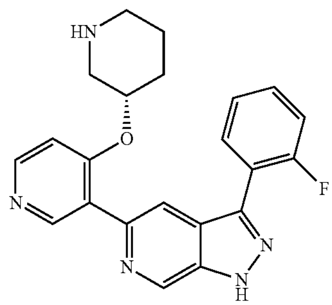 [SMILES: Fc1ccccc1-c1n[nH]c2cnc(-c3cnccc3O[C@H]3CCCNC3)cc12] | (S)-3-(2-fluorophenyl)-5-(4-(piperidin-3-yloxy)pyridin-3-yl)-1H-pyrazolo[3,4-c]pyridin | 0.000342 |
| 149 | 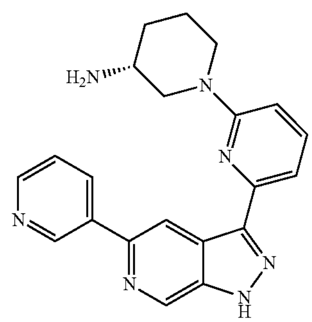 [SMILES: N[C@@H]1CCCN(c2cccc(-c3n[nH]c4cnc(-c5cccnc5)cc34)n2)C1] | (R)-1-(6-(5-(pyridin-3-yl)-1H-pyrazolo[3,4-c]pyridin-3-yl)pyridin-2-yl)piperidin-3-amine | 0.000027 |
| 150 | 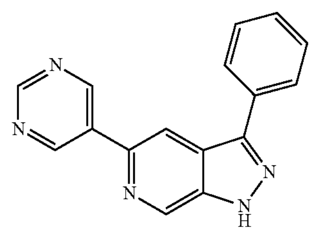 [SMILES: c1ccc(-c2n[nH]c3cnc(-c4cncnc4)cc23)cc1] | 3-phenyl-5-(pyrimidin-5-yl)-1H-pyrazolo[3,4-c]pyridine | 0.209 |
| 151 | 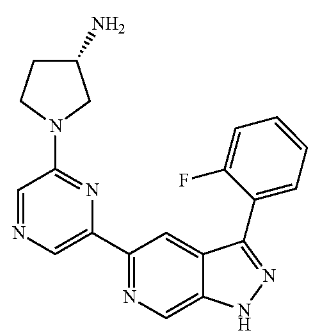 [SMILES: N[C@H]1CCN(c2cncc(-c3cc4c(-c5ccccc5F)n[nH]c4cn3)n2)C1] | (S)-1-(6-(3-(2-fluorophenyl)-1H-pyrazolo[3,4-c]pyridin-5-yl)pyrazin-2-yl)pyrrolidin-3-amine | 0.000179 |
| 152 | 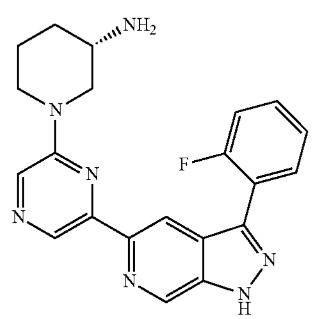 [SMILES: N[C@H]1CCCN(c2cncc(-c3cc4c(-c5ccccc5F)n[nH]c4cn3)n2)C1] | (S)-1-(6-(3-(2-fluorophenyl)-1H-pyrazolo[3,4-c]pyridin-5-yl)pyrazin-2-yl)piperidin-3-amine | 0.00012 |

TABLE 1-continued

| No. | Structure | Name | Pim-1 Ki (μm) |
|---|---|---|---|
| 153 | 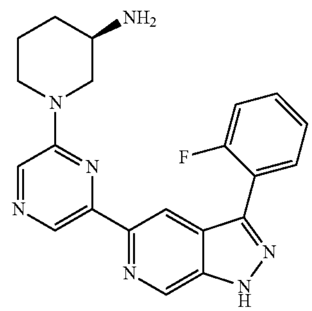 [SMILES: N[C@@H]1CCCN(c2cncc(-c3cc4c(-c5ccccc5F)n[nH]c4cn3)n2)C1] | (R)-1-(6-(3-(2-fluorophenyl)-1H-pyrazolo[3,4-c]pyridin-5-yl)pyrazin-2-yl)piperidin-3-amine | 0.000114 |
| 154 | 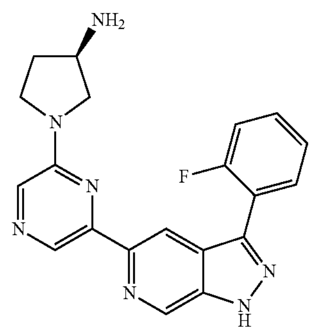 [SMILES: N[C@@H]1CCN(c2cncc(-c3cc4c(-c5ccccc5F)n[nH]c4cn3)n2)C1] | (R)-1-(6-(3-(2-fluorophenyl)-1H-pyrazolo[3,4-c]pyridin-5-yl)pyrazin-2-yl)pyrrolidin-3-amine | 0.000302 |
| 155 | 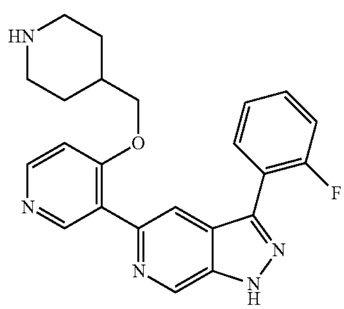 [SMILES: Fc1ccccc1-c1n[nH]c2cnc(-c3cnccc3OCC3CCNCC3)cc12] | 3-(2-fluorophenyl)-5-(4-(piperidin-4-ylmethoxy)pyridin-3-yl)-1H-pyrazolo[3,4-c]pyridine | 0.000614 |
| 156 | 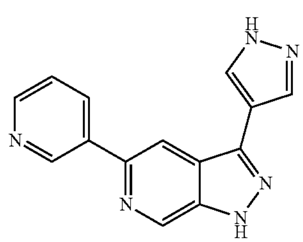 [SMILES: c1cncc(-c2cc3c(-c4cn[nH]c4)n[nH]c3cn2)c1] | 3-(1H-pyrazol-4-yl)-5-(pyridin-3-yl)-1H-pyrazolo[3,4-c]pyridine | 0.00231 |
| 157 | 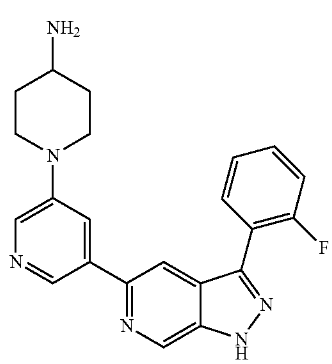 [SMILES: NC1CCN(c2cncc(-c3cc4c(-c5ccccc5F)n[nH]c4cn3)c2)CC1] | 1-(5-(3-(2-fluorophenyl)-1H-pyrazolo[3,4-c]pyridin-5-yl)pyridin-3-yl)piperidin-4-amine | 0.00131 |

TABLE 1-continued

| No. | Structure | Name | Pim-1 Ki (μm) |
|---|---|---|---|
| 158 | 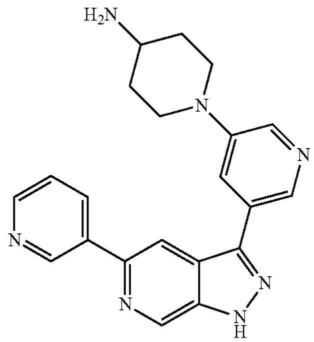 [SMILES: NC1CCN(c2cncc(-c3n[nH]c4cnc(-c5cccnc5)cc34)c2)CC1] | 1-(5-(5-(pyridin-3-yl)-1H-pyrazolo[3,4-c]pyridin-3-yl)pyridin-3-yl)piperidin-4-amine | 0.0021 |
| 159 | 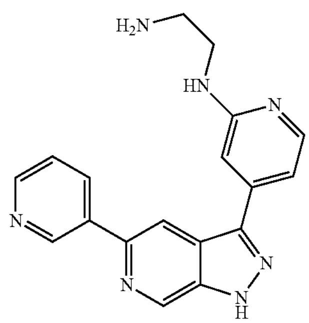 [SMILES: NCCNc1cc(-c2n[nH]c3cnc(-c4cccnc4)cc23)ccn1] | N1-(4-(5-(pyridin-3-yl)-1H-pyrazolo[3,4-c]pyridin-3-yl)pyridin-2-yl)ethane-1,2-diamine | 0.000941 |
| 160 | 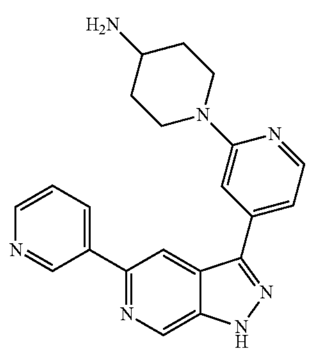 [SMILES: NC1CCN(c2cc(-c3n[nH]c4cnc(-c5cccnc5)cc34)ccn2)CC1] | 1-(4-(5-(pyridin-3-yl)-1H-pyrazolo[3,4-c]pyridin-3-yl)pyridin-2-yl)piperidin-4-amine | 0.00278 |
| 161 | 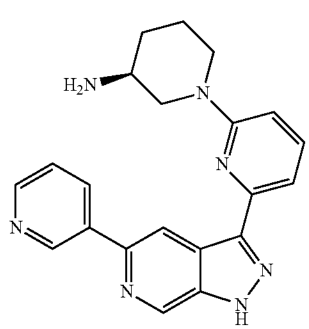 [SMILES: N[C@H]1CCCN(c2cccc(-c3n[nH]c4cnc(-c5cccnc5)cc34)n2)C1] | (S)-1-(6-(5-(pyridin-3-yl)-1H-pyrazolo[3,4-c]pyridin-3-yl)pyridin-2-yl)piperidin-3-amine | 0.0000411 |

TABLE 1-continued

| No. | Structure | Name | Pim-1 Ki (μm) |
|---|---|---|---|
| 162 | 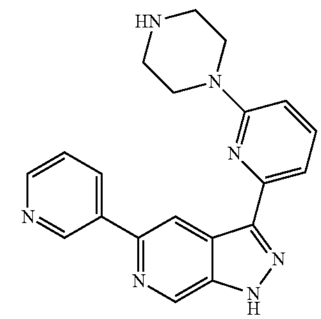 [SMILES: c1cncc(-c2cc3c(-c4cccc(N5CCNCC5)n4)n[nH]c3cn2)c1] | 3-(6-(piperazin-1-yl)pyridin-2-yl)-5-(pyridin-3-yl)-1H-pyrazolo[3,4-c]pyridine | 0.000037 |
| 163 | 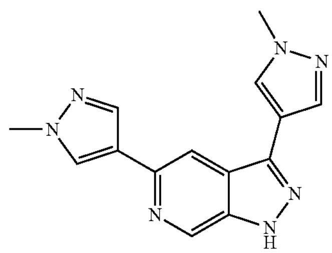 [SMILES: Cn1cc(-c2cc3c(-c4cnn(C)c4)n[nH]c3cn2)cn1] | 3,5-bis(1-methyl-1H-pyrazol-4-yl)-1H-pyrazolo[3,4-c]pyridine | 0.00192 |
| 164 | 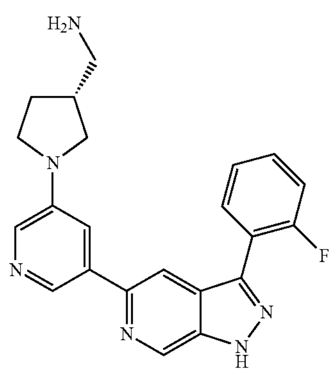 [SMILES: NC[C@H]1CCN(c2cncc(-c3cc4c(-c5ccccc5F)n[nH]c4cn3)c2)C1] | (R)-(1-(5-(3-(2-fluorophenyl)-1H-pyrazolo[3,4-c]pyridin-5-yl)pyridin-3-yl)pyrrolidin-3-yl)methanamine | 0.0019 |
| 165 | 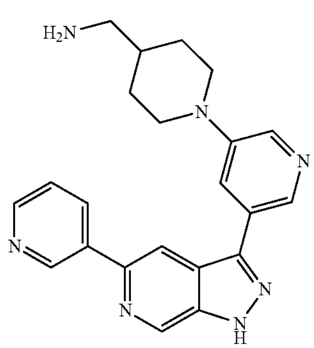 [SMILES: NCC1CCN(c2cncc(-c3n[nH]c4cnc(-c5cccnc5)cc34)c2)CC1] | (1-(5-(5-(pyridin-3-yl)-1H-pyrazolo[3,4-c]pyridin-3-yl)pyridin-3-yl)piperidin-4-yl)methanamine | 0.000985 |

TABLE 1-continued

| No. | Structure | Name | Pim-1 Ki (μm) |
|---|---|---|---|
| 166 | 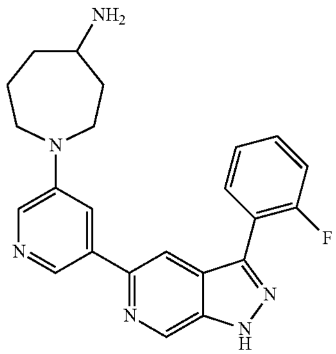 [SMILES: NC1CCCN(c2cncc(-c3cc4c(-c5ccccc5F)n[nH]c4cn3)c2)CC1] | 1-(5-(3-(2-fluorophenyl)-1H-pyrazolo[3,4-c]pyridin-5-yl)pyridin-3-yl)azepan-4-amine | 0.000574 |
| 167 | 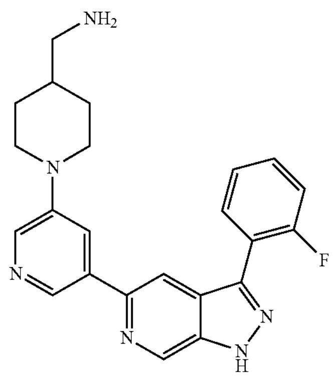 [SMILES: NCC1CCN(c2cncc(-c3cc4c(-c5ccccc5F)n[nH]c4cn3)c2)CC1] | (1-(5-(3-(2-fluorophenyl)-1H-pyrazolo[3,4-c]pyridin-5-yl)pyridin-3-yl)piperidin-4-yl)methanamine | 0.00171 |
| 168 | 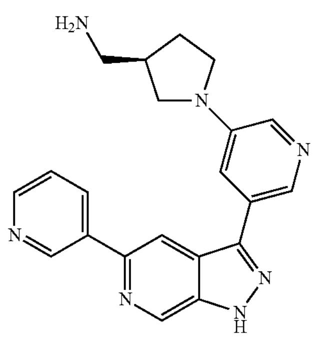 [SMILES: NC[C@H]1CCN(c2cncc(-c3n[nH]c4cnc(-c5cccnc5)cc34)c2)C1] | (R)-(1-(5-(5-(pyridin-3-yl)-1H-pyrazolo[3,4-c]pyridin-3-yl)pyridin-3-yl)pyrrolidin-3-yl)methanamine | 0.0016 |
| 169 | 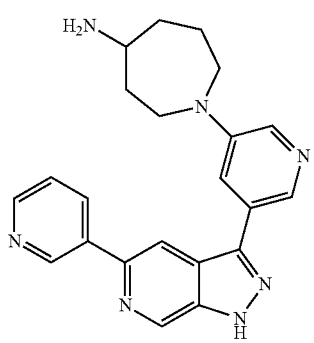 [SMILES: NC1CCCN(c2cncc(-c3n[nH]c4cnc(-c5cccnc5)cc34)c2)CC1] | 1-(5-(5-(pyridin-3-yl)-1H-pyrazolo[3,4-c]pyridin-3-yl)pyridin-3-yl)azepan-4-amine | 0.00135 |

TABLE 1-continued

| No. | Structure | Name | Pim-1 Ki (μm) |
|---|---|---|---|
| 170 | 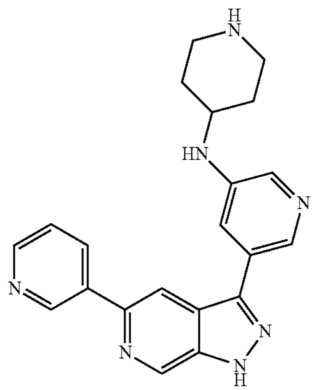 [SMILES: c1cncc(-c2cc3c(-c4cncc(NC5CCNCC5)c4)n[nH]c3cn2)c1] | N-(piperidin-4-yl)-5-(5-(pyridin-3-yl)-1H-pyrazolo[3,4-c]pyridin-3-yl)pyridin-3-amine | 0.000443 |
| 171 | 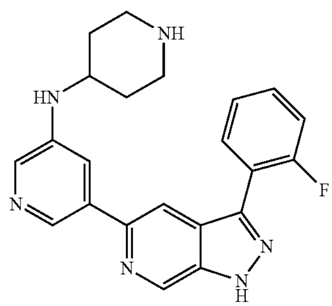 [SMILES: Fc1ccccc1-c1n[nH]c2cnc(-c3cncc(NC4CCNCC4)c3)cc12] | 5-(3-(2-fluorophenyl)-1H-pyrazolo[3,4-c]pyridin-5-yl)-N-(piperidin-4-yl)pyridin-3-amine | 0.00242 |
| 172 | 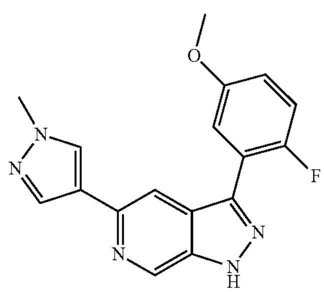 [SMILES: COc1ccc(F)c(-c2n[nH]c3cnc(-c4cnn(C)c4)cc23)c1] | 3-(2-fluoro-5-methoxyphenyl)-5-(1-methyl-1H-pyrazol-4-yl)-1H-pyrazolo[3,4-c]pyridine | 0.00376 |
| 173 | 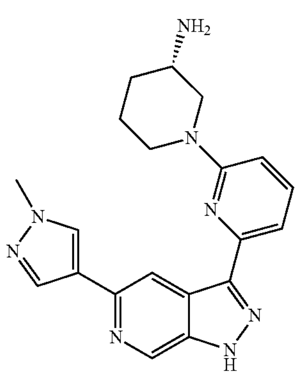 [SMILES: Cn1cc(-c2cc3c(-c4cccc(N5CCC[C@H](N)C5)n4)n[nH]c3cn2)cn1] | (S)-1-(6-(5-(1-methyl-1H-pyrazol-4-yl)-1H-pyrazolo[3,4-c]pyridin-3-yl)pyridin-2-yl)piperidin-3-amine | 0.000060 |

TABLE 1-continued

| No. | Name | Pim-1 Ki (μm) |
|---|---|---|
| 174 | 1-(6-(5-(1-methyl-1H-pyrazol-4-yl)-1H-pyrazolo[3,4-c]pyridin-3-yl)pyridin-2-yl)piperidin-4-amine | 0.000086 |
| 175 | 3-(1-(piperidin-4-yl)-1H-pyrazol-4-yl)-5-(pyridin-3-yl)-1H-pyrazolo[3,4-c]pyridine | 0.00030 |
| 176 | 3,5-di(pyridin-3-yl)-1H-pyrazolo[3,4-c]pyridine | 0.00646 |
| 177 | (R)-1-(6-(5-(1-methyl-1H-pyrazol-4-yl)-1H-pyrazolo[3,4-c]pyridin-3-yl)pyridin-2-yl)piperidin-3-amine | 0.0000355 |
| 178 | 2-(4-(3-(6-fluoropyridin-2-yl)-1H-pyrazolo[3,4-c]pyridin-5-yl)-1H-pyrazol-1-yl)acetamide | 0.0176 |

TABLE 1-continued

| No. | Structure | Name | Pim-1 Ki (μm) |
|---|---|---|---|
| 179 | 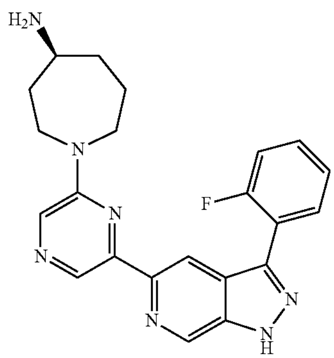 [SMILES: N[C@H]1CCCN(c2cncc(-c3cc4c(-c5ccccc5F)n[nH]c4cn3)n2)CC1] | (S)-1-(6-(3-(2-fluorophenyl)-1H-pyrazolo[3,4-c]pyridin-5-yl)pyrazin-2-yl)azepan-4-amine | 0.000061 |
| 180 | 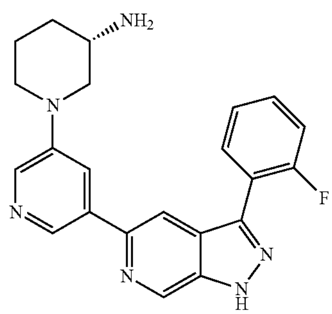 [SMILES: N[C@H]1CCCN(c2cncc(-c3cc4c(-c5ccccc5F)n[nH]c4cn3)c2)C1] | (S)-1-(5-(3-(2-fluorophenyl)-1H-pyrazolo[3,4-c]pyridin-5-yl)pyridin-3-yl)piperidin-3-amine | 0.000264 |
| 181 | 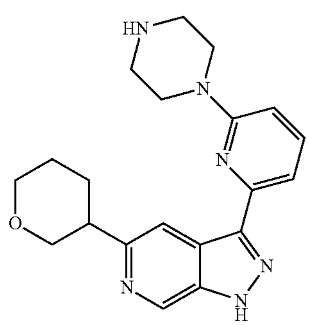 [SMILES: c1cc(-c2n[nH]c3cnc(C4CCCOC4)cc23)nc(N2CCNCC2)c1] | 3-(6-(piperazin-1-yl)pyridin-2-yl)-5-(tetrahydro-2H-pyran-3-yl)-1H-pyrazolo[3,4-c]pyridine | 0.00396 |
| 182 | 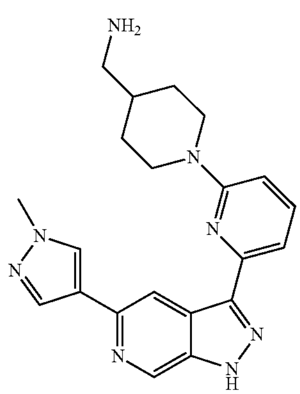 [SMILES: Cn1cc(-c2cc3c(-c4cccc(N5CCC(CN)CC5)n4)n[nH]c3cn2)cn1] | (1-(6-(5-(1-methyl-1H-pyrazol-4-yl)-1H-pyrazolo[3,4-c]pyridin-3-yl)pyridin-2-yl)piperidin-4-yl)methanamine | 0.000085 |

TABLE 1-continued

| No. | Structure | Name | Pim-1 Ki (μm) |
|---|---|---|---|
| 183 | 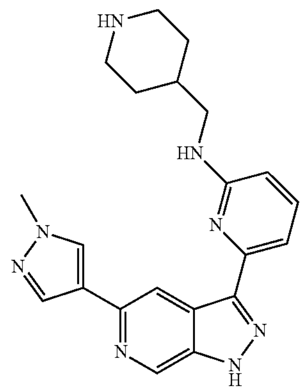 [SMILES: Cn1cc(-c2cc3c(-c4cccc(NCC5CCNCC5)n4)n[nH]c3cn2)cn1] | 6-(5-(1-methyl-1H-pyrazol-4-yl)-1H-pyrazolo[3,4-c]pyridin-3-yl)-N-(piperidin-4-ylmethyl)pyridin-2-amine | 0.000426 |
| 184 | 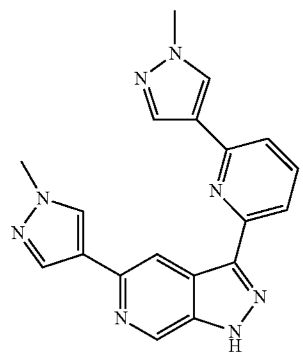 [SMILES: Cn1cc(-c2cc3c(-c4cccc(-c5cnn(C)c5)n4)n[nH]c3cn2)cn1] | 5-(1-methyl-1H-pyrazol-4-yl)-3-(6-(1-methyl-1H-pyrazol-4-yl)pyridin-2-yl)-1H-pyrazolo[3,4-c]pyridine | 0.000502 |
| 185 | 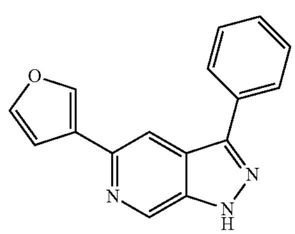 [SMILES: c1ccc(-c2n[nH]c3cnc(-c4ccoc4)cc23)cc1] | 5-(furan-3-yl)-3-phenyl-1H-pyrazolo[3,4-c]pyridine | 0.0709 |
| 186 | 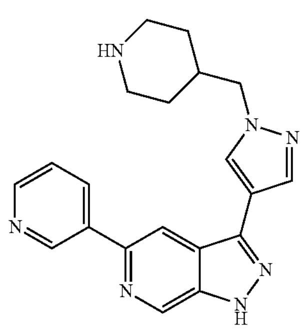 [SMILES: c1cncc(-c2cc3c(-c4cnn(CC5CCNCC5)c4)n[nH]c3cn2)c1] | 3-(1-(piperidin-4-ylmethyl)-1H-pyrazol-4-yl)-5-(pyridin-3-yl)-1H-pyrazolo[3,4-c]pyridine | 0.000717 |

TABLE 1-continued

| No. | Structure | Name | Pim-1 Ki (μm) |
|---|---|---|---|
| 187 | 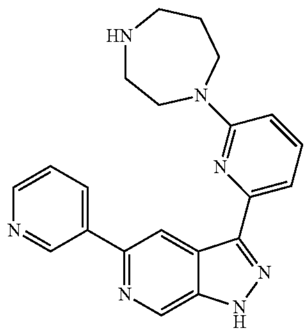 [SMILES: c1cncc(-c2cc3c(-c4cccc(N5CCCNCC5)n4)n[nH]c3cn2)c1] | 3-(6-(1,4-diazepan-1-yl)pyridin-2-yl)-5-(pyridin-3-yl)-1H-pyrazolo[3,4-c]pyridine | 0.000015 |
| 188 | 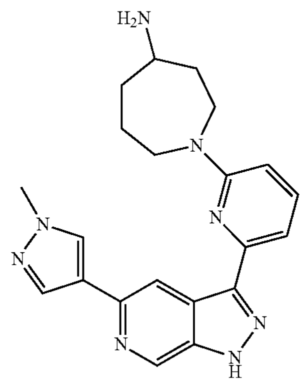 [SMILES: Cn1cc(-c2cc3c(-c4cccc(N5CCCC(N)CC5)n4)n[nH]c3cn2)cn1] | 1-(6-(5-(1-methyl-1H-pyrazol-4-yl)-1H-pyrazolo[3,4-c]pyridin-3-yl)pyridin-2-yl)azepan-4-amine | 0.000039 |
| 189 | 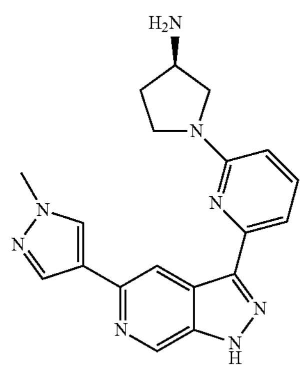 [SMILES: Cn1cc(-c2cc3c(-c4cccc(N5CC[C@@H](N)C5)n4)n[nH]c3cn2)cn1] | (R)-1-(6-(5-(1-methyl-1H-pyrazol-4-yl)-1H-pyrazolo[3,4-c]pyridin-3-yl)pyridin-2-yl)pyrrolidin-3-amine | 0.000136 |
| 190 | 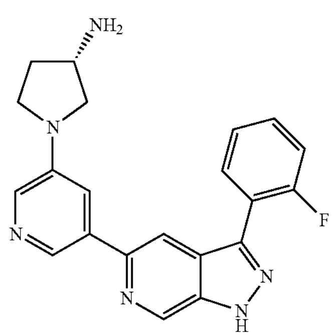 [SMILES: N[C@H]1CCN(c2cncc(-c3cc4c(-c5ccccc5F)n[nH]c4cn3)c2)C1] | (S)-1-(5-(3-(2-fluorophenyl)-1H-pyrazolo[3,4-c]pyridin-5-yl)pyridin-3-yl)pyrrolidin-3-amine | 0.00027 |

TABLE 1-continued

| No. | Structure | Name | Pim-1 Ki (μm) |
|---|---|---|---|
| 191 | 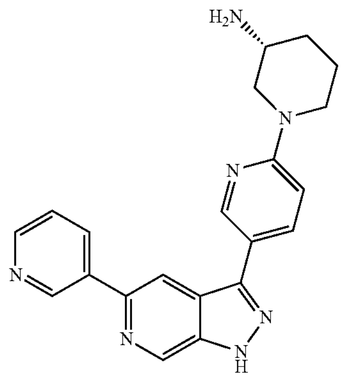 [SMILES: N[C@@H]1CCCN(c2ccc(-c3n[nH]c4cnc(-c5cccnc5)cc34)cn2)C1] | (R)-1-(5-(5-(pyridin-3-yl)-1H-pyrazolo[3,4-c]pyridin-3-yl)pyridin-2-yl)piperidin-3-amine | 0.000404 |
| 192 | 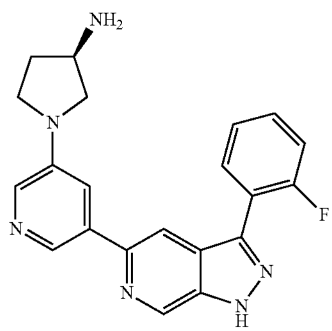 [SMILES: N[C@@H]1CCN(c2cncc(-c3cc4c(-c5ccccc5F)n[nH]c4cn3)c2)C1] | (R)-1-(5-(3-(2-fluorophenyl)-1H-pyrazolo[3,4-c]pyridin-5-yl)pyridin-3-yl)pyrrolidin-3-amine | 0.000511 |
| 193 | 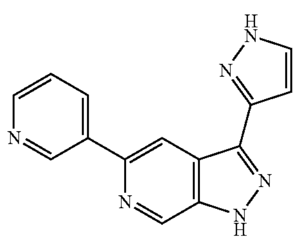 [SMILES: c1cncc(-c2cc3c(-c4cc[nH]n4)n[nH]c3cn2)c1] | 3-(1H-pyrazol-3-yl)-5-(pyridin-3-yl)-1H-pyrazolo[3,4-c]pyridine | 0.00263 |
| 194 | 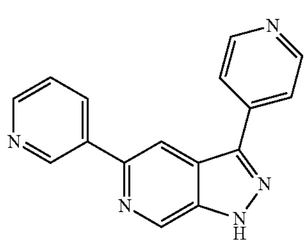 [SMILES: c1cncc(-c2cc3c(-c4ccncc4)n[nH]c3cn2)c1] | 5-(pyridin-3-yl)-3-(pyridin-4-yl)-1H-pyrazolo[3,4-c]pyridine | 0.00877 |
| 195 | 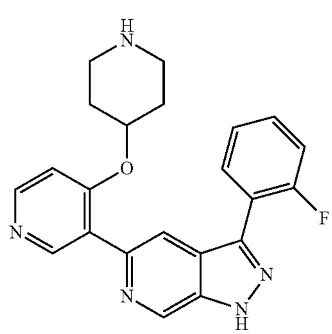 [SMILES: Fc1ccccc1-c1n[nH]c2cnc(-c3cnccc3OC3CCNCC3)cc12] | 3-(2-fluorophenyl)-5-(4-(piperidin-4-yloxy)pyridin-3-yl)-1H-pyrazolo[3,4-c]pyridine | 0.000567 |

TABLE 1-continued

| No. | Structure | Name | Pim-1 Ki (μm) |
|---|---|---|---|
| 196 | 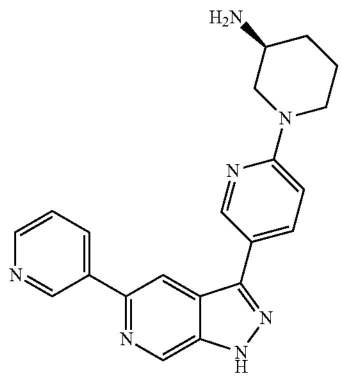 [SMILES: N[C@H]1CCCN(c2ccc(-c3n[nH]c4cnc(-c5cccnc5)cc34)cn2)C1] | (S)-1-(5-(5-(pyridin-3-yl)-1H-pyrazolo[3,4-c]pyridin-3-yl)pyridin-2-yl)piperidin-3-amine | 0.000774 |
| 197 | 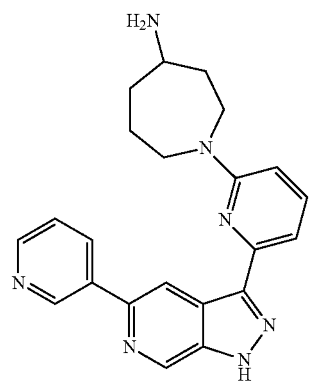 [SMILES: NC1CCCN(c2cccc(-c3n[nH]c4cnc(-c5cccnc5)cc34)n2)CC1] | 1-(6-(5-(pyridin-3-yl)-1H-pyrazolo[3,4-c]pyridin-3-yl)pyridin-2-yl)azepan-4-amine | 0.000038 |
| 198 | 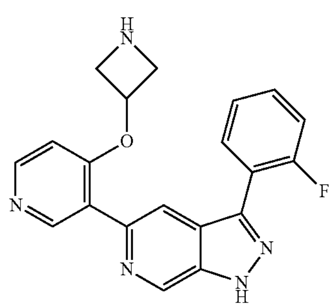 [SMILES: Fc1ccccc1-c1n[nH]c2cnc(-c3cnccc3OC3CNC3)cc12] | 5-(4-(azetidin-3-yloxy)pyridin-3-yl)-3-(2-fluorophenyl)-1H-pyrazolo[3,4-c]pyridine | 0.00312 |
| 199 | 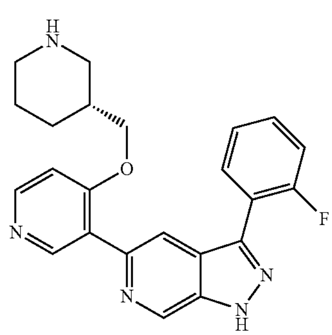 [SMILES: Fc1ccccc1-c1n[nH]c2cnc(-c3cnccc3OC[C@@H]3CCCNC3)cc12] | (R)-3-(2-fluorophenyl)-5-(4-(piperidin-3-ylmethoxy)pyridin-3-yl)-1H-pyrazolo[3,4-c]pyridine | 0.000354 |

TABLE 1-continued

| No. | Structure | Name | Pim-1 Ki (μm) |
|---|---|---|---|
| 200 | 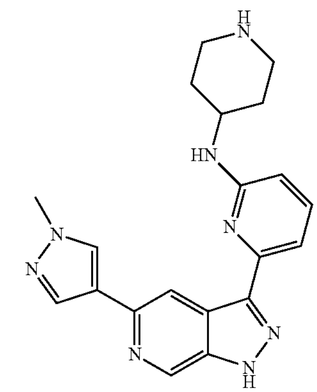 [SMILES: Cn1cc(-c2cc3c(-c4cccc(NC5CCNCC5)n4)n[nH]c3cn2)cn1] | 6-(5-(1-methyl-1H-pyrazol-4-yl)-1H-pyrazolo[3,4-c]pyridin-3-yl)-N-(piperidin-4-yl)pyridin-2-amine | 0.000092 |
| 201 | 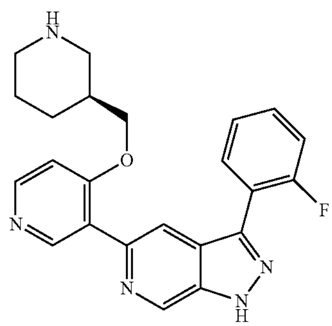 [SMILES: Fc1ccccc1-c1n[nH]c2cnc(-c3cnccc3OC[C@H]3CCCNC3)cc12] | (S)-3-(2-fluorophenyl)-5-(4-(piperidin-3-ylmethoxy)pyridin-3-yl)-1H-pyrazolo[3,4-c]pyridine | 0.00152 |
| 202 | 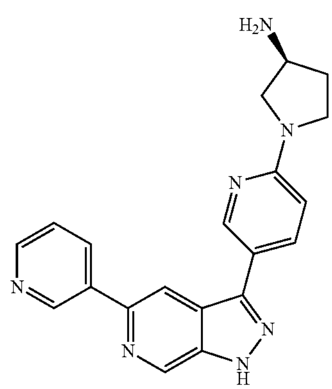 [SMILES: N[C@H]1CCN(c2ccc(-c3n[nH]c4cnc(-c5cccnc5)cc34)cn2)C1] | (S)-1-(5-(5-(pyridin-3-yl)-1H-pyrazolo[3,4-c]pyridin-3-yl)pyridin-2-yl)pyrrolidin-3-amine | 0.0010 |
| 203 | 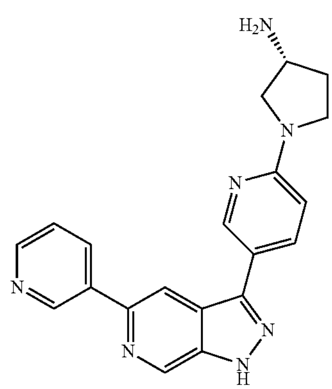 [SMILES: N[C@@H]1CCN(c2ccc(-c3n[nH]c4cnc(-c5cccnc5)cc34)cn2)C1] | (R)-1-(5-(5-(pyridin-3-yl)-1H-pyrazolo[3,4-c]pyridin-3-yl)pyridin-2-yl)pyrrolidin-3-amine | 0.00102 |

TABLE 1-continued

| No. | Structure | Name | Pim-1 Ki (μm) |
|---|---|---|---|
| 204 | 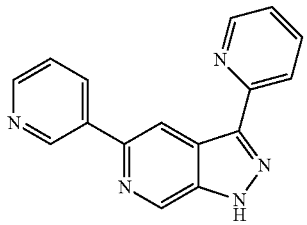 [SMILES: c1ccc(-c2n[nH]c3cnc(-c4cccnc4)cc23)nc1] | 3-(pyridin-2-yl)-5-(pyridin-3-yl)-1H-pyrazolo[3,4-c]pyridine | 0.0116 |
| 205 | 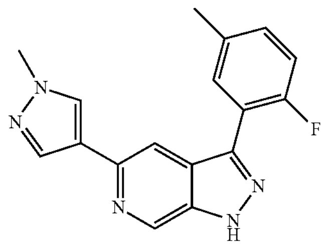 [SMILES: Cc1ccc(F)c(-c2n[nH]c3cnc(-c4cnn(C)c4)cc23)c1] | 3-(2-fluoro-5-methylphenyl)-5-(1-methyl-1H-pyrazol-4-yl)-1H-pyrazolo[3,4-c]pyridine | 0.00608 |
| 206 | 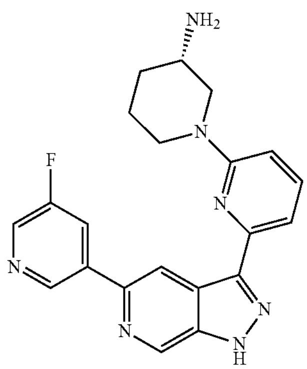 [SMILES: N[C@H]1CCCN(c2cccc(-c3n[nH]c4cnc(-c5cncc(F)c5)cc34)n2)C1] | (S)-1-(6-(5-(5-fluoropyridin-3-yl)-1H-pyrazolo[3,4-c]pyridin-3-yl)pyridin-2-yl)piperidin-3-amine | 0.000172 |
| 207 | 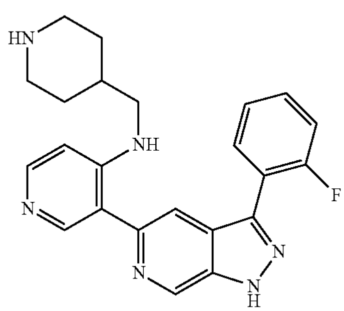 [SMILES: Fc1ccccc1-c1n[nH]c2cnc(-c3cnccc3NCC3CCNCC3)cc12] | 3-(3-(2-fluorophenyl)-1H-pyrazolo[3,4-c]pyridin-5-yl)-N-(piperidin-4-ylmethyl)pyridin-4-amine | 0.0227 |
| 208 | 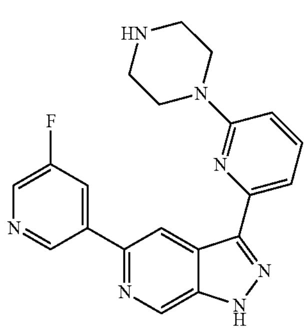 | 5-(5-fluoropyridin-3-yl)-3-(6-(piperazin-1-yl)pyridin-2-yl)-1H-pyrazolo[3,4-c]pyridine | 0.000284 |

TABLE 1-continued

| No. | Structure | Name | Pim-1 Ki (μm) |
|---|---|---|---|
| 209 | 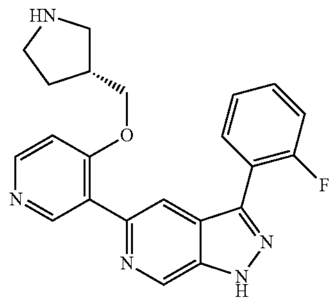 [SMILES: Fc1ccccc1-c1n[nH]c2cnc(-c3cnccc3OC[C@@H]3CCNC3)cc12] | (R)-3-(2-fluorophenyl)-5-(4-(pyrrolidin-3-ylmethoxy)pyridin-3-yl)-1H-pyrazolo[3,4-c]pyridine | 0.000189 |
| 210 | 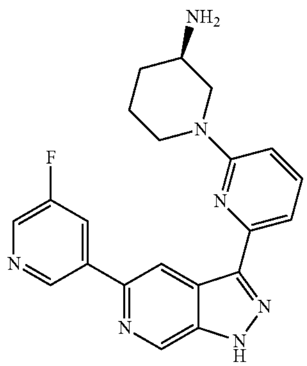 [SMILES: N[C@@H]1CCCN(c2cccc(-c3n[nH]c4cnc(-c5cncc(F)c5)cc34)n2)C1] | (R)-1-(6-(5-(5-fluoropyridin-3-yl)-1H-pyrazolo[3,4-c]pyridin-3-yl)pyridin-2-yl)piperidin-3-amine | 0.000206 |
| 211 | 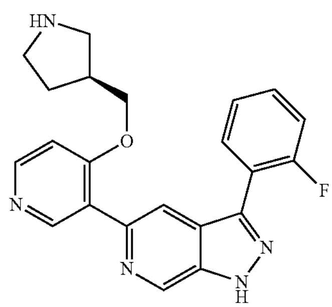 [SMILES: Fc1ccccc1-c1n[nH]c2cnc(-c3cnccc3OC[C@H]3CCNC3)cc12] | (S)-3-(2-fluorophenyl)-5-(4-(pyrrolidin-3-ylmethoxy)pyridin-3-yl)-1H-pyrazolo[3,4-c]pyridine | 0.00128 |
| 212 | 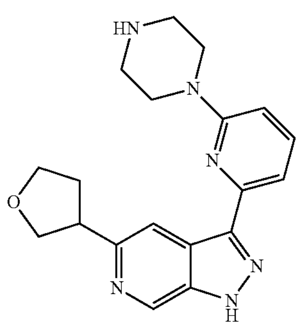 [SMILES: c1cc(-c2n[nH]c3cnc(C4CCOC4)cc23)nc(N2CCNCC2)c1] | 3-(6-(piperazin-1-yl)pyridin-2-yl)-5-(tetrahydrofuran-3-yl)-1H-pyrazolo[3,4-c]pyridine | 0.00848 |
| 213 | 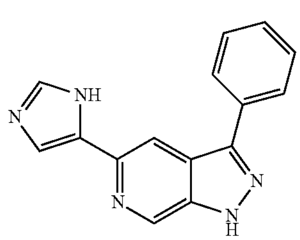 [SMILES: c1ccc(-c2n[nH]c3cnc(-c4cnc[nH]4)cc23)cc1] | 5-(1H-imidazol-5-yl)-3-phenyl-1H-pyrazolo[3,4-c]pyridine | |

TABLE 1-continued

| No. | Structure | Name | Pim-1 Ki (μm) |
|---|---|---|---|
| 214 | 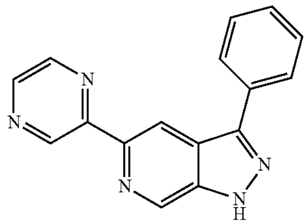 [SMILES: c1ccc(-c2n[nH]c3cnc(-c4cnccn4)cc23)cc1] | 3-phenyl-5-(pyrazin-2-yl)-1H-pyrazolo[3,4-c]pyridine | 0.0416 |
| 215 | 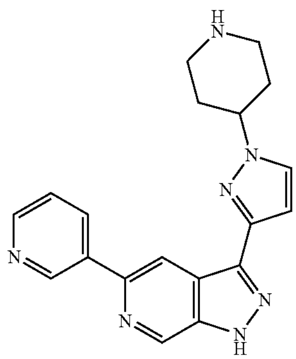 [SMILES: c1cncc(-c2cc3c(-c4ccn(C5CCNCC5)n4)n[nH]c3cn2)c1] | 3-(1-(piperidin-4-yl)-1H-pyrazol-3-yl)-5-(pyridin-3-yl)-1H-pyrazolo[3,4-c]pyridine | 0.000313 |
| 216 | 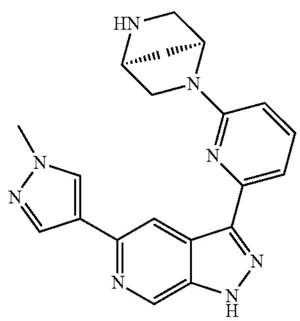 [SMILES: Cn1cc(-c2cc3c(-c4cccc(N5C[C@@H]6C[C@H]5CN6)n4)n[nH]c3cn2)cn1] | 3-(6-((1S,4S)-2,5-diazabicyclo[2.2.1]heptan-2-yl)pyridin-2-yl)-5-(1-methyl-1H-pyrazol-4-yl)-1H-pyrazolo[3,4-c]pyridine | 0.000126 |
| 217 | 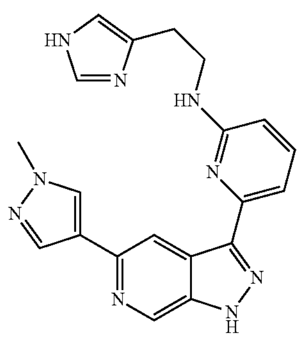 [SMILES: Cn1cc(-c2cc3c(-c4cccc(NCCc5c[nH]cn5)n4)n[nH]c3cn2)cn1] | N-(2-(1H-imidazol-4-yl)ethyl)-6-(5-(1-methyl-1H-pyrazol-4-yl)-1H-pyrazolo[3,4-c]pyridin-3-yl)pyridin-2-amine | −.000297 |
| 218 | 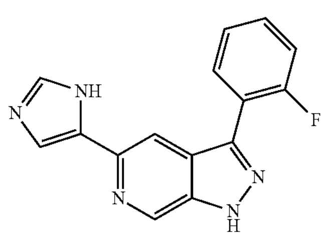 [SMILES: Fc1ccccc1-c1n[nH]c2cnc(-c3cnc[nH]3)cc12] | 3-(2-fluorophenyl)-5-(1H-imidazol-5-yl)-1H-pyrazolo[3,4-c]pyridine | 0.0309 |

TABLE 1-continued

| No. | Structure | Name | Pim-1 Ki (μm) |
|---|---|---|---|
| 219 | 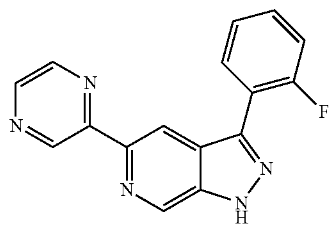 [SMILES: Fc1ccccc1-c1n[nH]c2cnc(-c3cnccn3)cc12] | 3-(2-fluorophenyl)-5-(pyrazin-2-yl)-1H-pyrazolo[3,4-c]pyridine | 0.0335 |
| 220 | 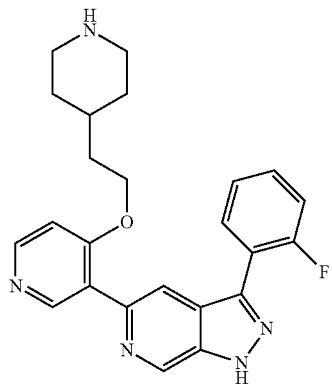 [SMILES: Fc1ccccc1-c1n[nH]c2cnc(-c3cnccc3OCCC3CCNCC3)cc12] | 3-(2-fluorophenyl)-5-(4-(2-(piperidin-4-yl)ethoxy)pyridin-3-yl)-1H-pyrazolo[3,4-c]pyridine | 0.000379 |
| 221 | 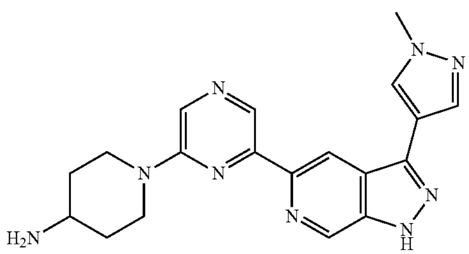 [SMILES: Cn1cc(-c2n[nH]c3cnc(-c4cncc(N5CCC(N)CC5)n4)cc23)cn1] | 1-(6-(3-(1-methyl-1H-pyrazol-4-yl)-1H-pyrazolo[3,4-c]pyridin-5-yl)pyrazin-2-yl)piperidin-4-amine | 0.000096 |
| 222 | 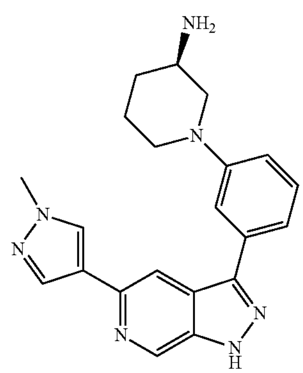 [SMILES: Cn1cc(-c2cc3c(-c4cccc(N5CCC[C@@H](N)C5)c4)n[nH]c3cn2)cn1] | (R)-1-(3-(5-(1-methyl-1H-pyrazol-4-yl)-1H-pyrazolo[3,4-c]pyridin-3-yl)phenyl)piperidin-3-amine | 0.000387 |
| 223 | 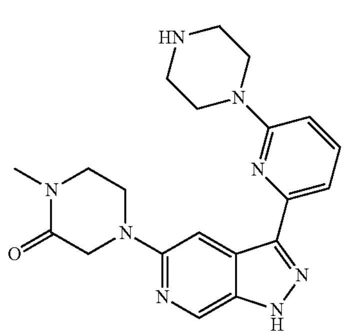 [SMILES: CN1CCN(c2cc3c(-c4cccc(N5CCNCC5)n4)n[nH]c3cn2)CC1=O] | 1-methyl-4-(3-(6-(piperazin-1-yl)pyridin-2-yl)-1H-pyrazolo[3,4-c]pyridin-5-yl)piperazin-2-one | 0.0385 |

TABLE 1-continued
| No. | Structure | Name | Pim-1 Ki (μm) |
|---|---|---|---|
| 224 | 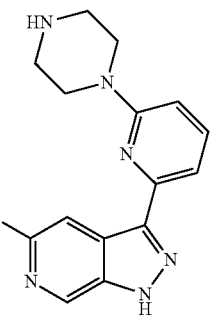 | 1-(3-(6-(piperazin-1-yl)pyridin-2-yl)-1H-pyrazolo[3,4-c]pyridin-5-yl)urea | 0.00196 |
| 225 | 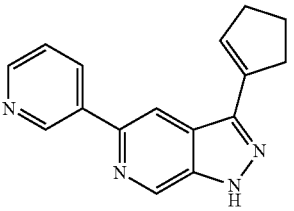 [SMILES: C1=C(c2n[nH]c3cnc(-c4cccnc4)cc23)CCC1] | 3-cyclopentenyl-5-(pyridin-3-yl)-1H-pyrazolo[3,4-c]pyridine | 0.00283 |
| 226 | 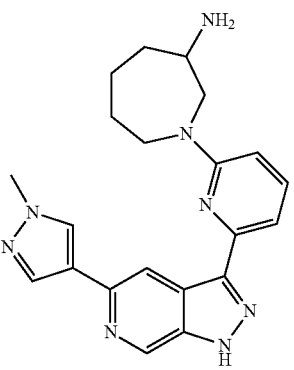 [SMILES: Cn1cc(-c2cc3c(-c4cccc(N5CCCCC(N)C5)n4)n[nH]c3cn2)cn1] | 1-(6-(5-(1-methyl-1H-pyrazol-4-yl)-1H-pyrazolo[3,4-c]pyridin-3-yl)pyridin-2-yl)azepan-3-amine | 0.000051 |
| 227 | 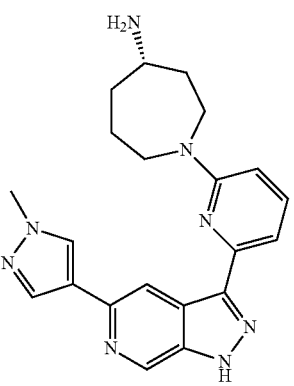 [SMILES: Cn1cc(-c2cc3c(-c4cccc(N5CCC[C@H](N)CC5)n4)n[nH]c3cn2)cn1] | (S)-1-(6-(5-(1-methyl-1H-pyrazol-4-yl)-1H-pyrazolo[3,4-c]pyridin-3-yl)pyridin-2-yl)azepan-4-amine | 0.000069 |
| 228 | 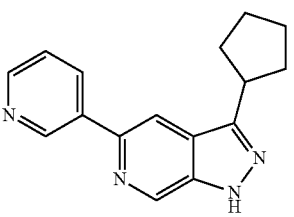 [SMILES: c1cncc(-c2cc3c(C4CCCC4)n[nH]c3cn2)c1] | 3-cyclopentyl-5-(pyridin-3-yl)-1H-pyrazolo[3,4-c]pyridine | 0.043 |

TABLE 1-continued

| No. | Structure | Name | Pim-1 Ki (μm) |
|---|---|---|---|
| 229 | 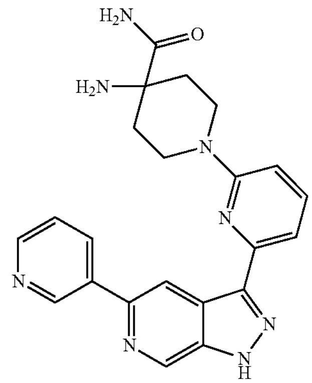 [SMILES: NC(=O)C1(N)CCN(c2cccc(-c3n[nH]c4cnc(-c5cccnc5)cc34)n2)CC1] | 4-amino-1-(6-(5-(pyridin-3-yl)-1H-pyrazolo[3,4-c]pyridin-3-yl)pyridin-2-yl)piperidine-4-carboxamide | 0.00022 |
| 230 | 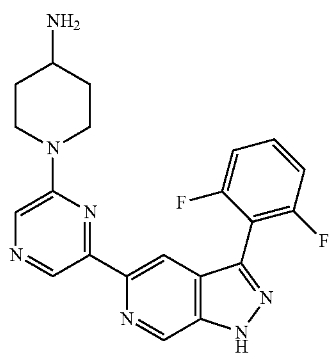 [SMILES: NC1CCN(c2cncc(-c3cc4c(-c5c(F)cccc5F)n[nH]c4cn3)n2)CC1] | 1-(6-(3-(2,6-difluorophenyl)-1H-pyrazolo[3,4-c]pyridin-5-yl)pyrazin-2-yl)piperidin-4-amine | |
| 231 | 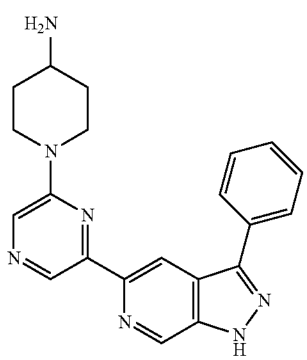 [SMILES: NC1CCN(c2cncc(-c3cc4c(-c5ccccc5)n[nH]c4cn3)n2)CC1] | 1-(6-(3-phenyl-1H-pyrazolo[3,4-c]pyridin-5-yl)pyrazin-2-yl)piperidin-4-amine | |
| 232 | 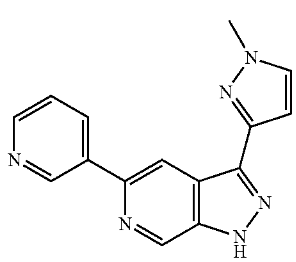 [SMILES: Cn1ccc(-c2n[nH]c3cnc(-c4cccnc4)cc23)n1] | 3-(1-methyl-1H-pyrazol-3-yl)-5-(pyridin-3-yl)-1H-pyrazolo[3,4-c]pyridine | 0.00716 |

TABLE 1-continued

| No. | Structure | Name | Pim-1 Ki (μm) |
|---|---|---|---|
| 233 | 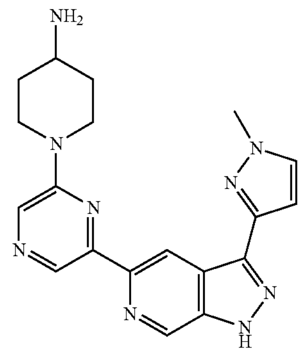 [SMILES: Cn1ccc(-c2n[nH]c3cnc(-c4cncc(N5CCC(N)CC5)n4)cc23)n1] | 1-(6-(3-(1-methyl-1H-pyrazol-3-yl)-1H-pyrazolo[3,4-c]pyridin-5-yl)pyrazin-2-yl)piperidin-4-amine | 0.000051 |
| 234 | 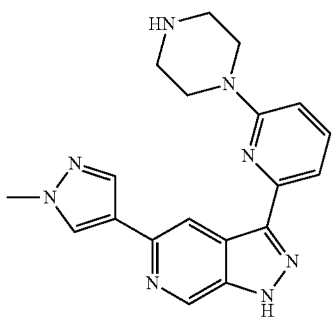 | 5-(1-methyl-1H-pyrazol-4-yl)-3-(6-(piperazin-1-yl)pyridin-2-yl)-1H-pyrazolo[3,4-c]pyridine | 0.000036 |
| 235 | 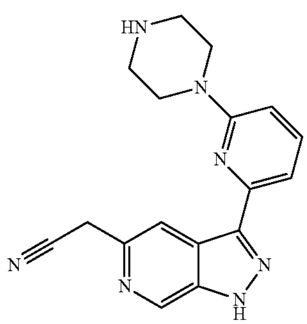 [SMILES: N#CCc1cc2c(-c3cccc(N4CCNCC4)n3)n[nH]c2cn1] | 2-(3-(6-(piperazin-1-yl)pyridin-2-yl)-1H-pyrazolo[3,4-c]pyridin-5-yl)acetonitrile | 0.583 |
| 236 | 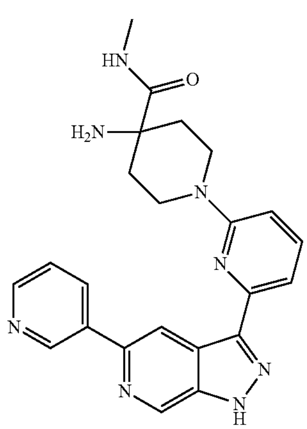 [SMILES: CNC(=O)C1(N)CCN(c2cccc(-c3n[nH]c4cnc(-c5cccnc5)cc34)n2)CC1] | 4-amino-N-methyl-1-(6-(5-(pyridin-3-yl)-1H-pyrazolo[3,4-c]pyridin-3-yl)pyridin-2-yl)piperidine-4-carboxamide | 0.000353 |

TABLE 1-continued

| No. | Structure | Name | Pim-1 Ki (μm) |
|-----|-----------|------|---------------|
| 237 | 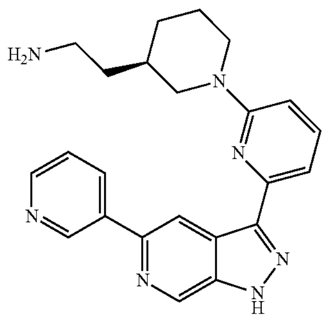 [SMILES: NCC[C@H]1CCCN(c2cccc(-c3n[nH]c4cnc(-c5cccnc5)cc34)n2)C1] | (R)-2-(1-(6-(5-(pyridin-3-yl)-1H-pyrazolo[3,4-c]pyridin-3-yl)pyridin-2-yl)piperidin-3-yl)ethanamine | 0.000042 |
| 238 | 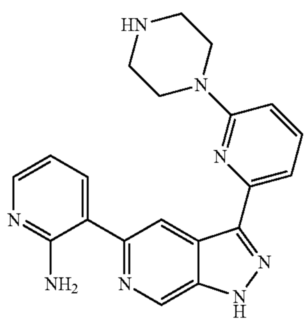 [SMILES: Nc1ncccc1-c1cc2c(-c3cccc(N4CCNCC4)n3)n[nH]c2cn1] | 3-(3-(6-(piperazin-1-yl)pyridin-2-yl)-1H-pyrazolo[3,4-c]pyridin-5-yl)pyridin-2-amine | 0.000267 |
| 239 | 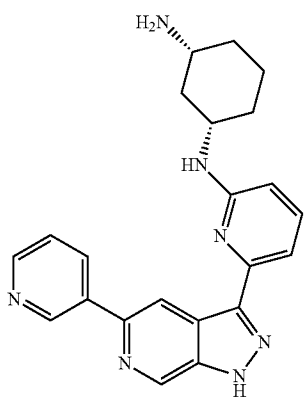 [SMILES: N[C@@H]1CCC[C@H](Nc2cccc(-c3n[nH]c4cnc(-c5cccnc5)cc34)n2)C1] | (1S,3R)-N1-(6-(5-(pyridin-3-yl)-1H-pyrazolo[3,4-c]pyridin-3-yl)pyridin-2-yl)cyclohexane-1,3-diamine | 0.00030 |
| 240 | 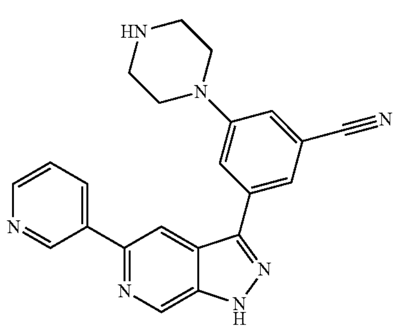 [SMILES: N#Cc1cc(-c2n[nH]c3cnc(-c4cccnc4)cc23)cc(N2CCNCC2)c1] | 3-(piperazin-1-yl)-5-(5-(pyridin-3-yl)-1H-pyrazolo[3,4-c]pyridin-3-yl)benzonitrile | 0.00528 |

TABLE 1-continued

| No. | Structure | Name | Pim-1 Ki (μm) |
|---|---|---|---|
| 241 | 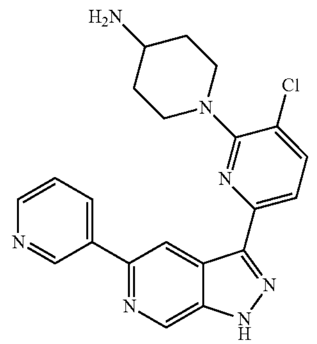 [SMILES: NC1CCN(c2nc(-c3n[nH]c4cnc(-c5cccnc5)cc34)ccc2Cl)CC1] | 1-(3-chloro-6-(5-(pyridin-3-yl)-1H-pyrazolo[3,4-c]pyridin-3-yl)pyridin-2-yl)piperidin-4-amine | 0.000096 |
| 242 | 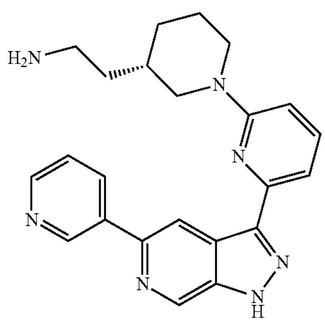 [SMILES: NCC[C@@H]1CCCN(c2cccc(-c3n[nH]c4cnc(-c5cccnc5)cc34)n2)C1] | (S)-2-(1-(6-(5-(pyridin-3-yl)-1H-pyrazolo[3,4-c]pyridin-3-yl)pyridin-2-yl)piperidin-3-yl)ethanamine | 0.000030 |
| 243 | 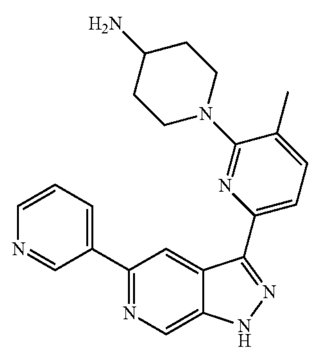 [SMILES: Cc1ccc(-c2n[nH]c3cnc(-c4cccnc4)cc23)nc1N1CCC(N)CC1] | 1-(3-methyl-6-(5-(pyridin-3-yl)-1H-pyrazolo[3,4-c]pyridin-3-yl)pyridin-2-yl)piperidin-4-amine | 0.000049 |
| 244 | 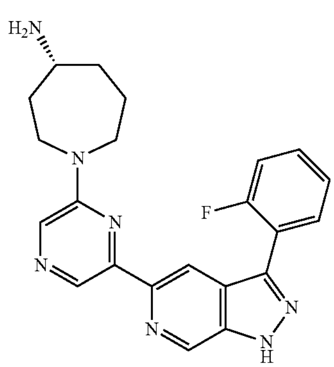 [SMILES: N[C@@H]1CCCN(c2cncc(-c3cc4c(-c5ccccc5F)n[nH]c4cn3)n2)CC1] | (R)-1-(6-(3-(2-fluorophenyl)-1H-pyrazolo[3,4-c]pyridin-5-yl)pyrazin-2-yl)azepan-4-amine | 0.000030 |

TABLE 1-continued

| No. | Structure | Name | Pim-1 Ki (μm) |
|---|---|---|---|
| 245 | 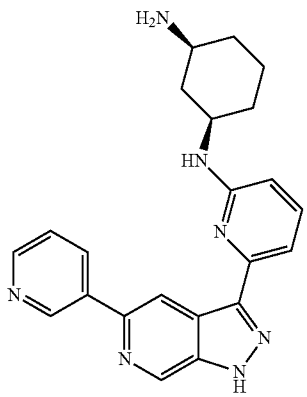 [SMILES: N[C@H]1CCC[C@@H](Nc2cccc(-c3n[nH]c4cnc(-c5cccnc5)cc34)n2)C1] | (1R,3S)-N1-(6-(5-(pyridin-3-yl)-1H-pyrazolo[3,4-c]pyridin-3-yl)pyridin-2-yl)cyclohexane-1,3-diamine | 0.0000079 |
| 246 | 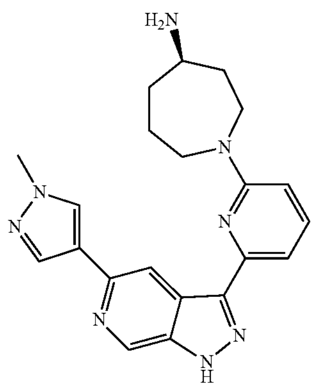 [SMILES: Cn1cc(-c2cc3c(-c4cccc(N5CCC[C@@H](N)CC5)n4)n[nH]c3cn2)cn1] | (R)-1-(6-(5-(1-methyl-1H-pyrazol-4-yl)-1H-pyrazolo[3,4-c]pyridin-3-yl)pyridin-2-yl)azepan-4-amine | 0.000030 |
| 247 | 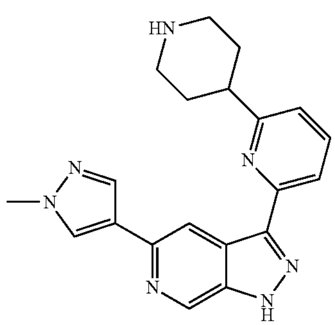 [SMILES: Cn1cc(-c2cc3c(-c4cccc(C5CCNCC5)n4)n[nH]c3cn2)cn1] | 5-(1-methyl-1H-pyrazol-4-yl)-3-(6-(piperidin-4-yl)pyridin-2-yl)-1H-pyrazolo[3,4-c]pyridine | 0.000224 |
| 248 | 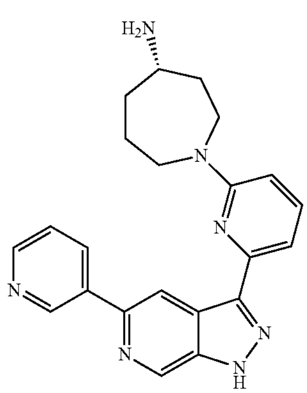 | (S)-1-(6-(5-(pyridin-3-yl)-1H-pyrazolo[3,4-c]pyridin-3-yl)pyridin-2-yl)azepan-4-amine | 0.000048 |

TABLE 1-continued
| No. | Structure | Name | Pim-1 Ki (μm) |
|---|---|---|---|
| 249 | 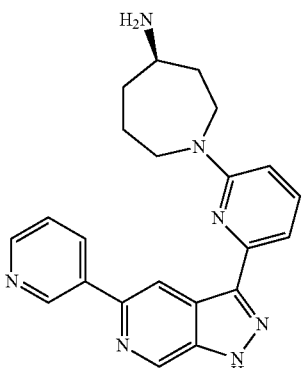 | (R)-1-(6-(5-(pyridin-3-yl)-1H-pyrazolo[3,4-c]pyridin-3-yl)pyridin-2-yl)azepan-4-amine | 0.000020 |
| 250 | 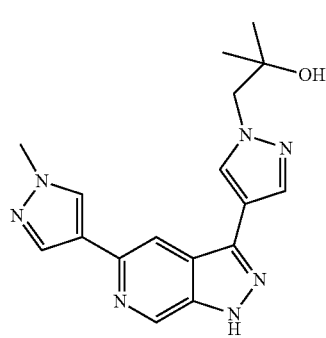 [SMILES: Cn1cc(-c2cc3c(-c4cnn(CC(C)(C)O)c4)n[nH]c3cn2)cn1] | 2-methyl-1-(4-(5-(1-methyl-1H-pyrazol-4-yl)-1H-pyrazolo[3,4-c]pyridin-3-yl)-1H-pyrazol-1-yl)propan-2-ol | 0.000389 |
| 251 | 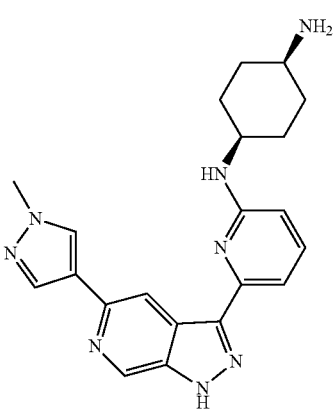 [SMILES: Cn1cc(-c2cc3c(-c4cccc(N[C@H]5CC[C@@H](N)CC5)n4)n[nH]c3cn2)cn1] | (1s,4s)-N1-(6-(5-(1-methyl-1H-pyrazol-4-yl)-1H-pyrazolo[3,4-c]pyridin-3-yl)pyridin-2-yl)cyclohexane-1,4-diamine | 0.000040 |
| 252 | 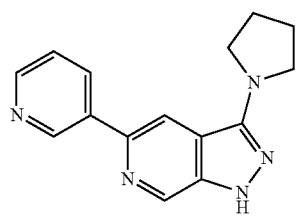 [SMILES: c1cncc(-c2cc3c(N4CCCC4)n[nH]c3cn2)c1] | 5-(pyridin-3-yl)-3-(pyrrolidin-1-yl)-1H-pyrazolo[3,4-c]pyridine | 0.010 |

TABLE 1-continued

| No. | Structure | Name | Pim-1 Ki (μm) |
|---|---|---|---|
| 253 | 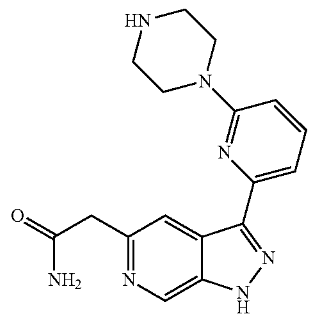 [SMILES: NC(=O)Cc1cc2c(-c3cccc(N4CCNCC4)n3)n[nH]c2cn1] | 2-(3-(6-(piperazin-1-yl)pyridin-2-yl)-1H-pyrazolo[3,4-c]pyridin-5-yl)acetamide | 0.171 |
| 254 | 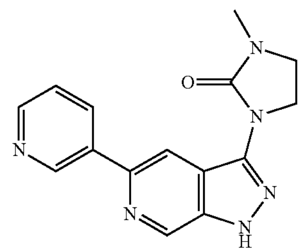 [SMILES: CN1CCN(c2n[nH]c3cnc(-c4cccnc4)cc23)C1=O] | 1-methyl-3-(5-(pyridin-3-yl)-1H-pyrazolo[3,4-c]pyridin-3-yl)imidazolidin-2-one | 0.0185 |
| 255 | 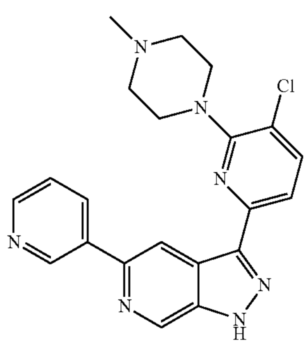 [SMILES: CN1CCN(c2nc(-c3n[nH]c4cnc(-c5cccnc5)cc34)ccc2Cl)CC1] | 3-(5-chloro-6-(4-methylpiperazin-1-yl)pyridin-2-yl)-5-(pyridin-3-yl)-1H-pyrazolo[3,4-c]pyridine | 0.000113 |
| 256 | 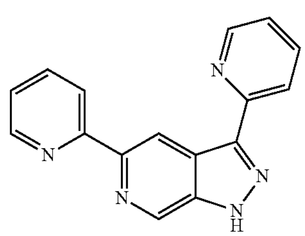 [SMILES: c1ccc(-c2cc3c(-c4ccccn4)n[nH]c3cn2)nc1] | 3,5-di(pyridin-2-yl)-1H-pyrazolo[3,4-c]pyridine | 1.5 |
| 257 | 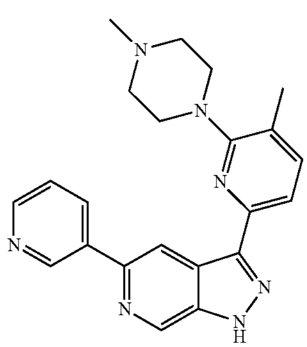 [SMILES: Cc1ccc(-c2n[nH]c3cnc(-c4cccnc4)cc23)nc1N1CCN(C)CC1] | 3-(5-methyl-6-(4-methylpiperazin-1-yl)pyridin-2-yl)-5-(pyridin-3-yl)-1H-pyrazolo[3,4-c]pyridine | 0.000032 |

TABLE 1-continued

| No. | Structure | Name | Pim-1 Ki (μm) |
|---|---|---|---|
| 258 | 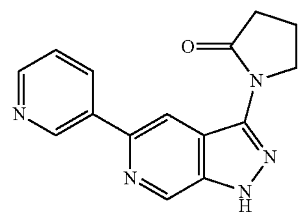 [SMILES: O=C1CCCN1c1n[nH]c2cnc(-c3cccnc3)cc12] | 1-(5-(pyridin-3-yl)-1H-pyrazolo[3,4-c]pyridin-3-yl)pyrrolidin-2-one | 0.0809 |
| 259 | 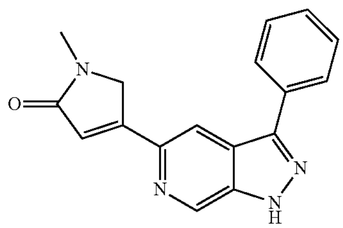 [SMILES: CN1CC(c2cc3c(-c4ccccc4)n[nH]c3cn2)=CC1=O] | 1-methyl-4-(3-phenyl-1H-pyrazolo[3,4-c]pyridin-5-yl)-1H-pyrrol-2(5H)-one | 0.92 |
| 260 | 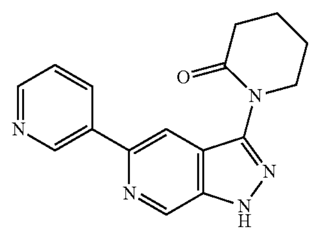 [SMILES: O=C1CCCCN1c1n[nH]c2cnc(-c3cccnc3)cc12] | 1-(5-(pyridin-3-yl)-1H-pyrazolo[3,4-c]pyridin-3-yl)piperidin-2-one | 1.1 |
| 261 | 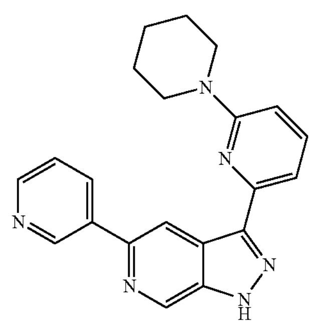 [SMILES: c1cncc(-c2cc3c(-c4cccc(N5CCCCC5)n4)n[nH]c3cn2)c1] | 3-(6-(piperidin-1-yl)pyridin-2-yl)-5-(pyridin-3-yl)-1H-pyrazolo[3,4-c]pyridine | 0.000415 |
| 262 | 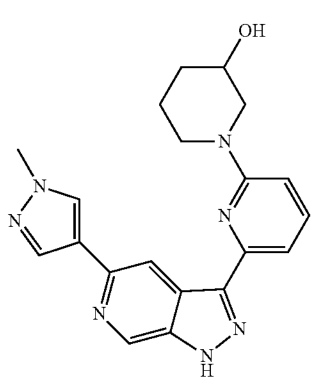 [SMILES: Cn1cc(-c2cc3c(-c4cccc(N5CCCC(O)C5)n4)n[nH]c3cn2)cn1] | 1-(6-(5-(1-methyl-1H-pyrazol-4-yl)-1H-pyrazolo[3,4-c]pyridin-3-yl)pyridin-2-yl)piperidin-3-ol | 0.000071 |

TABLE 1-continued

| No. | Name | Pim-1 Ki (μm) |
|---|---|---|
| 263 | 1-methyl-4-(3-phenyl-1H-pyrazolo[3,4-c]pyridin-5-yl)pyrrolidin-2-one | 0.241 |
| 264 | (R)-5-(1-methyl-1H-pyrazol-4-yl)-3-(6-(piperidin-3-yloxy)pyridin-2-yl)-1H-pyrazolo[3,4-c]pyridine | 0.00027 |
| 265 | (S)-1-(3-chloro-6-(5-(pyridin-3-yl)-1H-pyrazolo[3,4-c]pyridin-3-yl)pyridin-2-yl)piperidin-3-amine | 0.000019 |
| 266 | (R)-1-(3-chloro-6-(5-(pyridin-3-yl)-1H-pyrazolo[3,4-c]pyridin-3-yl)pyridin-2-yl)piperidin-3-amine | 0.000060 |
| 267 | 4-(6-(5-(pyridin-3-yl)-1H-pyrazolo[3,4-c]pyridin-3-yl)pyridin-2-yl)morpholine | 0.000262 |

TABLE 1-continued

| No. | Structure | Name | Pim-1 Ki (μm) |
|---|---|---|---|
| 268 | 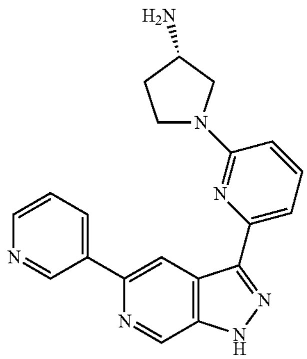 [SMILES: N[C@H]1CCN(c2cccc(-c3n[nH]c4cnc(-c5cccnc5)cc34)n2)C1] | (S)-1-(6-(5-(pyridin-3-yl)-1H-pyrazolo[3,4-c]pyridin-3-yl)pyridin-2-yl)pyrrolidin-3-amine | 0.0000268 |
| 269 | 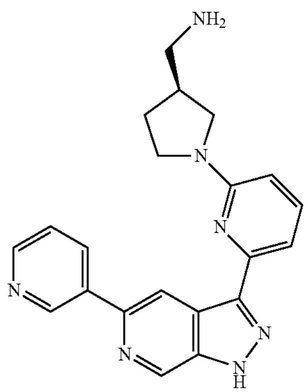 [SMILES: NC[C@@H]1CCN(c2cccc(-c3n[nH]c4cnc(-c5cccnc5)cc34)n2)C1] | (S)-(1-(6-(5-(pyridin-3-yl)-1H-pyrazolo[3,4-c]pyridin-3-yl)pyridin-2-yl)pyrrolidin-3-yl)methanamine | 0.000113 |
| 270 | 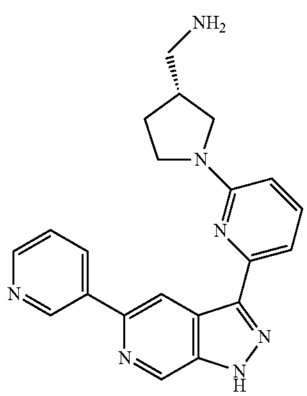 [SMILES: NC[C@H]1CCN(c2cccc(-c3n[nH]c4cnc(-c5cccnc5)cc34)n2)C1] | (R)-(1-(6-(5-(pyridin-3-yl)-1H-pyrazolo[3,4-c]pyridin-3-yl)pyridin-2-yl)pyrrolidin-3-yl)methanamine | 0.000085 |
| 271 | 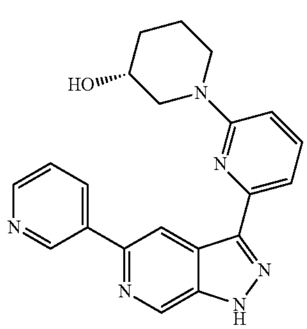 [SMILES: O[C@@H]1CCCN(c2cccc(-c3n[nH]c4cnc(-c5cccnc5)cc34)n2)C1] | (R)-1-(6-(5-(pyridin-3-yl)-1H-pyrazolo[3,4-c]pyridin-3-yl)pyridin-2-yl)piperidin-3-ol | 0.000073 |

TABLE 1-continued

| No. | Structure | Name | Pim-1 Ki (μm) |
|---|---|---|---|
| 272 | 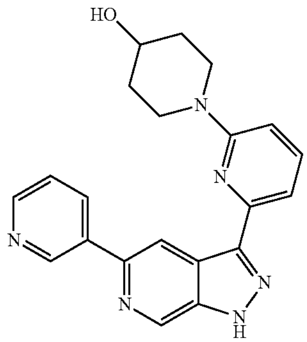 [SMILES: OC1CCN(c2cccc(-c3n[nH]c4cnc(-c5cccnc5)cc34)n2)CC1] | 1-(6-(5-(pyridin-3-yl)-1H-pyrazolo[3,4-c]pyridin-3-yl)pyridin-2-yl)piperidin-4-ol | 0.000149 |
| 273 | 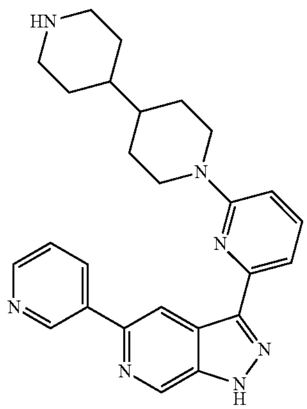 [SMILES: c1cncc(-c2cc3c(-c4cccc(N5CCC(C6CCNCC6)CC5)n4)n[nH]c3cn2)c1] | 3-(6-(4,4'-bipiperidin-1-yl)pyridin-2-yl)-5-(pyridin-3-yl)-1H-pyrazolo[3,4-c]pyridine | 0.00007 |
| 274 | 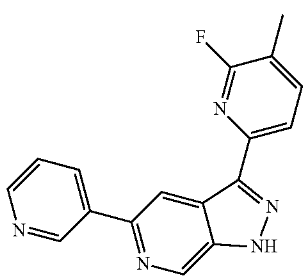 [SMILES: Cc1ccc(-c2n[nH]c3cnc(-c4cccnc4)cc23)nc1F] | 3-(6-fluoro-5-methylpyridin-2-yl)-5-(pyridin-3-yl)-1H-pyrazolo[3,4-c]pyridine | 0.00477 |
| 275 | 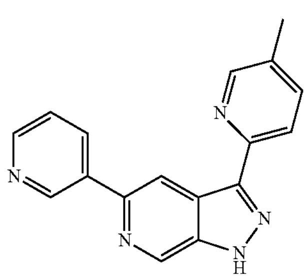 [SMILES: Cc1ccc(-c2n[nH]c3cnc(-c4cccnc4)cc23)nc1] | 3-(5-methylpyridin-2-yl)-5-(pyridin-3-yl)-1H-pyrazolo[3,4-c]pyridine | 0.00692 |

TABLE 1-continued

| No. | Structure | Name | Pim-1 Ki (μm) |
|---|---|---|---|
| 276 | 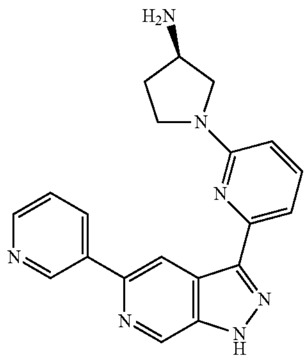 [SMILES: N[C@@H]1CCN(c2cccc(-c3n[nH]c4cnc(-c5cccnc5)cc34)n2)C1] | (R)-1-(6-(5-(pyridin-3-yl)-1H-pyrazolo[3,4-c]pyridin-3-yl)pyridin-2-yl)pyrrolidin-3-amine | 0.000188 |
| 277 | 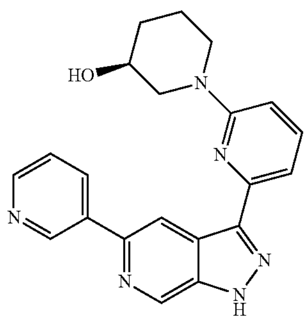 [SMILES: O[C@H]1CCCN(c2cccc(-c3n[nH]c4cnc(-c5cccnc5)cc34)n2)C1] | (S)-1-(6-(5-(pyridin-3-yl)-1H-pyrazolo[3,4-c]pyridin-3-yl)pyridin-2-yl)piperidin-3-ol | |
| 278 | 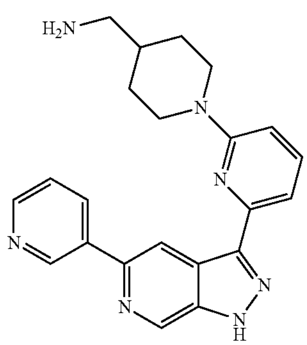 [SMILES: NCC1CCN(c2cccc(-c3n[nH]c4cnc(-c5cccnc5)cc34)n2)CC1] | (1-(6-(5-(pyridin-3-yl)-1H-pyrazolo[3,4-c]pyridin-3-yl)pyridin-2-yl)piperidin-4-yl)methanamine | 0.00010 |
| 279 | 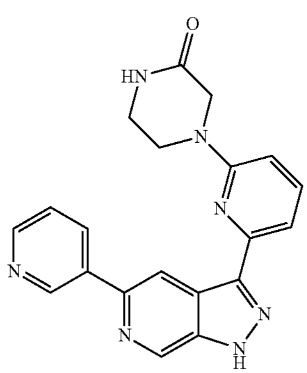 [SMILES: O=C1CN(c2cccc(-c3n[nH]c4cnc(-c5cccnc5)cc34)n2)CCN1] | 4-(6-(5-(pyridin-3-yl)-1H-pyrazolo[3,4-c]pyridin-3-yl)pyridin-2-yl)piperazin-2-one | 0.000351 |

TABLE 1-continued

| No. | Structure | Name | Pim-1 Ki (μm) |
|---|---|---|---|
| 280 | 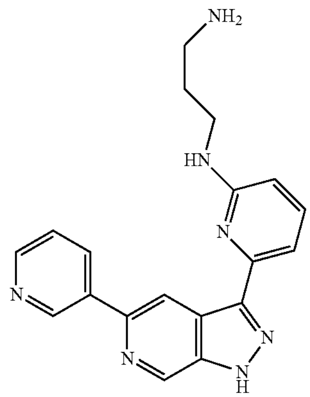 [SMILES: NCCCNc1cccc(-c2n[nH]c3cnc(-c4cccnc4)cc23)n1] | N1-(6-(5-(pyridin-3-yl)-1H-pyrazolo[3,4-c]pyridin-3-yl)pyridin-2-yl)propane-1,3-diamine | |
| 281 | 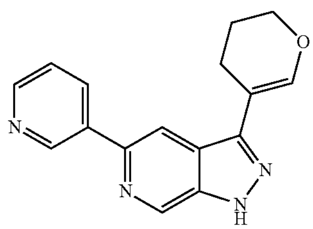 [SMILES: C1=C(c2n[nH]c3cnc(-c4cccnc4)cc23)CCCO1] | 3-(3,4-dihydro-2H-pyran-5-yl)-5-(pyridin-3-yl)-1H-pyrazolo[3,4-c]pyridine | 0.0288 |
| 282 | 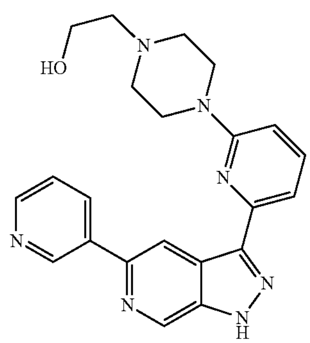 [SMILES: OCCN1CCN(c2cccc(-c3n[nH]c4cnc(-c5cccnc5)cc34)n2)CC1] | 2-(4-(6-(5-(pyridin-3-yl)-1H-pyrazolo[3,4-c]pyridin-3-yl)pyridin-2-yl)piperazin-1-yl)ethanol | 0.000164 |
| 283 | 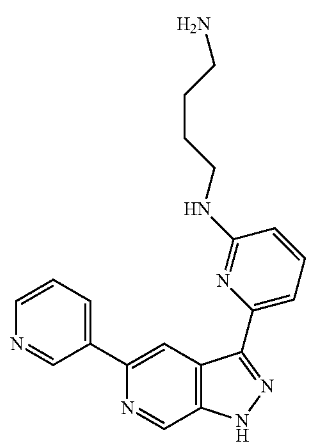 [SMILES: NCCCCNc1cccc(-c2n[nH]c3cnc(-c4cccnc4)cc23)n1] | N1-(6-(5-(pyridin-3-yl)-1H-pyrazolo[3,4-c]pyridin-3-yl)pyridin-2-yl)butane-1,4-diamine | 0.000257 |

TABLE 1-continued

| No. | Structure | Name | Pim-1 Ki (μm) |
|---|---|---|---|
| 284 | 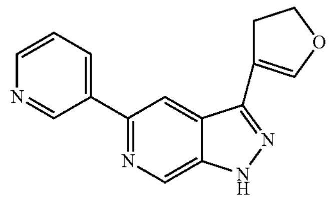 [SMILES: C1=C(c2n[nH]c3cnc(-c4cccnc4)cc23)CCO1] | 3-(4,5-dihydrofuran-3-yl)-5-(pyridin-3-yl)-1H-pyrazolo[3,4-c]pyridine | 0.0106 |
| 285 | 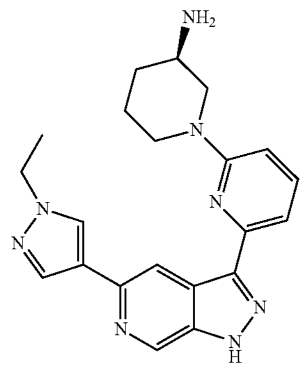 [SMILES: CCn1cc(-c2cc3c(-c4cccc(N5CCC[C@@H](N)C5)n4)n[nH]c3cn2)cn1] | (R)-1-(6-(5-(1-ethyl-1H-pyrazol-4-yl)-1H-pyrazolo[3,4-c]pyridin-3-yl)pyridin-2-yl)piperidin-3-amine | 0.0000473 |
| 286 | 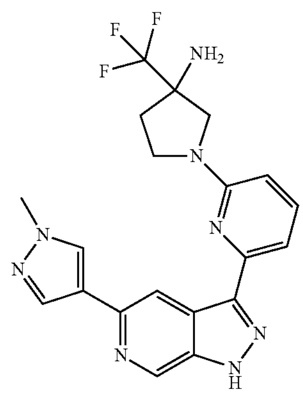 [SMILES: Cn1cc(-c2cc3c(-c4cccc(N5CCC(N)(C(F)(F)F)C5)n4)n[nH]c3cn2)cn1] | 1-(6-(5-(1-methyl-1H-pyrazol-4-yl)-1H-pyrazolo[3,4-c]pyridin-3-yl)pyridin-2-yl)-3-(trifluoromethyl)pyrrolidin-3-amine | 0.000093 |
| 287 | 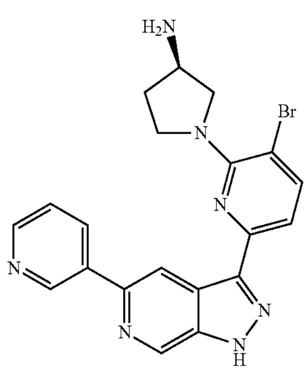 [SMILES: N[C@@H]1CCN(c2nc(-c3n[nH]c4cnc(-c5cccnc5)cc34)ccc2Br)C1] | (R)-1-(3-bromo-6-(5-(pyridin-3-yl)-1H-pyrazolo[3,4-c]pyridin-3-yl)pyridin-2-yl)pyrrolidin-3-amine | 0.000118 |

TABLE 1-continued

| No. | Structure | Name | Pim-1 Ki (μm) |
|---|---|---|---|
| 288 | 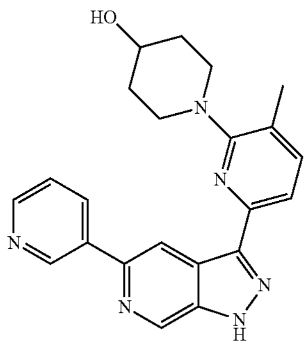 [SMILES: Cc1ccc(-c2n[nH]c3cnc(-c4cccnc4)cc23)nc1N1CCC(O)CC1] | 1-(3-methyl-6-(5-(pyridin-3-yl)-1H-pyrazolo[3,4-c]pyridin-3-yl)pyridin-2-yl)piperidin-4-ol | 0.000086 |
| 289 | 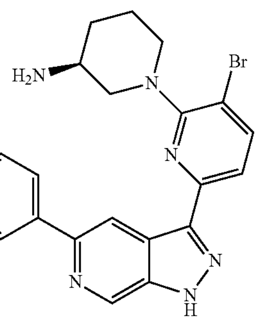 | (S)-1-(3-bromo-6-(5-(pyridin-3-yl)-1H-pyrazolo[3,4-c]pyridin-3-yl)pyridin-2-yl)piperidin-3-amine | 0.000017 |
| 290 | 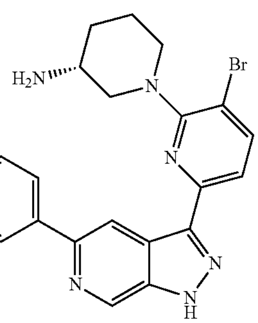 | (R)-1-(3-bromo-6-(5-(pyridin-3-yl)-1H-pyrazolo[3,4-c]pyridin-3-yl)pyridin-2-yl)piperidin-3-amine | 0.000082 |
| 291 | 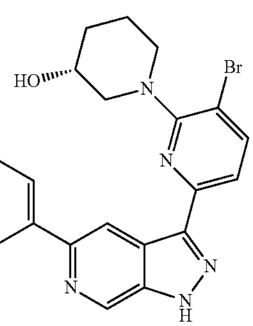 | (R)-1-(3-bromo-6-(5-(pyridin-3-yl)-1H-pyrazolo[3,4-c]pyridin-3-yl)pyridin-2-yl)piperidin-3-ol | 0.000261 |

TABLE 1-continued

| No. | Structure | Name | Pim-1 Ki (µm) |
|---|---|---|---|
| 292 | 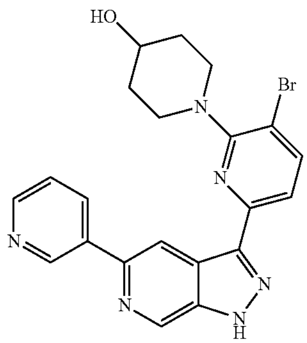 [SMILES: OC1CCN(c2nc(-c3n[nH]c4cnc(-c5cccnc5)cc34)ccc2Br)CC1] | 1-(3-bromo-6-(5-(pyridin-3-yl)-1H-pyrazolo[3,4-c]pyridin-3-yl)pyridin-2-yl)piperidin-4-ol | 0.000181 |
| 293 | 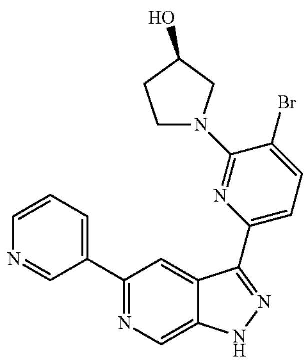 [SMILES: O[C@@H]1CCN(c2nc(-c3n[nH]c4cnc(-c5cccnc5)cc34)ccc2Br)C1] | (R)-1-(3-bromo-6-(5-(pyridin-3-yl)-1H-pyrazolo[3,4-c]pyridin-3-yl)pyridin-2-yl)pyrrolidin-3-ol | 0.000412 |
| 294 | 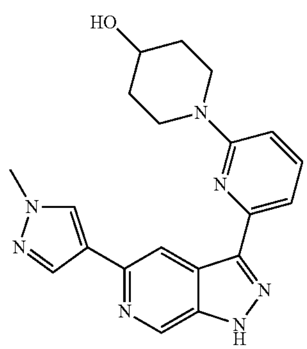 [SMILES: Cn1cc(-c2cc3c(-c4cccc(N5CCC(O)CC5)n4)n[nH]c3cn2)cn1] | 1-(6-(5-(1-methyl-1H-pyrazol-4-yl)-1H-pyrazolo[3,4-c]pyridin-3-yl)pyridin-2-yl)piperidin-4-ol | 0.000168 |
| 295 | 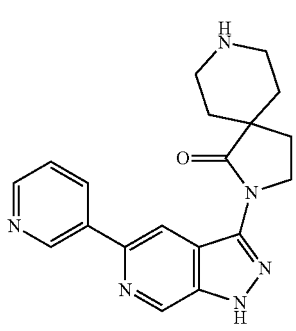 [SMILES: O=C1N(c2n[nH]c3cnc(-c4cccnc4)cc23)CCC12CCNCC2] | 2-(5-(pyridin-3-yl)-1H-pyrazolo[3,4-c]pyridin-3-yl)-2,8-diazaspiro[4.5]decan-1-one | 0.0399 |

TABLE 1-continued

| No. | Structure | Name | Pim-1 Ki (μm) |
|---|---|---|---|
| 296 | 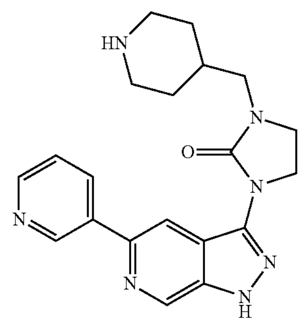 [SMILES: O=C1N(CC2CCNCC2)CCN1c1n[nH]c2cnc(-c3cccnc3)cc12] | 1-(piperidin-4-ylmethyl)-3-(5-(pyridin-3-yl)-1H-pyrazolo[3,4-c]pyridin-3-yl)imidazolidin-2-one | 0.00974 |
| 297 | 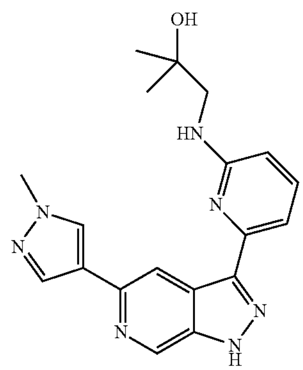 [SMILES: Cn1cc(-c2cc3c(-c4cccc(NCC(C)(C)O)n4)n[nH]c3cn2)cn1] | 2-methyl-1-(6-(5-(1-methyl-1H-pyrazol-4-yl)-1H-pyrazolo[3,4-c]pyridin-3-yl)pyridin-2-ylamino)propan-2-ol | 0.000034 |
| 298 | 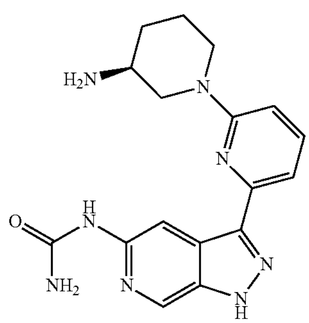 [SMILES: NC(=O)Nc1cc2c(-c3cccc(N4CCC[C@H](N)C4)n3)n[nH]c2cn1] | (S)-1-(3-(6-(3-aminopiperidin-1-yl)pyridin-2-yl)-1H-pyrazolo[3,4-c]pyridin-5-yl)urea | 0.0141 |
| 299 | 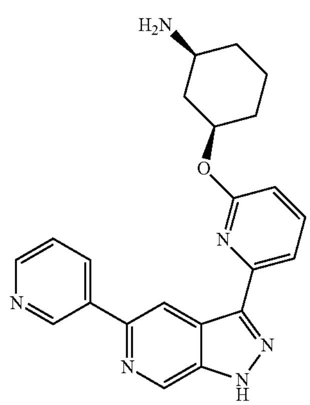 [SMILES: N[C@H]1CCC[C@@H](Oc2cccc(-c3n[nH]c4cnc(-c5cccnc5)cc34)n2)C1] | (1S,3R)-3-(6-(5-(pyridin-3-yl)-1H-pyrazolo[3,4-c]pyridin-3-yl)pyridin-2-yloxy)cyclohexanamine | 0.000664 |

TABLE 1-continued

| No. | Name | Pim-1 Ki (μm) |
|---|---|---|
| 300 | (R)-1-(4-(5-(pyridin-3-yl)-1H-pyrazolo[3,4-c]pyridin-3-yl)pyrimidin-2-yl)piperidin-3-amine | 0.000070 |
| 301 | 1-(6-(5-(pyridin-3-yl)-1H-pyrazolo[3,4-c]pyridin-3-yl)pyridin-2-yl)piperazin-2-one | 0.00295 |
| 302 | 2-(5-(pyridin-3-yl)-1H-pyrazolo[3,4-c]pyridin-3-yl)isonicotinamide | 0.0060 |
| 303 | 1-(5-(pyridin-3-yl)-1H-pyrazolo[3,4-c]pyridin-3-yl)-3-(pyrrolidin-3-ylmethyl)imidazolidin-2-one | 0.00411 |
| 304 | (S)-3-amino-1-(6-(5-(pyridin-3-yl)-1H-pyrazolo[3,4-c]pyridin-3-yl)pyridin-2-yl)pyrrolidin-2-one | 0.000556 |

TABLE 1-continued

| No. | Structure | Name | Pim-1 Ki (μm) |
|---|---|---|---|
| 305 | 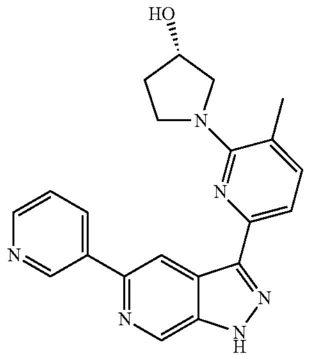 [SMILES: Cc1ccc(-c2n[nH]c3cnc(-c4cccnc4)cc23)nc1N1CC[C@H](O)C1] | (S)-1-(3-methyl-6-(5-(pyridin-3-yl)-1H-pyrazolo[3,4-c]pyridin-3-yl)pyridin-2-yl)pyrrolidin-3-ol | 0.000091 |
| 306 | 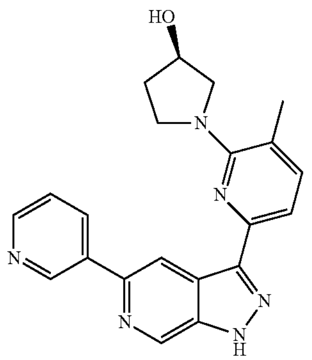 [SMILES: Cc1ccc(-c2n[nH]c3cnc(-c4cccnc4)cc23)nc1N1CC[C@@H](O)C1] | (R)-1-(3-methyl-6-(5-(pyridin-3-yl)-1H-pyrazolo[3,4-c]pyridin-3-yl)pyridin-2-yl)pyrrolidin-3-ol | 0.00022 |
| 307 | 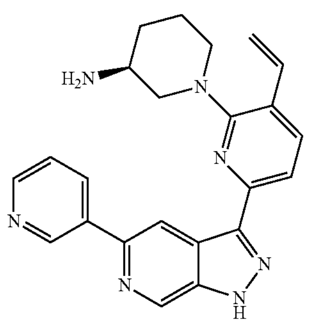 [SMILES: C=Cc1ccc(-c2n[nH]c3cnc(-c4cccnc4)cc23)nc1N1CCC[C@H](N)C1] | (S)-1-(6-(5-(pyridin-3-yl)-1H-pyrazolo[3,4-c]pyridin-3-yl)-3-vinylpyridin-2-yl)piperidin-3-amine | 0.000014 |
| 308 | 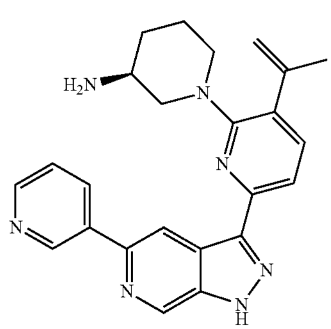 [SMILES: C=C(C)c1ccc(-c2n[nH]c3cnc(-c4cccnc4)cc23)nc1N1CCC[C@H](N)C1] | (S)-1-(3-(prop-1-en-2-yl)-6-(5-(pyridin-3-yl)-1H-pyrazolo[3,4-c]pyridin-3-yl)pyridin-2-yl)piperidin-3-amine | 0.000010 |

TABLE 1-continued

| No. | Structure | Name | Pim-1 Ki (µm) |
|---|---|---|---|
| 309 | 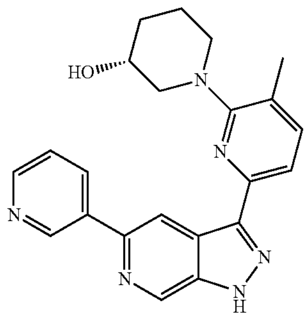 [SMILES: Cc1ccc(-c2n[nH]c3cnc(-c4cccnc4)cc23)nc1N1CCC[C@@H](O)C1] | (R)-1-(3-methyl-6-(5-(pyridin-3-yl)-1H-pyrazolo[3,4-c]pyridin-3-yl)pyridin-2-yl)piperidin-3-ol | 0.000112 |
| 310 | 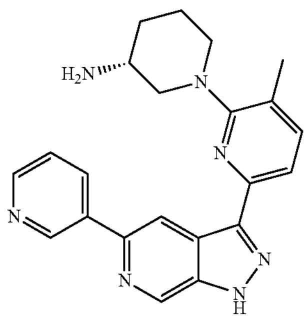 [SMILES: Cc1ccc(-c2n[nH]c3cnc(-c4cccnc4)cc23)nc1N1CCC[C@@H](N)C1] | (R)-1-(3-methyl-6-(5-(pyridin-3-yl)-1H-pyrazolo[3,4-c]pyridin-3-yl)pyridin-2-yl)piperidin-3-amine | 0.000137 |
| 311 | 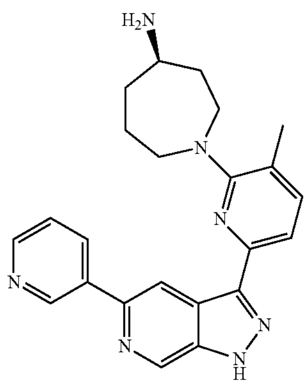 [SMILES: Cc1ccc(-c2n[nH]c3cnc(-c4cccnc4)cc23)nc1N1CCC[C@@H](N)CC1] | (R)-1-(3-methyl-6-(5-(pyridin-3-yl)-1H-pyrazolo[3,4-c]pyridin-3-yl)pyridin-2-yl)azepan-4-amine | 0.000030 |
| 312 | 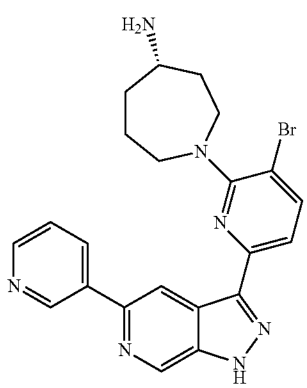 [SMILES: N[C@H]1CCCN(c2nc(-c3n[nH]c4cnc(-c5cccnc5)cc34)ccc2Br)CC1] | (S)-1-(3-bromo-6-(5-(pyridin-3-yl)-1H-pyrazolo[3,4-c]pyridin-3-yl)pyridin-2-yl)azepan-4-amine | 0.000029 |

TABLE 1-continued

| No. | Structure | Name | Pim-1 Ki (μm) |
|---|---|---|---|
| 313 | 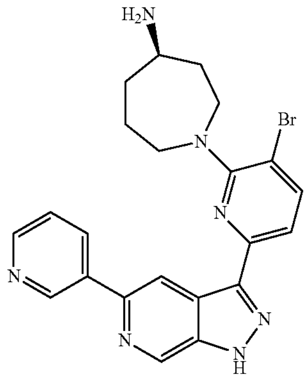 [SMILES: N[C@@H]1CCCN(c2nc(-c3n[nH]c4cnc(-c5cccnc5)cc34)ccc2Br)CC1] | (R)-1-(3-bromo-6-(5-(pyridin-3-yl)-1H-pyrazolo[3,4-c]pyridin-3-yl)pyridin-2-yl)azepan-4-amine | 0.000028 |
| 314 | 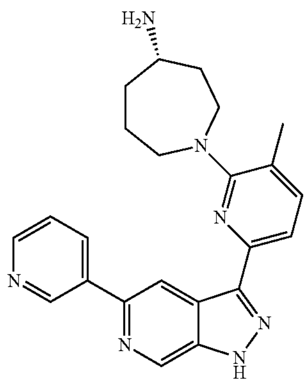 [SMILES: Cc1ccc(-c2n[nH]c3cnc(-c4cccnc4)cc23)nc1N1CCC[C@H](N)CC1] | (S)-1-(3-methyl-6-(5-(pyridin-3-yl)-1H-pyrazolo[3,4-c]pyridin-3-yl)pyridin-2-yl)azepan-4-amine | 0.000025 |
| 315 | 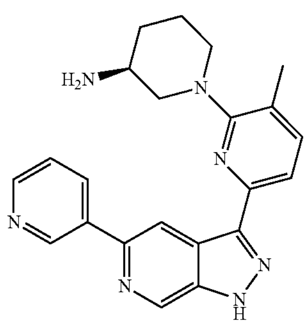 [SMILES: Cc1ccc(-c2n[nH]c3cnc(-c4cccnc4)cc23)nc1N1CCC[C@H](N)C1] | (S)-1-(3-methyl-6-(5-(pyridin-3-yl)-1H-pyrazolo[3,4-c]pyridin-3-yl)pyridin-2-yl)piprridin-3-amine | 0.00000806 |
| 316 | 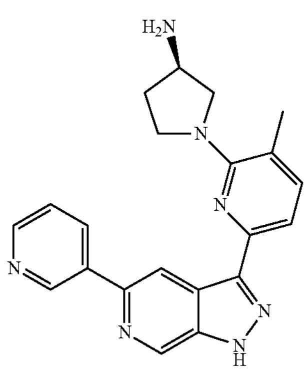 [SMILES: Cc1ccc(-c2n[nH]c3cnc(-c4cccnc4)cc23)nc1N1CC[C@@H](N)C1] | (R)-1-(3-methyl-6-(5-(pyridin-3-yl)-1H-pyrazolo[3,4-c]pyridin-3-yl)pyridin-2-yl)pyrrolidin-3-amine | 0.0000549 |

TABLE 1-continued

| No. | Structure | Name | Pim-1 Ki (μm) |
|---|---|---|---|
| 317 | 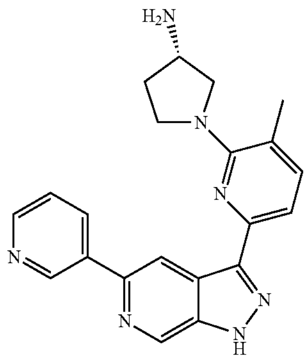 [SMILES: Cc1ccc(-c2n[nH]c3cnc(-c4cccnc4)cc23)nc1N1CC[C@H](N)C1] | (S)-1-(3-methyl-6-(5-(pyridin-3-yl)-1H-pyrazolo[3,4-c]pyridin-3-yl)pyridin-2-yl)pyrrolidin-3-amine | 0.000059 |
| 318 | 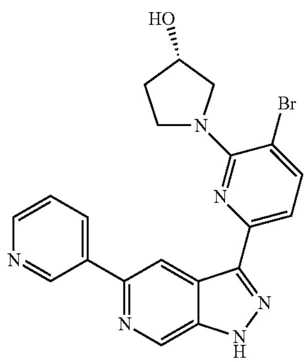 [SMILES: O[C@H]1CCN(c2nc(-c3n[nH]c4cnc(-c5cccnc5)cc34)ccc2Br)C1] | (S)-1-(3-bromo-6-(5-(pyridin-3-yl)-1H-pyrazolo[3,4-c]pyridin-3-yl)pyridin-2-yl)pyrrolidin-3-ol | 0.000059 |
| 319 | 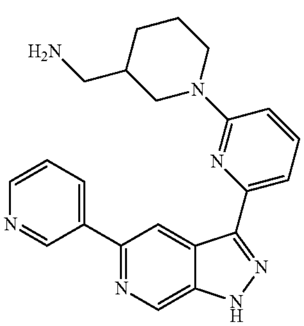 [SMILES: NCC1CCCN(c2cccc(-c3n[nH]c4cnc(-c5cccnc5)cc34)n2)C1] | (1-(6-(5-(pyridin-3-yl)-1H-pyrazolo[3,4-c]pyridin-3-yl)pyridin-2-yl)piperidin-3-yl)methanamine | |
| 320 | 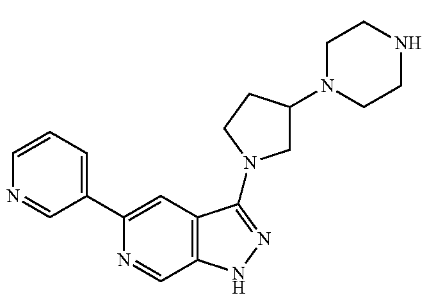 [SMILES: c1cncc(-c2cc3c(N4CCC(N5CCNCC5)C4)n[nH]c3cn2)c1] | 3-(3-(piperazin-1-yl)pyrrolidin-1-yl)-5-(pyridin-3-yl)-1H-pyrazolo[3,4-c]pyridine | 0.00386 |

TABLE 1-continued

| No. | Structure | Name | Pim-1 Ki (μm) |
|---|---|---|---|
| 321 | 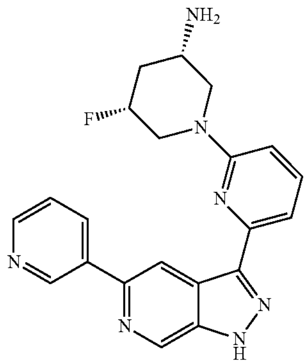 [SMILES: N[C@H]1C[C@@H](F)CN(c2cccc(-c3n[nH]c4cnc(-c5cccnc5)cc34)n2)C1] | (3S,5R)-5-fluoro-1-(6-(5-(pyridin-3-yl)-1H-pyrazolo[3,4-c]pyridin-3-yl)pyridin-2-yl)piperidin-3-amine | 0.0000662 |
| 322 | 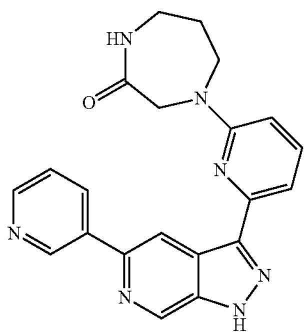 [SMILES: O=C1CN(c2cccc(-c3n[nH]c4cnc(-c5cccnc5)cc34)n2)CCCN1] | 4-(6-(5-(pyridin-3-yl)-1H-pyrazolo[3,4-c]pyridin-3-yl)pyridin-2-yl)-1,4-diazepan-2-one | 0.000322 |
| 323 | 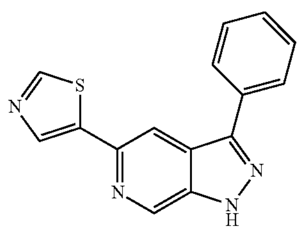 [SMILES: c1ccc(-c2n[nH]c3cnc(-c4cncs4)cc23)cc1] | 5-(3-phenyl-1H-pyrazolo[3,4-c]pyridin-5-yl)thiazole | 0.0330.033 |
| 324 | 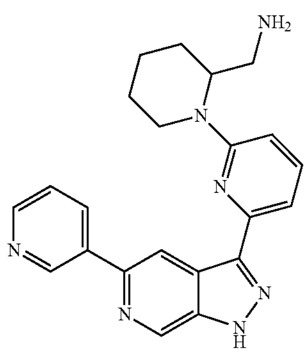 [SMILES: NCC1CCCCN1c1cccc(-c2n[nH]c3cnc(-c4cccnc4)cc23)n1] | (1-(6-(5-(pyridin-3-yl)-1H-pyrazolo[3,4-c]pyridin-3-yl)pyridin-2-yl)piperidin-2-yl)methanamine | 0.000296 |
| 325 | 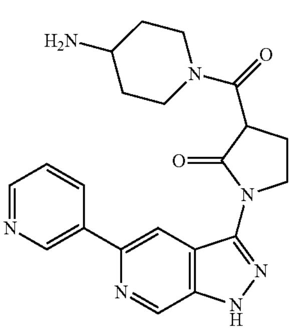 [SMILES: NC1CCN(C(=O)C2CCN(c3n[nH]c4cnc(-c5cccnc5)cc34)C2=O)CC1] | 3-(4-aminopiperidine-1-carbonyl)-1-(5-(pyridin-3-yl)-1H-pyrazolo[3,4-c]pyridin-3-yl)pyrrolidin-2-one | 0.106 |

TABLE 1-continued

| No. | Structure | Name | Pim-1 Ki (μm) |
|---|---|---|---|
| 326 | 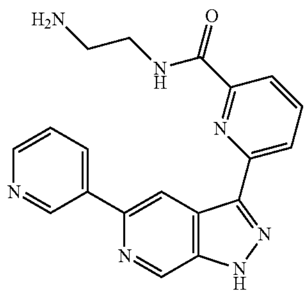 [SMILES: NCCNC(=O)c1cccc(-c2n[nH]c3cnc(-c4cccnc4)cc23)n1] | N-(2-aminoethyl)-6-(5-(pyridin-3-yl)-1H-pyrazolo[3,4-c]pyridin-3-yl)picolinamide | 0.0177 |
| 327 | 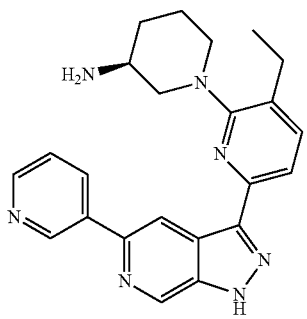 [SMILES: CCc1ccc(-c2n[nH]c3cnc(-c4cccnc4)cc23)nc1N1CCC[C@H](N)C1] | (S)-1-(3-ethyl-6-(5-(pyridin-3-yl)-1H-pyrazolo[3,4-c]pyridin-3-yl)pyridin-2-yl)piperidin-3-amine | 0.000035 |
| 328 | 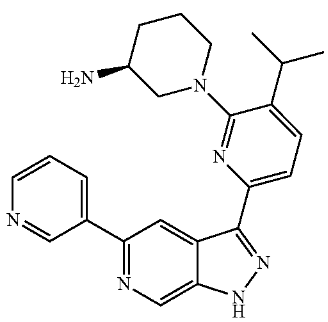 [SMILES: CC(C)c1ccc(-c2n[nH]c3cnc(-c4cccnc4)cc23)nc1N1CCC[C@H](N)C1] | (S)-1-(3-isopropyl-6-(5-(pyridin-3-yl)-1H-pyrazolo[3,4-c]pyridin-3-yl)pyridin-2-yl)piperidin-3-amine | 0.000046 |
| 329 | 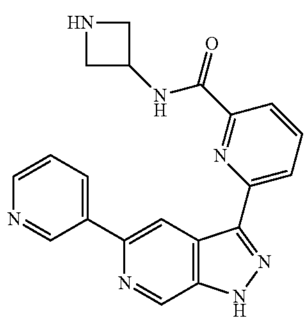 [SMILES: O=C(NC1CNC1)c1cccc(-c2n[nH]c3cnc(-c4cccnc4)cc23)n1] | N-(azetidin-3-yl)-6-(5-(pyridin-3-yl)-1H-pyrazolo[3,4-c]pyridin-3-yl)picolinamide | 0.0165 |
| 330 | 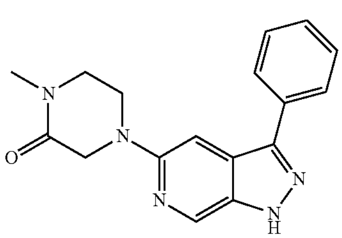 [SMILES: CN1CCN(c2cc3c(-c4ccccc4)n[nH]c3cn2)CC1=O] | 1-methyl-4-(3-phenyl-1H-pyrazolo[3,4-c]pyridin-5-yl)piperazin-2-one | 0.66 |

TABLE 1-continued

| No. | Structure | Name | Pim-1 Ki (μm) |
|---|---|---|---|
| 331 | 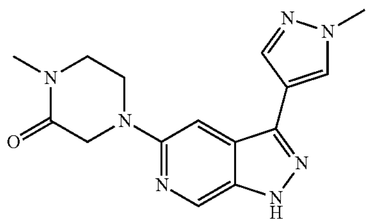 [SMILES: CN1CCN(c2cc3c(-c4cnn(C)c4)n[nH]c3cn2)CC1=O] | 1-methyl-4-(3-(1-methyl-1H-pyrazol-4-yl)-1H-pyrazolo[3,4-c]pyridin-5-yl)piperazin-2-one | 0.721 |
| 332 | 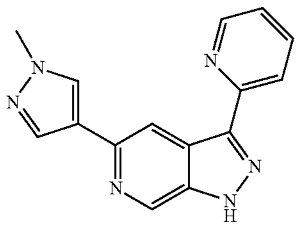 [SMILES: Cn1cc(-c2cc3c(-c4ccccn4)n[nH]c3cn2)cn1] | 5-(1-methyl-1H-pyrazol-4-yl)-3-(pyridin-2-yl)-1H-pyrazolo[3,4-c]pyridine | 0.00771 |
| 333 | 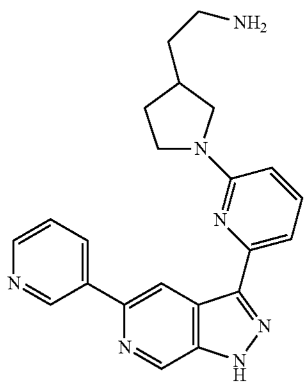 [SMILES: NCCC1CCN(c2cccc(-c3n[nH]c4cnc(-c5cccnc5)cc34)n2)C1] | 2-(1-(6-(5-(pyridin-3-yl)-1H-pyrazolo[3,4-c]pyridin-3-yl)pyridin-2-yl)pyrrolidin-3-yl)ethanamine | 0.00013 |
| 334 | 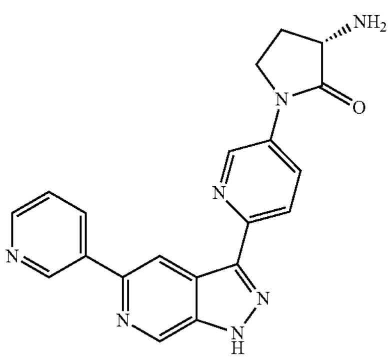 [SMILES: N[C@H]1CCN(c2ccc(-c3n[nH]c4cnc(-c5cccnc5)cc34)nc2)C1=O] | (S)-3-amino-1-(6-(5-(pyridin-3-yl)-1H-pyrazolo[3,4-c]pyridin-3-yl)pyridin-3-yl)pyrrolidin-2-one | 0.00157 |
| 335 | 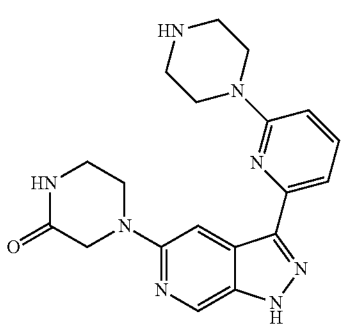 [SMILES: O=C1CN(c2cc3c(-c4cccc(N5CCNCC5)n4)n[nH]c3cn2)CCN1] | 4-(3-(6-(piperazin-1-yl)pyridin-2-yl)-1H-pyrazolo[3,4-c]pyridin-5-yl)piperazin-2-one | 0.0126 |

TABLE 1-continued

| No. | Name | Pim-1 Ki (μm) |
|---|---|---|
| 336 | (4-aminopiperidin-1-yl)(6-(5-(pyridin-3-yl)-1H-pyrazolo[3,4-c]pyridin-3-yl)pyridin-2-yl)methanone | 0.0127 |
| 337 | N-(piperidin-4-yl)-6-(5-(pyridin-3-yl)-1H-pyrazolo[3,4-c]pyridin-3-yl)picolinamide | 0.0305 |
| 338 | 5-(3-(pyridin-2-yl)-1H-pyrazolo[3,4-c]pyridin-5-yl)thiazole | 0.0245 |
| 339 | 4-(3-(2-fluorophenyl)-1H-pyrazolo[3,4-c]pyridin-5-yl)-1-methylpiperazin-2-one | 5.5 |

TABLE 1-continued

| No. | Structure | Name | Pim-1 Ki (μm) |
|---|---|---|---|
| 340 | 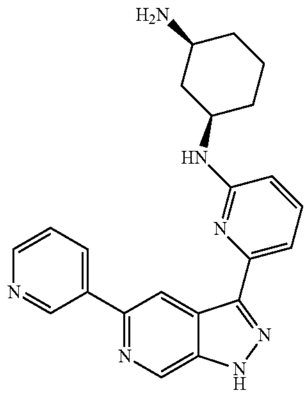 [SMILES: N[C@H]1CCC[C@@H](Nc2cccc(-c3n[nH]c4cnc(-c5cccnc5)cc34)n2)C1] | (1R,3S)-N1-(6-(5-(pyridin-3-yl)-1H-pyrazolo[3,4-c]pyridin-3-yl)pyridin-2-yl)cyclohexane-1,3-diamine | 0.000044 |
| 341 | 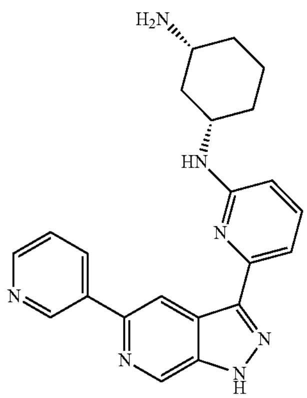 [SMILES: N[C@@H]1CCC[C@H](Nc2cccc(-c3n[nH]c4cnc(-c5cccnc5)cc34)n2)C1] | (1S,3R)-N1-(6-(5-(pyridin-3-yl)-1H-pyrazolo[3,4-c]pyridin-3-yl)pyridin-2-yl)cyclohexane-1,3-diamine | 0.000077 |
| 342 | 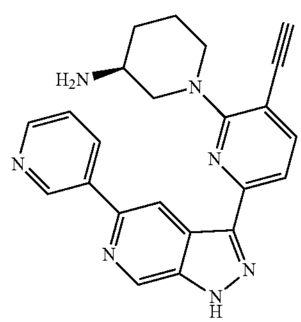 [SMILES: C#Cc1ccc(-c2n[nH]c3cnc(-c4cccnc4)cc23)nc1N1CCC[C@H](N)C1] | (S)-1-(3-ethynyl-6-(5-(pyridin-3-yl)-1H-pyrazolo[3,4-c]pyridin-3-yl)pyridin-2-yl)piperidin-3-amine | 0.0000100 |
| 343 | 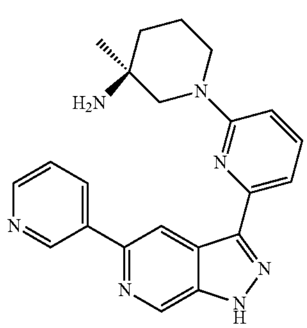 [SMILES: C[C@]1(N)CCCN(c2cccc(-c3n[nH]c4cnc(-c5cccnc5)cc34)n2)C1] | (S)-3-methyl-1-(6-(5-(pyridin-3-yl)-1H-pyrazolo[3,4-c]pyridin-3-yl)pyridin-2-yl)piperidin-3-amine | 0.000045 |

TABLE 1-continued

| No. | Structure | Name | Pim-1 Ki (μm) |
|---|---|---|---|
| 344 | 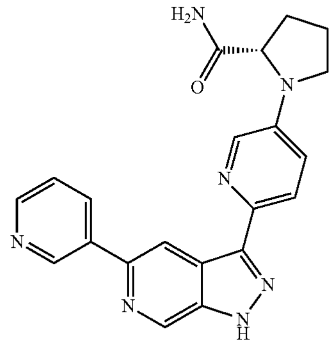 [SMILES: NC(=O)[C@@H]1CCCN1c1ccc(-c2n[nH]c3cnc(-c4cccnc4)cc23)nc1] | (S)-1-(6-(5-(pyridin-3-yl)-1H-pyrazolo[3,4-c]pyridin-3-yl)pyridin-3-yl)pyrrolidine-2-carboxamide | 0.0039 |
| 345 | 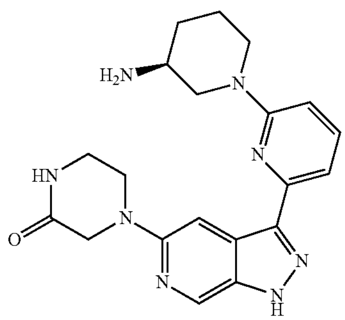 [SMILES: N[C@H]1CCCN(c2cccc(-c3n[nH]c4cnc(N5CCNC(=O)C5)cc34)n2)C1] | (S)-4-(3-(6-(3-aminopiperidin-1-yl)pyridin-2-yl)-1H-pyrazolo[3,4-c]pyridin-5-yl)piperazin-2-one | 0.0137 |
| 346 | 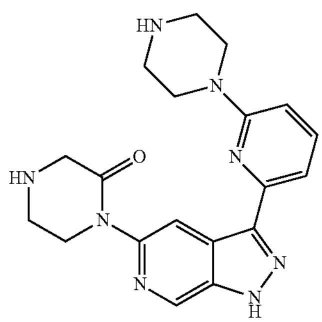 [SMILES: O=C1CNCCN1c1cc2c(-c3cccc(N4CCNCC4)n3)n[nH]c2cn1] | 1-(3-(6-(piperazin-1-yl)pyridin-2-yl)-1H-pyrazolo[3,4-c]pyridin-5-yl)piperazin-2-one | 0.219 |
| 347 | 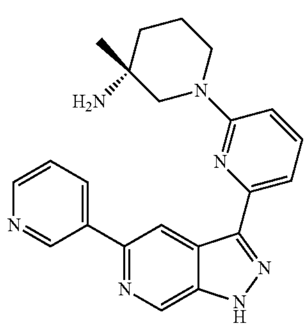 [SMILES: C[C@@]1(N)CCCN(c2cccc(-c3n[nH]c4cnc(-c5cccnc5)cc34)n2)C1] | (R)-3-methyl-1-(6-(5-(pyridin-3-yl)-1H-pyrazolo[3,4-c]pyridin-3-yl)pyridin-2-yl)piperidin-3-amine | 0.00011 |
| 348 | 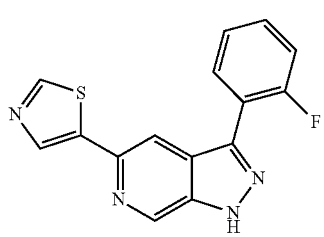 [SMILES: Fc1ccccc1-c1n[nH]c2cnc(-c3cncs3)cc12] | 5-(3-(2-fluorophenyl)-1H-pyrazolo[3,4-c]pyridin-5-yl)thiazole | 0.0268 |

TABLE 1-continued

| No. | Structure | Name | Pim-1 Ki (μm) |
|---|---|---|---|
| 349 | 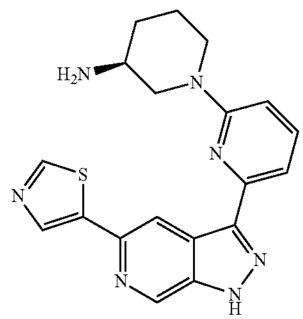 [SMILES: N[C@H]1CCCN(c2cccc(-c3n[nH]c4cnc(-c5cncs5)cc34)n2)C1] | (S)-1-(6-(5-(thiazol-5-yl)-1H-pyrazolo[3,4-c]pyridin-3-yl)pyridin-2-yl)piperidin-3-amine | 0.000035 |
| 350 | 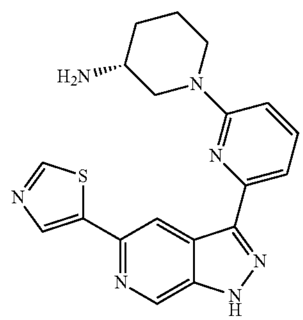 [SMILES: N[C@@H]1CCCN(c2cccc(-c3n[nH]c4cnc(-c5cncs5)cc34)n2)C1] | (R)-1-(6-(5-(thiazol-5-yl)-1H-pyrazolo[3,4-c]pyridin-3-yl)pyridin-2-yl)piperidin-3-amine | 0.000036 |
| 351 | 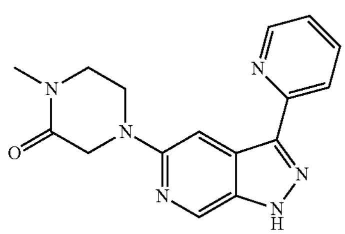 | 1-methyl-4-(3-(pyridin-2-yl)-1H-pyrazolo[3,4-c]pyridin-5-yl)piperazin-2-one | 4.8 |
| 352 | 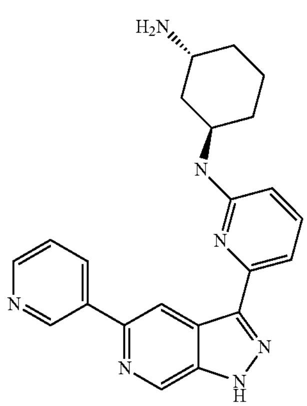 [SMILES: N[C@@H]1CCC[C@@H](Nc2cccc(-c3n[nH]c4cnc(-c5cccnc5)cc34)n2)C1] | (1R,3R)-N1-(6-(5-(pyridin-3-yl)-1H-pyrazolo[3,4-c]pyridin-3-yl)pyridin-2-yl)cyclohexane-1,3-diamine | 0.000025 |

TABLE 1-continued

| No. | Structure | Name | Pim-1 Ki (μm) |
|---|---|---|---|
| 353 | 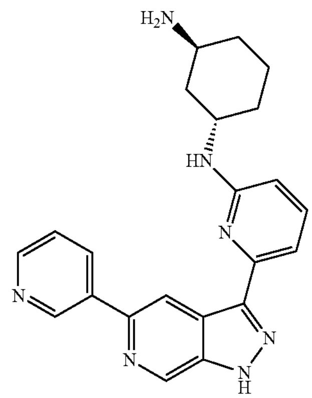 [SMILES: N[C@H]1CCC[C@H](Nc2cccc(-c3n[nH]c4cnc(-c5cccnc5)cc34)n2)C1] | (1S,3S)-N1-(6-(5-(pyridin-3-yl)-1H-pyrazolo[3,4-c]pyridin-3-yl)pyridin-2-yl)cyclohexane-1,3-diamine | 0.000397 |
| 354 | 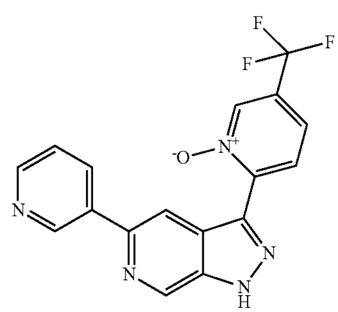 | 2-(5-(pyridin-3-yl)-1H-pyrazolo[3,4-c]pyridin-3-yl)-5-(trifluoromethyl(pyridine 1-oxide | 0.0979 |
| 355 | 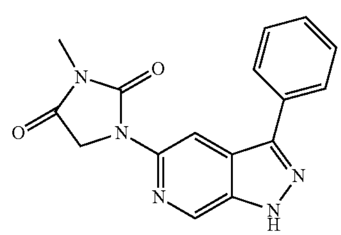 [SMILES: CN1C(=O)CN(c2cc3c(-c4ccccc4)n[nH]c3cn2)C1=O] | 3-methyl-1-(3-phenyl-1H-pyrazolo[3,4-c]pyridin-5-yl)imidazolidine-2,4-dione | 0.809 |
| 356 | 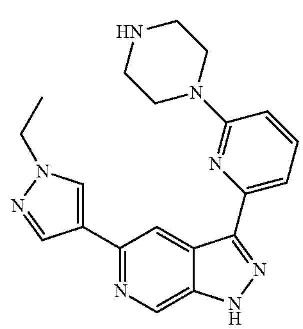 [SMILES: CCn1cc(-c2cc3c(-c4cccc(N5CCNCC5)n4)n[nH]c3cn2)cn1] | 5-(1-ethyl-1H-pyrazol-4-yl)-3-(6-(piperazin-1-yl)pyridin-2-yl)-1H-pyrazolo[3,4-c]pyridine | 0.000073 |

| No. | Structure | Name | Pim-1 Ki (μm) |
|---|---|---|---|
| 357 | 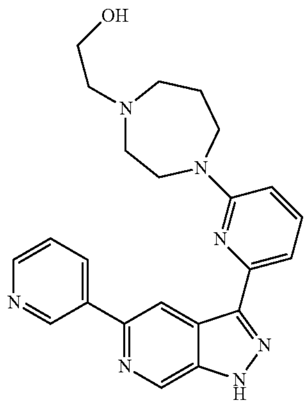 [SMILES: OCCN1CCCN(c2cccc(-c3n[nH]c4cnc(-c5cccnc5)cc34)n2)CC1] | 2-(4-(6-(5-(pyridin-3-yl)-1H-pyrazolo[3,4-c]pyridin-3-yl)pyridin-2-yl)-1,4-diazepan-1-yl)ethanol | 0.00026 |
| 358 | 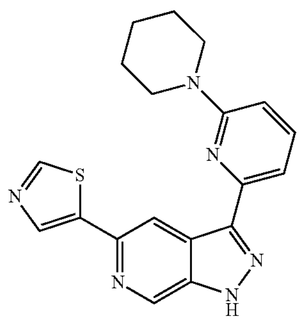 [SMILES: c1cc(-c2n[nH]c3cnc(-c4cncs4)cc23)nc(N2CCCCC2)c1] | 5-(3-(6-(piperidin-1-yl)pyridin-2-yl)-1H-pyrazolo[3,4-c]pyridin-5-yl)thiazole | 0.00122 |
| 359 | 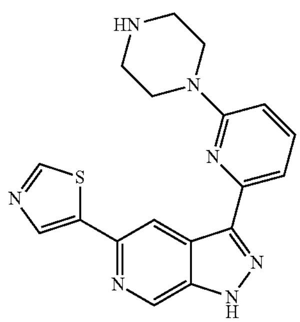 [SMILES: c1cc(-c2n[nH]c3cnc(-c4cncs4)cc23)nc(N2CCNCC2)c1] | 5-(3-(6-(piperazin-1-yl)pyridin-2-yl)-1H-pyrazolo[3,4-c]pyridin-5-yl)thiazole | 0.000074 |
| 360 | 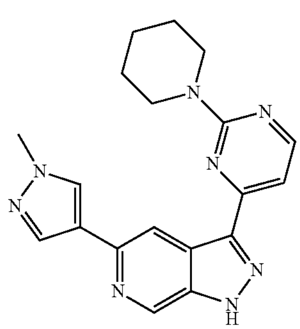 [SMILES: Cn1cc(-c2cc3c(-c4ccnc(N5CCCCC5)n4)n[nH]c3cn2)cn1] | 5-(1-methyl-1H-pyrazol-4-yl)-3-(2-(piperidin-1-yl)pyrimidin-4-yl)-1H-pyrazolo[3,4-c]pyridine | 0.000366 |

TABLE 1-continued

| No. | Structure | Name | Pim-1 Ki (μm) |
|---|---|---|---|
| 361 | 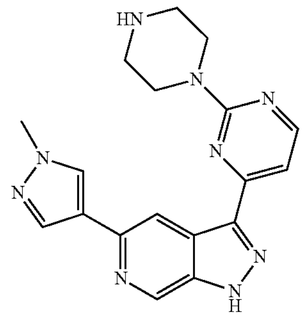 | 5-(1-methyl-1H-pyrazol-4-yl)-3-(2-(piperazin-1-yl)pyrimidin-4-yl)-1H-pyrazolo[3,4-c]pyridine | |
| 362 | 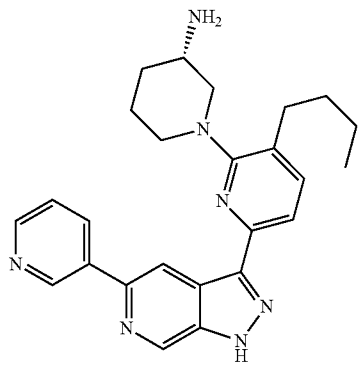 [SMILES: CCCCc1ccc(-c2n[nH]c3cnc(-c4cccnc4)cc23)nc1N1CCC[C@H](N)C1] | (S)-1-(3-butyl-6-(5-(pyridin-3-yl)-1H-pyrazolo[3,4-c]pyridin-3-yl)pyridin-2-yl)piperidin-3-amine | 0.000079 |
| 363 | 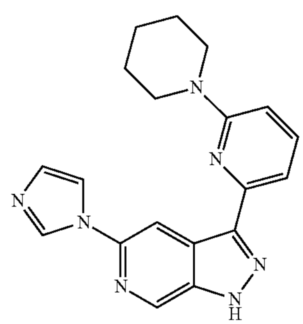 [SMILES: c1cc(-c2n[nH]c3cnc(-n4ccnc4)cc23)nc(N2CCCCC2)c1] | 5-(1H-imidazol-1-yl)-3-(6-(piperidin-1-yl)pyridin-2-yl)-1H-pyrazolo[3,4-c]pyridine | 0.00241 |
| 364 | 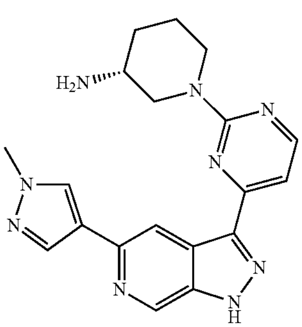 [SMILES: Cn1cc(-c2cc3c(-c4ccnc(N5CCC[C@@H](N)C5)n4)n[nH]c3cn2)cn1] | (R)-1-(4-(5-(1-methyl-1H-pyrazol-4-yl)-1H-pyrazolo[3,4-c]pyridin-3-yl)pyrimidin-2-yl)piperidin-3-amine | 0.000052 |

TABLE 1-continued

| No. | Structure | Name | Pim-1 Ki (μm) |
|---|---|---|---|
| 365 | 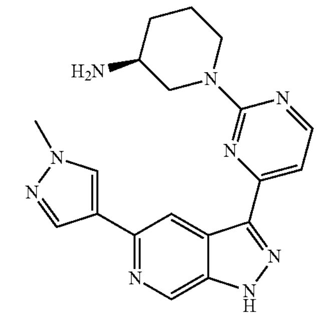 [SMILES: Cn1cc(-c2cc3c(-c4ccnc(N5CCC[C@H](N)C5)n4)n[nH]c3cn2)cn1] | (S)-1-(4-(5-(1-methyl-1H-pyrazol-4-yl)-1H-pyrazolo[3,4-c]pyridin-3-yl)pyrimidin-2-yl)piperidin-3-amine | 0.0000941 |
| 366 | 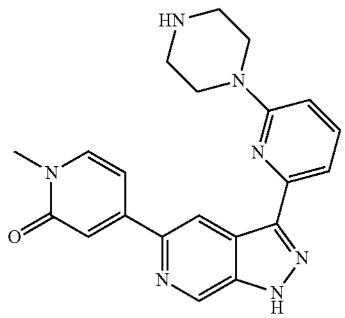 [SMILES: Cn1ccc(-c2cc3c(-c4cccc(N5CCNCC5)n4)n[nH]c3cn2)cc1=O] | 1-methyl-4-(3-(6-(piperazin-1-yl)pyridin-2-yl)-1H-pyrazolo[3,4-c]pyridin-5-yl)pyridin-2(1H)-one | 0.00097 |
| 367 | 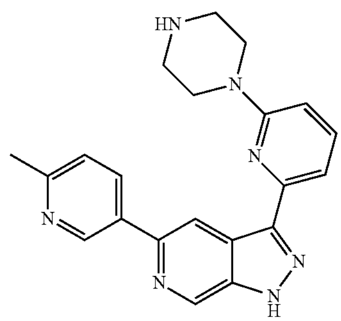 [SMILES: Cc1ccc(-c2cc3c(-c4cccc(N5CCNCC5)n4)n[nH]c3cn2)cn1] | 5-(6-methylpyridin-3-yl)-3-(6-(piperazin-1-yl(pyridin-2-yl)-1H-pyrazolo[3,4-c]pyridine | 0.000217 |
| 368 | 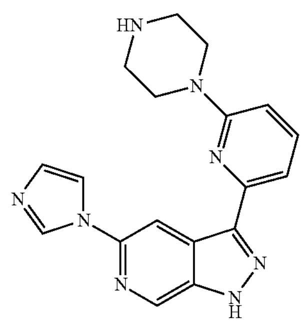 [SMILES: c1cc(-c2n[nH]c3cnc(-n4ccnc4)cc23)nc(N2CCNCC2)c1] | 5-(1H-imidazol-1-yl)-3-(6-(piperazin-1-yl)pyridin-2-yl)-1H-pyrazolo[3,4-c]pyridine | 0.00182 |
| 369 | 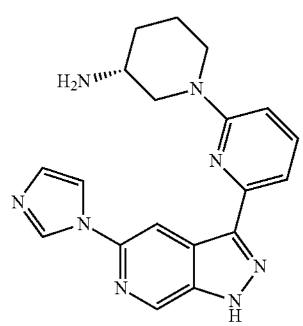 [SMILES: N[C@@H]1CCCN(c2cccc(-c3n[nH]c4cnc(-n5ccnc5)cc34)n2)C1] | (R)-1-(6-(5-(1H-imidazol-1-yl)-1H-pyrazolo[3,4-c]pyridin-3-yl)pyridin-2-yl)piperidin-3-amine | 0.00113 |

TABLE 1-continued

| No. | Structure | Name | Pim-1 Ki (μm) |
|---|---|---|---|
| 370 | 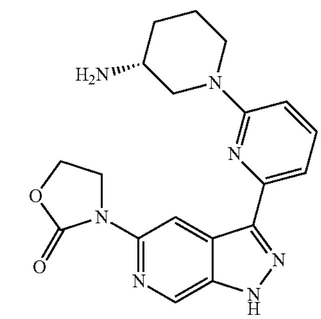 [SMILES: N[C@@H]1CCCN(c2cccc(-c3n[nH]c4cnc(N5CCOC5=O)cc34)n2)C1] | (R)-3-(3-(6-(3-aminopiperidin-1-yl)pyridin-2-yl)-1H-pyrazolo[3,4-c]pyridin-5-yl)oxazolidin-2-one | 0.18 |
| 371 | 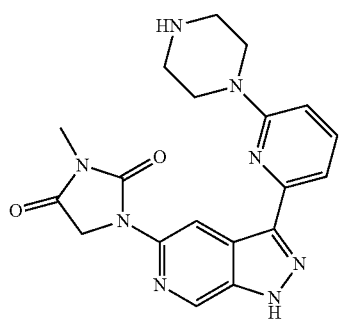 [SMILES: CN1C(=O)CN(c2cc3c(-c4cccc(N5CCNCC5)n4)n[nH]c3cn2)C1=O] | 3-methyl-1-(3-(6-(piperazin-1-yl)pyridin-2-yl)-1H-pyrazolo[3,4-c]pyridin-5-yl)imidazolidine-2,4-dione | 0.0311 |
| 372 | 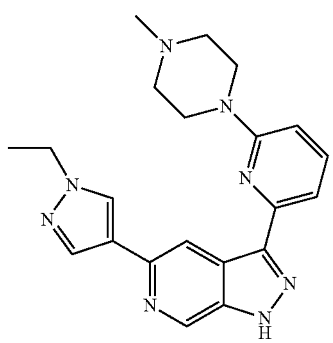 [SMILES: CCn1cc(-c2cc3c(-c4cccc(N5CCN(C)CC5)n4)n[nH]c3cn2)cn1] | 5-(1-ethyl-1H-pyrazol-4-yl)-3-(6-(4-methylpiperazin-1-yl)pyridin-2-yl)-1H-pyrazolo[3,4-c]pyridine | 0.000268 |
| 373 | 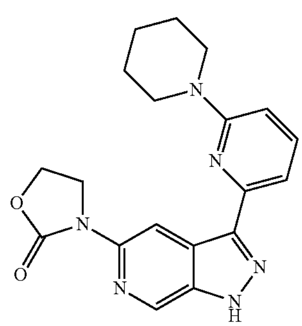 [SMILES: O=C1OCCN1c1cc2c(-c3cccc(N4CCCCC4)n3)n[nH]c2cn1] | 3-(3-(6-(piperidin-1-yl)pyridin-2-yl)-1H-pyrazolo[3,4-c]pyridin-5-yl)oxazolidin-2-one | 0.483 |

TABLE 1-continued

| No. | Structure | Name | Pim-1 Ki (μm) |
|---|---|---|---|
| 374 | 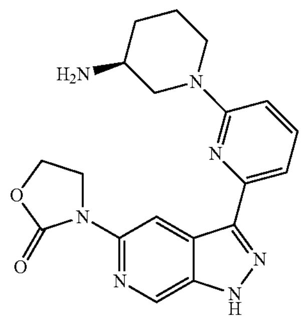 [SMILES: N[C@H]1CCCN(c2cccc(-c3n[nH]c4cnc(N5CCOC5=O)cc34)n2)C1] | (S)-3-(3-(6-(3-aminopiperidin-1-yl)pyridin-2-yl)-1H-pyrazolo[3,4-c]pyridin-5-yl)oxazolidin-2-one | 0.085 |
| 375 | 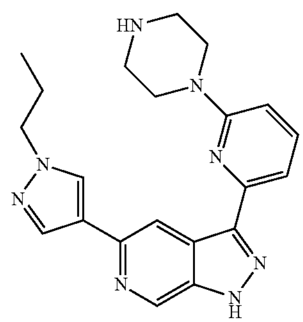 [SMILES: CCCn1cc(-c2cc3c(-c4cccc(N5CCNCC5)n4)n[nH]c3cn2)cn1] | 3-(6-(piperazin-1-yl)pyridin-2-yl)-5-(1-propyl-1H-pyrazol-4-yl)-1H-pyrazolo[3,4-c]pyridine | 0.000039 |
| 376 | 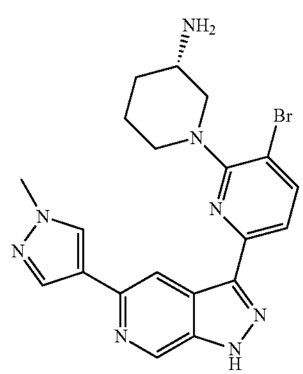 [SMILES: Cn1cc(-c2cc3c(-c4ccc(Br)c(N5CCC[C@H](N)C5)n4)n[nH]c3cn2)cn1] | (S)-1-(3-bromo-6-(5-(1-methyl-1H-pyrazol-4-yl)-1H-pyrazolo[3,4-c]pyridin-3-yl)pyridin-2-yl)piperidin-3-amine | 0.0000090 |
| 377 | 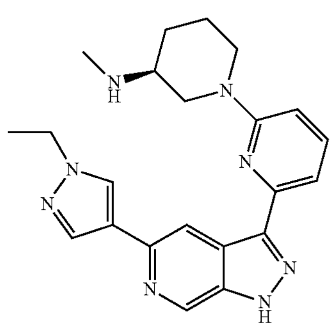 [SMILES: CCn1cc(-c2cc3c(-c4cccc(N5CCC[C@H](NC)C5)n4)n[nH]c3cn2)cn1] | (S)-1-(6-(5-(1-ethyl-1H-pyrazol-4-yl)-1H-pyrazolo[3,4-c]pyridin-3-yl)pyridin-2-yl)-N-methylpiperidin-3-amine | 0.000080 |

TABLE 1-continued

| No. | Structure | Name | Pim-1 Ki (μm) |
|---|---|---|---|
| 378 | 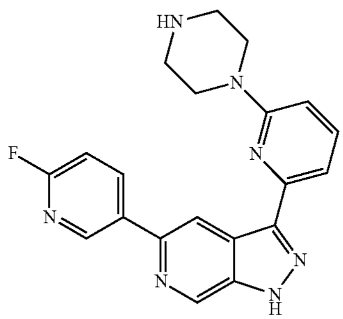 [SMILES: Fc1ccc(-c2cc3c(-c4cccc(N5CCNCC5)n4)n[nH]c3cn2)cn1] | 5-(6-fluoropyridin-3-yl)-3-(6-(piperazin-1-yl)pyridin-2-yl)-1H-pyrazolo[3,4-c]pyridine | 0.000796 |
| 379 | 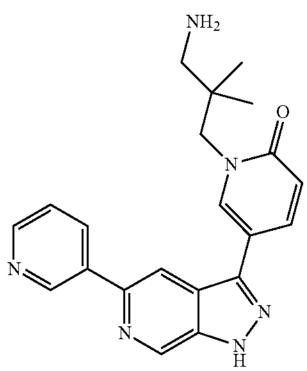 [SMILES: CC(C)(CN)Cn1cc(-c2n[nH]c3cnc(-c4cccnc4)cc23)ccc1=O] | 1-(3-amino-2,2-dimethylpropyl)-5-(5-(pyridin-3-yl)-1H-pyrazolo[3,4-c]pyridin-3-yl)pyridin-2(1H)-one | 0.00129 |
| 380 | 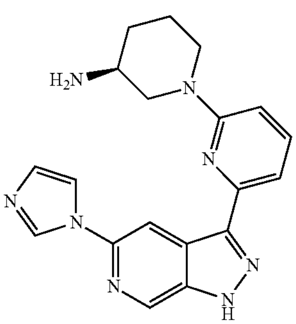 [SMILES: N[C@H]1CCCN(c2cccc(-c3n[nH]c4cnc(-n5ccnc5)cc34)n2)C1] | (S)-1-(6-(5-(1H-imidazol-1-yl)-1H-pyrazolo[3,4-c]pyridin-3-yl)pyridin-2-yl)piperidin-3-amine | 0.000523 |
| 381 | 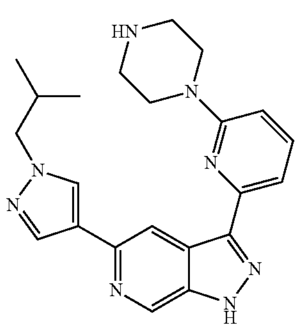 [SMILES: CC(C)Cn1cc(-c2cc3c(-c4cccc(N5CCNCC5)n4)n[nH]c3cn2)cn1] | 5-(1-isobutyl-1H-pyrazol-4-yl)-3-(6-(piperazin-1-yl)pyridin-2-yl)-1H-pyrazolo[3,4-c]pyridine | 0.000057 |

TABLE 1-continued

| No. | Structure | Name | Pim-1 Ki (μm) |
|---|---|---|---|
| 382 | 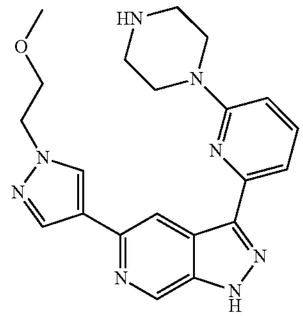 [SMILES: COCCn1cc(-c2cc3c(-c4cccc(N5CCNCC5)n4)n[nH]c3cn2)cn1] | 5-(1-(2-methoxyethyl)-1H-pyrazol-4-yl)-3-(6-(piperazin-1-yl)pyridin-2-yl)-1H-pyrazolo[3,4-c]pyridine | 0.000060 |
| 383 | 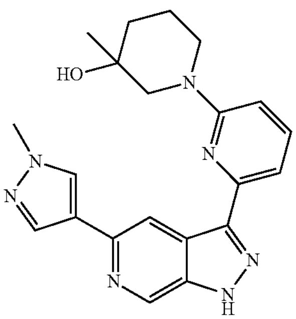 [SMILES: Cn1cc(-c2cc3c(-c4cccc(N5CCCC(C)(O)C5)n4)n[nH]c3cn2)cn1] | 3-methyl-1-(6-(5-(1-methyl-1H-pyrazol-4-yl)-1H-pyrazolo[3,4-c]pyridin-3-yl)pyridin-2-yl)piperidin-3-ol | 0.000078 |
| 384 | 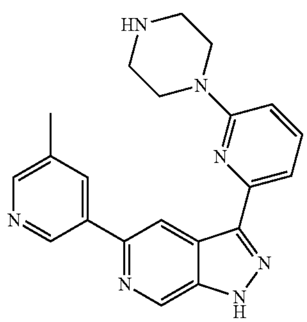 [SMILES: Cc1cncc(-c2cc3c(-c4cccc(N5CCNCC5)n4)n[nH]c3cn2)c1] | 5-(5-methylpyridin-3-yl)-3-(6-(piperazin-1-yl)pyridin-2-yl)-1H-pyrazolo[3,4-c]pyridine | 0.000041 |
| 385 | 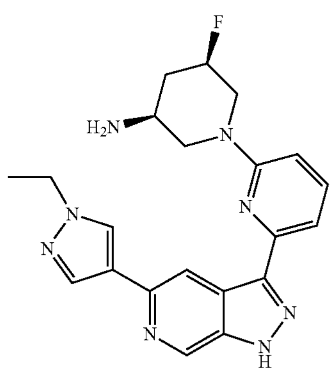 [SMILES: CCn1cc(-c2cc3c(-c4cccc(N5C[C@@H](N)C[C@@H](F)C5)n4)n[nH]c3cn2)cn1] | (3S,5R)-1-(6-(5-(1-ethyl-1H-pyrazol-4-yl)-1H-pyrazolo[3,4-c]pyridin-3-yl)pyridin-2-yl)-5-fluoropiperidin-3-amine | 0.000131 |

TABLE 1-continued

| No. | Structure | Name | Pim-1 Ki (μm) |
|---|---|---|---|
| 386 | 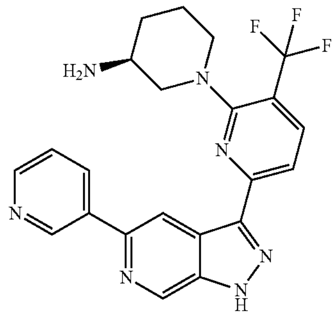 [SMILES: N[C@H]1CCCN(c2nc(-c3n[nH]c4cnc(-c5cccnc5)cc34)ccc2C(F)(F)F)C1] | (S)-1-(6-(5-(pyridin-3-yl)-1H-pyrazolo[3,4-c]pyridin-3-yl)-3-(trifluoromethyl)pyridin-2-yl)piperidin-3-amine | 0.000117 |
| 387 | 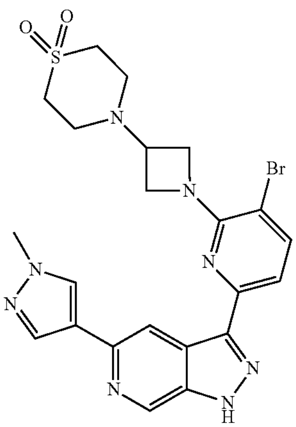 [SMILES: Cn1cc(-c2cc3c(-c4ccc(Br)c(N5CC(N6CCS(=O)(=O)CC6)C5)n4)n[nH]c3cn2)cn1] | 4-(1-(3-bromo-6-(5-(1-methyl-1H-pyrazol-4-yl)-1H-pyrazolo[3,4-c]pyridin-3-yl)pyridin-2-yl)azetidin-3-yl)-1,1-dioxothiomorpholine | 0.00159 |
| 388 | 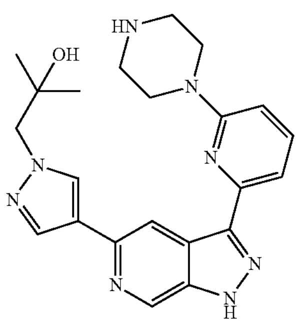 [SMILES: CC(C)(O)Cn1cc(-c2cc3c(-c4cccc(N5CCNCC5)n4)n[nH]c3cn2)cn1] | 2-methyl-1-(4-(3-(6-(piperazin-1-yl)pyridin-2-yl)-1H-pyrazolo[3,4-c]pyridin-5-yl)-1H-pyrazol-1-yl)propan-2-ol | 0.000138 |
| 389 | 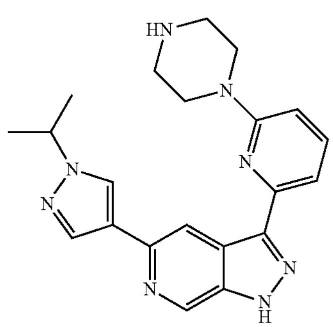 [SMILES: CC(C)n1cc(-c2cc3c(-c4cccc(N5CCNCC5)n4)n[nH]c3cn2)cn1] | 5-(1-isopropyl-1H-pyrazol-4-yl)-3-(6-(piperazin-1-yl)pyridin-2-yl)-1H-pyrazolo[3,4-c]pyridine | 0.000213 |

TABLE 1-continued

| No. | Structure | Name | Pim-1 Ki (μm) |
|---|---|---|---|
| 390 | 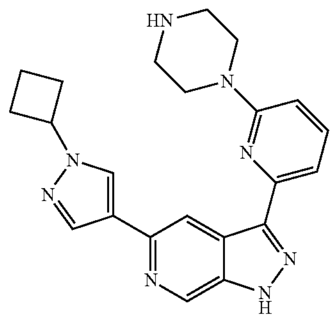 [SMILES: c1cc(-c2n[nH]c3cnc(-c4cnn(C5CCC5)c4)cc23)nc(N2CCNCC2)c1] | 5-(1-cyclobutyl-1H-pyrazol-4-yl)-3-(6-(piperazin-1-yl)pyridin-2-yl)-1H-pyrazolo[3,4-c]pyridine | 0.000132 |
| 391 | 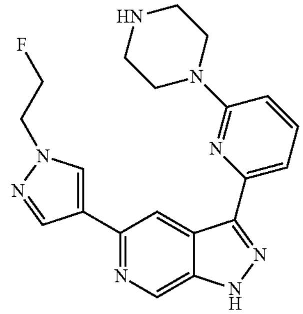 | 5-(1-(2-fluoroethyl)-1H-pyrazol-4-yl)-3-(6-(piperazin-1-yl)pyridin-2-yl)-1H-pyrazolo[3,4-c]pyridine | 0.000108 |
| 392 | 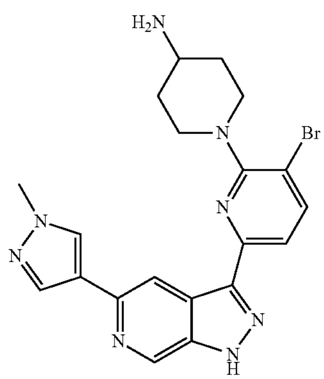 [SMILES: Cn1cc(-c2cc3c(-c4ccc(Br)c(N5CCC(N)CC5)n4)n[nH]c3cn2)cn1] | 1-(3-bromo-6-(5-(1-methyl-1H-pyrazol-4-yl)-1H-pyrazolo[3,4-c]pyridin-3-yl)pyridin-2-yl)piperidin-4-amine | 0.000030 |
| 393 | 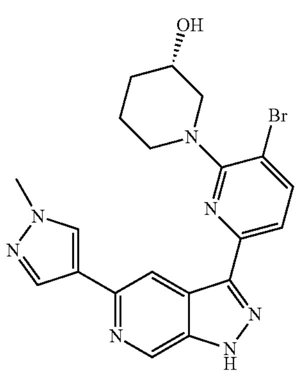 | (S)-1-(3-bromo-6-(5-(1-methyl-1H-pyrazol-4-yl)-1H-pyrazolo[3,4-c]pyridin-3-yl)pyridin-2-yl)piperidin-3-ol | 0.000333 |

TABLE 1-continued

| No. | Structure | Name | Pim-1 Ki (μm) |
|---|---|---|---|
| 394 | 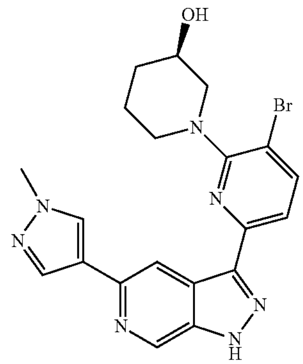 | (R)-1-(3-bromo-6-(5-(1-methyl-1H-pyrazol-4-yl)-1H-pyrazolo[3,4-c]pyridin-3-yl)pyridin-2-yl)piperidin-3-ol | 0.000316 |
| 395 | 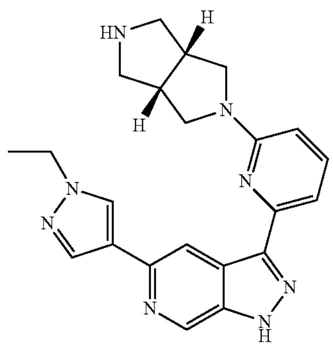 [SMILES: CCn1cc(-c2cc3c(-c4cccc(N5C[C@H]6CNC[C@H]6C5)n4)n[nH]c3cn2)cn1] | 5-(1-ethyl-1H-pyrazol-4-yl)-3-(6-((3aR,6aS)-hexahydropyrrolo[3,4-c]pyrrol-2(1H)-yl(pyridin-2-yl)-1H-pyrazolo[3,4-c]pyridine | 0.000404 |
| 396 | 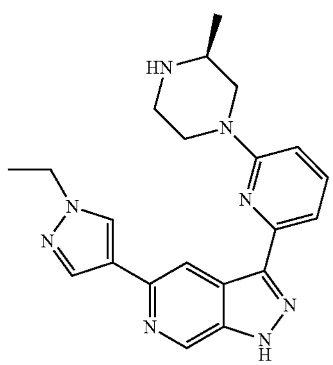 [SMILES: CCn1cc(-c2cc3c(-c4cccc(N5CCN[C@@H](C)C5)n4)n[nH]c3cn2)cn1] | (S)-5-(1-ethyl-1H-pyrazol-4-yl)-3-(6-(3-methylpiperazin-1-yl)pyridin-2-yl)-1H-pyrazolo[3,4-c]pyridine | 0.000081 |
| 397 | 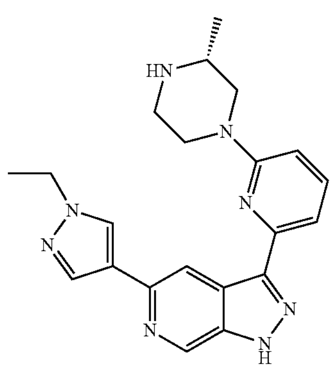 [SMILES: CCn1cc(-c2cc3c(-c4cccc(N5CCN[C@H](C)C5)n4)n[nH]c3cn2)cn1] | (R)-5-(1-ethyl-1H-pyrazol-4-yl)-3-(6-(3-methylpiperazin-1-yl)pyridin-2-yl)-1H-pyrazolo[3,4-c]pyridine | 0.000046 |

TABLE 1-continued

| No. | Structure | Name | Pim-1 Ki (μm) |
|---|---|---|---|
| 398 | 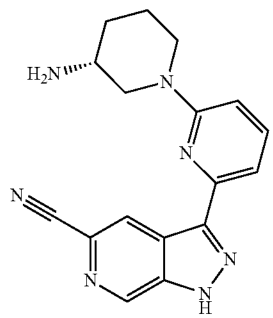 [SMILES: N#Cc1cc2c(-c3cccc(N4CCC[C@@H](N)C4)n3)n[nH]c2cn1] | (R)-3-(6-(3-aminopiperidin-1-yl)pyridin-2-yl)-1H-pyrazolo[3,4-c]pyridine-5-carbonitrile | 0.0391 |
| 399 | 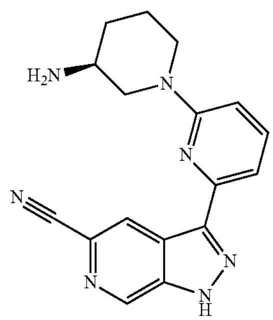 [SMILES: N#Cc1cc2c(-c3cccc(N4CCC[C@H](N)C4)n3)n[nH]c2cn1] | (S)-3-(6-(3-aminopiperidin-1-yl)pyridin-2-yl)-1H-pyrazolo[3,4-c]pyridine-5-carbonitrile | 0.0226 |
| 400 | 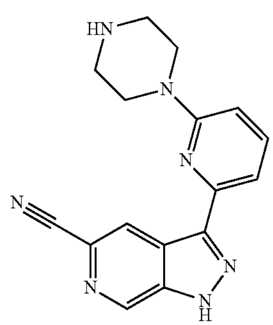 [SMILES: N#Cc1cc2c(-c3cccc(N4CCNCC4)n3)n[nH]c2cn1] | 3-(6-(piperazin-1-yl)pyridin-2-yl)-1H-pyrazolo[3,4-c]pyridine-5-carbonitrile | 0.0511 |
| 401 | 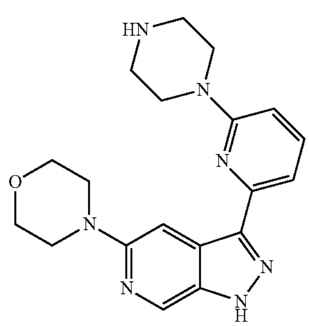 [SMILES: c1cc(-c2n[nH]c3cnc(N4CCOCC4)cc23)nc(N2CCNCC2)c1] | 4-(3-(6-(piperazin-1-yl)pyridin-2-yl)-1H-pyrazolo[3,4-c]pyridin-5-yl)morpholine | 0.00329 |

TABLE 1-continued

| No. | Structure | Name | Pim-1 Ki (μm) |
|---|---|---|---|
| 402 | 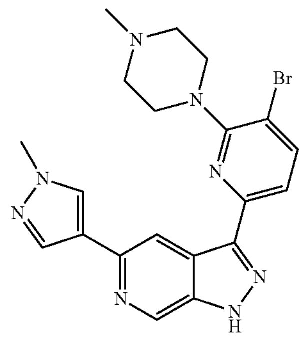 [SMILES: CN1CCN(c2nc(-c3n[nH]c4cnc(-c5cnn(C)c5)cc34)ccc2Br)CC1] | 3-(5-bromo-6-(4-methylpiperazin-1-yl)pyridin-2-yl)-5-(1-methyl-1H-pyrazol-4-yl)-1H-pyrazolo[3,4-c]pyridine | 0.000070 |
| 403 | 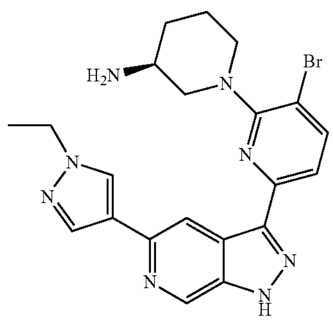 [SMILES: CCn1cc(-c2cc3c(-c4ccc(Br)c(N5CCC[C@H](N)C5)n4)n[nH]c3cn2)cn1] | (S)-1-(3-bromo-6-(5-(1-ethyl-1H-pyrazol-4-yl)-1H-pyrazolo[3,4-c]pyridin-3-yl)pyridin-2-yl)piperidin-3-amine | 0.000040 |
| 404 | 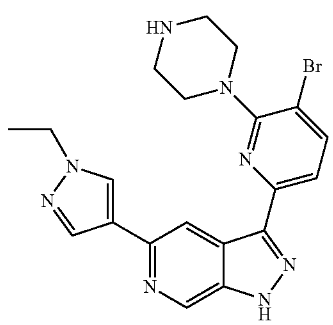 [SMILES: CCn1cc(-c2cc3c(-c4ccc(Br)c(N5CCNCC5)n4)n[nH]c3cn2)cn1] | 3-(5-bromo-6-(piperazin-1-yl)pyridin-2-yl)-5-(1-ethyl-1H-pyrazol-4-yl)-1H-pyrazolo[3,4-c]pyridine | 0.000090 |
| 405 | 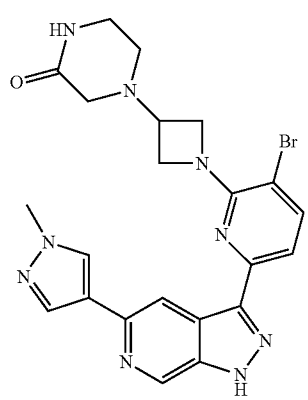 [SMILES: Cn1cc(-c2cc3c(-c4ccc(Br)c(N5CC(N6CCNC(=O)C6)C5)n4)n[nH]c3cn2)cn1] | 4-(1-(3-bromo-6-(5-(1-methyl-1H-pyrazol-4-yl)-1H-pyrazolo[3,4-c]pyridin-3-yl)pyridin-2-yl)azetidin-3-yl)piperazin-2-one | 0.000527 |

TABLE 1-continued

| No. | Structure | Name | Pim-1 Ki (μm) |
|---|---|---|---|
| 406 | 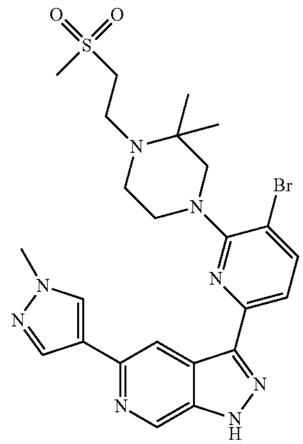 [SMILES: Cn1cc(-c2cc3c(-c4ccc(Br)c(N5CCN(CCS(C)(=O)=O)C(C)(C)C5)n4)n[nH]c3cn2)cn1] | 3-(5-bromo-6-(3,3-dimethyl-4-(2-(methylsulfonyl)ethyl)piperazin-1-yl)pyridin-2-yl)-5-(1-methyl-1H-pyrazol-4-yl)-1H-pyrazolo[3,4-c]pyridine | 0.000259 |
| 407 | 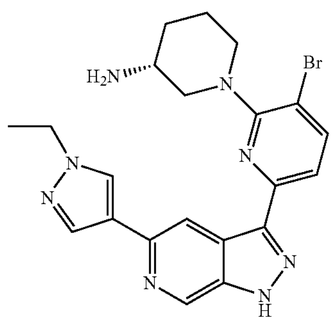 [SMILES: CCn1cc(-c2cc3c(-c4ccc(Br)c(N5CCC[C@@H](N)C5)n4)n[nH]c3cn2)cn1] | (R)-1-(3-bromo-6-(5-(1-ethyl-1H-pyrazol-4-yl)-1H-pyrazolo[3,4-c]pyridin-3-yl)pyridin-2-yl)piperidin-3-amine | |
| 408 | 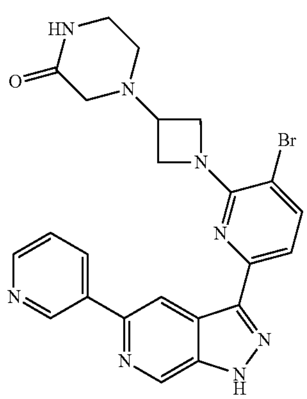 [SMILES: O=C1CN(C2CN(c3nc(-c4n[nH]c5cnc(-c6cccnc6)cc45)ccc3Br)C2)CCN1] | 4-(1-(3-bromo-6-(5-(pyridin-3-yl)-1H-pyrazolo[3,4-c]pyridin-3-yl)pyridin-2-yl)azetidin-3-yl)piperazin-2-one | |
| 409 | 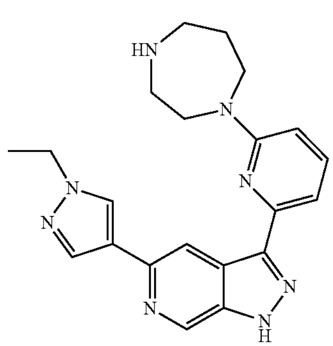 [SMILES: CCn1cc(-c2cc3c(-c4cccc(N5CCCNCC5)n4)n[nH]c3cn2)cn1] | 3-(6-(1,4-diazepan-1-yl)pyridin-2-yl)-5-(1-ethyl-1H-pyrazol-4-yl)-1H-pyrazolo[3,4-c]pyridine | 0.000020 |

TABLE 1-continued

| No. | Structure | Name | Pim-1 Ki (μm) |
|---|---|---|---|
| 410 | 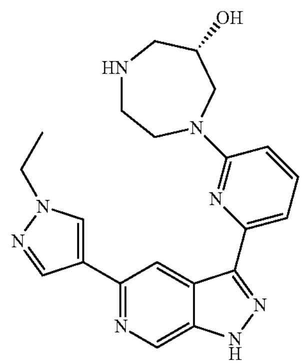 [SMILES: CCn1cc(-c2cc3c(-c4cccc(N5CCNC[C@H](O)C5)n4)n[nH]c3cn2)cn1] | (S)-1-(6-(5-(1-ethyl-1H-pyrazol-4-yl)-1H-pyrazolo[3,4-c]pyridin-3-yl)pyridin-2-yl)-1,4-diazepan-6-ol | 0.000039 |
| 411 | 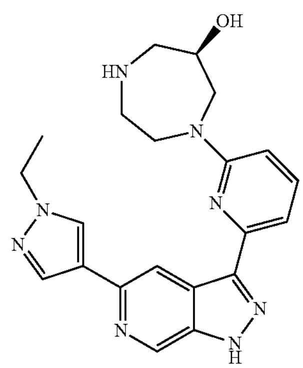 [SMILES: CCn1cc(-c2cc3c(-c4cccc(N5CCNC[C@@H](O)C5)n4)n[nH]c3cn2)cn1] | (R)-1-(6-(5-(1-ethyl-1H-pyrazol-4-yl)-1H-pyrazolo[3,4-c]pyridin-3-yl)pyridin-2-yl)-1,4-diazepan-6-ol | 0.000014 |
| 412 | 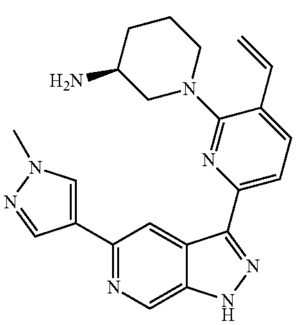 [SMILES: C=Cc1ccc(-c2n[nH]c3cnc(-c4cnn(C)c4)cc23)nc1N1CCC[C@H](N)C1] | (S)-1-(6-(5-(1-methyl-1H-pyrazol-4-yl)-1H-pyrazolo[3,4-c]pyridin-3-yl)-3-vinylpyridin-2-yl)piperidin-3-amine | 0.000036 |
| 413 | 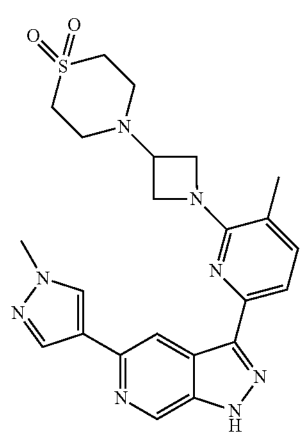 [SMILES: Cc1ccc(-c2n[nH]c3cnc(-c4cnn(C)c4)cc23)nc1N1CC(N2CCS(=O)(=O)CC2)C1] | 4-(1-(3-methyl-6-(5-(1-methyl-1H-pyrazol-4-yl)-1H-pyrazolo[3,4-c]pyridin-3-yl)pyridin-2-yl)azetidin-3-yl)-1,1-dioxo thiomorpholine | 0.00102 |

TABLE 1-continued

| No. | Structure | Name | Pim-1 Ki (µm) |
|---|---|---|---|
| 414 | 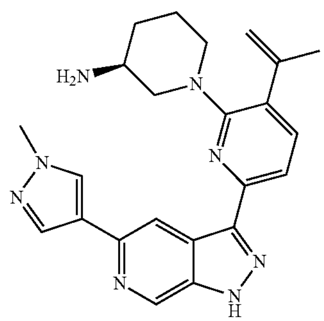 [SMILES: C=C(C)c1ccc(-c2n[nH]c3cnc(-c4cnn(C)c4)cc23)nc1N1CCC[C@H](N)C1] | (S)-1-(6-(5-(1-methyl-1H-pyrazol-4-yl)-1H-pyrazolo[3,4-c]pyridin-3-yl)-3-(prop-1-en-2-yl)pyridin-2-yl)piperidin-3-amine | 0.000028 |
| 415 | 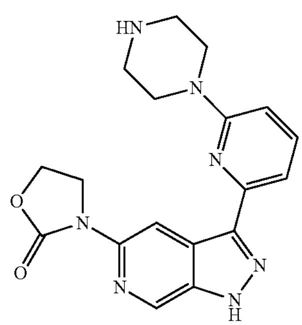 [SMILES: O=C1OCCN1c1cc2c(-c3cccc(N4CCNCC4)n3)n[nH]c2cn1] | 3-(3-(6-(piperazin-1-yl)pyridin-2-yl)-1H-pyrazolo[3,4-c]pyridin-5-yl)oxazolidin-2-one | 0.104 |
| 416 | 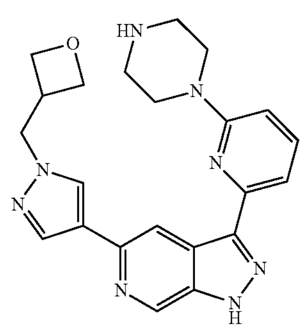 [SMILES: c1cc(-c2n[nH]c3cnc(-c4cnn(CC5COC5)c4)cc23)nc(N2CCNCC2)c1] | 5-(1-(oxetan-3-ylmethyl)-1H-pyrazol-4-yl)-3-(6-(piperazin-1-yl)pyridin-2-yl)-1H-pyrazolo[3,4-c]pyridine | 0.0113 |
| 417 | 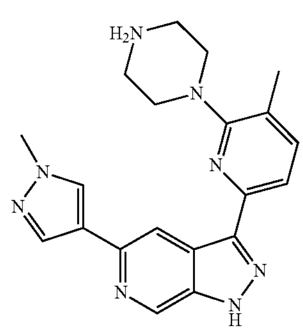 [SMILES: Cc1ccc(-c2n[nH]c3cnc(-c4cnn(C)c4)cc23)nc1N1CCNCC1] | 1-(3-methyl-6-(5-(1-methyl-1H-pyrazol-4-yl)-1H-pyrazolo[3,4-c]pyridin-3-yl)pyridin-2-yl)piperidin-4-amine | 0.000051 |

TABLE 1-continued

| No. | Structure | Name | Pim-1 Ki (μm) |
|---|---|---|---|
| 418 | 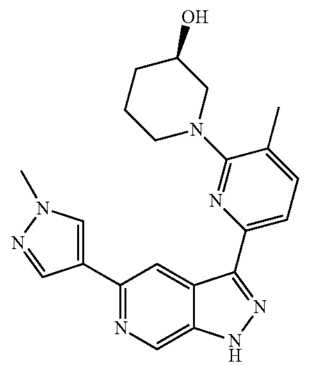 [SMILES: Cc1ccc(-c2n[nH]c3cnc(-c4cnn(C)c4)cc23)nc1N1CCC[C@@H](O)C1] | (R)-1-(3-methyl-6-(5-(1-methyl-1H-pyrazol-4-yl)-1H-pyrazolo[3,4-c]pyridin-3-yl)pyridin-2-yl)piperidin-3-ol | 0.00011 |
| 419 | 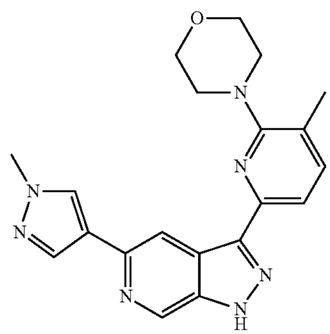 | 4-(3-methyl-6-(5-(1-methyl-1H-pyrazol-4-yl)-1H-pyrazolo[3,4-c]pyridin-3-yl)pyridin-2-yl)morpholine | 0.00016 |
| 420 | 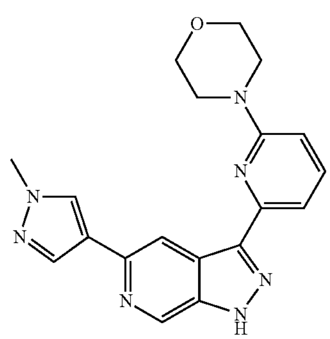 [SMILES: Cn1cc(-c2cc3c(-c4cccc(N5CCOCC5)n4)n[nH]c3cn2)cn1] | 4-(6-(5-(1-methyl-1H-pyrazol-4-yl)-1H-pyrazolo[3,4-c]pyridin-3-yl)pyridin-2-yl)morpholine | 0.000368 |
| 421 | 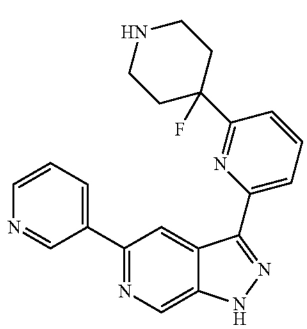 [SMILES: FC1(c2cccc(-c3n[nH]c4cnc(-c5cccnc5)cc34)n2)CCNCC1] | 3-(6-(4-fluoropiperidin-4-yl)pyridin-2-yl)-5-(pyridin-3-yl)-1H-pyrazolo[3,4-c]pyridine | 0.000105 |

TABLE 1-continued

| No. | Structure | Name | Pim-1 Ki (μm) |
|---|---|---|---|
| 422 | 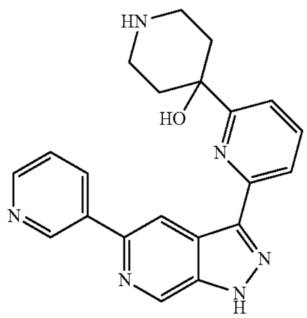 [SMILES: OC1(c2cccc(-c3n[nH]c4cnc(-c5cccnc5)cc34)n2)CCNCC1] | 4-(6-(5-(pyridin-3-yl)-1H-pyrazolo[3,4-c]pyridin-3-yl)pyridin-2-yl)piperidin-4-ol | 0.3000684 |
| 423 | 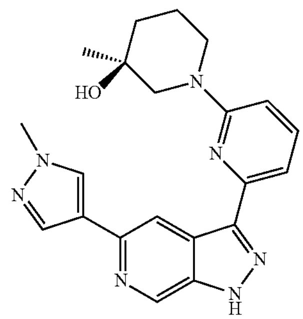 [SMILES: Cn1cc(-c2cc3c(-c4cccc(N5CCC[C@](C)(O)C5)n4)n[nH]c3cn2)cn1] | (S)-3-methyl-1-(6-(5-(1-methyl-1H-pyrazol-4-yl)-1H-pyrazolo[3,4-c]pyridin-3-yl)pyridin-2-yl)piperidin-3-ol | 0.000128 |
| 424 | 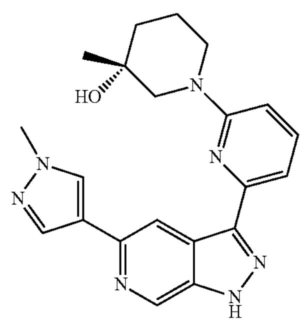 [SMILES: Cn1cc(-c2cc3c(-c4cccc(N5CCC[C@@](C)(O)C5)n4)n[nH]c3cn2)cn1] | (R)-3-methyl-1-(6-(5-(1-methyl-1H-pyrazol-4-yl)-1H-pyrazolo[3,4-c]pyridin-3-yl)pyridin-2-yl)piperidin-3-ol | 0.000073 |
| 425 | 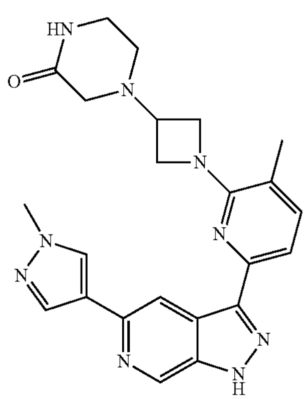 [SMILES: Cc1ccc(-c2n[nH]c3cnc(-c4cnn(C)c4)cc23)nc1N1CC(N2CCNC(=O)C2)C1] | 4-(1-(3-methyl-6-(5-(1-methyl-1H-pyrazol-4-yl)-1H-pyrazolo[3,4-c]pyridin-3-yl)pyridin-2-yl)azetidin-3-yl)piperazin-2-one | 0.000618 |

TABLE 1-continued

| No. | Structure | Name | Pim-1 Ki (μm) |
|---|---|---|---|
| 426 | 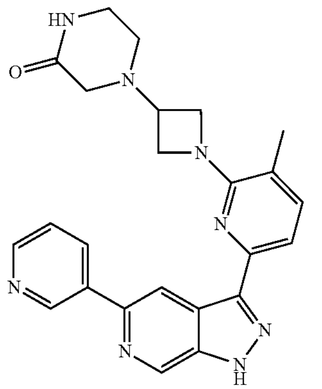 [SMILES: Cc1ccc(-c2n[nH]c3cnc(-c4cccnc4)cc23)nc1N1CC(N2CCNC(=O)C2)C1] | 4-(1-(3-methyl-6-(5-(pyridin-3-yl)-1H-pyrazolo[3,4-c]pyridin-3-yl)pyridin-2-yl)azetidin-3-yl)piperazin-2-one | 0.00046 |
| 427 | 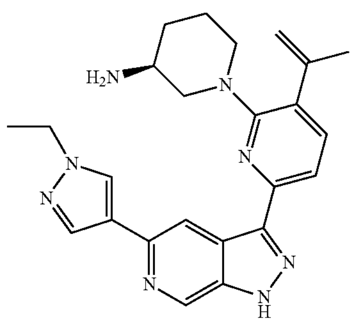 [SMILES: C=C(C)c1ccc(-c2n[nH]c3cnc(-c4cnn(CC)c4)cc23)nc1N1CCC[C@H](N)C1] | (S)-1-(6-(5-(1-ethyl-1H-pyrazol-4-yl)-1H-pyrazolo[3,4-c]pyridin-3-yl)-3-(prop-1-en-2-yl)pyridin-2-yl)piperidin-3-amine | 0.000016 |
| 428 | 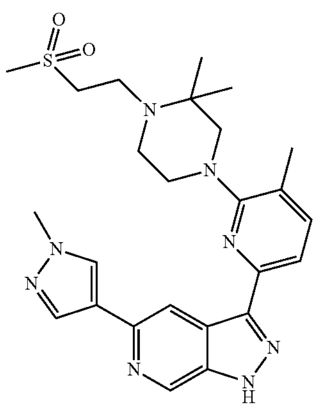 [SMILES: Cc1ccc(-c2n[nH]c3cnc(-c4cnn(C)c4)cc23)nc1N1CCN(CCS(C)(=O)=O)C(C)(C)C1] | 3-(6-(3,3-dimethyl-4-(2-(methylsulfonyl)ethyl)piperazin-1-yl)-5-methylpyridin-2-yl)-5-(1-methyl-1H-pyrazol-4-yl)-1H-pyrazolo[3,4-c]pyridine | 0.000112 |
| 429 | 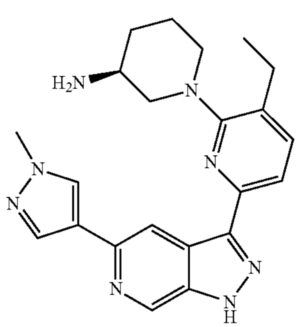 [SMILES: CCc1ccc(-c2n[nH]c3cnc(-c4cnn(C)c4)cc23)nc1N1CCC[C@H](N)C1] | (S)-1-(3-ethyl-6-(5-(1-methyl-1H-pyrazol-4-yl)-1H-pyrazolo[3,4-c]pyridin-3-yl)pyridin-2-yl)piperidin-3-amine | 0.000022 |

TABLE 1-continued

| No. | Structure | Name | Pim-1 Ki (μm) |
|---|---|---|---|
| 430 | 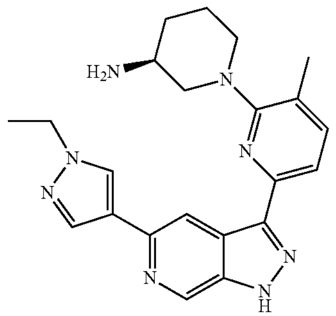 [SMILES: CCn1cc(-c2cc3c(-c4ccc(C)c(N5CCC[C@H](N)C5)n4)n[nH]c3cn2)cn1] | (S)-1-(6-(5-(1-ethyl-1H-pyrazol-4-yl)-1H-pyrazolo[3,4-c]pyridin-3-yl)-3-methylpyridin-2-yl)piperidin-3-amine | 0.000027 |
| 431 | 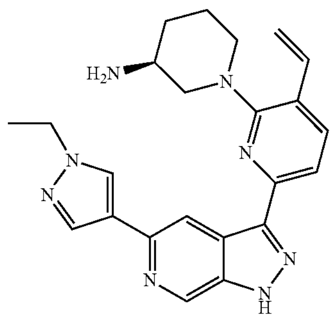 [SMILES: C=Cc1ccc(-c2n[nH]c3cnc(-c4cnn(CC)c4)cc23)nc1N1CCC[C@H](N)C1] | (S)-1-(6-(5-(1-ethyl-1H-pyrazol-4-yl)-1H-pyrazolo[3,4-c]pyridin-3-yl)-3-vinylpyridin-2-yl)piperidin-3-amine | 0.000023 |
| 432 | 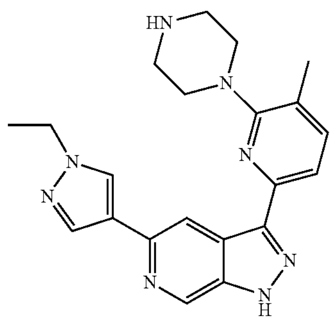 [SMILES: CCn1cc(-c2cc3c(-c4ccc(C)c(N5CCNCC5)n4)n[nH]c3cn2)cn1] | 5-(1-ethyl-1H-pyrazol-4-yl)-3-(5-methyl-6-(piperazin-1-yl)pyridin-2-yl)-1H-pyrazolo[3,4-c]pyridine | 0.000055 |
| 433 | 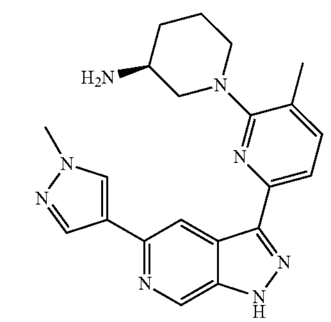 [SMILES: Cc1ccc(-c2n[nH]c3cnc(-c4cnn(C)c4)cc23)nc1N1CCC[C@H](N)C1] | (S)-1-(3-methyl-6-(5-(1-methyl-1H-pyrazol-4-yl)-1H-pyrazolo[3,4-c]pyridin-3-yl)pyridin-2-yl)piperidin-3-amine | 0.000013 |
| 434 | 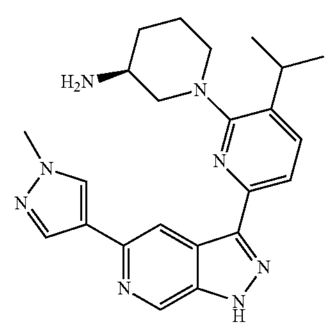 [SMILES: CC(C)c1ccc(-c2n[nH]c3cnc(-c4cnn(C)c4)cc23)nc1N1CCC[C@H](N)C1] | (S)-1-(3-isopropyl-6-(5-(1-methyl-1H-pyrazol-4-yl)-1H-pyrazolo[3,4-c]pyridin-3-yl)pyridin-2-yl)piperidin-3-amine | |

TABLE 1-continued

| No. | Name | Pim-1 Ki (μm) |
|---|---|---|
| 435 | 4-fluoro-1-(6-(5-(pyridin-3-yl)-1H-pyrazolo[3,4-c]pyridin-3-yl)pyridin-2-yl)piperidin-3-ol | 0.000089 |
| 436 | 5-(5-methoxypyridin-3-yl)-3-(6-(piperazin-1-yl)pyridin-2-yl)-1H-pyrazolo[3,4-c]pyridine | 0.000021 |
| 437 | N-methyl-6-(5-(pyridin-3-yl)-1H-pyrazolo[3,4-c]pyridin-3-yl)pyridin-2-amine | 0.000409 |
| 438 | 5-(5-ethylpyridin-3-yl)-3-(6-(piperazin-1-yl)pyridin-2-yl)-1H-pyrazolo[3,4-c]pyridine | 0.0000040 |
| 439 | 5-(1-methyl-1H-pyrazol-4-yl)-3-(2-(piperidin-4-yl)pyrimidin-4-yl)-1H-pyrazolo[3,4-c]pyridine | 0.000571 |

TABLE 1-continued

| No. | Structure | Name | Pim-1 Ki (μm) |
|---|---|---|---|
| 440 | 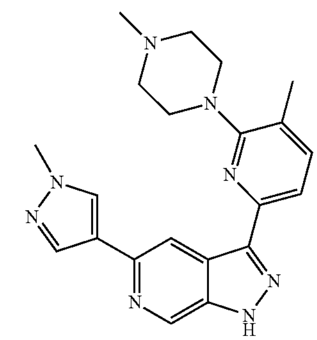 [SMILES: Cc1ccc(-c2n[nH]c3cnc(-c4cnn(C)c4)cc23)nc1N1CCN(C)CC1] | 5-(1-methyl-1H-pyrazol-4-yl)-3-(5-methyl-6-(4-methylpiperazin-1-yl)pyridin-2-yl)-1H-pyrazolo[3,4-c]pyridine | 0.000029 |
| 441 | 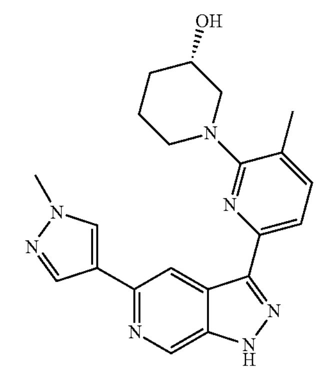 [SMILES: Cc1ccc(-c2n[nH]c3cnc(-c4cnn(C)c4)cc23)nc1N1CCC[C@H](O)C1] | (S)-1-(3-methyl-6-(5-(1-methyl-1H-pyrazol-4-yl)-1H-pyrazolo[3,4-c]pyridin-3-yl)pyridin-2-yl)piperidin-3-ol | 0.000062 |
| 442 | 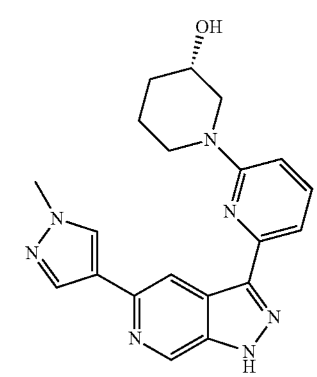 [SMILES: Cn1cc(-c2cc3c(-c4cccc(N5CCC[C@H](O)C5)n4)n[nH]c3cn2)cn1] | (S)-1-(6-(5-(1-methyl-1H-pyrazol-4-yl)-1H-pyrazolo[3,4-c]pyridin-3-yl)pyridin-2-yl)piperidin-3-ol | 0.000154 |
| 443 | 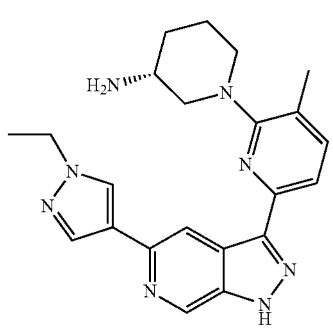 [SMILES: CCn1cc(-c2cc3c(-c4ccc(C)c(N5CCC[C@@H](N)C5)n4)n[nH]c3cn2)cn1] | (R)-1-(6-(5-(1-ethyl-1H-pyrazol-4-yl)-1H-pyrazolo[3,4-c]pyridin-3-yl)-3-methylpyridin-2-yl)piperidin-3-amine | 0.00010 |

TABLE 1-continued

| No. | Structure | Name | Pim-1 Ki (μm) |
|---|---|---|---|
| 444 | 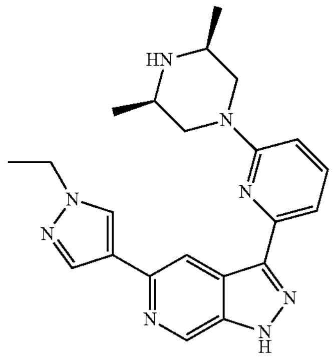 [SMILES: CCn1cc(-c2cc3c(-c4cccc(N5C[C@@H](C)N[C@@H](C)C5)n4)n[nH]c3cn2)cn1] | 3-(6-((3S,5R)-3,5-dimethylpiperazin-1-yl)pyridin-2-yl)-5-(1-ethyl-1H-pyrazol-4-yl)-1H-pyrazolo[3,4-c]pyridine | 0.000070 |
| 445 | 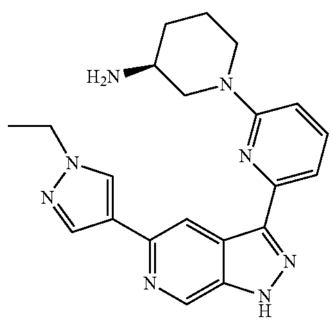 [SMILES: CCn1cc(-c2cc3c(-c4cccc(N5CCC[C@H](N)C5)n4)n[nH]c3cn2)cn1] | (S)-1-(6-(5-(1-ethyl-1H-pyrazol-4-yl)-1H-pyrazolo[3,4-c]pyridin-3-yl)pyridin-2-yl)piperidin-3-amine | 0.000031 |
| 446 | 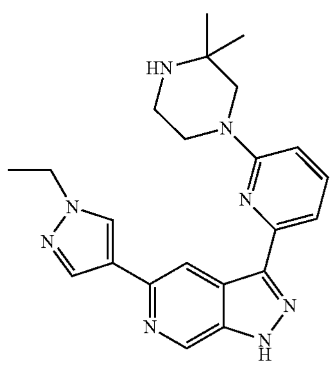 [SMILES: CCn1cc(-c2cc3c(-c4cccc(N5CCNC(C)(C)C5)n4)n[nH]c3cn2)cn1] | 3-(6-(3,3-dimethylpiperazin-1-yl)pyridin-2-yl)-5-(1-ethyl-1H-pyrazol-4-yl)-1H-pyrazolo[3,4-c]pyridine | 0.000029 |
| 447 | 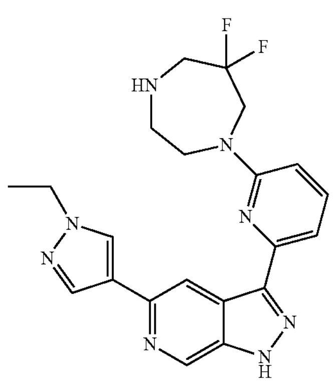 [SMILES: CCn1cc(-c2cc3c(-c4cccc(N5CCNCC(F)(F)C5)n4)n[nH]c3cn2)cn1] | 3-(6-(6,6-difluoro-1,4-diazepan-1-yl)pyridin-2-yl)-5-(1-ethyl-1H-pyrazol-4-yl)-1H-pyrazolo[3,4-c]pyridine | 0.000029 |

TABLE 1-continued

| No. | Name | Pim-1 Ki (μm) |
|---|---|---|
| 448 | 5-(1-tert-butyl-1H-pyrazol-4-yl)-3-(6-(piperazin-1-yl)pyridin-2-yl)-1H-pyrazolo[3,4-c]pyridine | 0.000376 |
| 449 | 4-(3-bromo-6-(5-(1-methyl-1H-pyrazol-4-yl)-1H-pyrazolo[3,4-c]pyridin-3-yl)pyridin-2-yl)morpholine | 0.000191 |
| 450 | 4-(6-(5-(1-ethyl-1H-pyrazol-4-yl)-1H-pyrazolo[3,4-c]pyridin-3-yl)pyridin-2-yl)morpholine | 0.000581 |
| 451 | (R)-1-(6-(5-(1-methyl-1H-pyrazol-4-yl)-1H-pyrazolo[3,4-c]pyridin-3-yl)pyridin-2-yl)piperidin-3-ol | 0.000106 |

TABLE 1-continued

| No. | Structure | Name | Pim-1 Ki (μm) |
|---|---|---|---|
| 452 | 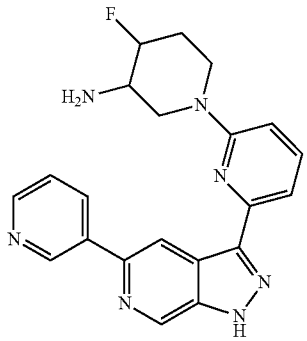 [SMILES: NC1CN(c2cccc(-c3n[nH]c4cnc(-c5cccnc5)cc34)n2)CCC1F] | cis-4-fluoro-1-(6-(5-(pyridin-3-yl)-1H-pyrazolo[3,4-c]pyridin-3-yl)pyridin-2-yl)piperidin-3-amine | 0.000046 |
| 453 | 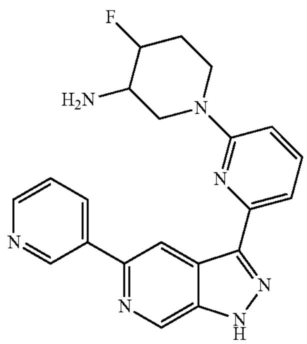 [SMILES: NC1CN(c2cccc(-c3n[nH]c4cnc(-c5cccnc5)cc34)n2)CCC1F] | trans-4-fluoro-1-(6-(5-(pyridin-3-yl)-1H-pyrazolo[3,4-c]pyridin-3-yl)pyridin-2-yl)piperidin-3-amine | 0.000296 |
| 454 | 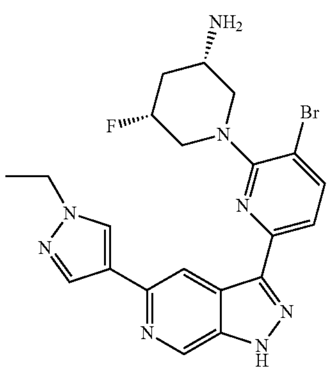 [SMILES: CCn1cc(-c2cc3c(-c4ccc(Br)c(N5C[C@@H](N)C[C@@H](F)C5)n4)n[nH]c3cn2)cn1] | (3S,5R)-1-(3-bromo-6-(5-(1-ethyl-1H-pyrazol-4-yl)-1H-pyrazolo[3,4-c]pyridin-3-yl)pyridin-2-yl)-5-fluoropiperidin-3-amine | 0.000026 |
| 455 | 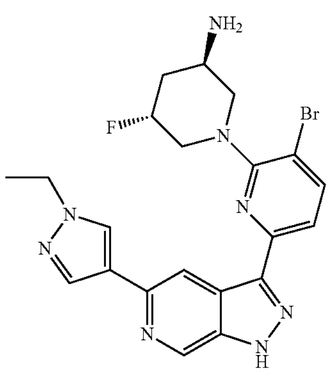 [SMILES: CCn1cc(-c2cc3c(-c4ccc(Br)c(N5C[C@H](N)C[C@@H](F)C5)n4)n[nH]c3cn2)cn1] | (3R,5R)-1-(3-bromo-6-(5-(1-ethyl-1H-pyrazol-4-yl)-1H-pyrazolo[3,4-c]pyridin-3-yl)pyridin-2-yl)-5-fluoropiperidin-3-amine | 0.000028 |

TABLE 1-continued

| No. | Structure | Name | Pim-1 Ki (μm) |
|---|---|---|---|
| 456 | 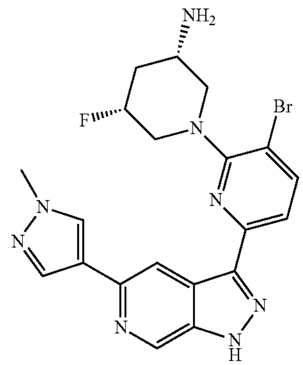 [SMILES: Cn1cc(-c2cc3c(-c4ccc(Br)c(N5C[C@@H](N)C[C@@H](F)C5)n4)n[nH]c3cn2)cn1] | (3S,5R)-1-(3-bromo-6-(5-(1-methyl-1H-pyrazol-4-yl)-1H-pyrazolo[3,4-c]pyridin-3-yl)pyridin-2-yl)-5-fluoropiperidin-3-amine | 0.000030 |
| 457 | 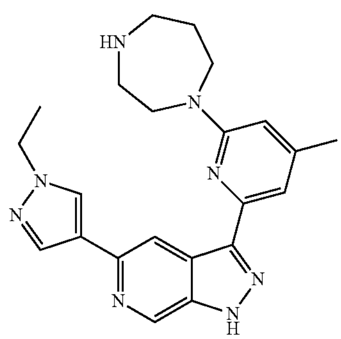 [SMILES: CCn1cc(-c2cc3c(-c4cc(C)cc(N5CCCNCC5)n4)n[nH]c3cn2)cn1] | 3-(6-(1,4-diazepan-1-yl)-4-methylpyridin-2-yl)-5-(1-ethyl-1H-pyrazol-4-yl)-1H-pyrazolo[3,4-c]pyridine | 0.000049 |
| 458 | 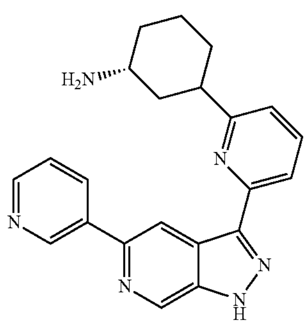 [SMILES: N[C@@H]1CCCC(c2cccc(-c3n[nH]c4cnc(-c5cccnc5)cc34)n2)C1] | (1R)-3-(6-(5-(pyridin-3-yl)-1H-pyrazolo[3,4-c]pyridin-3-yl)pyridin-2-yl)cyclohexanamine | 0.000030 |
| 459 | 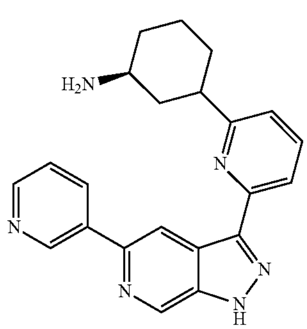 [SMILES: N[C@H]1CCCC(c2cccc(-c3n[nH]c4cnc(-c5cccnc5)cc34)n2)C1] | (1S)-3-(6-(5-(pyridin-3-yl)-1H-pyrazolo[3,4-c]pyridin-3-yl)pyridin-2-yl)cyclohexanamine | 0.000045 |

TABLE 1-continued

| No. | Structure | Name | Pim-1 Ki (μm) |
|---|---|---|---|
| 460 | 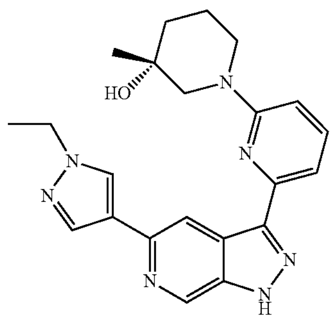 [SMILES: CCn1cc(-c2cc3c(-c4cccc(N5CCC[C@@](C)(O)C5)n4)n[nH]c3cn2)cn1] | (R)-1-(6-(5-(1-ethyl-1H-pyrazol-4-yl)-1H-pyrazolo[3,4-c]pyridin-3-yl)pyridin-2-yl)-3-methylpiperidin-3-ol | 0.000265 |
| 461 | 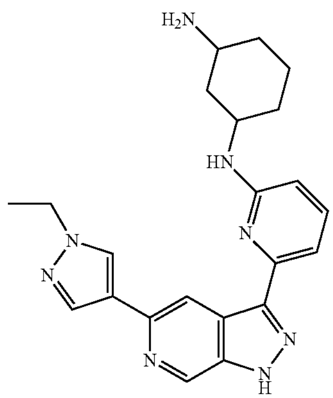 [SMILES: CCn1cc(-c2cc3c(-c4cccc(NC5CCCC(N)C5)n4)n[nH]c3cn2)cn1] | N1-(6-(5-(1-ethyl-1H-pyrazol-4-yl)-1H-pyrazolo[3,4-c]pyridin-3-yl)pyridin-2-yl)cyclohexane-1,3-diamine | 0.0000593 |
| 462 | 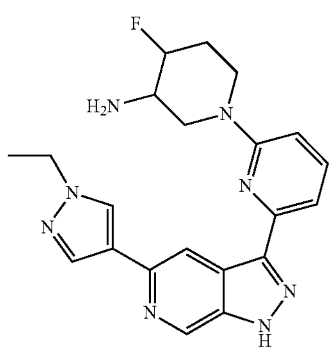 [SMILES: CCn1cc(-c2cc3c(-c4cccc(N5CCC(F)C(N)C5)n4)n[nH]c3cn2)cn1] | trans-1-(6-(5-(1-ethyl-1H-pyrazol-4-yl)-1H-pyrazolo[3,4-c]pyridin-3-yl)pyridin-2-yl)-4-fluoropiperidin-3-amine | 0.00055 |
| 463 | 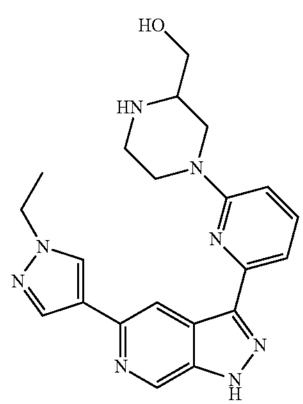 [SMILES: CCn1cc(-c2cc3c(-c4cccc(N5CCNC(CO)C5)n4)n[nH]c3cn2)cn1] | (4-(6-(5-(1-ethyl-1H-pyrazol-4-yl)-1H-pyrazolo[3,4-c]pyridin-3-yl)pyridin-2-yl)piperazin-2-yl)methanol | 0.000084 |

TABLE 1-continued

| No. | Structure | Name | Pim-1 Ki (μm) |
|---|---|---|---|
| 464 | 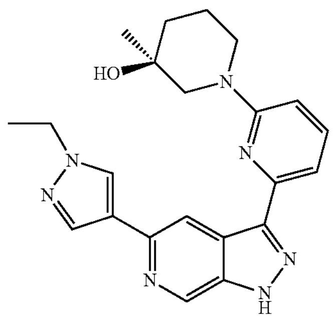 [SMILES: CCn1cc(-c2cc3c(-c4cccc(N5CCC[C@](C)(O)C5)n4)n[nH]c3cn2)cn1] | (S)-1-(6-(5-(1-ethyl-1H-pyrazol-4-yl)-1H-pyrazolo[3,4-c]pyridin-3-yl)pyridine-2-yl)-3-methylpiperidin-3-ol | 0.0000721 |
| 465 | 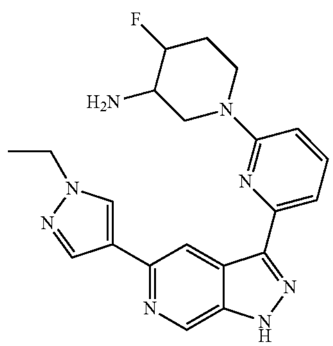 [SMILES: CCn1cc(-c2cc3c(-c4cccc(N5CCC(F)C(N)C5)n4)n[nH]c3cn2)cn1] | cis-1-(6-(5-(1-ethyl-1H-pyrazol-4-yl)-1H-pyrazolo[3,4-c]pyridin-3-yl)pyridin-2-yl)-4-fluoropiperidin-3-amine | 0.000063 |
| 466 | 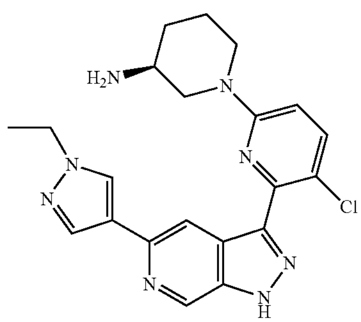 [SMILES: CCn1cc(-c2cc3c(-c4nc(N5CCC[C@H](N)C5)ccc4Cl)n[nH]c3cn2)cn1] | (S)-1-(5-chloro-6-(5-(1-ethyl-1H-pyrazol-4-yl)-1H-pyrazolo[3,4-c]pyridin-3-yl)pyridin-2-yl)piperidin-3-amine | 0.000389 |
| 467 | 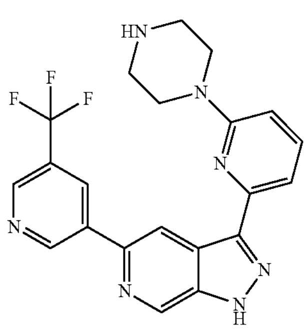 [SMILES: FC(F)(F)c1cncc(-c2cc3c(-c4cccc(N5CCNCC5)n4)n[nH]c3cn2)c1] | 3-(6-(piperazin-1-yl)pyridin-2-yl)-5-(5-(trifluoromethyl)pyridin-3-yl)-1H-pyrazolo[3,4-c]pyridine | 0.000093 |

TABLE 1-continued

| No. | Structure | Name | Pim-1 Ki (μm) |
|---|---|---|---|
| 468 | 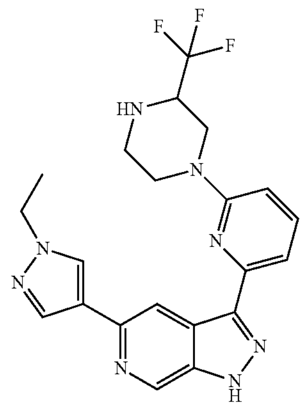 [SMILES: CCn1cc(-c2cc3c(-c4cccc(N5CCNC(C(F)(F)F)C5)n4)n[nH]c3cn2)cn1] | 5-(1-ethyl-1H-pyrazol-4-yl)-3-(6-(3-(trifluoromethyl)piperazin-1-yl)pyridin-2-yl)-1H-pyrazolo[3,4-c]pyridine | 0.000060 |
| 469 | 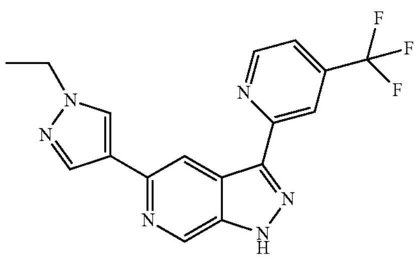 [SMILES: CCn1cc(-c2cc3c(-c4cc(C(F)(F)F)ccn4)n[nH]c3cn2)cn1] | 5-(1-ethyl-1H-pyrazol-4-yl)-3-(4-(trifluoromethyl)pyridin-2-yl)-1H-pyrazolo[3,4-c]pyridine | 0.0656 |
| 470 | 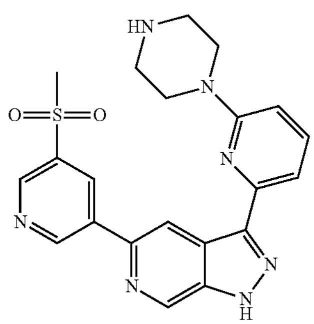 [SMILES: CS(=O)(=O)c1cncc(-c2cc3c(-c4cccc(N5CCNCC5)n4)n[nH]c3cn2)c1] | 5-(5-(methylsulfonyl)pyridin-3-yl)-3-(6-(piperazin-1-yl)pyridin-2-yl)-1H-pyrazolo[3,4-c]pyridine | 0.000049 |
| 471 | 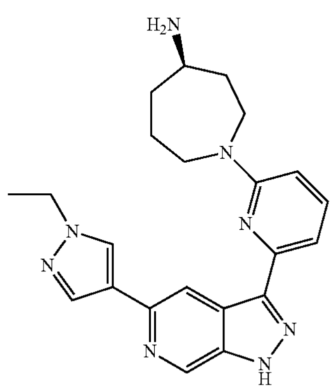 [SMILES: CCn1cc(-c2cc3c(-c4cccc(N5CCC[C@@H](N)CC5)n4)n[nH]c3cn2)cn1] | (R)-1-(6-(5-(1-ethyl-1H-pyrazol-4-yl)-1H-pyrazolo[3,4-c]pyridin-3-yl)pyridin-2-yl)azepan-4-amine | 0.000073 |

TABLE 1-continued

| No. | Structure | Name | Pim-1 Ki (μm) |
|---|---|---|---|
| 472 | 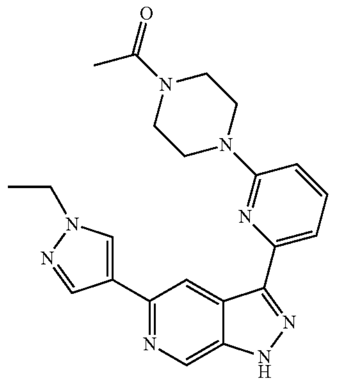 [SMILES: CCn1cc(-c2cc3c(-c4cccc(N5CCN(C(C)=O)CC5)n4)n[nH]c3cn2)cn1] | 1-(4-(6-(5-(1-ethyl-1H-pyrazol-4-yl)-1H-pyrazolo[3,4-c]pyridin-3-yl)pyridin-2-yl)piperazin-1-yl)ethanone | 0.000107 |
| 473 | 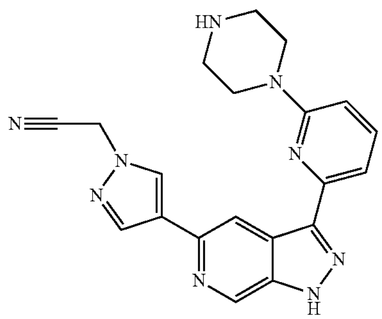 [SMILES: N#CCn1cc(-c2cc3c(-c4cccc(N5CCNCC5)n4)n[nH]c3cn2)cn1] | 2-(4-(3-(6-(piperazin-1-yl)pyridin-2-yl)-1H-pyrazolo[3,4-c]pyridin-5-yl)-1H-pyrazol-1-yl)acetonitrile | 0.000022 |
| 474 | 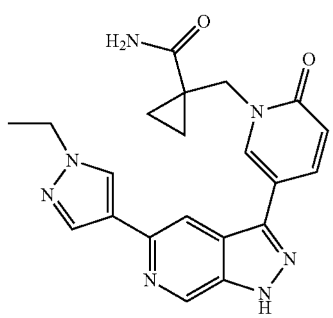 [SMILES: CCn1cc(-c2cc3c(-c4ccc(=O)n(CC5(C(N)=O)CC5)c4)n[nH]c3cn2)cn1] | 1-((5-(5-(1-ethyl-1H-pyrazol-4-yl)-1H-pyrazolo[3,4-c]pyridin-3-yl)-2-oxopyridin-1(2H)-yl)methyl) cyclopropanecarboxamide | 0.00141 |
| 475 | 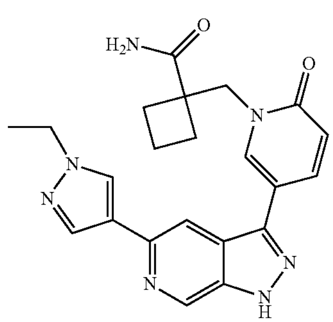 [SMILES: CCn1cc(-c2cc3c(-c4ccc(=O)n(CC5(C(N)=O)CCC5)c4)n[nH]c3cn2)cn1] | 1-((5-(5-(1-ethyl-1H-pyrazol-4-yl)-1H-pyrazolo[3,4-c]pyridin-3-yl)-2-oxopyridin-1(2H)-yl)methyl) cyclobutanecarboxamide | 0.00449 |
| 476 | 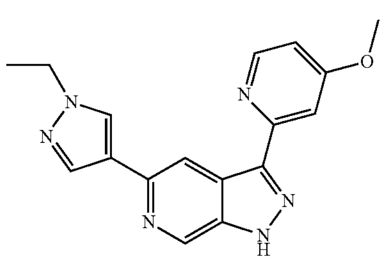 [SMILES: CCn1cc(-c2cc3c(-c4cc(OC)ccn4)n[nH]c3cn2)cn1] | 5-(1-ethyl-1H-pyrazol-4-yl)-3-(4-methoxypyridin-2-yl)-1H-pyrazolo[3,4-c]pyridine | 0.0157 |

TABLE 1-continued

| No. | Structure | Name | Pim-1 Ki (μm) |
|---|---|---|---|
| 477 | 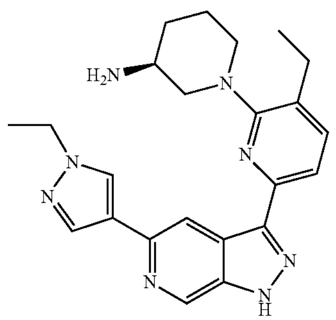 [SMILES: CCc1ccc(-c2n[nH]c3cnc(-c4cnn(CC)c4)cc23)nc1N1CCC[C@H](N)C1] | (S)-1-(3-ethyl-6-(5-(1-ethyl-1H-pyrazol-4-yl)-1H-pyrazolo[3,4-c]pyridin-3-yl)pyridin-2-yl)piperidin-3-amine | 0.000013 |
| 478 | 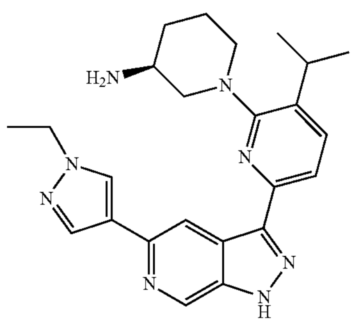 [SMILES: CCn1cc(-c2cc3c(-c4ccc(C(C)C)c(N5CCC[C@H](N)C5)n4)n[nH]c3cn2)cn1] | (S)-1-(6-(5-(1-ethyl-1H-pyrazol-4-yl)-1H-pyrazolo[3,4-c]pyridin-3-yl)-3-isopropylpyridin-2-yl)piperidin-3-amine | 0.000020 |
| 479 | 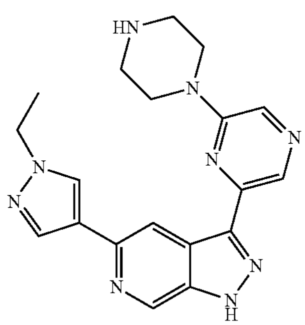 [SMILES: CCn1cc(-c2cc3c(-c4cncc(N5CCNCC5)n4)n[nH]c3cn2)cn1] | 5-(1-ethyl-1H-pyrazol-4-yl)-3-(6-(piperazin-1-yl)pyrazin-2-yl)-1H-pyrazolo[3,4-c]pyridine | 0.000064 |
| 480 | 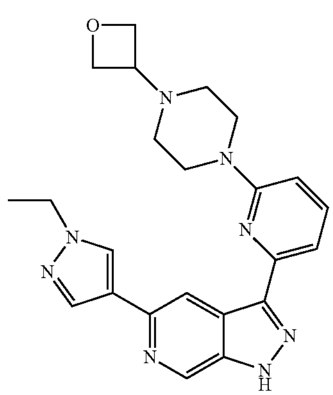 [SMILES: CCn1cc(-c2cc3c(-c4cccc(N5CCN(C6COC6)CC5)n4)n[nH]c3cn2)cn1] | 5-(1-ethyl-1H-pyrazol-4-yl)-3-(6-(4-(oxetan-3-yl)piperazin-1-yl)pyridin-2-yl)-1H-pyrazolo[3,4-c]pyridine | 0.000311 |

TABLE 1-continued

| No. | Structure | Name | Pim-1 Ki (μm) |
|---|---|---|---|
| 481 | 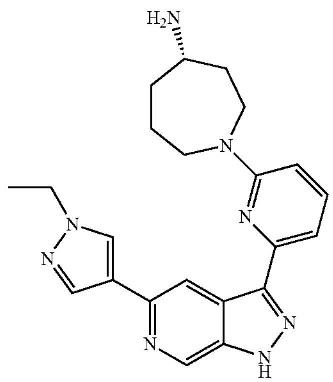 [SMILES: CCn1cc(-c2cc3c(-c4cccc(N5CCC[C@H](N)CC5)n4)n[nH]c3cn2)cn1] | (S)-1-(6-(5-(1-ethyl-1H-pyrazol-4-yl)-1H-pyrazolo[3,4-c]pyridin-3-yl)pyridin-2-yl)azepan-4-amine | 0.000034 |
| 482 | 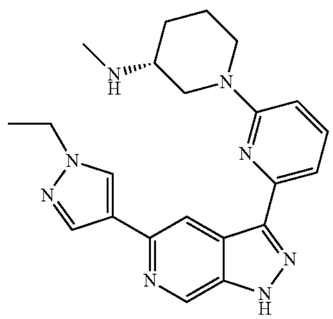 [SMILES: CCn1cc(-c2cc3c(-c4cccc(N5CCC[C@@H](NC)C5)n4)n[nH]c3cn2)cn1] | (R)-1-(6-(5-(1-ethyl-1H-pyrazol-4-yl)-1H-pyrazolo[3,4-c]pyridin-3-yl)pyridin-2-yl)-N-methylpiperidin-3-amine | 0.000147 |
| 483 | 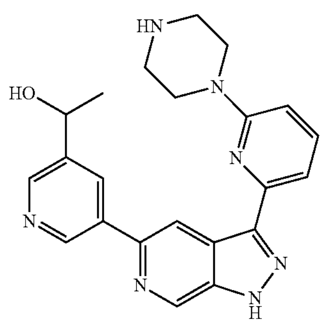 [SMILES: CC(O)c1cncc(-c2cc3c(-c4cccc(N5CCNCC5)n4)n[nH]c3cn2)c1] | 1-(5-(3-(6-(piperazin-1-yl)pyridin-2-yl)-1H-pyrazolo[3,4-c]pyridin-5-yl)pyridin-3-yl)ethanol | 0.000027 |
| 484 | 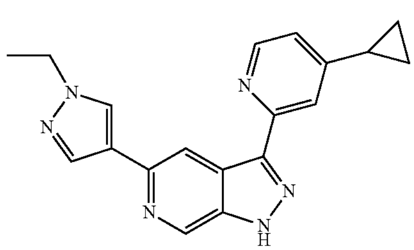 [SMILES: CCn1cc(-c2cc3c(-c4cc(C5CC5)ccn4)n[nH]c3cn2)cn1] | 3-(4-cyclopropylpyridin-2-yl)-5-(1-ethyl-1H-pyrazol-4-yl)-1H-pyrazolo[3,4-c]pyridine | 0.0115 |
| 485 | 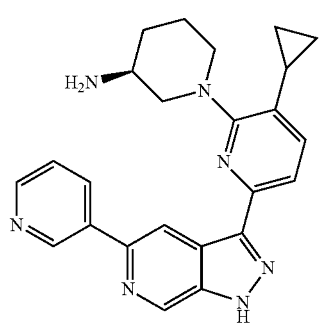 [SMILES: N[C@H]1CCCN(c2nc(-c3n[nH]c4cnc(-c5cccnc5)cc34)ccc2C2CC2)C1] | (S)-1-(3-cyclopropyl-6-(5-(pyridin-3-yl)-1H-pyrazolo[3,4-c]pyridin-3-yl)pyridin-2-yl)piperidin-3-amine | 0.000022 |

TABLE 1-continued

| No. | Structure | Name | Pim-1 Ki (μm) |
|---|---|---|---|
| 486 | 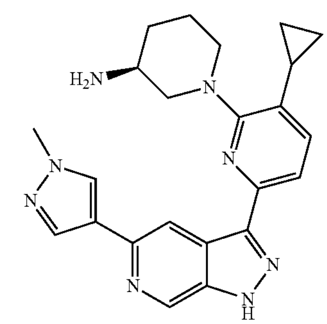 [SMILES: Cn1cc(-c2cc3c(-c4ccc(C5CC5)c(N5CCC[C@H](N)C5)n4)n[nH]c3cn2)cn1] | (S)-1-(3-cyclopropyl-6-(5-(1-methyl-1H-pyrazol-4-yl)-1H-pyrazolo[3,4-c]pyridin-3-yl)pyridin-2-yl)piperidin-3-amine | 0.0000090 |
| 487 | 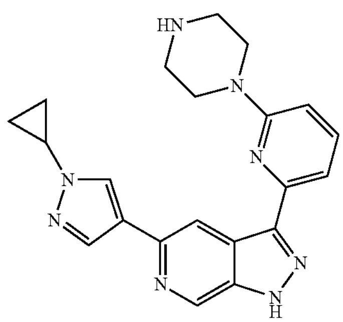 [SMILES: c1cc(-c2n[nH]c3cnc(-c4cnn(C5CC5)c4)cc23)nc(N2CCNCC2)c1] | 5-(1-cyclopropyl-1H-pyrazol-4-yl)-3-(6-(piperazin-1-yl)pyridin-2-yl)-1H-pyrazolo[3,4-c]pyridine | 0.000106 |
| 488 | 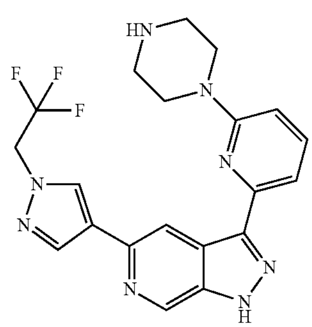 [SMILES: FC(F)(F)Cn1cc(-c2cc3c(-c4cccc(N5CCNCC5)n4)n[nH]c3cn2)cn1] | 3-(6-(piperazin-1-yl)pyridin-2-yl)-5-(1-(2,2,2-trifluoroethyl)-1H-pyrazol-4-yl)-1H-pyrazolo[3,4-c]pyridine | 0.000022 |
| 489 | 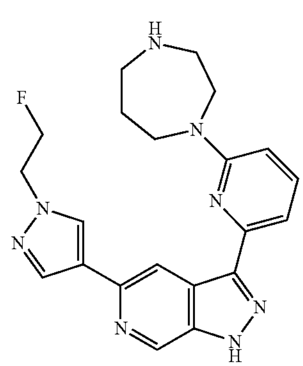 [SMILES: FCCn1cc(-c2cc3c(-c4cccc(N5CCCNCC5)n4)n[nH]c3cn2)cn1] | 3-(6-(1,4-diazepan-1-yl)pyridin-2-yl)-5-(1-(2-fluoroethyl)-1H-pyrazol-4-yl)-1H-pyrazolo[3,4-c]pyridine | 0.000014 |

TABLE 1-continued

| No. | Structure | Name | Pim-1 Ki (μm) |
|---|---|---|---|
| 490 | 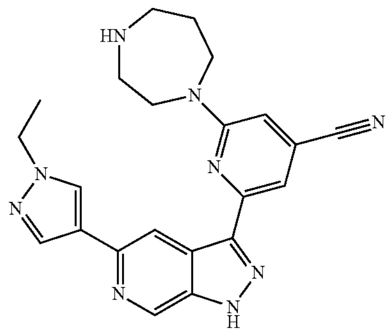 [SMILES: CCn1cc(-c2cc3c(-c4cc(C#N)cc(N5CCCNCC5)n4)n[nH]c3cn2)cn1] | 2-(1,4-diazepan-1-yl)-6-(5-(1-ethyl-1H-pyrazol-4-yl)-1H-pyrazolo[3,4-c]pyridin-3-yl)isonicotinonitrile | 0.000107 |
| 491 | 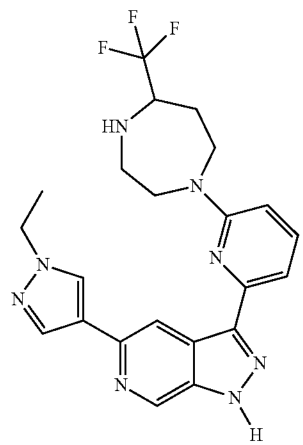 [SMILES: CCn1cc(-c2cc3c(-c4cccc(N5CCNC(C(F)(F)F)CC5)n4)n[nH]c3cn2)cn1] | 5-(1-ethyl-1H-pyrazol-4-yl)-3-(6-(5-(trifluoromethyl)-1,4-diazepan-1-yl)pyridin-2-yl)-1H-pyrazolo[3,4-c]pyridine | 0.000181 |
| 492 | 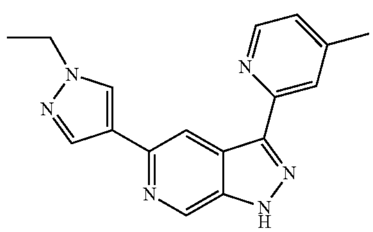 [SMILES: CCn1cc(-c2cc3c(-c4cc(C)ccn4)n[nH]c3cn2)cn1] | 5-(1-ethyl-1H-pyrazol-4-yl)-3-(4-methylpyridin-2-yl)-1H-pyrazolo[3,4-c]pyridine | 0.0232 |
| 493 | 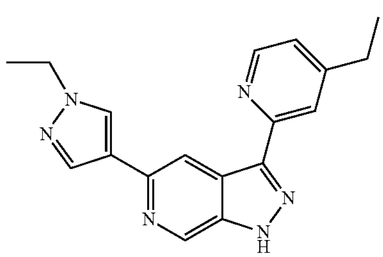 [SMILES: CCc1ccnc(-c2n[nH]c3cnc(-c4cnn(CC)c4)cc23)c1] | 5-(1-ethyl-1H-pyrazol-4-yl)-3-(4-ethylpyridin-2-yl)-1H-pyrazolo[3,4-c]pyridine | 0.0436 |

TABLE 1-continued

| No. | Structure | Name | Pim-1 Ki (μm) |
|---|---|---|---|
| 494 | 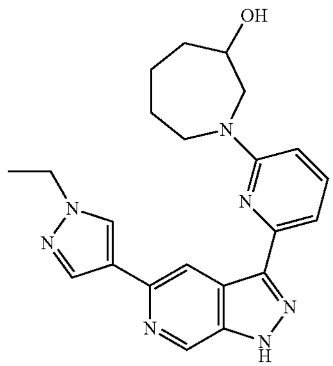 [SMILES: CCn1cc(-c2cc3c(-c4cccc(N5CCCCC(O)C5)n4)n[nH]c3cn2)cn1] | 1-(6-(5-(1-ethyl-1H-pyrazol-4-yl)-1H-pyrazolo[3,4-c]pyridin-3-yl)pyridin-2-yl)azepan-3-ol | 0.000122 |
| 495 | 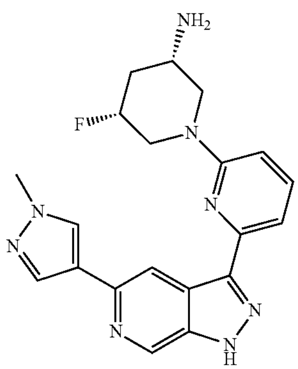 [SMILES: Cn1cc(-c2cc3c(-c4cccc(N5C[C@@H](N)C[C@@H](F)C5)n4)n[nH]c3cn2)cn1] | (3S,5R)-5-fluoro-1-(6-(5-(1-methyl-1H-pyrazol-4-yl)-1H-pyrazolo[3,4-c]pyridin-3-yl)pyridin-2-yl)piperidin-3-amine | 0.000122 |
| 496 | 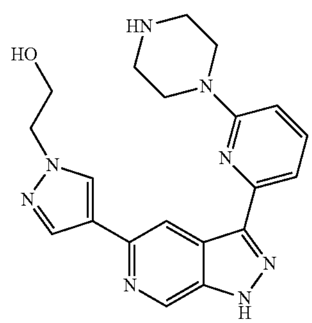 [SMILES: OCCn1cc(-c2cc3c(-c4cccc(N5CCNCC5)n4)n[nH]c3cn2)cn1] | 2-(4-(3-(6-(piperazin-1-yl)pyridin-2-yl)-1H-pyrazolo[3,4-c]pyridin-5-yl)-1H-pyrazol-1-yl)ethanol | 0.00013 |
| 497 | 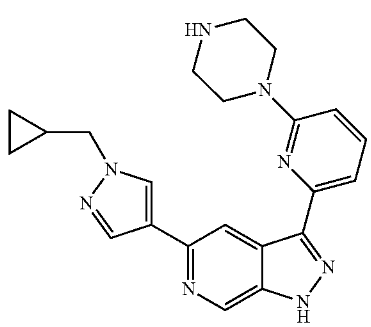 [SMILES: c1cc(-c2n[nH]c3cnc(-c4cnn(CC5CC5)c4)cc23)nc(N2CCNCC2)c1] | 5-(1-(cyclopropylmethyl)-1H-pyrazol-4-yl)-3-(6-(piperazin-1-yl)pyridin-2-yl)-1H-pyrazolo[3,4-c]pyridine | 0.000021 |

TABLE 1-continued

| No. | Structure | Name | Pim-1 Ki (μm) |
|---|---|---|---|
| 498 | 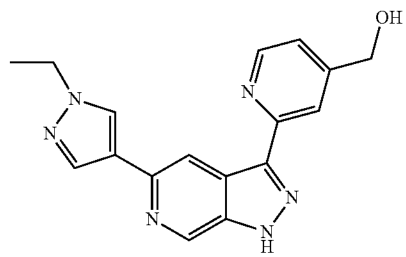 [SMILES: CCn1cc(-c2cc3c(-c4cc(CO)ccn4)n[nH]c3cn2)cn1] | (2-(5-(1-ethyl-1H-pyrazol-4-yl)-1H-pyrazolo[3,4-c]pyridin-3-yl)pyridin-4-yl)methanol | 0.0172 |
| 499 | 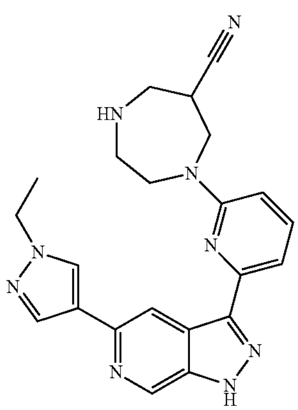 [SMILES: CCn1cc(-c2cc3c(-c4cccc(N5CCNCC(C#N)C5)n4)n[nH]c3cn2)cn1] | 1-(6-(5-(1-ethyl-1H-pyrazol-4-yl)-1H-pyrazolo[3,4-c]pyridin-3-yl)pyridin-2-yl)-1,4-diazepane-6-carbonitrile | 0.000072 |
| 500 | 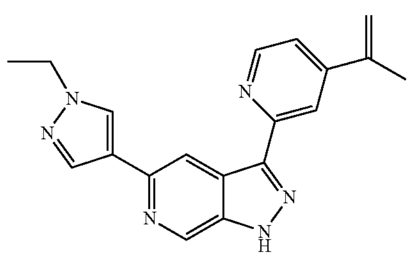 [SMILES: C=C(C)c1ccnc(-c2n[nH]c3cnc(-c4cnn(CC)c4)cc23)c1] | 5-(1-ethyl-1H-pyrazol-4-yl)-3-(4-(prop-1-en-2-yl)pyridin-2-yl)-1H-pyrazolo[3,4-c]pyridine | 0.0541 |
| 501 | 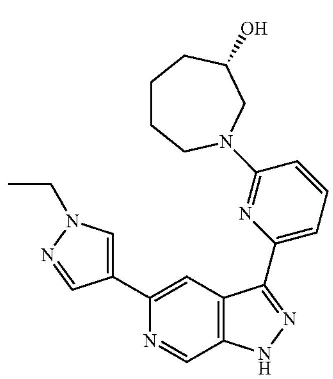 [SMILES: CCn1cc(-c2cc3c(-c4cccc(N5CCCC[C@H](O)C5)n4)n[nH]c3cn2)cn1] | (S)-1-(6-(5-(1-ethyl-1H-pyrazol-4-yl)-1H-pyrazolo[3,4-c]pyridin-3-yl)pyridin-2-yl)azepan-3-ol | 0.000103 |

TABLE 1-continued

| No. | Structure | Name | Pim-1 Ki (μm) |
|---|---|---|---|
| 502 | 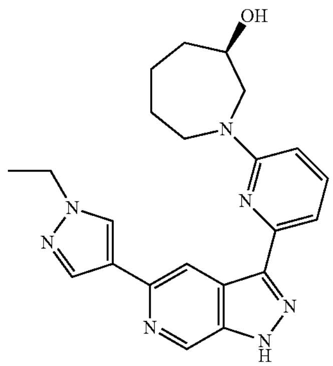 [SMILES: CCn1cc(-c2cc3c(-c4cccc(N5CCCC[C@@H](O)C5)n4)n[nH]c3cn2)cn1] | (R)-1-(6-(5-(1-ethyl-1H-pyrazol-4-yl)-1H-pyrazolo[3,4-c]pyridin-3-yl)pyridin-2-yl)azepan-3-ol | 0.000139 |
| 503 | 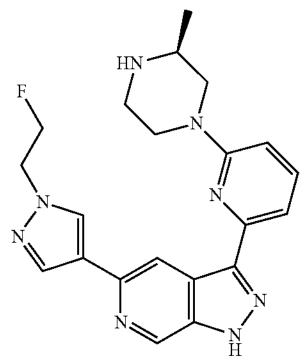 [SMILES: C[C@H]1CN(c2cccc(-c3n[nH]c4cnc(-c5cnn(CCF)c5)cc34)n2)CCN1] | (S)-5-(1-(2-fluoroethyl)-1H-pyrazol-4-yl)-3-(6-(3-methylpiperazin-1-yl)pyridin-2-yl)-1H-pyrazolo[3,4-c]pyridine | 0.0000294 |
| 504 | 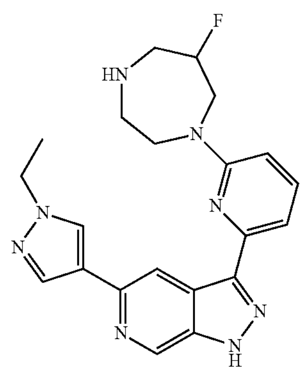 [SMILES: CCn1cc(-c2cc3c(-c4cccc(N5CCNCC(F)C5)n4)n[nH]c3cn2)cn1] | 5-(1-ethyl-1H-pyrazol-4-yl)-3-(6-(6-fluoro-1,4-diazepan-1-yl)pyridin-2-yl)-1H-pyrazolo[3,4-c]pyridine | 0.000076 |
| 505 | 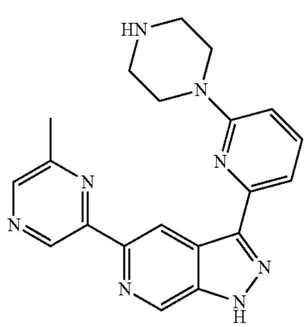 [SMILES: Cc1cncc(-c2cc3c(-c4cccc(N5CCNCC5)n4)n[nH]c3cn2)n1] | 5-(6-methylpyrazin-2-yl)-3-(6-(piperazin-1-yl)pyridin-2-yl)-1H-pyrazolo[3,4-c]pyridine | 0.0000100 |

TABLE 1-continued

| No. | Structure | Name | Pim-1 Ki (μm) |
|---|---|---|---|
| 506 | 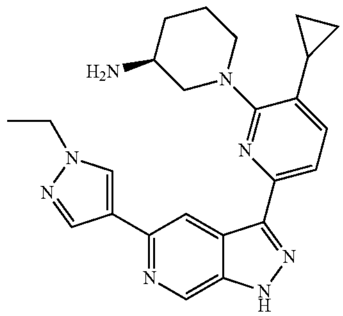 [SMILES: CCn1cc(-c2cc3c(-c4ccc(C5CC5)c(N5CCC[C@H](N)C5)n4)n[nH]c3cn2)cn1] | (S)-1-(3-cyclopropyl-6-(5-(1-ethyl-1H-pyrazol-4-yl)-1H-pyrazolo[3,4-c]pyridin-3-yl)pyridin-2-yl)piperidin-3-amine | 0.000021 |
| 507 | 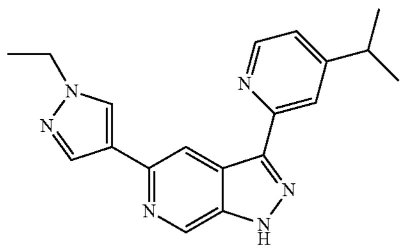 [SMILES: CCn1cc(-c2cc3c(-c4cc(C(C)C)ccn4)n[nH]c3cn2)cn1] | 5-(1-ethyl-1H-pyrazol-4-yl)-3-(4-isopropylpyridin-2-yl)-1H-pyrazolo[3,4-c]pyridine | 0.0298 |
| 508 | 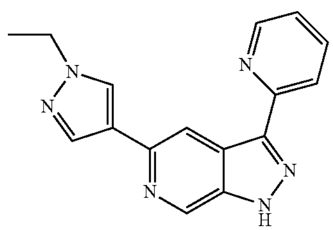 [SMILES: CCn1cc(-c2cc3c(-c4ccccn4)n[nH]c3cn2)cn1] | 5-(1-ethyl-1H-pyrazol-4-yl)-3-(pyridin-2-yl)-1H-pyrazolo[3,4-c]pyridine | 0.0106 |
| 509 | 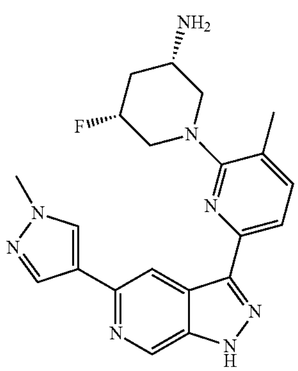 [SMILES: Cc1ccc(-c2n[nH]c3cnc(-c4cnn(C)c4)cc23)nc1N1C[C@@H](N)C[C@@H](F)C1] | (3S,5R)-5-fluoro-1-(3-methyl-6-(5-(1-methyl-1H-pyrazol-4-yl)-1H-pyrazolo[3,4-c]pyridin-3-yl)pyridin-2-yl)piperidin-3-amine | 0.000056 |
| 510 | 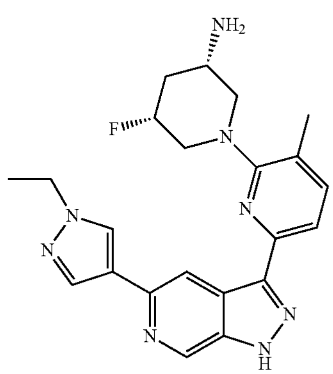 [SMILES: CCn1cc(-c2cc3c(-c4ccc(C)c(N5C[C@@H](N)C[C@@H](F)C5)n4)n[nH]c3cn2)cn1] | (3S,5R)-1-(6-(5-(1-ethyl-1H-pyrazol-4-yl)-1H-pyrazolo[3,4-c]pyridin-3-yl)-3-methylpyridin-2-yl)-5-fluoropiperidin-3-amine | 0.000030 |

TABLE 1-continued

| No. | Structure | Name | Pim-1 Ki (μm) |
|---|---|---|---|
| 511 | 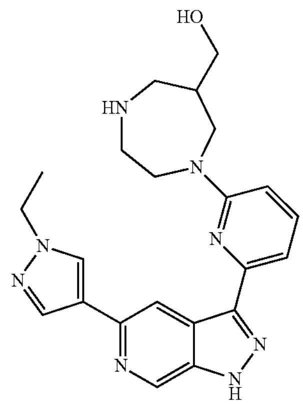 [SMILES: CCn1cc(-c2cc3c(-c4cccc(N5CCNCC(CO)C5)n4)n[nH]c3cn2)cn1] | (1-(6-(5-(1-ethyl-1H-pyrazol-4-yl)-1H-pyrazolo[3,4-c]pyridin-3-yl)pyridin-2-yl)-1,4-diazepan-6-yl)methanol | 0.000016 |
| 512 | 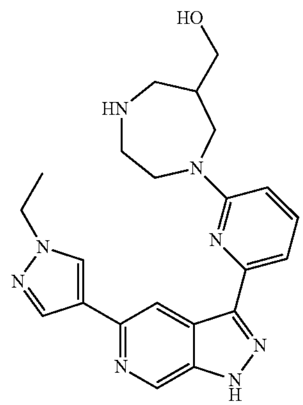 [SMILES: CCn1cc(-c2cc3c(-c4cccc(N5CCNCC(CO)C5)n4)n[nH]c3cn2)cn1] | (1-(6-(5-(1-ethyl-1H-pyrazol-4-yl)-1H-pyrazolo[3,4-c]pyridin-3-yl)pyridin-2-yl)-1,4-diazepan-6-yl)methanol | 0.000040 |
| 513 | 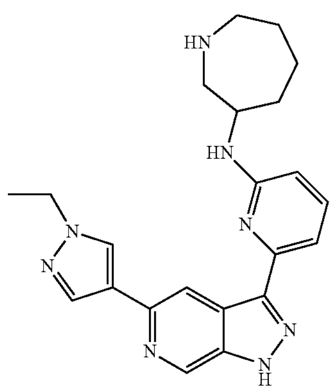 [SMILES: CCn1cc(-c2cc3c(-c4cccc(NC5CCCCNC5)n4)n[nH]c3cn2)cn1] | N-(6-(5-(1-ethyl-1H-pyrazol-4-yl)-1H-pyrazolo[3,4-c]pyridin-3-yl)pyridin-2-yl)azepan-3-amine | 0.000055 |
| 514 | 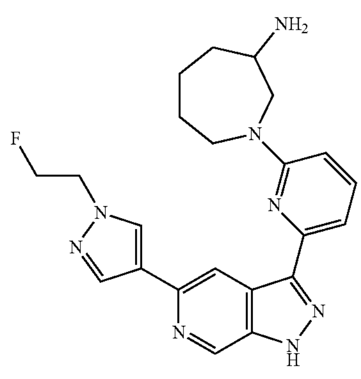 [SMILES: NC1CCCCN(c2cccc(-c3n[nH]c4cnc(-c5cnn(CCF)c5)cc34)n2)C1] | 1-(6-(5-(1-(2-fluoroethyl)-1H-pyrazol-4-yl)-1H-pyrazolo[3,4-c]pyridin-3-yl)pyridin-2-yl)azepan-3-amine | 0.000077 |

TABLE 1-continued

| No. | Structure | Name | Pim-1 Ki (μm) |
|---|---|---|---|
| 515 | 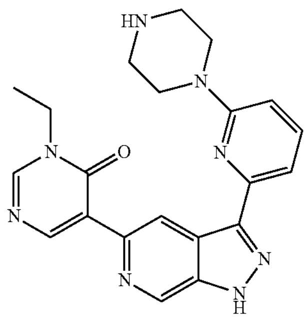 [SMILES: CCn1cncc(-c2cc3c(-c4cccc(N5CCNCC5)n4)n[nH]c3cn2)c1=O] | 3-ethyl-5-(3-(6-(piperazin-1-yl)pyridin-2-yl)-1H-pyrazolo[3,4-c]pyridin-5-yl)pyrimidin-4(3H)-one | 0.000015 |
| 516 | 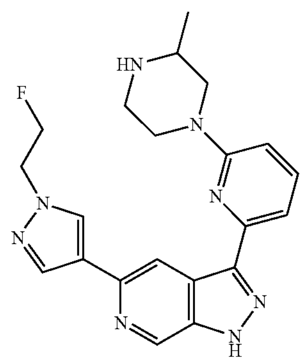 [SMILES: CC1CN(c2cccc(-c3n[nH]c4cnc(-c5cnn(CCF)c5)cc34)n2)CCN1] | 5-(1-(2-fluoroethyl)-1H-pyrazol-4-yl)-3-(6-(3-methylpiperazin-1-yl)pyridin-2-yl)-1H-pyrazolo[3,4-c]pyridine | 0.000024 |
| 517 | 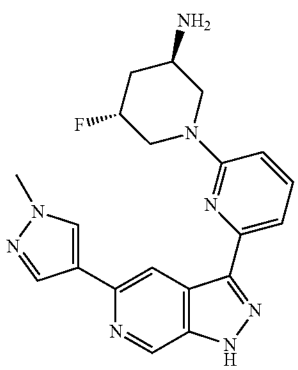 [SMILES: Cn1cc(-c2cc3c(-c4cccc(N5C[C@H](N)C[C@@H](F)C5)n4)n[nH]c3cn2)cn1] | (3R,5R)-5-fluoro-1-(6-(5-(1-methyl-1H-pyrazol-4-yl)-1H-pyrazolo[3,4-c]pyridin-3-yl)pyridin-2-yl)piperidin-3-amine | 0.00117 |
| 518 | 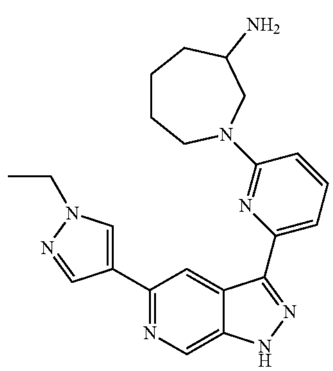 [SMILES: CCn1cc(-c2cc3c(-c4cccc(N5CCCCC(N)C5)n4)n[nH]c3cn2)cn1] | 1-(6-(5-(1-ethyl-1H-pyrazol-4-yl)-1H-pyrazolo[3,4-c]pyridin-3-yl)pyridin-2-yl)azepan-3-amine | 0.000082 |

TABLE 1-continued

| No. | Structure | Name | Pim-1 Ki (μm) |
|---|---|---|---|
| 519 | 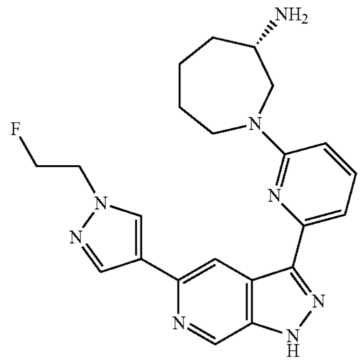 [SMILES: N[C@H]1CCCCN(c2cccc(-c3n[nH]c4cnc(-c5cnn(CCF)c5)cc34)n2)C1] | (S)-1-(6-(5-(1-(2-fluoroethyl)-1H-pyrazol-4-yl)-1H-pyrazolo[3,4-c]pyridin-3-yl)pyridin-2-yl)azepan-3-amine | 0.000025 |
| 520 | 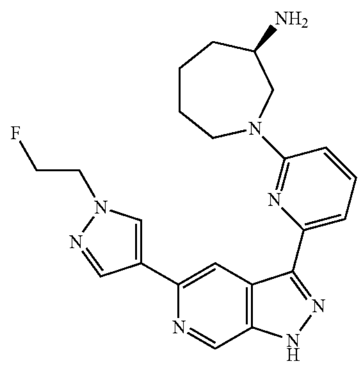 [SMILES: N[C@@H]1CCCCN(c2cccc(-c3n[nH]c4cnc(-c5cnn(CCF)c5)cc34)n2)C1] | (R)-1-(6-(5-(1-(2-fluoroethyl)-1H-pyrazol-4-yl)-1H-pyrazolo[3,4-c]pyridin-3-yl)pyridin-2-yl)azepan-3-amine | 0.000098 |
| 521 | 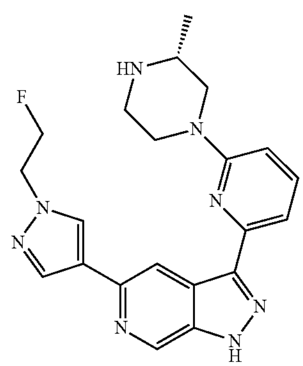 [SMILES: C[C@@H]1CN(c2cccc(-c3n[nH]c4cnc(-c5cnn(CCF)c5)cc34)n2)CCN1] | (R)-5-(1-(2-fluoroethyl)-1H-pyrazol-4-yl)-3-(6-(3-methylpiperazin-1-yl)pyridin-2-yl)-1H-pyrazolo[3,4-c]pyridine | 0.000026 |

TABLE 2

| No. | Structure | Name | Pim-1 Ki (μm) |
|---|---|---|---|
| 522 | 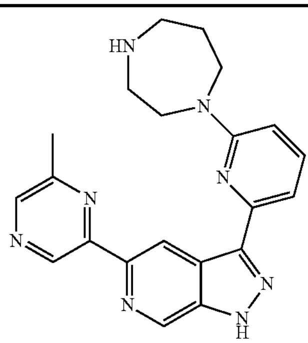 | 3-(6-(1,4-diazepan-1-yl)pyridin-2-yl)-5-(6-methylpyrazin-2-yl)-1H-pyrazolo[3,4-c]pyridine | 0.000019 |

TABLE 2-continued

| No. | Structure | Name | Pim-1 Ki (μm) |
|---|---|---|---|
| 523 | 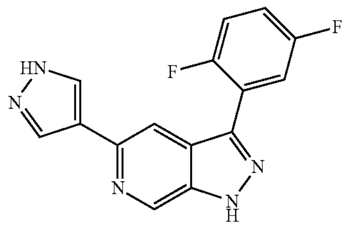 [SMILES: Fc1ccc(F)c(-c2n[nH]c3cnc(-c4cn[nH]c4)cc23)c1] | 3-(2,5-difluorophenyl)-5-(1H-pyrazol-4-yl)-1H-pyrazolo[3,4-c]pyridine | |
| 524 | 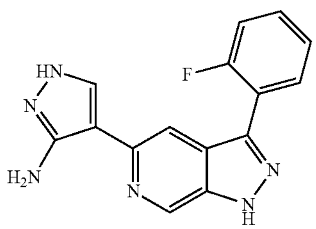 [SMILES: Nc1n[nH]cc1-c1cc2c(-c3ccccc3F)n[nH]c2cn1] | 4-(3-(2-fluorophenyl)-1H-pyrazolo[3,4-c]pyridin-5-yl)-1H-pyrazol-3-amine | |
| 525 | 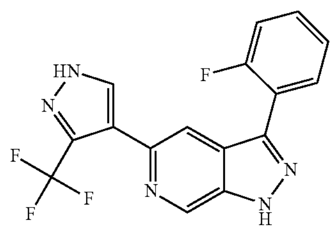 [SMILES: Fc1ccccc1-c1n[nH]c2cnc(-c3c[nH]nc3C(F)(F)F)cc12] | 3-(2-fluorophenyl)-5-(3-(trifluoromethyl)-1H-pyrazol-4-yl)-1H-pyrazolo[3,4-c]pyridine | |
| 526 | 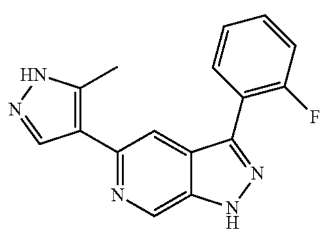 [SMILES: Cc1[nH]ncc1-c1cc2c(-c3ccccc3F)n[nH]c2cn1] | 3-(2-fluorophenyl)-5-(5-methyl-1H-pyrazol-4-yl)-1H-pyrazolo[3,4-c]pyridine | |
| 527 | 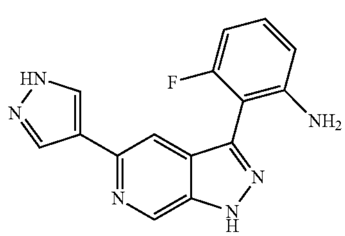 [SMILES: Nc1cccc(F)c1-c1n[nH]c2cnc(-c3cn[nH]c3)cc12] | 2-(5-(1H-pyrazol-4-yl)-1H-pyrazolo[3,4-c]pyridin-3-yl)-3-fluoroaniline | |

The compounds of the present invention were tested for their capacity to inhibit Pim kinase activity and for their biological effects on growing cells as described below in Examples 901 and 902. Formula I compounds having $Ki/IC_{50}/EC_{50}$ of less than 1 μM in assays described in Examples 901 and 902, may be useful therapeutically as Pim kinase inhibitors (Pim-1, Pim-2 and/or Pim-3).

The present invention includes a composition (e.g., a pharmaceutical composition) comprising a compound of Formula I, and/or solvates, hydrates and/or salts thereof, and a carrier (a pharmaceutically acceptable carrier). The present invention also includes a composition (e.g., a pharmaceutical composition) comprising a compound of Formula I and/or solvates, hydrates and/or salts thereof, and a carrier (a pharmaceutically acceptable carrier), further comprising a second chemotherapeutic agent such as those described herein. The present compositions are useful for inhibiting abnormal cell growth or treating a hyperproliferative disorder such as cancer in a mammal (e.g., human). For example, the present compounds and compositions are useful for treating multiple myeloma, lymphoma, acute myeloid leukemia, prostate cancer, breast cancer, hepatocellular carcinoma, pancreatic cancer, and/or colorectal cancer in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof, in combination with a second chemotherapeutic agent such as those described herein. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof, or a composition thereof, in combination with a second chemotherapeutic agent such as those described herein.

The present invention includes a method of treating lymphoma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as an anti-B-cell antibody therapeutic (e.g., Rituxan and/or Dacetuzumab), gemcitabine, corticosteroids (e.g., prednisolone and/or dexamethasone), chemotherapy cocktails (e.g., CHOP (cyclophosphamide, doxorubicin, vincristine, prednisolone) and/or ICE (isfosfamide, cytoxan, etoposide)), a combination of biologics and chemotherapy (e.g., Rituxan-ICE, Dacetuzumab-Rituxan-ICE, R-Gem, and/or D-R-Gem), an Akt inhibitor, a PI3K inhibitor (e.g, GDC-0941 (Genentech) and/or GDC-0980 (Genentech)), rapamycin, a MEK inhibitor (GDC-0973), a Bcl-2 inhibitor (ABT-263), and lymphoma directed antibody drug conjugate (e.g., antiCD22 antibody drug conjugate including but not limited to antiCD22-vcMMAE, and/or antiCD79b-antibody drug conjugate including but not limited to antiCD79b-vcMMAE).

The present invention includes a method of treating multiple myeloma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as melphalan, thalidomide, lenalidomide, pomolidamide, corticosteroids, dexamethasone, prednisolone, and bortezomib or other proteasome inhibitor.

The present invention includes a method of treating multiple myeloma, chronic lymphocytic leukemia (CLL), or acute myeloid leukemia (AML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as cytarabine (araC), anthracyclines (e.g., daunorubicin and/or idarubicin), anti-myeloid antibody therapeutics (e.g., SGN-33), anti-myeloid antibody-drug conjugates (e.g., MYLOTARG®).

The present invention includes a method of treating chronic lymphocytic leukemia (CLL) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as fludarabine, cyclophosphamide, anti-B-cell antibody therapeutics (e.g., Rituxan and/or Dacetuzumab).

The present invention includes a method of treating chronic myeloid leukemia (CML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as a BCR-abl inhibitor (e.g., imatinib, nilotinib, and/or dasatinib).

The present invention includes a method of treating myelodysplastic diseases (MDS) and myeloproliferative disorders including polycythemia vera (PV), essential thrombocytosis (ET) or myelofibrosis (MF), in a mammal (e.g., human) comprising administering to said mammal a therapeutically effective amount of a compound of Formula I, and/or solvates, hydrates and/or salts thereof, or a composition thereof, either alone or in combination.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension for parenteral injection as a sterile solution, suspension or emulsion for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of Formula I compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tabletting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of Pim kinases, e.g. Pim-1, Pim-2 and Pim-3 kinases. Accordingly, another aspect of this invention includes methods of treating or preventing diseases or conditions that can be treated or prevented by inhibiting Pim kinase. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit Pim kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or oil, or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Figures, General Procedures, and Examples, other starting materials and reagents can be easily substituted to provide a variety of derivatives and/or reaction conditions.

In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate of the racemic mixture and analyzing the $^1$H NMR spectrum for the presence of the two atropisomeric enantiomers or diastereomers (Jacob III. J. Org. Chem. (1982) 47:4165). Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

Scheme 1 shows a general synthesis of compounds 13. 4-$R^1$ Substituted 6-azaindazole 5 may be made through a 3-step synthesis starting from 2-bromo-4-methyl-5-nitropyridine 1. Installment of $R^1$ group by Suzuki reaction, followed by nitro group reduction and oxidative indazole ring formation furnishes compound 5. Subsequent iodination and SEM protection may provide a mixture of regioisomers 7a and 8a. Other suitable protection groups such as tetrahydropyran, Boc groups, etc, may be alternatives to SEM groups. The addition of $R^2$ group may be accomplished either through direct Suzuki, Buchwald or Goldberg reaction or starting from tin reagents 7b and 8b through Stille reaction. Further modification of $R^2$ group may be rendered by either direct SnAr or Buchwald reaction. Compounds 13 may be made from a mixture of 11 and 12 by using acidic, basic or fluorinated reagents in a suitable solvent.

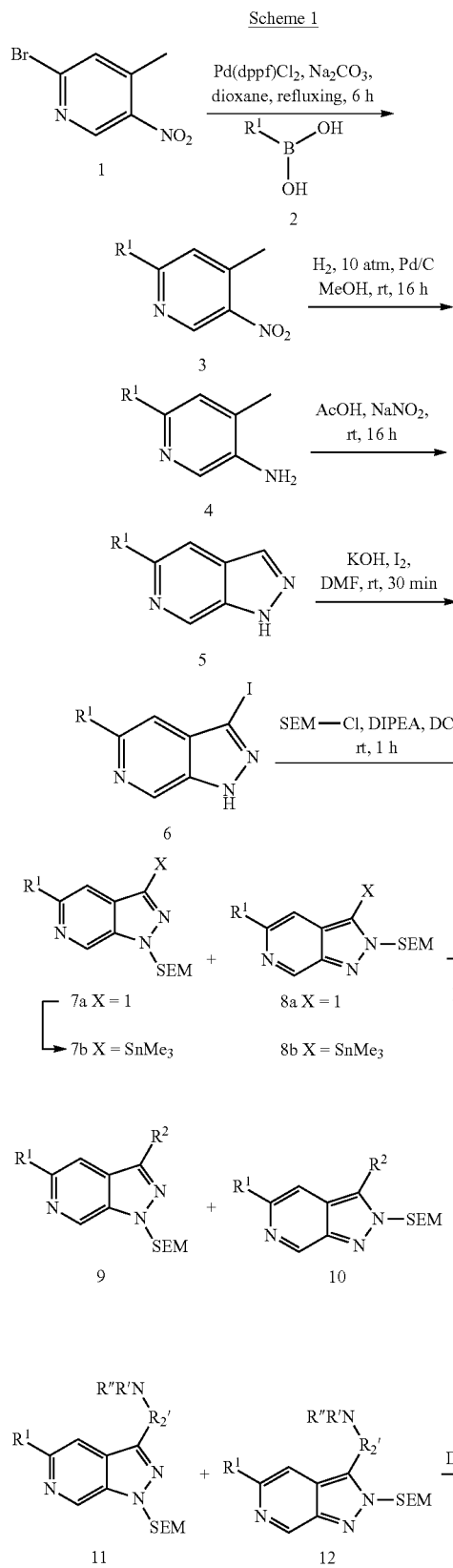

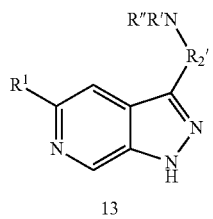

Scheme 2 describes a general synthesis of compounds 20. 5-Bromo-6-azaindazole 15 may be made from 2-bromo-4-methyl-5-aminopyridine 14 by an oxidative cyclization, described in J. Chem. Soc., Perkin Trans. 1, (1980), 2398-2404 and Bioorganic & Medicinal Chemistry (2007), 15/6: 2441-2452. Compound 17 may be made by iodination of compound 15, followed by tetrahydropyran protection. Compound 18 may be synthesized from compound 17 either by Suzuki, Stille or Buchwald reaction regioselectively. Compound 19 may be made from compound 18 through direct SnAr, Suzuki or Buchwald reaction. Compound 20 may be made from compound 19 through acid mediated removal of tetrahydropyran protecting group. Other alternative protecting groups, e.g. SEM, Boc, etc, may be used instead of tetrahydropyran.

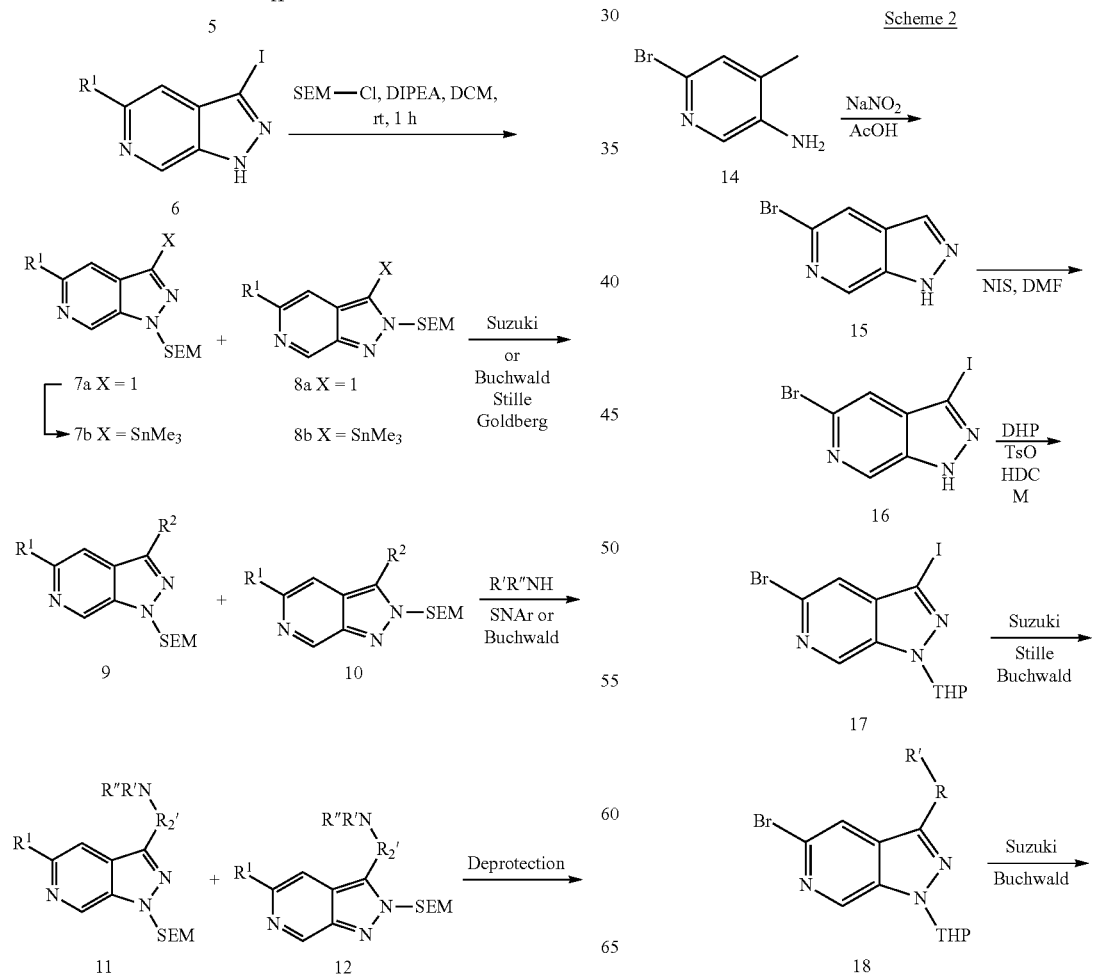

-continued

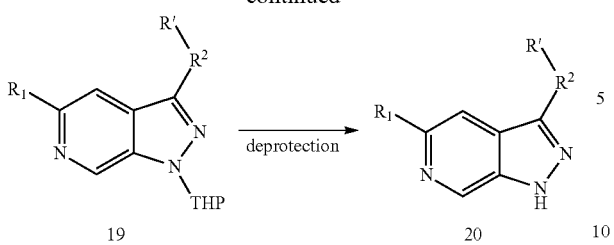

EXAMPLES

Intermediates

Example 1

4-methyl-5-nitro-2,3'-bipyridine

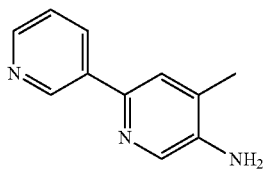

To a solution of 2-bromo-4-methyl-5-nitropyridine (217 g, 1 mol) in DMF (2000 mL) was added Pd(dppf)Cl$_2$ (5 g), saturated solution of Na$_2$CO$_3$ (200 mL) and pyridin-3-ylboronic acid (147 g, 1.2 mol). The mixture was stirred under argon for 6 h at 100. After cooling down, the solvent was removed under reduced pressure evaporation and the residue was purified by silica-gel column chromatography (mobile phase: EA:PE=1:1) to afford 4-methyl-5-nitro-2,3'-bipyridine (172 g, 80%).

Example 2

4-methyl-2,3'-bipyridin-5-amine

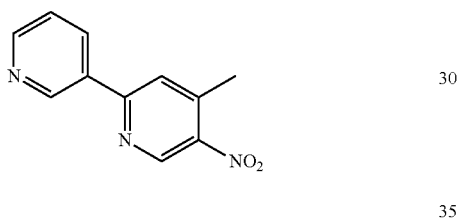

A mixture of 4-methyl-5-nitro-2,3'-bipyridine (215 g, 1 mol), Pd/C (10 g, 10%) and MeOH (1000 mL) was stirred at room temperature for 16 h under 10 atm of hydrogen. After reaction, the mixture was filtered. The filtrate was evaporated at reduced pressure to afford 4-methyl-2,3'-bipyridin-5-amine as a yellow solid (152 g, 82%)

Example 3

5-(pyridin-3-yl)-1H-pyrazolo[3,4-c]pyridine

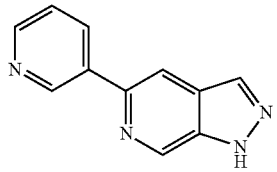 [SMILES: c1cncc(-c2cc3cn[nH]c3cn2)c1]

To a solution of 4-methyl-2,3'-bipyridin-5-amine (185 g, 1 mol) in AcOH (27 L) was added aq. NaNO$_2$ solution (82 g, 1.2 mol, 100 mL). The mixture was stirred for 16 h at room temperature. After reaction, the solvent was removed and the residue was purified by silica-gel column chromatography (mobile phase: EA:PE=1:1) to give 5-(pyridin-3-yl)-1H-pyrazolo[3,4-c]pyridine as a yellow solid (98 g, 50%)

Example 4

3-iodo-5-(pyridin-3-yl)-1H-pyrazolo[3,4-c]pyridine 5-(Pyridin-3-yl)-1H-pyrazolo[3,4-c]pyridine (196 g, 1 mol) was dissolved in 1000 mL DMF. KOH (112 g, 2 mol) was added. After stirring for 30 min, I$_2$ (303 g, 1.2 mol) was added. The mixture was stirred for 1 h at room temperature. After reaction, the reaction was quenched with saturated aq. Na$_2$S$_2$O$_5$ solution followed by the addition water (5 L). The solid was filtered and washed with water to give 3-iodo-5-(pyridin-3-yl)-1H-pyrazolo[3,4-c]pyridine as a yellow solid (290 g, 90%)

Example 5

3-iodo-5-(pyridin-3-yl)-1-((2-(trimethylsilyl)ethoxy)methyl)-1H-pyrazolo[3,4-c]pyridine and 3-iodo-5-(pyridin-3-yl)-2-((2-(trimethylsilyl)ethoxy)methyl)-2H-pyrazolo[3,4-c]pyridine

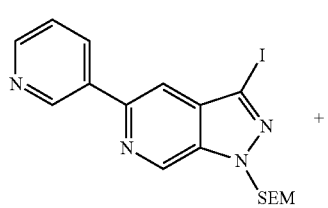

231

-continued

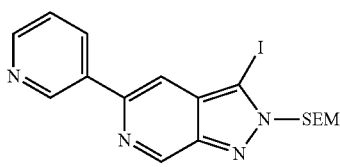

To a solution of 3-iodo-5-(pyridin-3-yl)-1H-pyrazolo[3,4-c]pyridine (100 g, 0.31 mol) in $CH_2Cl_2$ (500 mL) was added DIPEA (120 g, 0.93 mol) and SEM-Cl (77 g, 0.46 mol). The mixture was stirred at room temperature for 1 hr. After removing the solvent, the residue was purified by silica-gel column chromatography (mobile phase: EA:PE=1:1) to afford a mixture of 3-iodo-5-(pyridin-3-yl)-1-((2-(trimethylsilyl)ethoxy)methyl)-1H-pyrazolo[3,4-c]pyridine and 3-iodo-5-(pyridin-3-yl)-2-((2-(trimethylsilyl)ethoxy)methyl)-2H-pyrazolo[3,4-c]pyridine as a white solid (50 g, 35%)

Example 6

5-bromo-1H-pyrazolo[3,4-c]pyridine

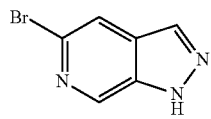

To a solution of 6-bromo-4-methylpyridin-3-amine (7.76 g, 0.0415 mol) in acetic acid (412.8 mL, 7.260 mol) was added Sodium nitrite (2.87 g, 0.0416 mol) in 4.0 ml water (Bioorg. Med. Chem. 15 (2007) 2441-2452). The reaction was stirred for 15 min and allowed to stand at room temperature (rt) for 2 days (d). The reaction was concentrated and diluted EtOAc then washed with $NaHCO_3$ and brine. The organic layer was dried $Na_2SO_4$, filtered and concentrated. The crude was purified by chromatography (DCM/MeOH) eluted at 5% MeOH to give 5-bromo-1H-pyrazolo[3,4-c]pyridine (79.1% yield)

Example 7

5-bromo-3-iodo-1H-pyrazolo[3,4-c]pyridine

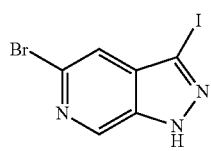

A solution containing 5-bromo-1H-pyrazolo[3,4-c]pyridine (168.0 g, 848.4 mmol) and NIS (286.3 g, 1.27 mol) in DMF (1.2 L) was stirred on at room temperature. The reaction mixture was poured into water then filtered. The solid was washed with water and 5% $Na_2S_2O_5$. The crude product was dried under high vacuum overnight to give 5-bromo-3-iodo-1H-pyrazolo[3,4-c]pyridine.

Example 8

5-bromo-3-iodo-1-(tetrahydro-2H-pyran-2-yl)-1H-pyrazolo[3,4-c]pyridine

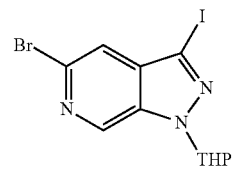

To a solution of Bromo-iodo-azaindazole (50 g, 154.36 mmol) in Methylene chloride (500 mL) was added Dihydropyran (28.57 g, 339.59 mmol) and TsOH (2.06 g, 10.81 mmol). The reaction was stirred at 20° C. overnight. LCMS showed that the reaction was complete, then the reaction was quenched with saturated $NaHCO_3$. The organic layer was dried and concentrated to give crude product which was purified by silica gel chromatography to afford 5-bromo-3-iodo-1-(tetrahydro-2H-pyran-2-yl)-1H-pyrazolo[3,4-c]pyridine (40 g, 71%) as a pale yellow solid.

Example 9

Bromo-3-(6-fluoropyridin-2-yl)-1-(tetrahydro-2H-pyran-2-yl)-1H-pyrazolo[3,4-c]pyridine

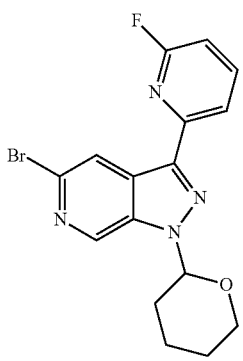 [SMILES: Fc1cccc(-c2nn(C3CCCCO3)c3cnc(Br)cc23)n1]

A mixture of 2.0 g (4.90 mmol) of 5-bromo-3-iodo-1H-pyrazolo[3,4-c]pyridine, 2.0 g (5.17 mmol) of 2-Fluoro-6-tributylstannanyl-pyridine and 566.4 mg (0.4902 mmol) of Tetrakis(triphenylphosphine)palladium(0) in 45 ml of Toluene was degassed an heated at 120° C. for 24 hours. Clear solution was concentrated in vacuum; the crystalline residue was mixed with 30 ml of ethyl ether and stirred for 20 min. The yellow precipitate was filtered out, washed with ether and dried on air to give bromo-3-(6-fluoropyridin-2-yl)-1-(tet-

Example 10

3-(6-Fluoropyridin-2-yl)-5-(pyridin-3-yl)-1-(tetrahydro-2H-pyran-2-yl)-1H-pyrazolo[3,4-c]pyridine

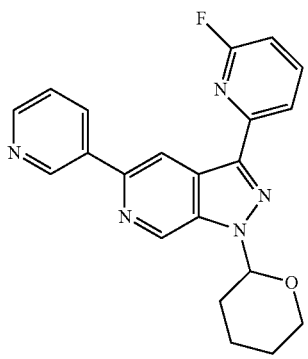 [SMILES: Fc1cccc(-c2nn(C3CCCCO3)c3cnc(-c4cccnc4)cc23)n1]

A mixture of 1.356 g (3.60 mmol) of 5-bromo-3-(6-fluoropyridin-2-yl)-1-(tetrahydro-2H-pyran-2-yl)-1H-pyrazolo[3,4-c]pyridine, 3.445 g, (16.80 mmol) of 3-pyridineboronic acid pinacol ester and 0.457 g (0.560 mmol) of 1,1'bis(diphenylphosphino)ferrocenepalladium (II) chloride and 7.2 ml of 1.0 M of Cesium Carbonate in water in 60 ml of Acetonitrile was degassed an heated in a sealed glass vial at 95° C. for 2 hours. The mixture was filtered through Celite and the filtrate concentrated in vacuum. The residue was redissolved in dichloromethane, the organic layer washed with water, brine, dried over MgSO4 and concentrated. The crude residue was purified on a 80 g silica gel column eluting with 3-4% of methanol in dichloromethane. Pooled fractions were concentrated. The residue was triturated with 7 ml of cold methanol and filtered to give 3-(6-Fluoropyridin-2-yl)-5-(pyridin-3-yl)-1-(tetrahydro-2H-pyran-2-yl)-1H-pyrazolo[3,4-c]pyridine. Yield 1.147 g (85%). ESI MS m/z=376.1 (M+1)

Example 11

5-(1H-pyrazol-4-yl)-1H-pyrazolo[3,4-c]pyridine

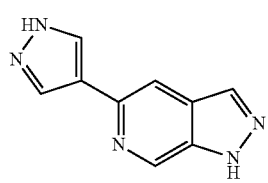 [SMILES: c1n[nH]cc1-c1cc2cn[nH]c2cn1]

To a solution of 5-bromo-1H-pyrazolo[3,4-c]pyridine (100 mg, 0.5 mmol) in DME:EtOH (5:1, 5 mL) was added Pd(dppf)Cl$_2$ (20 mg), saturated solution of Na$_2$CO$_3$ (1 mL) and 4-(4,4,5,5-tetramethyl-1,3,2-dioxaborolan-2-yl)-1H-pyrazole (116 mg, 0.6 mmol). Under argon, the mixture was stirred under microwave irradiation for 60 min at 150. After cooling down, the solvent was removed under reduced pressure and the residue was purified by silica-gel column chromatography (mobile phase: EA:PE=1:1) to afford 5-(1H-pyrazol-4-yl)-1H-pyrazolo[3,4-c]pyridine (40 mg, 43%). $^1$H NMR (500 MHz, MeOD) δ 9.17 (s, 1H), 8.98 (s, 1H), 8.17 (m, 3H), 8.05 (d, J=1.5, 1H). ESI MS m/z=186.1 (M+1).

Example 12

5-(1H-pyrazol-4-yl)-1H-pyrazolo[3,4-c]pyridine (P2-040)

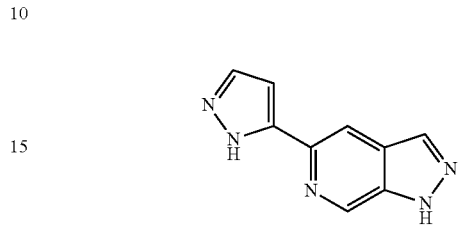

To a solution of 5-bromo-1H-pyrazolo[3,4-c]pyridine (100 mg, 0.5 mmol) in DME:EtOH (5:1, 5 mL) was added Pd(dppf)Cl$_2$ (20 mg), saturated solution of Na$_2$CO$_3$ (1 mL) and 5-(4,4,5,5-tetramethyl-1,3,2-dioxaborolan-2-yl)-1H-pyrazole (116 mg, 0.6 mmol). Under argon the mixture was stirred under microwave irradiation at 150° C. for 60 min. After cooling down, the solvent was removed under reduced pressure and the residue was purified by silica-gel column chromatography (mobile phase: EA:PE=1:1) to afford 5-(1H-pyrazol-4-yl)-1H-pyrazolo[3,4-c]pyridine (20 mg, 22%). $^1$H NMR (500 MHz, MeOD) δ 9.05 (s, 1H), 8.24 (m, 2H), 7.75 (s, 1H), 6.89 (s, 1H). ESI MS m/z=186.1 (M+1)

Table 1 Formula I Compounds

Example 101

3-methyl-5-(pyridin-3-yl)-1H-pyrazolo[3,4-c]pyridine 101

Step 1: 5-(pyridin-3-yl)-1H-pyrazolo[3,4-c]pyridine

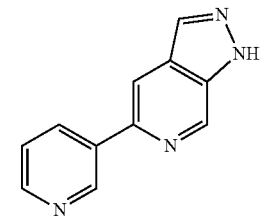 [SMILES: c1cncc(-c2cc3cn[nH]c3cn2)c1]

To a solution of 5-bromo-1H-pyrazolo[3,4-c]pyridine from Example 6 (100 mg, 0.5 mmol) in DMF (5 mL) was added Pd(dppf)Cl$_2$ (20 mg), saturated solution of Na$_2$CO$_3$ (1 mL) and pyridin-3-ylboronic acid (74 mg, 0.6 mmol). The mixture was stirred under argon for 16 h at 80° C. After cooling down, the solvent was removed under reduced pressure and the residue was purified by silica-gel column chromatography (mobile phase: EA:PE=1:1) to afford 5-(pyridin-3-yl)-1H-pyrazolo[3,4-c]pyridine (59 mg, 60%). $^1$H NMR (500 MHz, MeOD) δ 9.17 (s, 1H), 9.09 (s, 1H), 8.52 (d, J=3.5, 1H), 8.44 (q, J=7, 2, 1H), 8.29 (d, J=5, 1H), 8.23 (s, 1H), 7.53 (q, J=9.5, 5.5, 1H). ESI MS m/z=197.1 (M+1).

Step 2: 3-Bromo-1H-pyrazolo[3,4-c]pyridine

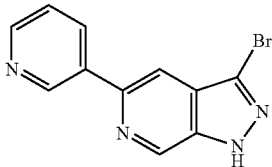 [SMILES: Brc1n[nH]c2cnc(-c3cccnc3)cc12]

1H-pyrazolo[3,4-c]pyridine (1 g), bromine (1.33 g), and water (40 mL) were stirred for 1 h. Basification with 20% sodium hydroxide solution, and adjustment to pH 7 by addition of acetic acid, yielded 3-Bromo-1H-pyrazolo[3,4-c]pyridine (1.1 g, 67%). ESI MS m/z=275 (M+1)

Step 3

To a solution of 90 mg (0.6 mmol) of 9-methoxy-9-borabicyclo[3.3.1]nonane in 5 mL of anhydrous tetrahydrofuran was added dropwise 0.37 mL (0.6 mmol) of a solution 1 N of methyl lithium in diethylether. After few minutes of stirring, a mixture of 3-bromo-1H-pyrazolo[3,4-c]pyridine (0.16 g, 0.6 mmol), and 10 mg (0.015 mmol) of bis(triphenylphosphine) palladium(II) dichloride in 10 mL of anhydrous tetrahydrofuran was added. The reaction mixture was stirred in a microwave oven at 150° C. for 15 minutes. After filtration over celite and concentration in vacuo, the residue is purified by flash chromatography (SiO$_2$, PE/ethyl acetate 1:1) to afford 47 mg of 101 (37%). $^1$H NMR (500 MHz, DMSO-d6) δ 9.34 (d, J=2, 1H), 9.09 (s, 1H), 8.57 (dd, J=4.5, 1.5, 1H), 8.48 (d, J=7.5, 1H), 8.44 (s, 1H), 7.51 (q, J=8, 5, 1H), 2.60 (s, 3H). ESI MS m/z=211.1 (M+1)

Example 102

3-methyl-5-(1H-pyrazol-4-yl)-1H-pyrazolo[3,4-c]pyridine 102

Step 1: 1-(2-bromo-5-fluoropyridin-4-yl)ethanol

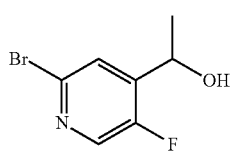

To a 1000 mL 3-neck flask was added 2-bromo-5-fluoropyridine (8.80 g, 50 mmol) and THF (200 mL) at −78° C. followed by dropwise addition of LDA (20.0 mL, 50 mmol, 2.5 M). After stirring at −78° C. for 4 h, acetaldehyde (3.1 mL, 55 mmol) was added dropwise via syringe. The contents were removed from the cold bath and stirred at room temperature overnight. The mixture was diluted with H2O (150 mL), and vigorously stirred for 5 min. The contents were extracted with ethyl ether (3×150 mL), the combined organic layers were dried over MgSO4, filtered, and concentrated in vacuo to afford a yellow oil. The crude product was passed through a short silica column (eluent: 3:1 PE/EtOAc) to afford 1-(2-bromo-5-fluoropyridin-4-yl)ethanol as a white solid (9.5 g, 86%). ESI MS m/z=220 (M+1)

Step 2: 1-(2-bromo-5-fluoropyridin-4-yl)ethanone

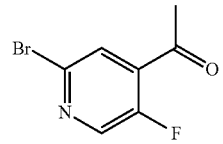

To a 350 mL sealed flask was dissolved 1-(2-bromo-5-fluoro-4-pyridinyl)ethanol (9.4 g, 42.3 mmol) in 60 mL dry CHCl3. Added next to the stirring solution was manganese (IV)oxide (14.7 g, 169 mmol). The vigorously stirred contents were sealed and heated at 95° C. for 2.5 h. After cooling to room temperature, the black heterogeneous mixture was vacuum filtered through a pad of Celite, and the filter pad washed with CH$_2$Cl$_2$ (10 mL). The yellow colored filtrate was concentrated in vacuo to a yellow oil, which was purified by silica gel column chromatography (eluent: 9:1 PE/EtOAc) to afford 1-(2-bromo-5-fluoropyridin-4-yl)ethanone as a pale yellow oil (8.2 g, 88%). ESI MS m/z=218 (M+1)

Step 3: 5-Bromo-3-methyl-1H-pyrazolo[3,4-c]pyridine

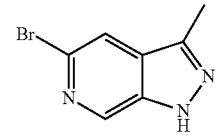

To a 150 mL sealed flask containing 50 mL dry ethylene glycol was dissolved 1-(2-bromo-5-fluoro-4-pyridinyl)ethanone (8.2 g, 37.6 mmol). Added dropwise via syringe next was anhydrous hydrazine (1.24 mL, 39.5 mmol). The stirred light yellow mixture was sealed, and heated at 165° C. After 3.5 h, the orange-tan reaction mixture was removed from heating. After cooling to room temperature, the contents were poured onto a stirring mixture of 300 g ice/water (1:1), wherein solid precipitation occurred. After stirring for 10 min, the off-white precipitate was collected. This solid was dried in vacuo and collected 5-Bromo-3-methyl-1H-pyrazolo[3,4-c]pyridine as an off-white solid (7.9 g, 99%). ESI MS m/z=212 (M+1).

Step 4

To a solution of 5-bromo-3-methyl-1H-pyrazolo[3,4-c]pyridine (106 mg, 0.5 mmol) in DMF (5 mL) was added Pd(dppf)Cl$_2$ (20 mg), saturated solution of Na$_2$CO$_3$ (1 mL) and 1H-pyrazol-4-ylboronic acid (67 mg, 0.6 mmol). Under argon, the mixture was stirred under microwave irradiation for 1 h at 150° C. After cooling down, the solvent was removed under reduced pressure and the residue was purified by silica-gel column chromatography (mobile phase: EA:PE=1:1) to afford 102 (15 mg, 15%). $^1$H NMR (500 MHz, MeOD) δ 8.88 (s, 1H), 8.16 (m, 2H), 8.00 (s, 1H), 2.61 (s, 3H); ESI MS m/z=200.1 (M+1)

Example 103

3-methyl-5-(1H-pyrazol-5-yl)-1H-pyrazolo[3,4-c]pyridine 103

To a solution of 5-Bromo-3-methyl-1H-pyrazolo[3,4-c]pyridine from Example 102 (106 mg, 0.5 mmol) in DMF (5 mL) was added Pd(dppf)Cl$_2$ (20 mg), saturated solution of Na$_2$CO$_3$ (1 mL) and 1H-pyrazol-3-ylboronic acid (67 mg, 0.6 mmol). The mixture was stirred under argon for 16 h at 80° C. After cooling down, the solvent was removed under reduced pressure and the residue was purified by silica-gel column chromatography (mobile phase: EA:PE=1:1) to afford 103 (15 mg, 15%). $^1$H NMR (500 MHz, MeOD) δ 8.96 (s, 1H), 8.23 (s, 1H), 7.71 (s, 1H), 6.90 (d, J=1.5, 1H), 2.65 (s, 3H). ESI MS m/z=200.1 (M+1)

Example 115

3-methyl-5-(pyrimidin-5-yl)-1H-pyrazolo[3,4-c]pyridine 115

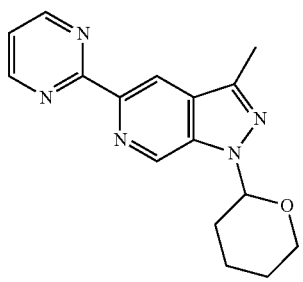 [SMILES: Cc1nn(C2CCCCO2)c2cnc(-c3ncccn3)cc12]

In a microwave reaction vials was charged with 5-bromo-3-methyl-1-(tetrahydro-2H-pyran-2-yl)-1H-pyrazolo[3,4-c]pyridine (296 mg, 1.0 mmol), Pyrimidine-5-boronic acid (185 mg, 1.5 mmol), 1,1'-Bis(diphenylphosphino)ferrocene-palladium (II) chloride (81.7 mg, 0.1 mmol), 1.00 M of Potassium acetate in Water (1.5 mL, 1.5 mmol), 1.00 M of Sodium carbonate in Water (1.5 mL, 1.5 mmol), and Acetonitrile (10 mL). The reaction mixture was heated under microwave at 130° C. for 30 minutes. The mixture was concentrated and the residue was purified on silica eluted with 0 to 5% MeOH in DCM with 1% NH4OH to afford 3-methyl-5-(pyrimidin-2-yl)-1-(tetrahydro-2H-pyran-2-yl)-1H-pyrazolo[3,4-c]pyridine (281.9 mg, 95.45%).

A solution of 3-methyl-5-(pyrimidin-2-yl)-1-(tetrahydro-2H-pyran-2-yl)-1H-pyrazolo[3,4-c]pyridine (281.2 mg, 0.9521 mmol) in 4.0 M of Hydrogen chloride in 1,4-Dioxane (5 mL) and 1,4-Dioxane (5 mL, 60 mmol) was stirred at room temperature overnight. The reaction mixture was concentrated and the residue was purified by reverse phase HPLC to afford 115 as an off-white solid (73.30 mg, 37%). 1H NMR (400 MHz, DMSO) δ 13.39 (s, 1H), 9.50 (s, 2H), 9.18 (s, 1H), 9.11 (d, J=1.1 Hz, 1H), 8.56 (d, J=1.2 Hz, 1H), 2.60 (s, 3H); ESI MS m/z=212.1 (M+1)

Example 116

3-phenyl-5-(pyridin-3-yl)-1H-pyrazolo[3,4-c]pyridine 116

To a solution of 3-iodo-5-(pyridin-3-yl)-1H-pyrazolo[3,4-c]pyridine from Example 4 (161 mg, 0.5 mmol) in DME:EtOH (5:1, 5 mL) was added Pd(dppf)Cl$_2$ (20 mg), saturated solution of Na$_2$CO$_3$ (1 mL) and phenylboronic acid (74 mg, 0.6 mmol). The mixture was heated in argon under microwave radiation at 135 for 60 min. After cooling down, the solvent was removed under reduced pressure and the residue was purified by silica-gel column chromatography (mobile phase: EA:PE=1:1) to afford 116 (82 mg, 60%). $^1$H NMR (400 MHz, DMSO) δ 9.33 (s, 1H), 9.21 (s, 1H), 8.56 (s, 1H), 8.53-8.51 (m, 2H), 8.12-8.10 (m, 2H), 7.57-7.44 (m, 4H). ESI MS m/z=273.7 (M+1

Example 117

3-(2-fluorophenyl)-5-(pyridin-3-yl)-1H-pyrazolo[3,4-c]pyridine 117

Following the procedures as described in Example 116, 3-iodo-5-(pyridin-3-yl)-1H-pyrazolo[3,4-c]pyridine from Example 4 and 2-fluorophenylboronic acid were converted to 117 as a yellow solid (86 mg, 56%) over two steps. $^1$H NMR (400 MHz, DMSO) δ 9.32 (s, 1H), 9.25 (s, 1H), 8.59-8.58 (m, 1H), 8.48-8.47 (m, 1H), 8.35 (s, 1H), 7.94-7.91 (m, 1H), 7.59-7.54 (m, 4H). ESI MS m/z=291.7 (M+1)

Example 118

3-methyl-5-(pyrazin-2-yl)-1H-pyrazolo[3,4-c]pyridine 118

Following the procedures as described in Example 115 and starting with 2-(4,4,5,5-tetramethyl-1,3,2-dioxaborolan-2-yl)pyrazine, 118 was obtained as an off-white solid (3.10 mg, 13%) over two steps. 1H NMR (400 MHz, DMSO) δ 13.42 (s, 1H), 9.56 (d, J=1.3 Hz, 1H), 9.11 (s, 1H), 8.73-8.70 (m, 2H), 8.64 (d, J=2.5 Hz, 1H), 2.61 (s, 3H); ESI MS m/z=212.1 (M+1)

Example 122

5-(3-fluorophenyl)-3-methyl-1H-pyrazolo[3,4-c]pyridine 122

Under nitrogen protection, to 6 mL of dioxane was added 5-bromo-3-methyl-1H-pyrazolo[3,4-c]pyridine from Example 102 (0.21 g, 1 mmol), 3-fluorophenylboronic acid (0.28 g, 2 mmol), PdCl$_2$(dppf) (87 mg, 0.1 mmol) and 2 M Na$_2$CO$_3$ (2 mmol, 1 mL). The suspension was heated under microwave radiation at 130° C. for 1 hour. It was cooled to room temperature and the solvent was removed the solvent. The crude product was purified by SGC (EtOAc/Petroleum: 1/1) to afford 79 mg (34%) of 122 as a white solid. $^1$H NMR (400 MHz, CDCl$_3$): δ 9.12 (s, 1H), 7.98 (s, 1H), 7.75-7.82 (m, 2H), 7.44-7.47 (m, 1H), 7.08-7.09 (m, 1H), 2.67 (s, 3H). ESI MS m/z=229 (M+1)

Example 123

5-(5-fluoropyridin-3-yl)-3-methyl-1H-pyrazolo[3,4-c]pyridine 123

To a mixture of 5-bromo-3-methyl-1-(tetrahydro-2H-pyran-2-yl)-1H-pyrazolo[3,4-c]pyridine (90.0 mg, 0.304 mmol), 5-fluoropyridin-3-ylboronic acid (128.6 mg, 0.9124 mmol) and 1,1'-Bis(diphenylphosphino)ferrocenepalladium (II) chloride (37.2 mg, 0.0456 mmol) in Acetonitrile (2.86 mL, 54.7 mmol) was added 1.0 M of Potassium acetate in Water (0.456 mL) and 1.0 M of Sodium carbonate in Water (0.456 mL). The reaction mixture was irradiated in microwave at 125° C. for 20 min. The reaction was filtered thru celite and concentrated. The crude product was purified by silica gel column using ethyl acetate/heptane to give 5-(5-fluoropyridin-3-yl)-3-methyl-1-(tetrahydro-2H-pyran-2-yl)-1H-pyrazolo[3,4-c]pyridine which was dissolved in 12M HCl (1.30 mL, 15.6 mmol) and Methanol (13.0 mL). The reaction mixture was stirred at RT (room temperature) for 18 h. The reaction was concentrated and then submitted for rHPLC to give 123 (27.9 mg, 40.2% yield). ESI MS m/z=229.1 (M+1). $^1$H NMR (400 MHz, DMSO) δ 9.25 (s, 1H), 9.08 (s, 1H), 8.62-8.49 (m, 2H), 8.47-8.30 (m, 1H), 2.60 (s, 3H)

Example 126

5-(pyridin-3-yl)-3-(3-(trifluoromethyl)phenyl)-1H-pyrazolo[3,4-c]pyridine 126

Following the Suzuki coupling procedure of Example 159, 5-bromo-3-iodo-1-(tetrahydro-2H-pyran-2-yl)-1H-pyrazolo[3,4-c]pyridine and 3-(trifluoromethyl)phenylboronic acid were reacted and the product was consequently reacted under Suzuki coupling procedure of Example 10 with 3-pyridineboronic acid pinacol ester and deprotected by the procedure of Example 131. The mixture was obtained as a base and purified by crystallization from ethyl acetate to afford 56 mg (33%) of 126 over three steps. ESI MS m/z 341.1 (M+1)

Example 127

3-methyl-5-(1-methyl-1H-pyrazol-4-yl)-1H-pyrazolo[3,4-c]pyridine 127

In a microwave vial was charged with tert-butyl 5-bromo-3-methyl-1H-pyrazolo[3,4-c]pyridine-1-carboxylate (53 mg, 0.17 mmol), 1-methyl-4-(4,4,5,5-tetramethyl-1,3,2-dioxaborolan-2-yl)-1H-pyrazole (70.6 mg, 0.34 mmol), potassium acetate (205.5 mg, 2.09 mmol), cesium carbonate (166.0 mg, 0.51 mmol), and bis(diphenylphosphino)ferrocene] dichloropalladium (II), complexed with dichloromethane (1:1) (13.9 mg, 0.017 mmol). DMF (2.6 mL) and water (0.5 mL) were added. Nitrogen was passed through the mixture for 15 minutes and the vial was capped. The reaction mixture was subjected to microwave irradiation at 125° C. for 20 min. The reaction mixture was filtered through a pad of Celite® and diluted with water and EtOAc. The organic layer was washed with brine, dried over Na$_2$SO$_4$, filtered, and evaporated in vacuo. The crude product was purified using flash chromatography (Si-PPC gradient elution, solvent: 50-100% ethyl acetate in heptanes, followed by 0-30% methanol in ethyl acetate) to give 127 as a foam (26.0 mg, 71.8%). $^1$H NMR (400 MHz, DMSO) δ 13.08 (broad s, 1H), 8.90 (s, 1H), 8.19 (s, 1H), 7.98 (s, 1H), 7.94 (s, 1H), 3.88 (s, 3H), 2.53 (s, 3H). LC/MS: m/z 214.1 [M+1]

Example 129

3-(2-fluorophenyl)-5-(1-methyl-1H-pyrazol-4-yl)-1H-pyrazolo[3,4-c]pyridine 129

Step 1: 3-(2-Fluorophenyl)-5-(1-methyl-1H-pyrazol-4-yl)-1-(tetrahydro-2H-pyran-2-yl)-1H-pyrazolo[3,4-c]pyridine

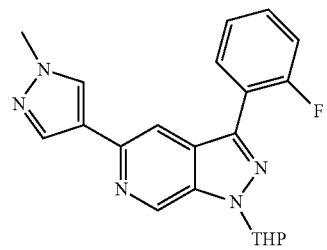

Following the procedures in Example 133, using 2-fluorobenzylboronic acid in place of phenylboronic acid, 3-(2-Fluorophenyl)-5-(1-methyl-1H-pyrazol-4-yl)-1-(tetrahydro-2H-pyran-2-yl)-1H-pyrazolo[3,4-c]pyridine was obtained as a foam (50.7% over two steps). $^1$H NMR (400 MHz, CDCl$_3$) δ 9.15 (s, 1H), 7.97 (d, J=5.6 Hz, 2H), 7.90-7.81 (m, 2H), 7.45 (ddd, J=7.3, 6.3, 1.7 Hz, 1H), 7.30 (dd, J=9.2, 5.9 Hz, 1H), 7.25 (d, J=6.6 Hz, 1H), 5.90 (dd, J=8.8, 2.5 Hz, 1H), 4.06 (dd, J=11.8, 4.1 Hz, 1H), 3.97 (s, 3H), 3.87-3.76 (m, 1H), 2.63-2.51 (m, 1H), 2.19 (d, J=9.5 Hz, 2H), 1.89-1.68 (m, 3H). LC/MS: m/z 378.3 [M+1]

Step 2

Following the procedure as described in Example 133, 3-(2-fluorophenyl)-5-(1-methyl-1H-pyrazol-4-yl)-1-(tetrahydro-2H-pyran-2-yl)-1H-pyrazolo[3,4-c]pyridine in place of 5-(1-methyl-1H-pyrazol-4-yl)-3-phenyl-1-(tetrahydro-2H-pyran-2-yl)-1H-pyrazolo[3,4-c]pyridine was converted to 129 as a white solid (69.1%). $^1$H NMR (400 MHz, DMSO) δ 13.95 (broad s, 1H), 9.06 (s, 1H), 8.26 (s, 1H), 7.99 (s, 1H), 7.91 (d, J=1.8 Hz, 1H), 7.89-7.82 (m, 1H), 7.54 (dd, J=13.2, 6.2 Hz, 1H), 7.47-7.35 (m, 2H), 3.87 (s, 3H). LC/MS: m/z 294.0 [M+1]

Example 131

3-(6-fluoropyridin-2-yl)-5-(pyridin-3-yl)-1H-pyrazolo[3,4-c]pyridine 131

To a mixture of 120 mg (0.32 mmol) of 3-(6-fluoropyridin-2-yl)-5-(pyridin-3-yl)-1-(tetrahydro-2H-pyran-2-yl)-1H-pyrazolo[3,4-c]pyridine from Example 10 in 3 ml of methanol, 12 ml of 4N HCl in dioxane was added. The mixture was stirred for 8 hours and concentrated in vacuum. The residue was triturated with ethyl ether. The solid material was filtered out, washed with ethyl ether and dried. The above solid was dispersed in 30 ml of saturated aqueous sodium bicarbonate and the suspension was stirred for 1 hour. The solid base was collected, washed with water and dried in high vacuum for 24 hours to yield 95 mg of 131 (90%). ESI MS m/z 292.1 (M+1). 1H NMR (400 MHz, DMSO): 9.32-9.21 (m, 1H), 8.81 (s, 1H), 8.61 (dd, J=4.7, 1.4 Hz, 1H), 8.42 (d, J=8.0 Hz, 1H), 8.21-8.06 (m, 1H), 7.55 (dd, J=7.9, 4.7 Hz, 1H), 7.18 (d, J=7.7 Hz, 1H), 6.53 (s, 1H), 6.28 (s, 1H)

Example 132

6-(5-(pyridin-3-yl)-1H-pyrazolo[3,4-c]pyridin-3-yl)pyridin-2(1H)-one 132

A mixture of 58.2 mg (0.200 mmol) of 3-(6-fluoropyridin-2-yl)-5-(pyridin-3-yl)-1H-pyrazolo[3,4-c]pyridine was heated in 15 ml of 1 N aq HCl for 4 hours. The product crystallized upon cooling. The precipitate was collected, washed with water and dried in high vacuum to give 132. Yield 48 mg (83%). ESI MS m/z 290.0 (M+1). 1H NMR (400 MHz, DMSO): 14.18 (s, 1H), 9.54 (s, 1H), 9.26 (s, 1H) 9.15 (s, 1H), 8.94 (d, J=6.5 Hz, 1H), 8.77 (d, J=5.0 Hz, 1H), 7.86 (s, 1H), 7.74 (t, J=7.7 Hz, 1H), 7.52 (s, 1H), 6.62 (d, J=8.2 Hz, 1H)

Example 133

5-(1-methyl-1H-pyrazol-4-yl)-3-phenyl-1H-pyrazolo[3,4-c]pyridine 133

Step 1: 5-bromo-3-phenyl-1-(tetrahydro-2H-pyran-2-yl)-1H-pyrazolo[3,4-c]pyridine

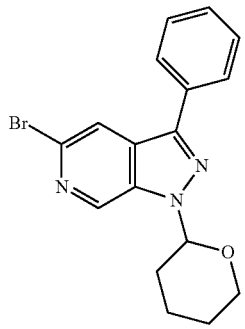 [SMILES: Brc1cc2c(-c3ccccc3)nn(C3CCCCO3)c2cn1]

In an oven-dried flask was placed 5-bromo-3-iodo-1-(tetrahydro-2H-pyran-2-yl)-1H-pyrazolo[3,4-c]pyridine (2.0 g, 4.90 mmol), phenylboronic acid (627.5 mg, 5.15 mmol), and bis(diphenylphosphino)ferrocene]dichloropalladium (II), complexed with dichloromethane (1:1) (200.14 mg, 0.24 mmol). Degassed acetonitrile (53 mL) was added, followed by 1.0 M aqueous sodium carbonate solution (7.4 mL) and 1.0 M aqueous potassium acetate solution (7.4 mL). The reaction mixture was degassed under N₂ for 5 minutes more and stirred at 80° C. under N₂ for 1 h. The reaction mixture was cooled to room temperature, partitioned between EtOAc and water and the layers were separated. The organic layer was washed with water (3×) and brine, dried over Na₂SO₄ and concentrated to an oil. The crude product was purified using flash column chromatography (Si-PPC gradient elution, solvent: 0-60% ethyl acetate in heptanes) to give 5-bromo-3-phenyl-1-(tetrahydro-2H-pyran-2-yl)-1H-pyrazolo[3,4-c]pyridine as a solid (1.45 g, 82.47%). ¹H NMR (400 MHz, CDCl₃) δ 8.95 (d, J=0.9 Hz, 1H), 8.08 (d, J=0.9 Hz, 1H), 7.94-7.88 (m, 2H), 7.55-7.48 (m, 2H), 7.48-7.41 (m, 1H), 5.86 (dd, J=8.6, 2.6 Hz, 1H), 4.07-3.97 (m, 1H), 3.80 (ddd, J=12.3, 8.9, 3.8 Hz, 1H), 2.54 (qd, J=9.0, 5.5 Hz, 1H), 2.24-2.11 (m, 2H), 1.89-1.67 (m, 3H). LC/MS: m/z 274.1 (des-THP) [M+1]

Step 2: 5-(1-Methyl-1H-pyrazol-4-yl)-3-phenyl-1-(tetrahydro-2H-pyran-2-yl)-1H-pyrazolo[3,4-c]pyridine

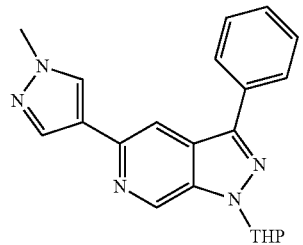

In a microwave vial was charged with 5-bromo-3-phenyl-1-(tetrahydro-2H-pyran-2-yl)-1H-pyrazolo[3,4-c]pyridine (500 mg, 1.39 mmol), 1-methyl-4-(4,4,5,5-tetramethyl-1,3,2-dioxaborolan-2-yl)-1H-pyrazole (435.6 mg, 2.09 mmol), potassium acetate (205.5 mg, 2.09 mmol), sodium carbonate (221.9 mg, 2.09 mmol), and bis(diphenylphosphino)ferrocene]dichloropalladium (II), complexed with dichloromethane (1:1) (108.3 mg, 0.13 mmol). Degassed acetonitrile (10.5 mL) and water (2.6 mL) were added. Nitrogen was passed through the mixture for 15 minutes and the vial was capped. The reaction mixture was subjected to microwave irradiation at 125° C. for 25 min. The reaction mixture was filtered through a pad of Celite® and diluted with water and EtOAc. The organic layer was washed with brine, dried over Na₂SO₄, filtered, and concentrated under reduced pressure. The crude product was purified using flash chromatography (Si-PPC gradient elution, solvent: 60-100% ethyl acetate in heptanes, followed by 0-30% methanol in ethyl acetate) to give 5-(1-methyl-1H-pyrazol-4-yl)-3-phenyl-1-(tetrahydro-2H-pyran-2-yl)-1H-pyrazolo[3,4-c]pyridine as a foam (340.0 mg, 67.8%). ¹H NMR (400 MHz, CDCl₃) δ 9.15 (s, 1H), 8.07-7.94 (m, 5H), 7.54 (t, J=7.6 Hz, 2H), 7.45 (t, J=7.4 Hz, 1H), 5.88 (dd, J=8.8, 2.2 Hz, 1H), 4.06 (dd, J=11.8, 4.0 Hz, 1H), 3.98 (s, 3H), 3.86-3.76 (m, 1H), 2.66-2.52 (m, 1H), 2.19 (d, J=10.8 Hz, 2H), 1.89-1.67 (m, 3H). LC/MS: m/z 378.3 [M+1]

Step 3

To a stirred solution of 5-(1-methyl-1H-pyrazol-4-yl)-3-phenyl-1-(tetrahydro-2H-pyran-2-yl)-1H-pyrazolo[3,4-c]pyridine (54.5 mg, 0.152 mmol) in MeOH (8 mL) was added 6 M HCl in water. The reaction mixture was stirred at 60° C. under N₂ for 16 h. The reaction mixture was cooled to room temperature. Volatile solvent was removed under reduced pressure. The crude was redissolved in EtOAc. The organic layer was washed with saturated aqueous sodium bicarbonate solution, water and brine, dried over Na₂SO₄, filtered, and evaporated in vacuo. Crystallization from DCM-heptanes afforded 133 as a solid (40 mg, 95.8%). ¹H NMR (400 MHz, DMSO) δ 13.71 (broad s, 1H), 9.04 (s, 1H), 8.32 (s, 1H), 8.24 (s, 1H), 8.09 (d, J=7.3 Hz, 3H), 7.55 (t, J=7.5 Hz, 2H), 7.44 (t, J=7.4 Hz, 1H), 3.90 (s, 3H). LC/MS: m/z 276.1 [M+1]

Example 136

3-(2-fluorophenyl)-5-(1H-pyrazol-4-yl)-1H-pyrazolo[3,4-c]pyridine 136

A microwave tube charged with 5-bromo-3-(2-fluorophenyl)-1-(tetrahydro-2H-pyran-2-yl)-1H-pyrazolo[3,4-c]pyridine (376 mg, 1 mmol), 1H-pyrazol-4-ylboronic acid (224 mg, 2 mmol), Pd(dppf)Cl$_2$ (50 mg, 0.0625 mmol), saturated solution of Na$_2$CO$_3$ (0.5 mL), and DME/EtOH (5 mL/0.5 mL) was irradiated under microwave at 140° C. for 1 h. After cooling down, ethyl acetate was added. The mixture was washed with water twice (2×20 mL), dried over anhydrous Na$_2$SO$_4$ and concentrated to afford the crude product. The crude product was purified by silica-gel column chromatography eluting with 50% ethyl acetate in heptane to afford 3-(2-fluorophenyl)-5-(1H-pyrazol-4-yl)-1-(tetrahydro-2H-pyran-2-yl)-1H-pyrazolo[3,4-c]pyridine as a white solid (300 mg, 82%, ESI MS m/z=364 (M+1) which was treated with HCl/dioxane (4 mL, 3 mol/L) and stirred for overnight. The crude product was received by filtration and washed with a little dioxane. It was further purified by prep-HPLC eluting with 5 to 95% CH$_3$CN in aqueous 10 mmol NH$_4$HCO$_3$ solution to afford 136 as a white solid (180 mg, 72%). $^1$H NMR (400 MHz, DMSO) δ 9.02 (s, 1H), 8.16 (s, 2H), 8.02 (m, 1H), 7.87 (m, 1H), 7.54 (m, 1H), 7.38 (m, 2H). ESI MS m/z=280 (M+1)

Example 137

3-phenyl-5-(1H-pyrazol-4-yl)-1H-pyrazolo[3,4-c]pyridine 137

Following the procedures as described in Example 136, 1H-pyrazol-4-ylboronic acid and 5-bromo-3-phenyl-1-(tetrahydro-2H-pyran-2-yl)-1H-pyrazolo[3,4-c]pyridine were reacted and the product was deprotected to give 137 as a yellow solid (26 mg, 23%) over two steps. $^1$H NMR (400 MHz, DMSO) δ 12.9 (s, 1H), 9.05 (s, 1H), 8.37-8.09 (m, 5H), 7.56 (m, 1H), 7.44 (m, 1H)

Example 138

3-(2-fluorophenyl)-5-(pyrimidin-5-yl)-1H-pyrazolo[3,4-c]pyridine 138

Following the procedures as described in Example 136, pyrimidin-5-ylboronic acid and 3-(2-fluorophenyl)-5-methyl-1-(tetrahydro-2H-pyran-2-yl)-1H-pyrazolo[3,4-c]pyridine were reacted and the product was deprotected to give 138 as a white solid (25 mg, 25%) over two steps. $^1$H NMR (400 MHz, DMSO) δ 14.2 (s, 1H), 9.51 (s, 2H), 9.28 (s, 1H), 9.21 (s, 1H), 8.50 (s, 1H), 7.92 (mt, 2H), 7.59 (t, 2H), 7.41 (t, 1H). ESI MS m/z=292 (M+1)

Example 142

3-phenyl-5-(1H-1,2,4-triazol-1-yl)-1H-pyrazolo[3,4-c]pyridine 142

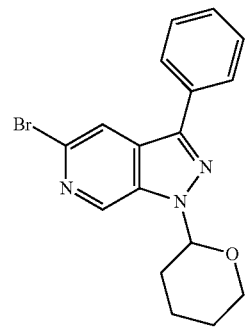 [SMILES: Brc1cc2c(-c3ccccc3)nn(C3CCCCO3)c2cn1]

Following the procedures of Examples 146 and 131, 5-bromo-3-phenyl-1-(tetrahydro-pyran-2-yl)-1H-pyrazolo[3,4-c]pyridine and 1,2,4-triazole were reacted to give 142 as a white solid (20 mg, 27%) over two steps. ESI MS m/z 263.0 (M+1). 1H NMR (400 MHz, DMSO): 14.32 (s, 1H), 9.36 (s, 1H), 9.09 (d, J=1.0 Hz, 1H), 8.38 (d, J=1.0 Hz, 1H), 8.30 (s, 1H), 8.07-8.00 (m, 2H), 7.60 (t, J=7.6 Hz, 2H), 7.48 (t, J=7.4 Hz, 1H)

Example 143

N1-(6-(5-(pyridin-3-yl)-1H-pyrazolo[3,4-c]pyridin-3-yl)pyridin-2-yl)ethane-1,2-diamine 143

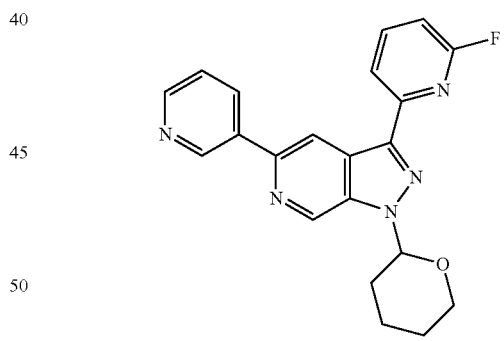

A mixture of 56.3 mg (0.150 mmol) of 3-(6-fluoropyridin-2-yl)-5-(pyridin-3-yl)-1-(tetrahydro-2H-pyran-2-yl)-1H-pyrazolo[3,4-c]pyridine and 1.0 ml (15.0 mmol) of 1,2-ethylenediamine was heated at 160° C. for 30 min. The mixture was mixed with water and extracted with ethyl acetate. The organic extracts were washed with water 3 times, brine, dried over MgSO4 and concentrated. The residue was heated in a mixture of 4 M of hydrogen chloride in 6 ml of dioxane and 2 ml of conc. hydrochloric acid at 60° C. for 18 hours. The mixture was concentrated in high vacuum and triturated with ethyl ether. The solid material was filtered out and washed with ethyl ether to give 143. Yield 37.5 mg (56%) over two steps. ESI MS m/z 332.1 (M+1). 1H NMR (400 MHz, DMSO): 14.27 (s, 1H), 9.57 (s, 1H), 9.30 (s, 1H), 9.19 (d, J=8.0 Hz, 1H), 9.11 (s, 1H), 8.90 (d, J=4.8 Hz, 1H), 8.23 (s, 3H), 8.11 (dd, J=7.9, 5.6 Hz, 1H), 7.68 (d, J=7.5 Hz, 1H), 7.53 (d, J=7.2 Hz, 1H), 6.71 (d, J=7.3 Hz, 1H), 3.75 (t, J=6.0 Hz, 2H), 3.17 (dd, J=11.4, 5.7 Hz, 2H)

Example 144

1-(6-(5-(pyridin-3-yl)-1H-pyrazolo[3,4-c]pyridin-3-yl)pyridin-2-yl)piperidin-4-amine 144

A mixture of 56.3 mg (0.150 mmol) of 3-(6-fluoropyridin-2-yl)-5-(pyridin-3-yl)-1-(tetrahydro-2H-pyran-2-yl)-1H-pyrazolo[3,4-c]pyridine and 211 mg, 0.90 mmol) of benzyl piperidin-4-ylcarbamate in 1.0 ml of dimethyl sulfoxide was heated at 100° C. for 24 hours. The mixture was mixed with water and extracted with ethyl acetate. The organic extracts were washed with water, 1% aqueous citric acid, water, brine, dried over MgSO4 and concentrated. The residue was heated in a mixture of 4 M of hydrogen chloride in 6 ml of dioxane and 2 ml of conc. hydrochloric acid at 60° C. for 18 hours. The mixture was concentrated in high vacuum and triturated with ethyl ether. The solid material was filtered out and washed with ethyl ether to give 144. Yield 13.7 mg (19%) over two steps. ESI MS m/z 372.1 (M+1). 1H NMR (400 MHz, DMSO): 14.17 (s, 1H), 9.41 (s, 1H), 9.29 (s, 1H), 8.99 (s, 1H), 8.93 (d, J=7.9 Hz, 1H), 8.87 (d, J=5.0 Hz, 1H), 8.14 (s, 3H), 8.07-7.99 (m, 1H), 7.76-7.69 (m, 1H), 7.51 (d, J=7.4 Hz, 1H), 6.99 (d, J=8.5 Hz, 1H), 4.52 (d, J=13.3 Hz, 3H), 3.40 (s, 2H), 3.12 (t, J=11.9 Hz, 2H), 2.08 (d, J=10.1 Hz, 2H), 1.66 (dt, J=12.0, 8.5 Hz, 2H)

Example 146

5-(1H-imidazol-1-yl)-3-phenyl-1H-pyrazolo[3,4-c]pyridine 146

A mixture of 100.0 mg (0.2791 mmol) of 5-bromo-3-phenyl-1-(tetrahydro-pyran-2-yl)-1H-pyrazolo[3,4-c]pyridine, 47.51 mg (0.6979 mmol) of 1H-Imidazole, 53.16 mg (0.2791 mmol) of Copper(I) iodide, 30.04 uL (0.2791 mmol) of N,N'-dimethylethylenediamine and 363.8 mg (1.116 mmol) of Cesium Carbonate in 3 ml of N,N-Dimethylformamide was heated at 120° C. for 48 hours. The mixture was filtered, the filtrate concentrated in high vacuum and the residue partitioned between ethyl acetate and water. The organic extracts were washed with water, brine, dried over MgSO4 and concentrated in vacuum. The residue was purified on 4 g of silica gel column, eluting 5-(1H-imidazol-1-yl)-3-phenyl-1-(tetrahydro-2H-pyran-2-yl)-1H-pyrazolo[3,4-c]pyridine with a gradient of ethyl acetate in heptane. Yield 67 mg (69%). ESI MS m/z 346.1 (M+1).

Deprotection of 5-(1H-imidazol-1-yl)-3-phenyl-1-(tetrahydro-2H-pyran-2-yl)-1H-pyrazolo[3,4-c]pyridine (67 mg, 0.193 mmol) yielded 60 mg of the crude hydrochloride salt product which was purified via reverse phase HPLC using a gradient of MeOH in water with 0.1% NH4OH to afford 25 mg (49%) of 146 as a white solid. ESI MS m/z 262.0 (M+1). 1H NMR (400 MHz, DMSO): 13.89 (s, 1H), 9.05 (d, J=0.9 Hz, 1H), 8.59 (s, 1H), 8.34 (d, J=1.1 Hz, 1H), 8.16-8.11 (m, 2H), 8.09 (t, J=1.3 Hz, 1H), 7.57 (t, J=7.6 Hz, 2H), 7.46 (t, J=7.4 Hz, 1H), 7.13 (s, 1H)

Example 149

(R)-1-(6-(5-(pyridin-3-yl)-1H-pyrazolo[3,4-c]pyridin-3-yl)pyridin-2-yl)piperidin-3-amine 149

Following the procedure of Example 144, 3-(6-fluoropyridin-2-yl)-5-(pyridin-3-yl)-1-(tetrahydro-2H-pyran-2-yl)-1H-pyrazolo[3,4-c]pyridine and (R)-benzyl piperidin-3-ylcarbamate were reacted to give 17 mg of 149 (15% over two steps). ESI MS m/z 372.1 (M+1). 1H NMR (400 MHz, DMSO): 14.24 (s, 1H), 9.49 (s, 1H), 9.30 (s, 1H), 9.10 (d, J=8.3 Hz, 1H), 9.06 (s, 1H), 8.36 (s, 3H), 8.21-8.12 (m, 1H), 7.78-7.72 (m, 1H), 7.56 (d, J=7.4 Hz, 1H), 6.99 (d, J=8.5 Hz, 1H), 4.49 (d, J=11.3 Hz, 2H), 3.53-3.44 (m, 3H), 3.35 (m, 1H), 3.22 (d, J=9.2 Hz, 1H), 2.10 (m, 1H), 1.95 (m, 1H)

Example 150

3-phenyl-5-(pyrimidin-5-yl)-1H-pyrazolo[3,4-c]pyridine 150

Following the procedures in Example 136, pyrimidin-5-ylboronic acid and 5-bromo-3-phenyl-1-(tetrahydro-2H-pyran-2-yl)-1H-pyrazolo[3,4-c]pyridine were reacted and the product was deprotected to give 150 as a yellow solid (25 mg, 25%) over two steps. $^1$H NMR (400 MHz, DMSO) δ 9.59 (s, 1H), 9.26 (s, 1H), 9.21 (s, 1H), 8.79 (s, 1H), 8.40 (s, 1H), 8.18 (d, 2H), 7.57 (t, 2H), 7.47 (t, 1H). ESI MS m/z=274 (M+1)

Example 156

3-(1H-pyrazol-4-yl)-5-(pyridin-3-yl)-1H-pyrazolo[3,4-c]pyridine 156

Step 1: 3-(1-Benzyl-1H-pyrazol-4-yl)-5-(pyridin-3-yl)-1-(tetrahydro-2H-pyran-2-yl)-1H-pyrazolo[3,4-c]pyridine

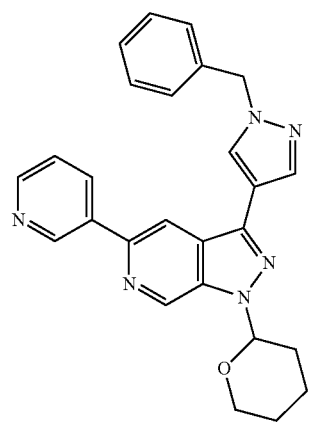 [SMILES: c1ccc(Cn2cc(-c3nn(C4CCCCO4)c4cnc(-c5cccnc5)cc34)cn2)cc1]

Following the Suzuki coupling procedure of Example 159, 5-bromo-3-iodo-1-(tetrahydro-2H-pyran-2-yl)-1H-pyrazolo[3,4-c]pyridine and 1-benzyl-4-(4,4,5,5-tetramethyl-1,3,2-dioxaborolan-2-yl)-1H-pyrazole were reacted and the product was consequently reacted by the Suzuki coupling procedure of Example 10 with 3-pyridineboronic acid pinacol ester. The product was purified via silica gel chromatography using a gradient of methanol in DCM to afford 236 mg (54%) of 3-(1-Benzyl-1H-pyrazol-4-yl)-5-(pyridin-3-yl)-1-

(tetrahydro-2H-pyran-2-yl)-1H-pyrazolo[3,4-c]pyridine over two steps. ESI MS m/z 437.1 (M+1).

Step 2: 3-(1H-Pyrazol-4-yl)-5-(pyridin-3-yl)-1-(tetrahydro-2H-pyran-2-yl)-1H-pyrazolo[3,4-c]pyridine

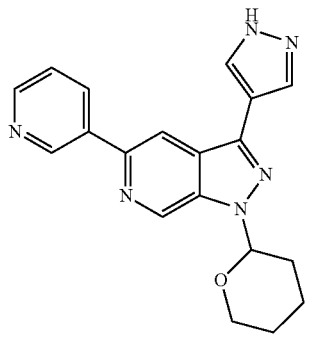 [SMILES: c1cncc(-c2cc3c(-c4cn[nH]c4)nn(C4CCCCO4)c3cn2)c1]

A mixture of 234 mg (0.54 mmol) of 3-(1-benzyl-1H-pyrazol-4-yl)-5-(pyridin-3-yl)-1-(tetrahydro-2H-pyran-2-yl)-1H-pyrazolo[3,4-c]pyridine, 3.0 ml (32 mmol) of 1,4-cyclohexadiene and 400 mg of 20% palladium hydroxide on carbon was heated to reflux for 8 hours. The mixture was filtered, the filtrate concentrated in vacuum to afford 106 mg (31%) of 3-(1H-Pyrazol-4-yl)-5-(pyridin-3-yl)-1-(tetrahydro-2H-pyran-2-yl)-1H-pyrazolo[3,4-c]pyridine over three steps. ESI MS m/z 347.1 (M+1).

Step 3

Following the deprotection of 3-(1H-Pyrazol-4-yl)-5-(pyridin-3-yl)-1-(tetrahydro-2H-pyran-2-yl)-1H-pyrazolo[3,4-c]pyridine by the procedure of Example 229, the product was purified by triturating with ethyl ether and collected by filtration to afford 24 mg (7%) of 156 over four steps. ESI MS m/z 263.0 (M+1). 1H NMR (400 MHz, DMSO): 9.70 (s, 1H), 9.37 (d, J=8.3 Hz, 1H), 9.22 (s, 1H), 8.94-8.84 (m, 2H), 8.48 (s, 2H), 8.19-8.11 (m, 1H)

Example 158

1-(5-(5-(pyridin-3-yl)-1H-pyrazolo[3,4-c]pyridin-3-yl)pyridin-3-yl)piperidin-4-amine 158

Step 1: tert-butyl 1-(5-bromopyridin-3-yl)piperidin-4-ylcarbamate

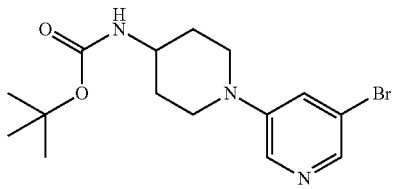 [SMILES: CC(C)(C)OC(=O)NC1CCN(c2cncc(Br)c2)CC1]

A solution of 3,5-dibromopyridine (0.400 g, 1.69 mmol), 4-(N-Boc-amino)-piperidine (0.238 g, 1.19 mmol), Tris(dibenzylideneacetone)dipalladium(0) (54 mg, 0.059 mmol), rac-2,2'-Bis(diphenylphosphino)-1,1'-binaphthyl (73.9 mg, 0.119 mmol), and Sodium-tert-butoxide (114 mg, 1.19 mmol) in Toluene (16.9 mL) was heated at 85° C. for 18 h. The reaction was filtered thru celite then rinsed with EtOAc. The crude product was purified by Isco (EtOAc/Hep eluted at 40%) to give tert-butyl 1-(5-bromopyridin-3-yl)piperidin-4-ylcarbamate (320 mg, 75.6% yield). ESI MS m/z=357.1 (M+1).

Step 2: tert-butyl 1-(5-(4,4,5,5-tetramethyl-1,3,2-dioxaborolan-2-yl)pyridin-3-yl)piperidin-4-ylcarbamate

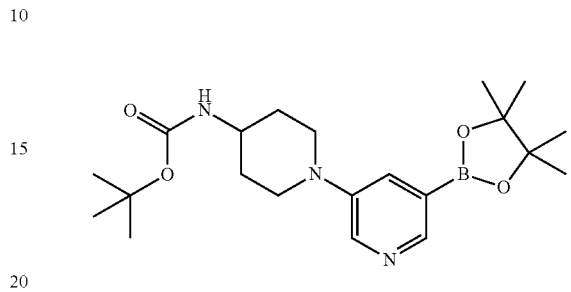

A solution of tert-butyl 1-(5-bromopyridin-3-yl)piperidin-4-ylcarbamate (0.120 g, 0.337 mmol;), Bispinacol ester boronate (0.13 g, 0.50 mmol), 1,1'-Bis(diphenylphosphino)ferrocenepalladium (II) chloride (13.75 mg, 0.01684 mmol) and Potassium acetate (99.17 mg, 1.010 mmol) in 1,4-Dioxane (5.00 mL) was purged N2 then heat at 85° C. 18 h. The reaction mixture was filtered thru celite and washed with EtOAc. The filtrate was washed water and brine. The organic layer was dried with Na2SO4 and concentrated. The crude tert-butyl 1-(5-(4,4,5,5-tetramethyl-1,3,2-dioxaborolan-2-yl)pyridin-3-yl)piperidin-4-ylcarbamate was carried to next step. ESI MS m/z=404.1 (M+1).

Step 3: tert-butyl 1-(5-(5-bromo-1-(tetrahydro-2H-pyran-2-yl)-1H-pyrazolo[3,4-c]pyridin-3-yl)pyridin-3-yl)piperidin-4-ylcarbamate

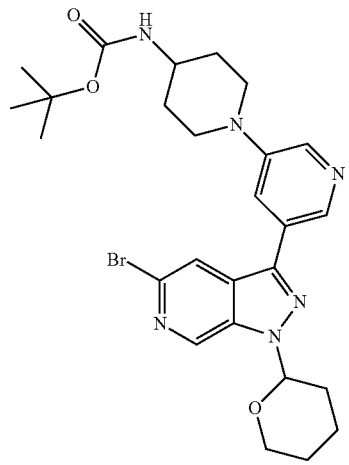 [SMILES: CC(C)(C)OC(=O)NC1CCN(c2cncc(-c3nn(C4CCCCO4)c4cnc(Br)cc34)c2)CC1]

5-bromo-3-iodo-1-(tetrahydro-2H-pyran-2-yl)-1H-pyrazolo[3,4-c]pyridine (0.0736 g, 0.180 mmol), tert-butyl 1-(5-(4,4,5,5-tetramethyl-1,3,2-dioxaborolan-2-yl)pyridin-3-yl)piperidin-4-ylcarbamate (0.080 g, 0.20 mmol) and 1,1'-Bis(diphenylphosphino)ferrocenepalladium (II) chloride (0.0221 g, 0.0270 mmol) were dissolved in Acetonitrile (3.00 mL), followed by the addition of 1.0 M of Potassium acetate in Water (0.270 mL) and 1.0 M of Sodium carbonate in Water (0.270 mL). The reaction was stirred at 80° C. for 1 h. After filtration, the crude was evaporated and purified by silica gel column using (EtOAc/Hep eluted at 75% EtOAc) to give tert-butyl 1-(5-(5-bromo-1-(tetrahydro-2H-pyran-2-yl)-1H-pyrazolo[3,4-c]pyridin-3-yl)pyridin-3-yl)piperidin-4-ylcarbamate (45 mg, 45% yield). ESI MS m/z=558.1 (M+1).

Step 4: tert-butyl 1-(5-(5-(pyridin-3-yl)-1-(tetrahydro-2H-pyran-2-yl)-1H-pyrazolo[3,4-c]pyridin-3-yl)pyridin-3-yl)piperidin-4-ylcarbamate

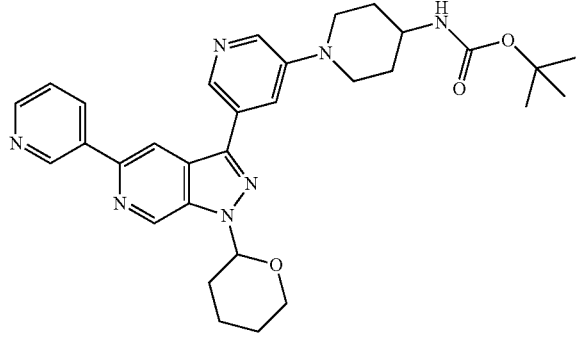 [SMILES: CC(C)(C)OC(=O)NC1CCN(c2cncc(-c3nn(C4CCCCO4)c4cnc(-c5cccnc5)cc34)c2)CC1]

To a mixture of tert-butyl 1-(5-(5-bromo-1-(tetrahydro-2H-pyran-2-yl)-1H-pyrazolo[3,4-c]pyridin-3-yl)pyridin-3-yl)piperidin-4-ylcarbamate (45.0 mg, 0.0807 mmol), 3-Pyridylboronic acid (29.8 mg, 0.242 mmol) and 1,1'-Bis(diphenylphosphino)ferrocenepalladium (II) chloride (9.888 mg, 0.01211 mmol) in Acetonitrile (1.01 mL, 19.4 mmol) was added 1.0 M of Potassium acetate in Water (0.121 mL) and 1.0 M of Sodium carbonate in Water (0.121 mL). The reaction mixture was irradiated in microwave at 125° C. for 20 min. The reaction was filtered thru celite. The filtrate was washed H2O and brine. The organic layer was dried with Na2SO4, filtered, and concentrated to give tert-butyl 1-(5-(5-(pyridin-3-yl)-1-(tetrahydro-2H-pyran-2-yl)-1H-pyrazolo[3,4-c]pyridin-3-yl)pyridin-3-yl)piperidin-4-ylcarbamate.

Step 5

To a solution of tert-butyl 1-(5-(5-(pyridin-3-yl)-1-(tetrahydro-2H-pyran-2-yl)-1H-pyrazolo[3,4-c]pyridin-3-yl)pyridin-3-yl)piperidin-4-ylcarbamate in methylene chloride (1.00 mL, 15.6 mmol) was added trifluoroacetic Acid (0.3109 mL, 4.036 mmol). The reaction was stirred at RT for 18 hours. The reaction was concentrated then submitted for rHPLC (reverse phase HPLC) to give 158 (10 mg, 33% yield). ESI MS m/z=372.1 (M+1). ¹H NMR (400 MHz, DMSO) δ 9.39 (s, 1H), 9.24 (s, 1H), 8.72 (s, 1H), 8.61-8.52 (m, 3H), 8.42 (s, 1H), 7.83 (s, 1H), 7.55-7.48 (m, 1H), 3.85 (d, J=13.0 Hz, 2H), 2.98-2.76 (m, 3H), 1.91-1.81 (m, 2H), 1.42 (dd, J=20.7, 10.2 Hz, 2H)

Example 159

N1-(4-(5-(pyridin-3-yl)-1H-pyrazolo[3,4-c]pyridin-3-yl)pyridin-2-yl)ethane-1,2-diamine 159

Step 1: 5-(3,4-Dihydro-2H-pyran-5-yl)-3-(6-fluoropyridin-2-yl)-1-(tetrahydro-2H-pyran-2-yl)-1H-pyrazolo[3,4-c]pyridine

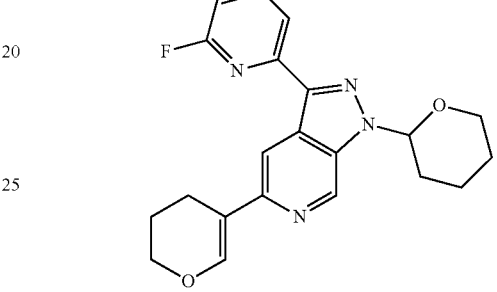

Following the Suzuki coupling procedure of Example 10, 5-bromo-3-(6-fluoropyridin-2-yl)-1-(tetrahydro-2H-pyran-2-yl)-1H-pyrazolo[3,4-c]pyridine and 2-(3,4-dihydro-2H-pyran-5-yl)-4,4,5,5-tetramethyl-1,3,2-dioxaborolane were reacted and purified via silica gel chromatography using a gradient of EtOAc in heptane to afford 68 mg (45%) of 5-(3,4-Dihydro-2H-pyran-5-yl)-3-(6-fluoropyridin-2-yl)-1-(tetrahydro-2H-pyran-2-yl)-1H-pyrazolo[3,4-c]pyridine. ESI MS m/z 381.1 (M+1).

Step 2: 3-(6-Fluoropyridin-2-yl)-1-(tetrahydro-2H-pyran-2-yl)-5-(tetrahydro-2H-pyran-3-yl)-1H-pyrazolo[3,4-c]pyridine

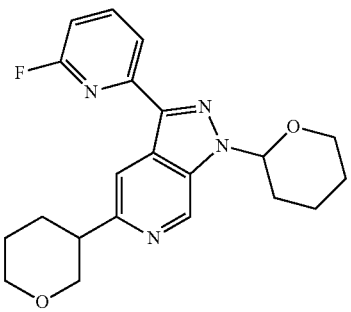 [SMILES: Fc1cccc(-c2nn(C3CCCCO3)c3cnc(C4CCCOC4)cc23)n1]

A mixture of 68 mg (0.18 mmol) of 5-(3,4-dihydro-2H-pyran-5-yl)-3-(6-fluoropyridin-2-yl)-1-(tetrahydro-2H-pyran-2-yl)-1H-pyrazolo[3,4-c]pyridine, 2.0 ml (21 mmol) of 1,4-cyclohexadiene and 300 mg of 10% palladium on carbon in 8 ml of ethanol was heated to reflux for 24 hours. The mixture was filtered through celite, the filtrate concentrated in vacuum to afford 70 mg (100%) of 3-(6-Fluoropyridin-2-yl)-

1-(tetrahydro-2H-pyran-2-yl)-5-(tetrahydro-2H-pyran-3-yl)-1H-pyrazolo[3,4-c]pyridine. ESI MS m/z 383.1 (M+1).

Step 3: 3-(6-(piperazin-1-yl)pyridin-2-yl)-5-(tetrahydro-2H-pyran-3-yl)-1H-pyrazolo[3,4-c]pyridine

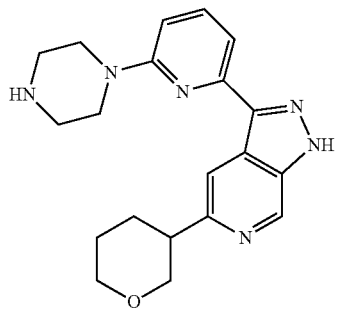 [SMILES: c1cc(-c2n[nH]c3cnc(C4CCCOC4)cc23)nc(N2CCNCC2)c1]

Following the procedure of Example 144, 3-(6-fluoropyridin-2-yl)-1-(tetrahydro-2H-pyran-2-yl)-5-(tetrahydro-2H-pyran-3-yl)-1H-pyrazolo[3,4-c]pyridine and piperazine were reacted and consequently deprotected by the procedure of Example 131, to give a racemic mixture purified via reverse phase HPLC using a gradient of MeOH in water with 0.1% $NH_4OH$ to afford 30 mg (20%) of 3-(6-(piperazin-1-yl)pyridin-2-yl)-5-(tetrahydro-2H-pyran-3-yl)-1H-pyrazolo[3,4-c]pyridine. ESI MS m/z 365.1 (M+1).

Step 4: 3-(2-Fluoropyridin-4-yl)-5-(pyridin-3-yl)-1-(tetrahydro-2H-pyran-2-yl)-1H-pyrazolo[3,4-c]pyridine

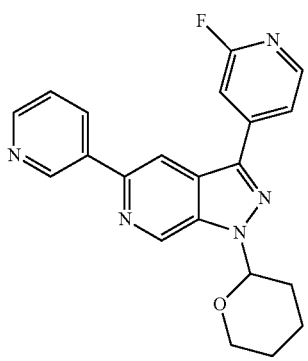 [SMILES: Fc1cc(-c2nn(C3CCCCO3)c3cnc(-c4cccnc4)cc23)ccn1]

A mixture of 0.408 g (1.00 mmol) of 5-bromo-3-(6-fluoropyridin-2-yl)-1-(tetrahydro-2H-pyran-2-yl)-1H-pyrazolo[3,4-c]pyridine, 0.162 g, (1.15 mmol) of 3-pyridineboronic acid pinacol ester and 0.817 g (0.10 mmol) of 1,1'bis(diphenylphosphino)ferrocenepalladium (II) chloride and 1.2 ml of 1.0 M of Cesium Carbonate in water in 12 ml of acetonitrile was degassed and heated in a sealed glass vial at 95° C. for 2 hours. The mixture was filtered and the filtrate concentrated in vacuum. The residue was dissolved in dichloromethane, the organic layer washed with water, brine, dried over $MgSO_4$ and concentrated to give 3-(2-Fluoropyridin-4-yl)-5-(pyridin-3-yl)-1-(tetrahydro-2H-pyran-2-yl)-1H-pyrazolo[3,4-c]pyridine.

Step 5

Following the procedure of Example 143, 3-(2-fluoropyridin-4-yl)-5-(pyridin-3-yl)-1-(tetrahydro-2H-pyran-2-yl)-1H-pyrazolo[3,4-c]pyridine and 1,2-ethylenediamine were reacted and purified via reverse phase HPLC using a gradient of MeOH in water with 0.1% $NH_4OH$ to afford 32 mg (64%) of 159. ESI MS m/z 332.1 (M+1). 1H NMR (400 MHz, DMSO): 9.38 (s, 1H), 9.23 (s, 1H), 8.60 (d, J=11.0 Hz, 2H), 8.53 (d, J=7.1 Hz, 1H), 8.10 (s, 1H), 7.54 (s, 1H), 7.25 (d, J=11.9 Hz, 2H), 6.67 (s, 1H), 2.78 (s, 2H)

Example 160

(S)-1-(6-(5-(pyridin-3-yl)-1H-pyrazolo[3,4-c]pyridin-3-yl)pyridin-2-yl)piperidin-3-amine 160

Following the procedure of Example 144, 3-(2-fluoropyridin-4-yl)-5-(pyridin-3-yl)-1-(tetrahydro-2H-pyran-2-yl)-1H-pyrazolo[3,4-c]pyridine and tert-butyl piperidin-4-ylcarbamate were reacted and consequently deprotected by the procedure of Example 229, the mixture was purified via reverse phase HPLC using a gradient of MeOH in water with 0.1% $NH_4OH$ to afford 50 mg (59%) of 160. ESI MS m/z 372.1 (M+1)

Example 161

(S)-1-(6-(5-(pyridin-3-yl)-1H-pyrazolo[3,4-c]pyridin-3-yl)pyridin-2-yl)piperidin-3-amine 161

Following the procedures of Example 144, 3-(6-fluoropyridin-2-yl)-5-(pyridin-3-yl)-1-(tetrahydro-2H-pyran-2-yl)-1H-pyrazolo[3,4-c]pyridine and (R)-benzyl piperidin-3-ylcarbamate were reacted. The reaction mixture was purified via reverse phase HPLC using a gradient of MeOH in water with 0.1% $NH_4OH$ to afford 20.0 mg (20%) of 161 over two steps. ESI MS m/z 372.1 (M+1). 1H NMR (400 MHz, DMSO): 9.30 (s, 1H), 9.21 (s, 1H), 9.00 (s, 1H), 8.60 (s, 1H), 8.48 (m, 1H), 7.66 (s, 1H) 7.53 (m, 1H), 7.46 (s, 1H), 6.87 (d, J=8.5 Hz, 1H), 4.37 (m, 1H), 4.29 (d, J=12.6 Hz, 1H), 3.06-2.97 (m, 1H), 2.79 (d, J=7.6 Hz, 2H), 1.94 (m, 1H), 1.80 (m, 1H), 1.61 (d, J=9.5 Hz, 1H), 1.34 (m, 1H)

Example 162

3-(6-(piperazin-1-yl)pyridin-2-yl)-5-(pyridin-3-yl)-1H-pyrazolo[3,4-c]pyridine 162

Following the procedures of Example 143, 3-(6-fluoropyridin-2-yl)-5-(pyridin-3-yl)-1-(tetrahydro-2H-pyran-2-yl)-1H-pyrazolo[3,4-c]pyridine and piperazine were reacted and purified via reverse phase HPLC using a gradient of MeOH in water with 0.1% $NH_4OH$ to afford 42 mg (78%) of 162. ESI MS m/z 358.1 (M+1). 1H NMR (400 MHz, DMSO): 9.24 (d, J=8.1 Hz, 1H), 8.90 (s, 1H), 8.61 (s, 1H), 8.42 (d, J=7.2 Hz, 1H), 7.74 (d, J=7.9 Hz, 1H), 7.56 (d, J=6.7 Hz, 1H), 6.96 (d, J=8.1 Hz, 1H), 3.82 (s, 2H), 3.17 (s, 2H)

Example 163

3,5-bis(1-methyl-1H-pyrazol-4-yl)-1H-pyrazolo[3,4-c]pyridine 163

3,5-bis(1-methyl-1H-pyrazol-4-yl)-1-(tetrahydro-2H-pyran-2-yl)-1H-pyrazolo[3,4-c]pyridine in methanol was treated with 4M HCl in 1,4-dioxane at 50° C. for 3 h. Volatile solvent was evaporated in vacuo. The resultant residue was purified by reverse phase HPLC to give 163 as a white solid (34.2%). 1H NMR (500 MHz, DMSO) δ 13.35 (s, 1H), 8.96

(s, 1H), 8.47 (s, 1H), 8.29 (s, 1H), 8.15 (s, 1H), 8.10 (d, J=5.6 Hz, 2H), 3.96 (s, 3H), 3.90 (s, 3H). LC/MS: m/z 280.0 [M+1]

Example 165

(1-(5-(5-(pyridin-3-yl)-1H-pyrazolo[3,4-c]pyridin-3-yl)pyridin-3-yl)piperidin-4-yl)methanamine 165

Following the procedures in Example 158, tert-butyl (1-(5-(5-bromo-1-(tetrahydro-2H-pyran-2-yl)-1H-pyrazolo[3,4-c]pyridin-3-yl)pyridin-3-yl)piperidin-4-yl)methylcarbamate was converted to 165. ESI MS m/z=386.1 (M+1). $^1$H NMR (400 MHz, DMSO) δ 9.37 (s, 1H), 9.23 (s, 1H), 8.59 (d, J=4.6 Hz, 1H), 8.55 (s, 1H), 8.52 (s, 1H), 8.06 (d, J=2.4 Hz, 1H), 7.56 (s, 1H), 7.51 (dd, J=8.0, 4.7 Hz, 1H), 6.13 (d, J=5.3 Hz, 1H), 3.15-3.00 (m, 4H), 2.62 (dd, J=25.8, 13.5 Hz, 2H), 1.90-1.76 (m, 3H), 1.21 (dd, J=10.6 Hz, 2H)

Example 168

(R)-(1-(5-(5-(pyridin-3-yl)-1H-pyrazolo[3,4-c]pyridin-3-yl)pyridin-3-yl)pyrrolidin-3-yl)methanamine 168

Following the procedures in Example 158, tert-butyl ((3R)-1-(5-(5-bromo-1-(tetrahydro-2H-pyran-2-yl)-1H-pyrazolo[3,4-c]pyridin-3-yl)pyridin-3-yl)pyrrolidin-3-yl)methylcarbamate was converted to 168. ESI MS m/z=372.1 (M+1). $^1$H NMR (400 MHz, DMSO) δ 9.39 (d, J=1.7 Hz, 1H), 9.24 (s, 1H), 8.70-8.52 (m, 4H), 8.03 (d, J=2.6 Hz, 1H), 7.51 (dd, J=7.9, 4.8 Hz, 1H), 7.43 (s, 1H), 3.59-3.45 (m, 4H), 2.81 (d, J=7.1 Hz, 2H), 2.20-2.12 (m, 1H), 1.87-1.74 (m, 1H)

Example 169

1-(5-(5-(pyridin-3-yl)-1H-pyrazolo[3,4-c]pyridin-3-yl)pyridin-3-yl)azepan-4-amine 169

Following the procedures in Example 158, tert-butyl 1-(5-(5-bromo-1-(tetrahydro-2H-pyran-2-yl)-1H-pyrazolo[3,4-c]pyridin-3-yl)pyridin-3-yl)azepan-4-ylcarbamate was converted to 169. ESI MS m/z=386.2 (M+1). $^1$H NMR (400 MHz, DMSO) δ 9.38 (s, 1H), 9.24 (s, 1H), 8.64-8.49 (m, 4H), 8.21 (d, J=2.7 Hz, 1H), 7.58 (s, 1H), 7.51 (dd, J=7.8, 4.8 Hz, 1H), 3.76-3.65 (m, 1H), 3.66-3.57 (m, 1H), 3.56-3.43 (m, 2H), 3.04 (dd, J=14.6, 9.5 Hz, 1H), 2.12-2.00 (m, 1H), 2.01-1.90 (m 1H), 1.83-1.59 (m, 2H), 1.53-1.37 (m, 1H), 1.25-1.15 (m, 1H)

Example 170

N-(piperidin-4-yl)-5-(5-(pyridin-3-yl)-1H-pyrazolo[3,4-c]pyridin-3-yl)pyridin-3-amine 170

Following the procedures in Example 158, tert-butyl 4-(5-(5-bromo-1-(tetrahydro-2H-pyran-2-yl)-1H-pyrazolo[3,4-c]pyridin-3-yl)pyridin-3-ylamino)piperidine-1-carboxylate was converted to 170. ESI MS m/z=372.1 (M+1). $^1$H NMR (400 MHz, DMSO) δ 9.37 (d, J=2.0 Hz, 1H), 9.23 (s, 1H), 8.59 (d, J=4.6 Hz, 1H), 8.56-8.47 (m, 3H), 8.05 (d, J=2.4 Hz, 1H), 7.57 (s, 1H), 7.51 (dd, J=7.9, 4.7 Hz, 1H), 5.90 (d, J=8.0 Hz, 1H), 2.99 (d, J=12.5 Hz, 2H), 2.60 (t, J=11.0 Hz, 2H), 1.95 (d, J=10.6 Hz, 2H), 1.30 (dd, J=19.6, 10.8 Hz, 2H)

Example 172

3-(2-fluoro-5-methoxyphenyl)-5-(1-methyl-1H-pyrazol-4-yl)-1H-pyrazolo[3,4-c]pyridine 172

Step 1: 3-(2-fluoro-5-methoxyphenyl)-5-(1-methyl-1H-pyrazol-4-yl)-1-(tetrahydro-2H-pyran-2-yl)-1H-pyrazolo[3,4-c]pyridine

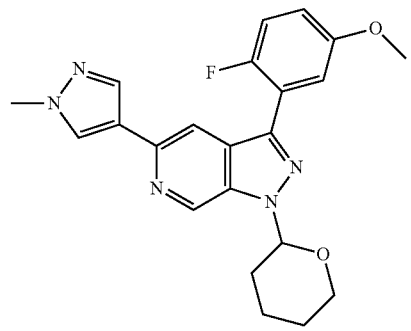

In a microwave vial was charged with 3-chloro-5-(1-methyl-1H-pyrazol-4-yl)-1-(tetrahydro-2H-pyran-2-yl)-1H-pyrazolo[3,4-c]pyridine (29.4 mg, 0.093 mmol), 2-(2-fluoro-5-methoxyphenyl)-4,4,5,5-tetramethyl-[1,3,2]dioxaborolane (35.0 mg, 0.139 mmol), potassium acetate (13.6 mg, 0.14 mmol), sodium carbonate (14.7 mg, 0.14 mmol), and bis(diphenylphosphino)ferrocene]dichloropalladium (II), complexed with dichloromethane (1:1) (7.5 mg, 9.2E$^{-3}$ mmol). Degassed acetonitrile (0.8 mL) and water (0.3 mL) were added. Nitrogen was passed through the mixture for 15 minutes and the vial was capped. The reaction mixture was subjected to microwave irradiation at 125° C. for 25 min. The reaction mixture was filtered through a pad of Celite® and diluted with water and EtOAc. The organic layer was washed with brine, dried over Na$_2$SO$_4$, filtered, and concentrated under reduced pressure. The crude product was purified using flash chromatography (Si-PPC gradient elution, solvent: 10-100% ethyl acetate in heptanes) to give 3-(2-fluoro-5-methoxyphenyl)-5-(1-methyl-1H-pyrazol-4-yl)-1-(tetrahydro-2H-pyran-2-yl)-1H-pyrazolo[3,4-c]pyridine as a foam (37.3 mg, 98.9%). $^1$H NMR (400 MHz, CDCl$_3$) δ 9.12 (s, 1H), 7.95 (s, 1H), 7.90 (s, 1H), 7.81 (d, J=2.8 Hz, 1H), 7.32 (dd, J=5.5, 3.2 Hz, 1H), 7.15 (t, J=9.4 Hz, 1H), 6.97-6.89 (m, 1H), 5.86 (dd, J=8.7, 2.1 Hz, 1H), 4.07-3.98 (m, 1H), 3.93 (s, 3H), 3.86-3.74 (m, 4H), 2.64-2.47 (m, 1H), 2.16 (d, J=9.7 Hz, 2H), 1.83-1.66 (m, 3H). LC/MS: m/z 408.2 [M+1].

Step 2

To a stirred mixture of 3-(2-fluoro-5-methoxyphenyl)-5-(1-methyl-1H-pyrazol-4-yl)-1-(tetrahydro-2H-pyran-2-yl)-

1H-pyrazolo[3,4-c]pyridine (37.0 mg, 0.09 mmol) in methanol (5.0 mL) was added 6 M HCl in water (0.66 mL). The reaction mixture was stirred at 60° C. for 3 days. Volatile solvent was evaporated in vacuo, and the crude was diluted into ethyl acetate (~30 mL). The organic layer was washed with saturated aqueous sodium bicarbonate solution, water and brine, dried over Na₂SO₄, filtered, and concentrated under reduced pressure. Trituration from ether-heptanes afforded 172 as a solid (15.3 mg, 52.1%). ¹H NMR (400 MHz, DMSO) δ 13.88 (s, 1H), 9.06 (s, 1H), 8.25 (s, 1H), 7.97 (s, 1H), 7.88 (s, 1H), 7.36 (t, J=9.6 Hz, 1H), 7.31 (dd, J=5.7, 3.2 Hz, 1H), 7.09 (s, 1H), 3.88 (s, 3H), 3.83 (s, 3H). LC/MS: m/z 324.0 [M+1]

Example 173

(S)-1-(6-(5-(1-methyl-1H-pyrazol-4-yl)-1H-pyrazolo [3,4-c]pyridin-3-yl)pyridin-2-yl)piperidin-3-amine 173

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and (S)-tert-butyl piperidin-3-ylcarbamate were reacted and the product was deprotected to give 173 as a white solid (71.7% over two steps). ¹H NMR (400 MHz, DMSO) δ 1H NMR (400 MHz, DMSO) δ 9.03 (d, J=1.2 Hz, 1H), 8.59 (d, J=1.2 Hz, 1H), 8.34 (s, 1H), 7.95 (s, 1H), 7.67-7.60 (m, 1H), 7.42 (d, J=7.3 Hz, 1H), 6.84 (d, J=8.5 Hz, 1H), 4.46 (d, J=8.9 Hz, 1H), 4.21 (d, J=12.7 Hz, 1H), 3.90 (s, 3H), 3.02-2.93 (m, 1H), 2.84-2.74 (m, 2H), 2.00-1.92 (m, 2H), 1.88-1.77 (m, 2H), 1.67-1.52 (m, 2H), 1.39-1.28 (m, 1H). LC/MS: m/z 375.1 [M+1]

Example 174

1-(6-(5-(1-methyl-1H-pyrazol-4-yl)-1H-pyrazolo[3, 4-c]pyridin-3-yl)pyridin-2-yl)piperidin-4-amine 174

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl piperidin-4-ylcarbamate were reacted and the product was deprotected to give 174 as a white solid (36.8% over two steps). ¹H NMR (400 MHz, DMSO) δ 1H NMR (400 MHz, DMSO) δ 9.03 (d, J=1.2 Hz, 1H), 8.54 (d, J=1.3 Hz, 1H), 8.12 (s, 1H), 7.82 (s, 1H), 7.63 (dd, J=8.4, 7.5 Hz, 1H), 7.41 (d, J=7.3 Hz, 1H), 6.86 (d, J=8.5 Hz, 1H), 4.37 (d, J=13.1 Hz, 2H), 3.91 (s, 3H), 3.51-3.20 (m, 3H), 3.14-3.04 (m, 2H), 2.96-2.83 (m, 1H), 1.87 (d, J=9.9 Hz, 2H), 1.45-1.27 (m, 2H). LC/MS: m/z 375.1 [M+1]

Example 175

3-(1-(piperidin-4-yl)-1H-pyrazol-4-yl)-5-(pyridin-3-yl)-1H-pyrazolo[3,4-c]pyridine 175

Step 1: tert-Butyl 4-(4-(5-(pyridin-3-yl)-1-(tetrahydro-2H-pyran-2-yl)-1H-pyrazolo[3,4-c]pyridin-3-yl)-1H-pyrazol-1-yl)piperidine-1-carboxylate

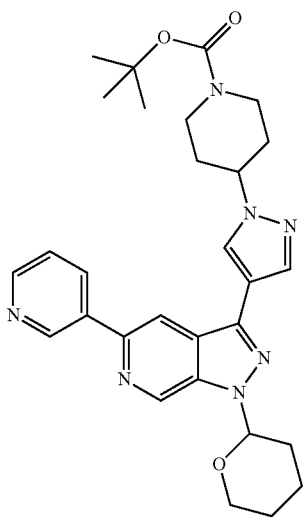 [SMILES: CC(C)(C)OC(=O)N1CCC(n2cc(-c3nn(C4CCCCO4)c4cnc(-c5cccnc5)cc34)cn2)CC1]

Following the Suzuki coupling procedure of Example 159, 5-bromo-3-iodo-1-(tetrahydro-2H-pyran-2-yl)-1H-pyrazolo [3,4-c]pyridine and tert-butyl 4-(4-(4,4,5,5-tetramethyl-1,3, 2-dioxaborolan-2-yl)-1H-pyrazol-1-yl)piperidine-1-carboxylate were reacted and the product was consequently reacted by the Suzuki coupling procedure of Example 10 with 3-pyridineboronic acid pinacol ester. The product mixture was purified via silica gel chromatography using a gradient of methanol in DCM to afford 230 mg (75%) of tert-Butyl 4-(4-(5-(pyridin-3-yl)-1-(tetrahydro-2H-pyran-2-yl)-1H-pyrazolo[3,4-c]pyridin-3-yl)-1H-pyrazol-1-yl)piperidine-1-carboxylate over two steps. ESI MS m/z 530.2 (M+1).

Step 2

Deprotection following the procedure of Example 229, of tert-Butyl 4-(4-(5-(pyridin-3-yl)-1-(tetrahydro-2H-pyran-2-yl)-1H-pyrazolo[3,4-c]pyridin-3-yl)-1H-pyrazol-1-yl)piperidine-1-carboxylate and purification via reverse phase HPLC using a gradient of MeOH in water with 0.1% NH₄OH gave 42 mg (21%) of 175. ESI MS m/z 346.1 (M+1). 1H NMR (400 MHz, DMSO): 13.75 (s, 1H), 9.44 (d, J=1.7 Hz, 1H), 9.15 (d, J=1.2 Hz, 1H), 8.64 (s, 1H), 8.61-8.56 (m, 3H), 4.36-4.26 (m, 1H), 3.09 (d, J=12.3 Hz, 2H), 2.68-2.57 (m, 2H), 2.05-1.87 (m, 4H)

Example 176

3,5-di(pyridin-3-yl)-1H-pyrazolo[3,4-c]pyridine 176

To a microwave tube was added 5-bromo-3-iodo-1H-pyrazolo[3,4-c]pyridine (100 mg, 0.31 mmol), pyridin-3-ylboronic acid (343 mg, 2.79 mmol), Pd(dppf)Cl₂ (24 mg, 0.03 mmol), sodium carbonate (131 mg, 1.24 mmol), 1,2-dimethoxyethane (2 mL), ethanol (0.5 mL) and water (0.5 mL). The tube was flushed with nitrogen for 2 minutes and heated in a Biotage microwave at 160° C. for 1 hour. The solvent was distilled off and the crude product was purified via reverse phase HPLC eluting with 15% CH₃CN in aqueous 10 mmol NH₄HCO₃ to afford 176 as a pale yellow solid (30 mg, 28%). ¹H NMR (500 MHz, DMSO) ¹H NMR (500 MHz, DMSO) δ 14.1 (s, 1H), 9.44 (s, 1H), 9.37 (s, 3H), 9.26 (s, 1H), 8.71 (s, 1H), 8.67-8.66 (m, 1H), 8.60-8.59 (m, 2H), 8.56-8.54 (m, 1H), 7.60-7.58 (m, 1H), 7.52-7.51 (m, 1H). ESI MS m/z=274 (M+1)

Example 177

(R)-1-(6-(5-(1-methyl-1H-pyrazol-4-yl)-1H-pyrazolo[3,4-c]pyridin-3-yl)pyridin-2-yl)piperidin-3-amine 177

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and (R)-tert-butyl piperidin-3-ylcarbamate were reacted and the product was deprotected to give 177 as a white solid (59.5% over two steps). ¹H NMR (400 MHz, DMSO) δ 9.03 (d, J=1.1 Hz, 1H), 8.60 (s, 1H), 8.34 (s, 1H), 7.95 (s, 1H), 7.69-7.56 (m, 1H), 7.42 (d, J=7.3 Hz, 1H), 6.83 (d, J=8.6 Hz, 1H), 4.47 (d, J=9.0 Hz, 1H), 4.22 (d, J=12.8 Hz, 1H), 3.89 (s, 3H), 3.04-2.90 (m, 1H), 2.81-2.66 (m, 2H), 2.01-1.92 (m, 2H), 1.88-1.74 (m, 2H), 1.56-1.52 (m, 2H), 1.37-1.27 (m, 1H). LC/MS: m/z 375.1 [M+1].

Example 178

2-(4-(3-(6-fluoropyridin-2-yl)-1H-pyrazolo[3,4-c]pyridin-5-yl)-1H-pyrazol-1-yl)acetamide 178

Step 1: Ethyl 2-(4-(3-(6-fluoropyridin-2-yl)-1-(tetrahydro-2H-pyran-2-yl)-1H-pyrazolo[3,4-c]pyridin-5-yl)-1H-pyrazol-1-yl)acetate

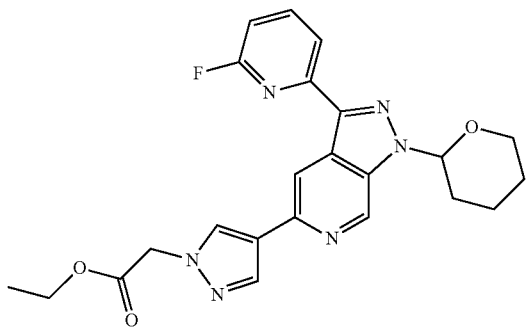 [SMILES: CCOC(=O)Cn1cc(-c2cc3c(-c4cccc(F)n4)nn(C4CCCCO4)c3cn2)cn1]

Following the Suzuki coupling procedure of Example 10, 5-bromo-3-(6-fluoropyridin-2-yl)-1-(tetrahydro-2H-pyran-2-yl)-1H-pyrazolo[3,4-c]pyridine and ethyl 2-(4-(4,4,5,5-tetramethyl-1,3,2-dioxaborolan-2-yl)-1H-pyrazol-1-yl)acetate, were reacted and purified via silica gel chromatography using a gradient of EtOAc in heptane to afford 100 mg (56%) of Ethyl 2-(4-(3-(6-fluoropyridin-2-yl)-1-(tetrahydro-2H-pyran-2-yl)-1H-pyrazolo[3,4-c]pyridin-5-yl)-1H-pyrazol-1-yl)acetate. ESI MS m/z 451.1 (M+1).

Step 2: 2-(4-(3-(6-Fluoropyridin-2-yl)-1-(tetrahydro-2H-pyran-2-yl)-1H-pyrazolo[3,4-c]pyridin-5-yl)-1H-pyrazol-1-yl)acetic acid

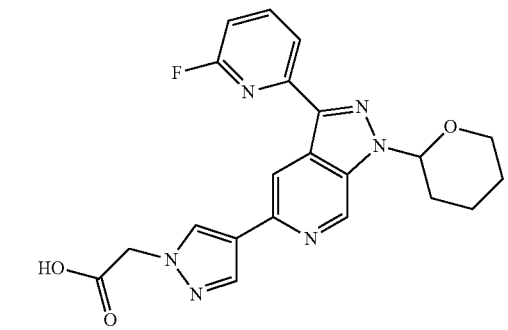 [SMILES: O=C(O)Cn1cc(-c2cc3c(-c4cccc(F)n4)nn(C4CCCCO4)c3cn2)cn1]

A mixture of 100 mg (0.22 mmol) of ethyl 2-(4-(3-(6-fluoropyridin-2-yl)-1-(tetrahydro-2H-pyran-2-yl)-1H-pyrazolo[3,4-c]pyridin-5-yl)-1H-pyrazol-1-yl)acetate and 1 ml of 1 M aqueous solution of lithium hydroxide in 6 ml of methanol and 2 ml of tetrahydrofuran was stirred for 2 hours. The mixture was concentrated in vacuum and neutralized to pH 5 by careful addition of 1 N aqueous HCl. The product was collected by filtration, washed with water and dried in high vacuum to afford 82 mg (85%) of 2-(4-(3-(6-Fluoropyridin-2-yl)-1-(tetrahydro-2H-pyran-2-yl)-1H-pyrazolo[3,4-c]pyridin-5-yl)-1H-pyrazol-1-yl)acetic acid. ESI MS m/z 423.0 (M+1).

Step 3: 2-(4-(3-(6-Fluoropyridin-2-yl)-1-(tetrahydro-2H-pyran-2-yl)-1H-pyrazolo[3,4-c]pyridin-5-yl)-1H-pyrazol-1-yl)acetamide

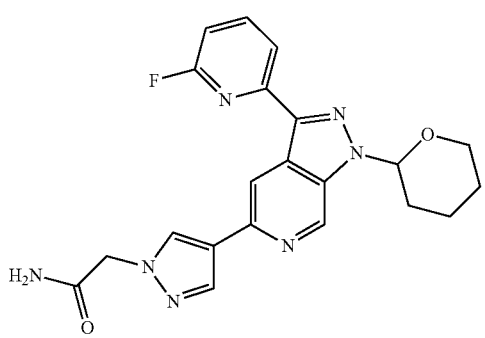 [SMILES: NC(=O)Cn1cc(-c2cc3c(-c4cccc(F)n4)nn(C4CCCCO4)c3cn2)cn1]

Following the procedure of Example 144, 2-(4-(3-(6-fluoropyridin-2-yl)-1-(tetrahydro-2H-pyran-2-yl)-1H-pyrazolo[3,4-c]pyridin-5-yl)-1H-pyrazol-1-yl)acetic acid and ammonium chloride were reacted to give 60 mg (75%) of 2-(4-(3-(6-Fluoropyridin-2-yl)-1-(tetrahydro-2H-pyran-2-yl)-1H-pyrazolo[3,4-c]pyridin-5-yl)-1H-pyrazol-1-yl)acetamide. ESI MS m/z 422.2 (M+1).

Step 4

A mixture of 60 mg (0.142 mmol) of 2-(4-(3-(6-fluoropyridin-2-yl)-1-(tetrahydro-2H-pyran-2-yl)-1H-pyrazolo[3,4- c]pyridin-5-yl)-1H-pyrazol-1-yl)acetamide and 2 ml of trifluoroacetic acid was stirred for 18 hours. The mixture was concentrated in vacuum, the residue stirred with 5 ml of saturated aqueous sodium bicarbonate for 30 min. The precipitate was collected by filtration, washed with water and recrystallized from methanol affording 35 mg (26%) of 178 over 4 steps. ESI MS m/z 338.0 (M+1). 1H NMR (400 MHz, DMSO): 14.02 (s, 1H), 9.10 (s, 1H), 8.46 (s, 1H), 8.28 (s, 1H), 8.17-8.09 (m, 2H), 7.99 (s, 1H), 7.51 (s, 1H), 7.28 (s, 1H), 7.20 (dt, J=5.4, 2.7 Hz, 1H), 4.84 (s, 2H)

Example 182

(1-(6-(5-(1-methyl-1H-pyrazol-4-yl)-1H-pyrazolo[3,4-c]pyridin-3-yl)pyridin-2-yl)piperidin-4-yl)methanamine 182

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl piperidin-4-ylmethylcarbamate were reacted and the product was deprotected to give 182 as a white solid (63% over two steps). $^1$H NMR (400 MHz, DMSO) δ 9.03 (s, 1H), 8.54 (s, 1H), 8.11 (s, 1H), 7.82 (s, 1H), 7.63 (t, J=8.0 Hz, 1H), 7.41 (d, J=7.4 Hz, 1H), 6.84 (d, J=8.5 Hz, 1H), 4.50 (d, J=12.1 Hz, 2H), 3.91 (s, 3H), 2.99 (t, J=12.5 Hz, 2H), 2.53-2.44 (m, 4H), 1.92-1.74 (m, 3H), 1.58 (s, 1H), 1.31-1.18 (m, 2H). LC/MS: m/z 389.2 [M+1]

Example 183

6-(5-(1-methyl-1H-pyrazol-4-yl)-1H-pyrazolo[3,4-c]pyridin-3-yl)-N-(piperidin-4-ylmethyl)pyridin-2-amine 183

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl 4-(aminomethyl)piperidine-1-carboxylate were reacted and the product was deprotected to give 183 as a white solid (55% over two steps). $^1$H NMR (400 MHz, DMSO) δ 9.01 (s, 1H), 8.66 (s, 1H), 8.16 (s, 1H), 7.92 (s, 1H), 7.47 (t, J=7.8 Hz, 1H), 7.30 (d, J=7.3 Hz, 1H), 6.76-6.70 (m, 1H), 6.50 (d, J=8.3 Hz, 1H), 3.90 (s, 3H), 3.44-3.34 (m, 4H), 2.99 (d, J=12.2 Hz, 2H), 2.55-2.44 (m, 2H), 1.85-1.71 (m, 3H), 1.27-1.09 (m, 2H). LC/MS: m/z 389.2 [M+1]

Example 184

5-(1-methyl-1H-pyrazol-4-yl)-3-(6-(1-methyl-1H-pyrazol-4-yl)pyridin-2-yl)-1H-pyrazolo[3,4-c]pyridine 184

Following the procedure in Example 189, 5-(1-methyl-1H-pyrazol-4-yl)-3-(6-(1-methyl-1H-pyrazol-4-yl)pyridin-2-yl)-1-(tetrahydro-2H-pyran-2-yl)-1H-pyrazolo[3,4-c]pyridine was deprotected to give 184 as a solid (52.1%). $^1$H NMR (400 MHz, DMSO) δ 13.85 (s, 1H), 9.08 (s, 1H), 8.66 (s, 1H), 8.43 (s, 1H), 8.25 (s, 1H), 8.16 (s, 1H), 7.98 (d, J=7.5 Hz, 2H), 7.90 (t, J=7.8 Hz, 1H), 7.65 (d, J=7.7 Hz, 1H), 3.98 (s, 3H), 3.93 (s, 3H). LC/MS: m/z 357.1 [M+1]

Example 185

5-(furan-3-yl)-3-phenyl-1H-pyrazolo[3,4-c]pyridine 185

Following the procedures as described in Example 176, pyrimidin-5-ylboronic acid and 5-bromo-3-phenyl-1-(tetrahydro-2H-pyran-2-yl)-1H-pyrazolo[3,4-c]pyridine were reacted and the product was deprotected to give 185 as a white solid (25 mg, 28%) over two step. $^1$H NMR (400 MHz, DMSO) δ 9.00 (s, 1H), 8.17 (t, 1H), 8.14 (t, 1H), 8.03 (t, 2H), 7.06-7.60 (m, 3H), 7.45 (t, 1H), 7.05 (s, 1H). ESI MS m/z=262 (M+1)

Example 186

3-(1-(piperidin-4-ylmethyl)-1H-pyrazol-4-yl)-5-(pyridin-3-yl)-1H-pyrazolo[3,4-c]pyridine 186

Step 1: tert-Butyl 4-((4-(4,4,5,5-tetramethyl-1,3,2-dioxaborolan-2-yl)-1H-pyrazol-1-yl)methyl)piperidine-1-carboxylate

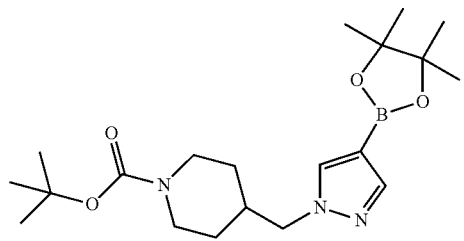 [SMILES: CC(C)(C)OC(=O)N1CCC(Cn2cc(B3OC(C)(C)C(C)(C)O3)cn2)CC1]

A solution of 630.8 mg (2.5 mmol) of 1,1'-(azodicarbonyl)-dipiperidine in 5 ml of THF was added dropwise to a mixture of 388 mg (2.0 mmol) of 4,4,5,5-Tetramethyl-2-(1H-pyrazol-4-yl)-1,3,2-dioxaborolane, 538 mg (2.5 mmol) of tert-butyl 4-(hydroxymethyl)piperidine-1-carboxylate and 0.62 ml (2.5 mmol) of tributylphosphine in 6 ml of tetrahydrofuran at 0° C. The mixture was stirred for 18 hours. The precipitate was filtered out and washed with ethyl ether. The filtrate was mixed with 50 ml of water and extracted with ethyl ether. The organic layer was washed with water, brine, dried over MgSO4 and concentrated. The residue was purified on 24 g silica column eluting with MeOH 0-4% gradient in DCM to afford 0.43 g (55%) of tert-Butyl 4-((4-(4,4,5,5-tetramethyl-1,3,2-dioxaborolan-2-yl)-1H-pyrazol-1-yl)methyl)piperidine-1-carboxylate. ESI MS m/z 392.1

Step 2

Following the Suzuki coupling procedure of Example 159, 5-bromo-3-iodo-1-(tetrahydro-2H-pyran-2-yl)-1H-pyrazolo[3,4-c]pyridine and tert-butyl 4-(4-(4,4,5,5-tetramethyl-1,3,2-dioxaborolan-2-yl)-1H-pyrazol-1-yl)piperidine-1-carboxylate were reacted. The product was subsequently reacted with 3-pyridineboronic acid pinacol ester by the Suzuki coupling procedure of Example 10 and deprotected by the procedure of Example 229. The mixture was purified via reverse phase HPLC using a gradient of MeOH in water with 0.1% NH$_4$OH to afford 25 mg (14%) of 186 over three steps. ESI MS m/z 360.1 (M+1). 1H NMR (400 MHz, DMSO) 9.44 (d, J=2.1 Hz, 1H), 9.15 (d, J=1.0 Hz, 1H), 8.64-8.54 (m, 4H), 8.17 (s, 1H), 7.53 (dd, J=8.0, 4.8 Hz, 1H), 4.08 (d, J=7.2 Hz, 2H), 2.91 (d, J=12.0 Hz, 2H), 2.41 (t, J=10.9 Hz, 2H), 1.98 (s, 1H), 1.45 (d, J=11.2 Hz, 2H), 1.18-1.05 (m, 2H)

Example 187

3-(6-(1,4-diazepan-1-yl)pyridin-2-yl)-5-(pyridin-3-yl)-1H-pyrazolo[3,4-c]pyridine 187

Following the procedures of Example 143 and starting with 3-(6-fluoropyridin-2-yl)-5-(pyridin-3-yl)-1-(tetrahydro-2H- pyran-2-yl)-1H-pyrazolo[3,4-c]pyridine and homopiperazine, 187 was obtained and lyophilized from water to afford 42 mg (78%). ESI MS m/z 372.1 (M+1). 1H NMR (400 MHz, DMSO)•9.58 (s, 1H), 9.44 (s, 1H), 9.36 (s, 2H), 9.31 (s, 1H), 9.11 (d, J=8.3 Hz, 1H), 8.99 (s, 1H), 8.94 (d, J=5.4 Hz, 1H), 8.23-8.15 (m, 1H), 7.73 (t, J=8.0 Hz, 1H), 7.52 (d, J=7.4 Hz, 1H), 6.83 (d, J=8.5 Hz, 1H), 4.12 (s, 2H), 3.89 (t, J=6.0 Hz, 2H), 3.43 (d, J=21.5 Hz, 2H), 3.27-3.17 (m, 2H), 2.24 (s, 2H)

Example 188

1-(6-(5-(1-methyl-1H-pyrazol-4-yl)-1H-pyrazolo[3,4-c]pyridin-3-yl)pyridin-2-yl)azepan-4-amine 188

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl azepan-4-ylcarbamate were reacted. The product was deprotected to give 188 as a white solid (47.1% over two steps). ¹H NMR (400 MHz, DMSO) δ 9.02 (s, 1H), 8.55 (s, 1H), 8.11 (s, 1H), 7.83 (s, 1H), 7.60 (t, J=8.0 Hz, 1H), 7.37 (d, J=7.3 Hz, 1H), 6.61 (d, J=8.5 Hz, 1H), 4.02-3.86 (m, 4H), 3.85-3.75 (m, 1H), 3.75-3.55 (m, 3H), 2.93-2.85 (s, 1H), 2.10-1.93 (m, 2H), 1.89-1.56 (m, 3H), 1.45-1.31 (m, 1H); 2 protons not seen. LC/MS: m/z 389.2 [M+1]

Example 189

(R)-1-(6-(5-(1-methyl-1H-pyrazol-4-yl)-1H-pyrazolo[3,4-c]pyridin-3-yl)pyridin-2-yl)pyrrolidin-3-amine 189

Step 1: tert-butyl (3R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)pyrrolidin-3-ylcarbamate

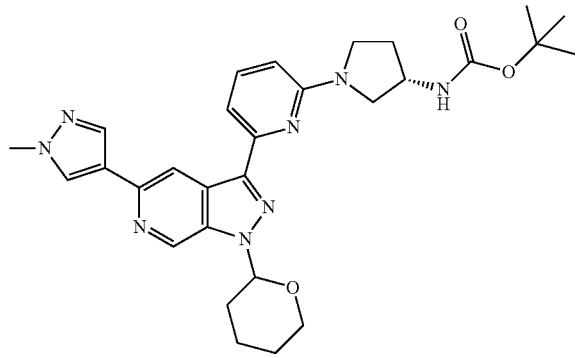 [SMILES: Cn1cc(-c2cc3c(-c4cccc(N5CC[C@H](NC(=O)OC(C)(C)C)C5)n4)nn(C4CCCCO4)c3cn2)cn1]

A mixture of 3-(6-fluoropyridin-2-yl)-5-(1-methyl-1H-pyrazol-4-yl)-1-(tetrahydro-2H-pyran-2-yl)-1H-pyrazolo[3,4-c]pyridine (50.0 mg, 0.13 mmol) and (R)-3-(Boc-amino)pyrrolidine (246.1 mg, 1.32 mmol) in DMSO (2.6 mL) in a sealed tube was stirred at 95° C. under N₂ for 3 days. The cooled reaction mixture was diluted into 1:1 ether-ethyl acetate. The organic layer was washed with 10% aqueous citric acid until pH ~4 to 5, water and brine, dried over Na₂SO₄, filtered, and evaporated in vacuo. The crude product was purified using flash chromatography (Si-PPC gradient elution, solvent: 0-20% methanol in ethyl acetate) to give tert-butyl (3R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)pyrrolidin-3-ylcarbamate as a foam (61.4 mg, 85.3%). ¹H NMR (400 MHz, CDCl₃) δ 1H NMR (400 MHz, CDCl₃) δ 9.11 (s, 1H), 8.79 (s, 1H), 8.05 (broad s, 1H), 7.97 (s, 1H), 7.62-7.50 (m, 2H), 6.37 (d, J=7.9 Hz, 1H), 5.86 (dd, J=8.5, 2.2 Hz, 1H), 4.79 (s, 1H), 4.44 (s, 1H), 4.07-3.95 (m, 4H), 3.92-3.84 (m, 1H), 3.84-3.69 (m, 3H), 3.63-3.51 (m, 1H), 2.64-2.49 (m, 1H), 2.37 (td, J=13.6, 7.7 Hz, 1H), 2.17 (d, J=9.8 Hz, 2H), 2.11-2.01 (m, 1H), 1.89-1.68 (m, 3H), 1.46 (s, 9H). LC/MS: m/z 545.3 [M+1].

Step 2

To a stirred solution of tert-butyl (3R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)pyrrolidin-3-ylcarbamate (60.0 mg, 0.12 mmol) in anhydrous DCM (5.0 mL) and methanol (2.5 mL) was added 4M HCl in 1,4-Dioxane (4.0 mL). The reaction mixture was stirred at 60° C. under N₂ for 18 h. Volatile solvent was evaporated in vacuo. The crude was redissolved in DMSO (1 mL) and was purified by reverse phase HPLC to give 189 as a white solid (25.5 mg, 58.4%). ¹H NMR (400 MHz, DMSO) δ 9.02 (s, 1H), 8.71 (s, 1H), 8.13 (s, 1H), 7.87 (s, 1H), 7.59 (t, J=7.9 Hz, 1H), 7.36 (d, J=7.4 Hz, 1H), 6.41 (d, J=8.4 Hz, 1H), 3.91 (s, 3H), 3.81-3.64 (m, 4H), 3.63-3.52 (m, 2H), 2.17 (dt, J=12.3, 6.5 Hz, 2H), 1.88-1.75 (m, 2H). LC/MS: m/z 361.1 [M+1]

Example 191

(R)-1-(5-(5-(pyridin-3-yl)-1H-pyrazolo[3,4-c]pyridin-3-yl)pyridin-2-yl)piperidin-3-amine 191

A solution containing 3-(6-fluoropyridin-3-yl)-5-(pyridin-3-yl)-1-(tetrahydro-2H-pyran-2-yl)-1H-pyrazolo[3,4-c]pyridine (0.070 g, 0.00019 mol) and (R)-tert-butyl piperidin-3-ylcarbamate (0.224 g, 0.00112 mol) in Dimethyl sulfoxide (1.40 mL, 0.0197 mol) was heated at 95° C. for 18 h. The reaction was quenched with water then filtered and washed with water. The crude product was dried under high vacuum overnight to give tert-butyl (3R)-1-(5-(5-(pyridin-3-yl)-1-(tetrahydro-2H-pyran-2-yl)-1H-pyrazolo[3,4-c]pyridin-3-yl)pyridin-2-yl)piperidin-3-ylcarbamate which was dissolved in Methylene chloride (1.4 mL, 0.022 mol) and treated with trifluoroacetic Acid (0.72 mL, 0.0093 mol). The reaction was stirred at RT 18 h. The reaction was concentrated then submitted for rHPLC to give 191 (50.6 mg, 73% yield). ESI MS m/z=372.1 (M+1). ¹H NMR (400 MHz, DMSO) δ 9.40 (d, J=1.7 Hz, 1H), 9.18 (s, 1H), 8.88 (d, J=2.3 Hz, 1H), 8.60-8.53 (m, 3H), 8.21 (dd, J=8.9, 2.4 Hz, 1H), 7.50 (dd, J=7.7, 5.1 Hz, 1H), 6.97 (d, J=9.0 Hz, 1H), 4.27 (dd, J=23.6, 12.1 Hz, 2H), 2.88 (dd, J=17.5, 7.2 Hz, 2H), 2.73-2.56 (m, 2H), 1.89 (d, J=12.0 Hz, 1H), 1.73 (d, J=13.5 Hz, 1H), 1.47 (dd, J=24.5, 12.1 Hz, 1H), 1.25 (ddd, J=16.2, 12.6, 4.0 Hz, 1H)

Example 193

3-(1H-pyrazol-3-yl)-5-(pyridin-3-yl)-1H-pyrazolo[3,4-c]pyridine 193

A mixture of 3-(1H-pyrazol-3-yl)-5-(pyridin-3-yl)-1-(tetrahydro-2H-pyran-2-yl)-1H-pyrazolo[3,4-c]pyridine (29.36 mg, 0.08476 mmol) in 4.0 M of Hydrogen chloride in 1,4-Dioxane (5 mL) and 1,4-Dioxane (5 mL) was stirred at room temperature overnight. The reaction mixture was concentrated and the residue was purified by reverse phase HPLC to afford 193 as an off-white solid (10.2 mg, 45.9%). 1H NMR (400 MHz, DMSO) δ 13.71 (s, 1H), 13.14 (s, 1H), 9.23 (d, J=31.1 Hz, 2H), 8.72-8.55 (m, 2H), 8.43 (s, 1H), 7.91 (s, 1H), 7.53 (dd, J=8.0, 4.8 Hz, 1H), 6.84 (s, 1H); ESI MS m/z=263.0 (M+1)

Example 194

5-(pyridin-3-yl)-3-(pyridin-4-yl)-1H-pyrazolo[3,4-c] pyridine 194

To a microwave tube was added 3-iodo-5-(pyridin-3-yl)-1H-pyrazolo[3,4-c]pyridine from Example 4 (100 mg, 0.31 mmol), pyridin-4-ylboronic acid (190 mg, 1.55 mmol), Pd(dppf)Cl$_2$ (50 mg, 0.06 mmol), sodium carbonate (131 mg, 1.24 mmol), 1,2-dimethoxyethane (2 mL), ethanol (0.3 mL) and water (0.3 mL). The tube was flushed with nitrogen for 2 minutes and heated in a Biotage microwave at 160° C. for 1 hour. The solvent was distilled off and the crude product was purified via reverse phase HPLC eluting with 15% CH$_3$CN aqueous 10 mmol NH$_4$HCO$_3$ solution to afford 194 as a white solid (18 mg, 21%). $^1$H NMR (400 MHz, DMSO) $^1$H NMR (500 MHz, DMSO) δ 9.44 (s, 1H), 9.28 (s, 1H), 8.76-8.73 (m, 3H), 8.62-8.59 (m, 2H), 8.19 (d, J=6.0 Hz, 2H), 7.55-7.53 (m, 1H). ESI MS m/z=274 (M+1)

Example 196

(S)-1-(5-(5-(pyridin-3-yl)-1H-pyrazolo[3,4-c]pyridin-3-yl)pyridin-2-yl)piperidin-3-amine 196

Following the procedures in Example 191, 3-(6-fluoropyridin-3-yl)-5-(pyridin-3-yl)-1-(tetrahydro-2H-pyran-2-yl)-1H-pyrazolo[3,4-c]pyridine was converted to 196. ESI MS m/z=372.1 (M+1). $^1$H NMR (400 MHz, DMSO) δ 9.40 (d, J=1.6 Hz, 1H), 9.18 (s, 1H), 8.87 (d, J=2.4 Hz, 1H), 8.62-8.50 (m, 3H), 8.21 (dd, J=8.9, 2.4 Hz, 1H), 7.50 (dd, J=8.0, 4.7 Hz, 1H), 6.97 (d, J=9.0 Hz, 1H), 4.27 (dd, J=23.4, 12.0 Hz, 2H), 2.94-2.82 (m, 1H), 2.65 (m, 2H), 1.90 (d, J=9.1 Hz, 1H), 1.78-1.64 (m, 2H), 1.55-1.37 (m, 1H), 1.33-1.17 (m, 1H)

Example 197

1-(6-(5-(pyridin-3-yl)-1H-pyrazolo[3,4-c]pyridin-3-yl)pyridin-2-yl)azepan-4-amine 197

Following the procedures in Example 191, 3-(6-fluoropyridin-2-yl)-5-(pyridin-3-yl)-1-(tetrahydro-2H-pyran-2-yl)-1H-pyrazolo[3,4-c]pyridine was converted to 197. ESI MS m/z=386.1 (M+1). $^1$H NMR (400 MHz, DMSO) δ 9.25-9.17 (m, 1H), 8.97 (s, 1H), 8.60 (d, J=4.7 Hz, 1H), 8.38 (d, J=7.9 Hz, 1H), 7.66-7.59 (m, 1H), 7.55 (dd, J=7.9, 4.7 Hz, 1H), 7.42 (d, J=7.3 Hz, 1H), 6.64 (d, J=8.6 Hz, 1H), 3.99-3.89 (m, 1H), 3.86-1.77 (m, 1H), 3.74-3.56 (m, 1H), 2.98-2.83 (m, 1H), 2.08-1.96 (m, 2H), 1.92-1.54 (m, 3H), 1.47-1.34 (m, 1H)

Example 200

6-(5-(1-methyl-1H-pyrazol-4-yl)-1H-pyrazolo[3,4-c] pyridin-3-yl)-N-(piperidin-4-yl)pyridin-2-amine 200

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl 4-aminopiperidine-1-carboxylate were reacted and the product was deprotected to give 200 as a white solid (5.4% over two steps). $^1$H NMR (400 MHz, MeOD) δ 8.97 (s, 1H), 8.61 (s, 1H), 8.47 (s, 2H), 8.12 (s, 1H), 8.01 (s, 1H), 7.55 (t, J=7.8 Hz, 1H), 7.44 (d, J=7.3 Hz, 1H), 6.57 (d, J=8.2 Hz, 1H), 4.69 (m, 1H), 4.41-4.32 (m, 1H), 3.99 (s, 3H), 3.52-3.43 (m, 2H), 3.12 (dd, J=16.9, 6.7 Hz, 2H), 2.44-2.33 (m, 2H), 1.97-1.85 (m, 2H). LC/MS: m/z 375.1 [M+1]

Example 202

(S)-1-(5-(5-(pyridin-3-yl)-1H-pyrazolo[3,4-c]pyridin-3-yl)pyridin-2-yl)pyrrolidin-3-amine 202

Following the procedures in Example 191, 3-(6-fluoropyridin-3-yl)-5-(pyridin-3-yl)-1-(tetrahydro-2H-pyran-2-yl)-1H-pyrazolo[3,4-c]pyridine was converted to 202. ESI MS m/z=358.1 (M+1). $^1$H NMR (400 MHz, DMSO) δ 9.41 (s, 1H), 9.17 (s, 1H), 8.89 (d, J=2.2 Hz, 1H), 8.62-8.54 (m, 3H), 8.20 (dd, J=8.8, 2.3 Hz, 1H), 7.54-7.46 (m, 1H), 6.58 (d, J=8.8 Hz, 1H), 3.66-3.56 (m, 3H), 3.52-3.44 (m, 1H), 3.19-3.11 (m, 1H), 2.15-2.03 (m, 1H), 1.80-1.70 (m, 1H)

Example 203

(R)-1-(5-(5-(pyridin-3-yl)-1H-pyrazolo[3,4-c]pyridin-3-yl)pyridin-2-yl)pyrrolidin-3-amine 203

Following the procedures in Example 191, 3-(6-fluoropyridin-3-yl)-5-(pyridin-3-yl)-1-(tetrahydro-2H-pyran-2-yl)-1H-pyrazolo[3,4-c]pyridine was converted to 203. ESI MS m/z=358.1 (M+1). $^1$H NMR (400 MHz, DMSO) δ 9.41 (s, 1H), 9.17 (s, 1H), 8.89 (d, J=2.2 Hz, 1H), 8.62-8.52 (m, 3H), 8.20 (dd, J=8.8, 2.3 Hz, 1H), 7.50 (dd, J=7.5, 5.1 Hz, 1H), 6.58 (d, J=8.8 Hz, 1H), 3.67-3.56 (m, 3H), 3.52-3.40 (m, 1H), 3.22-3.10 (m, 1H), 2.16-2.00 (m, 1H), 1.81-1.68 (m, 1H)

Example 204

3-(pyridin-2-yl)-5-(pyridin-3-yl)-1H-pyrazolo[3,4-c] pyridine 204

To a microwave tube was added 3-iodo-5-(pyridin-3-yl)-1H-pyrazolo[3,4-c]pyridine from Example 4 (120 mg, 0.37 mmol), 2-(butyldipentylstannyl)pyridine (168 mg, 0.45 mmol), Pd(PPh)$_3$ (12 mg, 0.015 mmol), LiCl (48 mg, 1.14 mmol), CuI (12 mg, 0.06 mmol) and 1,4-dioxane (0.3 mL). The tube was flushed with nitrogen for 2 minutes and heated in a Biotage microwave at 140° C. for 15 minutes. The solvent was distilled off and the crude product was purified via reverse phase combiflash eluting with 10% to 80% CH$_3$CN in aqueous 0.5% NH$_4$OH solution to afford 204 as a pale red solid (11 mg, 11%). $^1$H NMR (400 MHz, DMSO) $^1$H NMR (500 MHz, DMSO) δ 14.0 (s, 1H), 9.30 (s, 1H), 9.25 (s, 1H), 8.97 (s, 1H), 8.81 (d, J=4.0 Hz, 1H), 8.62-8.61 (m, 1H), 8.45 (d, J=8.5 Hz, 1H), 8.22 (d, J=7.5 Hz, 1H), 7.97-7.94 (m, 1H), 7.55-7.53 (m, 1H), 7.45-7.43 (m, 1H). ESI MS m/z=274 (M+1)

Example 205

3-(2-fluoro-5-methylphenyl)-5-(1-methyl-1H-pyrazol-4-yl)-1H-pyrazolo[3,4-c]pyridine 205

Following the procedures in Example 172, 2-fluoro-5-methylphenylboronic acid and 3-chloro-5-(1-methyl-1H-pyrazol-4-yl)-1-(tetrahydro-2H-pyran-2-yl)-1H-pyrazolo[3,4-c] pyridine were reacted and deprotected to give 205 as a white solid (21.3% over two steps). $^1$H NMR (400 MHz, DMSO) δ (400 MHz, DMSO) δ 13.86 (s, 1H), 9.05 (s, 1H), 8.25 (s, 1H), 7.98 (s, 1H), 7.88 (d, J=2.7 Hz, 1H), 7.63 (d, J=6.3 Hz, 1H), 7.36-7.27 (m, 2H), 3.88 (s, 3H), 2.40 (s, 3H). LC/MS: m/z 308.0 [M+1]

Example 206

(S)-1-(6-(5-(5-fluoropyridin-3-yl)-1H-pyrazolo[3,4-c]pyridin-3-yl)pyridin-2-yl)piperidin-3-amine 206

A solution containing 3-(6-fluoropyridin-2-yl)-5-(5-fluoropyridin-3-yl)-1-(tetrahydro-2H-pyran-2-yl)-1H-pyrazolo[3,4-c]pyridine (0.055 g, 0.14 mmol) and (S)-tert-butyl piperidin-3-ylcarbamate (0.196 g, 0.979 mmol) in Dimethyl sulfoxide (0.840 mL, 11.8 mmol) was heated at 95° C. for 18 h. The reaction was quenched with water and then extracted with EtOAc 2×. The combined organic layer was dried with Na2SO4, filtered and concentrated. The crude product was dried under high vacuum overnight to give tert-butyl (3S)-1-(6-(5-(5-fluoropyridin-3-yl)-1-(tetrahydro-2H-pyran-2-yl)-1H-pyrazolo[3,4-c]pyridin-3-yl)pyridin-2-yl)piperidin-3-ylcarbamate which was dissolved in 1,4-Dioxane (1.50 mL, 19.2 mmol) and treated with 4.0 M of Hydrogen chloride in 1,4-Dioxane (2.50 mL). The reaction was stirred at RT for 18 h. The reaction was concentrated then submitted for rHPLC to give 206 (37.8 mg, 69% yield). ESI MS m/z=390.1 (M+1). $^1$H NMR (400 MHz, DMSO) δ 9.22 (s, 1H), 9.18 (s, 1H), 9.03 (s, 1H), 8.60 (d, J=2.7 Hz, 1H), 8.32 (d, J=10.3 Hz, 1H), 7.66 (t, J=8.0 Hz, 1H), 7.45 (d, J=7.4 Hz, 1H), 6.87 (d, J=8.5 Hz, 1H), 4.37-4.25 (m, 2H), 3.08-2.96 (m, 1H), 2.85-2.75 (m, 2H), 2.00-1.88 (m, 1H), 1.85-1.75 (m, 1H), 1.68-1.56 (m, 1H), 1.42-1.25 (m, 1H)

Example 208

5-(5-fluoropyridin-3-yl)-3-(6-(piperazin-1-yl)pyridin-2-yl)-1H-pyrazolo[3,4-c]pyridine 208

Following the procedures in Example 206, 3-(6-fluoropyridin-2-yl)-5-(5-fluoropyridin-3-yl)-1-(tetrahydro-2H-pyran-2-yl)-1H-pyrazolo[3,4-c]pyridine was converted to 208. ESI MS m/z=376.1 (M+1). $^1$H NMR (400 MHz, DMSO) δ 9.23 (s, 1H), 9.12 (s, 1H), 9.02 (s, 1H), 8.61 (d, J=2.7 Hz, 1H), 8.23 (d, J=10.4 Hz, 1H), 7.69 (t, J=7.9 Hz, 1H), 7.49 (d, J=7.4 Hz, 1H), 6.88 (d, J=8.5 Hz, 1H), 3.67-3.60 (m, 4H), 2.94-2.86 (m, 4H Example 210

(R)-1-(6-(5-(5-fluoropyridin-3-yl)-1H-pyrazolo[3,4-c]pyridin-3-yl)pyridin-2-yl)piperidin-3-amine 210

Following the procedures in Example 206, 3-(6-fluoropyridin-2-yl)-5-(5-fluoropyridin-3-yl)-1-(tetrahydro-2H-pyran-2-yl)-1H-pyrazolo[3,4-c]pyridine was converted to 210. ESI MS m/z=390.1 (M+1). $^1$H NMR (400 MHz, DMSO) δ 9.23 (s, 1H), 9.18 (s, 1H), 9.02 (s, 1H), 8.60 (d, J=2.7 Hz, 1H), 8.32 (d, J=10.4 Hz, 1H), 7.66 (t, J=8.0 Hz, 1H), 7.45 (d, J=7.4 Hz, 1H), 6.87 (d, J=8.5 Hz, 1H), 4.39-4.23 (m, 2H), 3.08-2.98 (m, 1H), 2.86-2.74 (m, 2H), 1.99-1.88 (m, 1H), 1.71-1.65 (m, 1H), 1.62-1.58 (m, 1H), 1.38-1.30 (m, 1H)

Example 212

3-(6-(piperazin-1-yl)pyridin-2-yl)-5-(tetrahydrofuran-3-yl)-1H-pyrazolo[3,4-c]pyridine 212

Following the procedures in Example 206, 3-(6-fluoropyridin-2-yl)-1-(tetrahydro-2H-pyran-2-yl)-5-(tetrahydrofuran-3-yl)-1H-pyrazolo[3,4-c]pyridine was converted to 212. ESI MS m/z=351.1 (M+1). $^1$H NMR (400 MHz, DMSO) δ 9.02 (s, 1H), 8.29 (s, 1H), 7.66 (t, J=7.9 Hz, 1H), 7.46 (d, J=7.4 Hz, 1H), 6.84 (d, J=8.5 Hz, 1H), 4.13 (t, J=7.6 Hz, 1H), 3.99-3.83 (m, 2H), 3.80-3.60 (m, 2H), 3.65-3.60 (m, 4H), 3.00-2.92 (m, 4H), 2.45-2.35 (m, 1H), 2.25-2.15 (m, 1H)

Example 213

5-(1H-imidazol-5-yl)-3-phenyl-1H-pyrazolo[3,4-c]pyridine 213

Following the procedures in Example 204, 1-(tetrahydro-2H-pyran-2-yl)-5-(4,4,5,5-tetramethyl-1,3,2-dioxaborolan-2-yl)-1H-imidazole and 5-bromo-3-phenyl-1-(tetrahydro-2H-pyran-2-yl)-1H-pyrazolo[3,4-c]pyridine were reacted and the product was deprotected to give 213 as a yellow solid (30 mg, 25%) over two steps. $^1$H NMR (400 MHz, DMSO) δ 8.23 (s, 1H), 7.75 (s, 1H), 7.43 (m, 1H), 7.34 (m, 1H), 7.27 (m, 2H), 6.77 (m, 2H), 6.66 (m, 1H). ESI MS m/z=262 (M+1)

Example 214

3-phenyl-5-(pyrazin-2-yl)-1H-pyrazolo[3,4-c]pyridine 214

Following the procedures in Example 204, 2-(4,4,5,5-tetramethyl-1,3,2-dioxaborolan-2-yl)pyrazine and 5-bromo-3-phenyl-1-(tetrahydro-2H-pyran-2-yl)-1H-pyrazolo[3,4-c]pyridine were reacted and the product was deprotected to give 214 as a yellow solid (22 mg, 28%) over two steps. $^1$H NMR (400 MHz, DMSO) δ 9.61 (s, 1H), 9.26 (s, 1H), 8.97 (s, 1H), 8.76 (s, 1H), 8.67 (d, 1H), 8.05 (t, 2H), 7.61 (t, 2H), 7.48 (t, 1H). ESI MS m/z=274 (M+1)

Example 215

3-(1-(piperidin-4-yl)-1H-pyrazol-3-yl)-5-(pyridin-3-yl)-1H-pyrazolo[3,4-c]pyridine 215

Step 1: 5-bromo-3-(1H-pyrazol-3-yl)-1-(tetrahydro-2H-pyran-2-yl)-1H-pyrazolo[3,4-c]pyridine

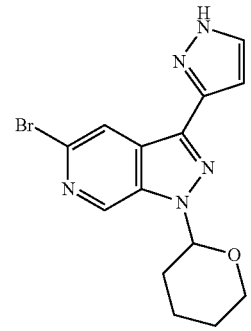 [SMILES: Brc1cc2c(-c3cc[nH]n3)nn(C3CCCCO3)c2cn1]

A microwave reaction vial was charged with 5-bromo-3-iodo-1-(tetrahydro-2H-pyran-2-yl)-1H-pyrazolo[3,4-c]pyridine (408.03 mg, 1.0 mmol), 1H-pyrazol-3-ylboronic acid (117.49 mg, 1.05 mmol), 1,1'-Bis(diphenylphosphino)ferrocenepalladium (II) chloride (81.66 mg, 0.1 mmol), 1.00 M of Potassium acetate in Water (1.5 mL, 1.5 mmol), 1.00 M of Sodium carbonate in Water (1.5 mL, 1.5 mmol), and Acetonitrile (3 mL). The reaction mixture was heated under microwave at 100° C. for 20 minutes. Added another 2 equivalents of 1H-pyrazol-3-ylboronic acid and continue heated under microwave at 100° C. for 20 minutes. The same procedure was repeated 2 more times. The mixture was concentrated and the residue was purified on silica eluted with 0 to 100% Ethyl acetate in Heptane to afford 5-bromo-3-(1H-pyrazol-3-yl)-1-(tetrahydro-2H-pyran-2-yl)-1H-pyrazolo[3,4-c]pyridine as an off-white solid (153.7 mg, 44%).

Step 2: 3-(1H-pyrazol-3-yl)-5-(pyridin-3-yl)-1-(tetrahydro-2H-pyran-2-yl)-1H-pyrazolo[3,4-c]pyridine

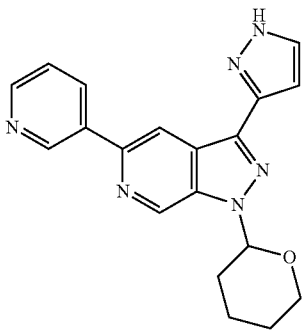 [SMILES: c1cncc(-c2cc3c(-c4cc[nH]n4)nn(C4CCCCO4)c3cn2)c1]

A microwave reaction vials was charged with 5-bromo-3-(1H-pyrazol-3-yl)-1-(tetrahydro-2H-pyran-2-yl)-1H-pyrazolo[3,4-c]pyridine as an off-white solid (153.7 mg 0.44 mmol), 3-Pyridylboronic acid (81.62 mg, 0.66 mmol), 1,1'-Bis(diphenylphosphino)ferrocenepalladium (II) chloride (36.15 mg, 0.044 mmol), 1.00 M of Potassium acetate in Water (0.66 mL, 0.66 mmol), 1.00 M of Sodium carbonate in Water (0.66 mL, 0.66 mmol), and Acetonitrile (3 mL). The reaction mixture was heated under microwave at 130° C. for 20 minutes The mixture was concentrated and the residue was purified on silica eluted with 0 to 7% MeOH in DCM with 1% NH4OH to afford 3-(1H-pyrazol-3-yl)-5-(pyridin-3-yl)-1-(tetrahydro-2H-pyran-2-yl)-1H-pyrazolo[3,4-c]pyridine (73.4 mg, 48%).

Step 3: tert-butyl 4-(3-(5-(pyridin-3-yl)-1-(tetrahydro-2H-pyran-2-yl)-1H-pyrazolo[3,4-c]pyridin-3-yl)-1H-pyrazol-1-yl)piperidine-1-carboxylate

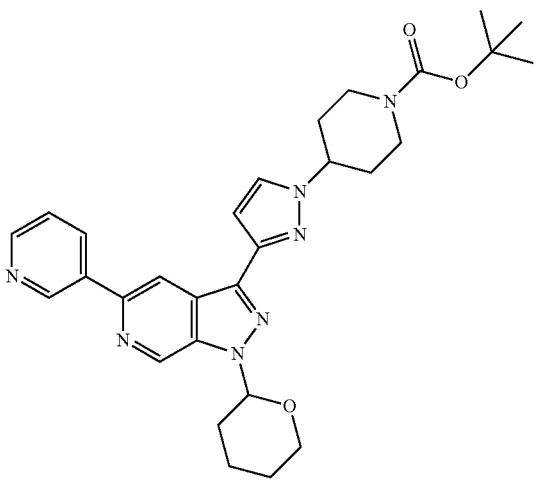 [SMILES: CC(C)(C)OC(=O)N1CCC(n2ccc(-c3nn(C4CCCCO4)c4cnc(-c5cccnc5)cc34)n2)CC1]

A mixture of 3-(1H-pyrazol-3-yl)-5-(pyridin-3-yl)-1-(tetrahydro-2H-pyran-2-yl)-1H-pyrazolo[3,4-c]pyridine (44.0 mg, 0.13 mmol), 1-N—BOC-4-bromopiperidine (100.8 mg, 0.38 mmol), and Cesium Carbonate (124.3 mg, 0.38 mmol) in N,N-Dimethylformamide (5 mL) was heated at 100° C. for 7 days. The mixture was concentrated to afford tert-butyl 4-(3-(5-(pyridin-3-yl)-1-(tetrahydro-2H-pyran-2-yl)-1H-pyrazolo[3,4-c]pyridin-3-yl)-1H-pyrazol-1-yl)piperidine-1-carboxylate, which was used without purification.

Step 4

Tert-butyl 4-(3-(5-(pyridin-3-yl)-1-(tetrahydro-2H-pyran-2-yl)-1H-pyrazolo[3,4-c]pyridin-3-yl)-1H-pyrazol-1-yl)piperidine-1-carboxylate (17.0 mg, 0.032 mmol) in Dioxane (5 mL) was treated with 4.0 M of Hydrogen chloride in 1,4-Dioxane (5 mL) overnight at room temperature. The reaction mixture was concentrated, and the residue was purified by reverse phase HPLC to afford 215 as an off-white solid (1.2 mg, 18%). 1H NMR (400 MHz, DMSO) δ 9.28 (s, 1H), 9.19 (s, 1H), 8.70-8.57 (m, 2H), 8.44 (d, J=7.6 Hz, 1H), 8.30 (s, 1H), 7.94 (s, 1H), 7.59-7.51 (m, 1H), 6.84 (s, 1H), 4.47 (s, 1H), 3.22 (d, J=12.7 Hz, 2H), 2.82 (t, J=12.0 Hz, 2H), 2.15 (d, J=11.5 Hz, 2H), 2.04 (d, J=9.0 Hz, 2H). ESI MS m/z=346.1 (M+1)

Example 216

3-(6-((1S,4S)-2,5-diazabicyclo[2.2.1]heptan-2-yl)pyridin-2-yl)-5-(1-methyl-1H-pyrazol-4-yl)-1H-pyrazolo[3,4-c]pyridine 216

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and 2-(1-trityl-1H-imidazol-4-yl)-ethylamine were reacted. The product was deprotected to give 216 as a white solid (69.7% over two steps). $^1$H NMR (400 MHz, DMSO) δ 9.02 (s, 1H), 8.59 (s, 1H), 8.11 (s, 1H), 7.84 (s, 1H), 7.59 (t, J=7.9 Hz, 1H), 7.36 (d, J=7.4 Hz, 1H), 6.64 (broad s, 1H), 6.50 (d, J=8.2 Hz, 1H), 4.76 (s, 1H), 3.91 (s, 3H), 3.75 (s, 1H), 3.69 (d, J=8.5 Hz, 1H), 3.49-3.32 (m, 2H), 3.00 (s, 2H), 1.89 (d, J=8.5 Hz, 1H), 1.78 (d, J=9.1 Hz, 1H). LC/MS: m/z 373.1 [M+1]

Example 217

N-(2-(1H-imidazol-4-yl)ethyl)-6-(5-(1-methyl-1H-pyrazol-4-yl)-1H-pyrazolo[3,4-c]pyridin-3-yl)pyridin-2-amine 217

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and 2-(1-trityl-1H-imidazol-4-yl)-ethylamine were reacted. The product was deprotected to give 217 as a white solid (37.6% over two steps). $^1$H NMR (400 MHz, DMSO) δ 9.01 (s, 1H), 8.62 (s, 1H), 8.26 (s, 1H), 8.03 (s, 1H), 7.88 (s, 1H), 7.56 (s, 1H), 7.49 (d, J=8.1 Hz, 1H), 7.34 (d, J=7.4 Hz, 1H), 6.86 (s, 1H), 6.80 (s, 1H), 6.49 (d, J=8.3 Hz, 1H), 3.88 (s, 3H), 3.78-3.70 (m, 2H), 2.92 (t, J=7.5 Hz, 2H), 2.54 (s, 1H). LC/MS: m/z 386.1 [M+1]

Example 218

3-(2-fluorophenyl)-5-(1H-imidazol-5-yl)-1H-pyrazolo[3,4-c]pyridine 218

Step 1: 5-bromo-3-(2-fluorophenyl)-1-(tetrahydro-2H-pyran-2-yl)-1H-pyrazolo[3,4-c]pyridine

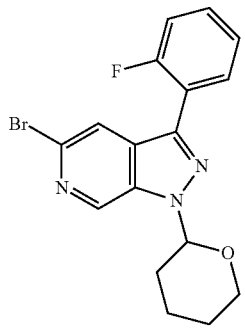 [SMILES: Fc1ccccc1-c1nn(C2CCCCO2)c2cnc(Br)cc12]

To a microwave tube was added 5-bromo-3-iodo-1-(tetrahydro-2H-pyran-2-yl)-1H-pyrazolo[3,4-c]pyridine (300 mg, 0.74 mmol), 2-fluorophenylboronic acid (134 mg, 0.96 mmol), Pd(dppf)Cl$_2$(60 mg, 0.07 mmol), sodium carbonate (314 mg, 2.96 mmol), 1,2-dimethoxyethane (3 mL), ethanol (0.3 mL) and water (0.3 mL). The tube was flushed with nitrogen for 2 minutes and heated in a Biotage microwave at 145° C. for 1 hour. The solvent was distilled off and the crude product was purified via flash chromatography eluting with 20% to 95% ethyl acetate in petroleum to afford 5-bromo-3-(2-fluorophenyl)-1-(tetrahydro-2H-pyran-2-yl)-1H-pyrazolo[3,4-c]pyridine as a yellow oil (105 mg, 38%). ESI MS m/z=377 (M+1).

Step 2: 3-(2-fluorophenyl)-1-(tetrahydro-2H-pyran-2-yl)-5-(1-(tetrahydro-2H-pyran-2-yl)-1H-imidazol-5-yl)-1H-pyrazolo[3,4-c]pyridine

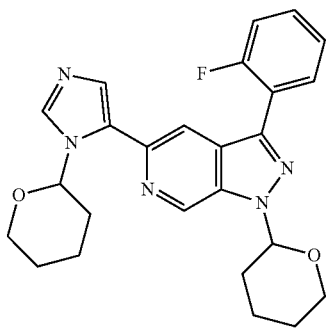 [SMILES: Fc1ccccc1-c1nn(C2CCCCO2)c2cnc(-c3cncn3C3CCCCO3)cc12]

To a 100 mL of round bottom flask was added 5-bromo-3-(2-fluorophenyl)-1-(tetrahydro-2H-pyran-2-yl)-1H-pyrazolo[3,4-c]pyridine (150 mg, 0.40 mmol), 1-(tetrahydro-2H-pyran-2-yl)-5-(4,4,5,5-tetramethyl-1,3,2-dioxaborolan-2-yl)-1H-imidazole (222 mg, 0.80 mmol), Pd(PPh$_3$)$_4$(33 mg, 0.04 mmol), CsF (152 mg, 1 mmol), CuI (8 mg, 0.04 mmol) and DMF (6 mL). The reaction mixture was heated at 90° C. under nitrogen for overnight. The resulting mixture was poured into 50 mL of water and extracted with ethyl acetate (50 mL×3). The combined organic layers were washed with brine, dried over anhydrous Na$_2$SO$_4$, filtered and concentrated. The residue was purified via flash chromatography eluting with 5% to 10% CH$_3$OH in CH$_2$Cl$_2$ to afford 3-(2-fluorophenyl)-1-(tetrahydro-2H-pyran-2-yl)-5-(1-(tetrahydro-2H-pyran-2-yl)-1H-imidazol-5-yl)-1H-pyrazolo[3,4-c]pyridine as a brown oil (100 mg, 84%). ESI MS m/z=448 (M+1).

Step 3

In a 50 mL round bottom flask was added 3-(2-fluorophenyl)-1-(tetrahydro-2H-pyran-2-yl)-5-(1-(tetrahydro-2H-pyran-2-yl)-1H-imidazol-5-yl)-1H-pyrazolo[3,4-c]pyridine (150 mg, 0.33 mmol) and 4 N HCl— dioxane (5 mL). The mixture was stirred at 25° C. for 2 h. The solvent was distilled off. The crude product was purified via reverse phase HPLC eluting with 35% CH$_3$CN in aqueous 10 mmol NH$_4$HCO$_3$ solution to afford 218 as a white solid (20 mg, 21%). $^1$H NMR (500 MHz, DMSO) δ 13.93 (s, 1H), 12.21 (s, 1H), 9.05 (s, 1H), 8.20 (s, 1H), 7.86 (t, J=7.0, 1H), 7.71 (s, 1H), 7.62 (s, 1H), 7.56-7.54 (m, 1H), 7.46 (t, J=10.0, 1H), 7.41 (t, J=7.5, 1H). ESI MS m/z=280 (M+1)

Example 219

3-(2-fluorophenyl)-5-(pyrazin-2-yl)-1H-pyrazolo[3,4-c]pyridine 219

Following the procedures as described in Example 218, and starting with 3-(2-fluorophenyl)-5-(pyrazin-2-yl)-1-(tetrahydro-2H-pyran-2-yl)-1H-pyrazolo[3,4-c]pyridine, 219 was obtained as a pale red solid (16 mg, 20%) over two steps. $^1$H NMR (500 MHz, DMSO) δ 9.60 (s, 1H), 9.27 (s, 1H), 8.77 (s, 1H), 8.73 (s, 1H), 8.67 (s, 1H), 7.93-7.90 (m, 1H), 7.60-7.56 (m, 1H), 7.49 (t, J=8.0, 1H), 7.43 (t, J=8.0, 1H). ESI MS m/z=292 (M+1)

Example 222

(R)-1-(3-(5-(1-methyl-1H-pyrazol-4-yl)-1H-pyrazolo[3,4-c]pyridin-3-yl)phenyl)piperidin-3-amine 222

Step 1: tert-butyl (3R)-1-(3-(5-(1-methyl-1H-pyrazol-4-yl)-1-(tetrahydro-2H-pyran-2-yl)-1H-pyrazolo[3,4-c]pyridin-3-yl)phenyl)piperidin-3-ylcarbamate

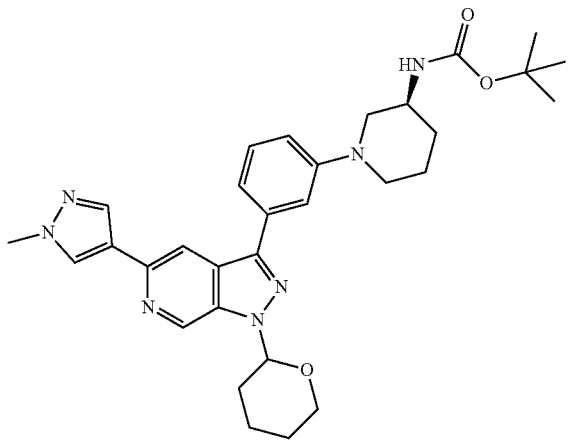 [SMILES: Cn1cc(-c2cc3c(-c4cccc(N5CCC[C@H](NC(=O)OC(C)(C)C)C5)c4)nn(C4CCCCO4)c3cn2)cn1]

271

Following the Suzuki coupling procedure in Example 172, (R)-tert-butyl 1-(3-(4,4,5,5-tetramethyl-1,3,2-dioxaborolan-2-yl)phenyl)piperidin-3-ylcarbamate and 3-chloro-5-(1-methyl-1H-pyrazol-4-yl)-1-(tetrahydro-2H-pyran-2-yl)-1H-pyrazolo[3,4-c]pyridine were reacted to give tert-butyl (3R)-1-(3-(5-(1-methyl-1H-pyrazol-4-yl)-1-(tetrahydro-2H-pyran-2-yl)-1H-pyrazo-lo[3,4-c]pyridin-3-yl)phenyl)piperidin-3-ylcarbamate as a solid (60%). $^{1}$H NMR (400 MHz, CDCl$_3$) δ 9.12 (s, 1H), 7.97 (s, 1H), 7.95 (s, 1H), 7.93 (s, 1H), 7.34 (t, J=7.8 Hz, 1H), 7.26 (s, 1H), 7.19 (s, 1H), 6.73 (d, J=8.4 Hz, 1H), 5.90-5.83 (m, 1H), 4.09-4.00 (m, 2H), 3.97 (s, 3H), 3.88-3.76 (m, 2H), 3.67 (s, 1H), 3.52 (s, 1H), 3.17 (s, 1H), 3.03 (s, 1H), 2.64-2.52 (m, 1H), 2.17 (d, J=10.1 Hz, 2H), 2.09-1.99 (m, 1H), 1.84-1.70 (m, 5H), 1.65-1.54 (m, 1H), 1.41 (s, 9H). LC/MS: m/z 558.2 [M+1].

Step 2

Following the procedure in Example 189, tert-butyl (3R)-1-(3-(5-(1-methyl-1H-pyrazol-4-yl)-1-(tetrahydro-2H-pyran-2-yl)-1H-pyra-zolo[3,4-c]pyridin-3-yl)phenyl)piperidin-3-ylcarbamate was deprotected to give 222 as a solid (55.4%). $^{1}$H NMR (400 MHz, DMSO) δ 9.02 (s, 1H), 8.31 (s, 1H), 8.28 (s, 1H), 8.13 (s, 1H), 8.05 (s, 1H), 7.34-7.21 (m, 3H), 6.70-6.65 (m, 1H), 5.74 (d, J=7.7 Hz, 1H), 3.90 (s, 3H), 3.24 (d, J=11.4 Hz, 1H), 2.96 (d, J=12.3 Hz, 1H), 2.62 (t, J=11.4 Hz, 1H), 2.45 (d, J=10.7 Hz, 1H), 2.05-1.96 (m, 1H), 1.82-1.73 (m, 1H), 1.63-1.39 (m, 2H); 2 protons not seen. LC/MS: m/z 374.1 [M+1]

Example 223

1-methyl-4-(3-(6-(piperazin-1-yl)pyridin-2-yl)-1H-pyrazolo[3,4-c]pyridin-5-yl)piperazin-2-one 223

Following the procedure of Example 224, tert-butyl (3S)-1-(6-bromo-1-(tetrahydro-2H-pyran-2-yl)-1H-pyrazolo[3,4-c]pyridin-3-yl)pyridin-2-yl)piperidin-3-ylcarbamate and 1-methylpiperazin-2-one were reacted and deprotected by the procedure of Example 229. The mixture was purified by lyophilization from water and trituration of the crude product with cold methanol. The solid material was collected by filtration to afford 52 mg (28%) of 223 over two steps. ESI MS m/z 393.2 (M+1). $^{1}$H NMR (400 MHz, DMSO) δ 13.55 (s, 1H), 9.07 (s, 2H), 8.81 (s, 1H), 7.73 (t, J=8.0 Hz, 1H), 7.60 (s, 1H), 7.52 (d, J=7.5 Hz, 1H), 6.92 (d, J=8.5 Hz, 1H), 3.95 (s, 2H), 3.88 (m, 6H), 3.48-3.44 (m, 2H), 3.31 (s, 4H), 2.91 (s, 3H)

Example 224

1-(3-(6-(piperazin-1-yl)pyridin-2-yl)-1H-pyrazolo[3,4-c]pyridin-5-yl)urea 224

Step 1: tert-Butyl 4-(6-(5-(3-tert-butylureido)-1-(tetrahydro-2H-pyran-2-yl)-1H-pyrazolo[3,4-c]pyridin-3-yl)pyridin-2-yl)piperazine-1-carboxylate

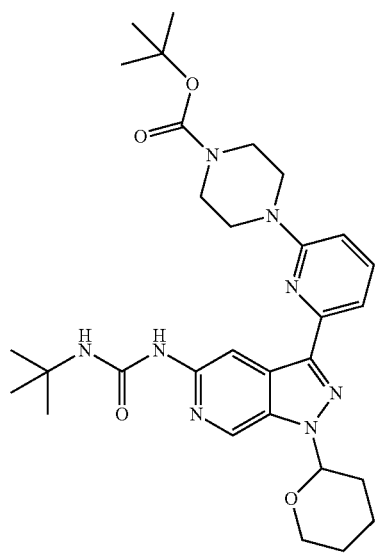 [SMILES: CC(C)(C)NC(=O)Nc1cc2c(-c3cccc(N4CCN(C(=O)OC(C)(C)C)CC4)n3)nn(C3CCCCO3)c2cn1]

A mixture of 109 mg (0.2 mmol) of tert-butyl 4-(6-(5-bromo-1-(tetrahydro-2H-pyran-2-yl)-1H-pyrazolo[3,4-c]pyridin-3-yl)pyridin-2-yl)piperazine-1-carboxylate, 46.5 mg (0.40 mmol) of (1,1-dimethylethyl)urea, 23 mg (0.040 mmol) of 4,5-bis(diphenylphosphino)-9,9-dimethylxantene and 130 mg (0.40 mmol) of cesium carbonate in 1 ml of dioxane was degassed and heated for at 95° C. for 30 min. The mixture was diluted with 10 ml of dichloromethane and filtered through celite. The filtrate was concentrated, the title compound was purified via silica gel chromatography using a gradient of ethyl acetate in heptane to afford 86 mg (74%). ESI MS m/z 579.2 (M+1) of tert-Butyl 4-(6-(5-(3-tert-butylureido)-1-(tetrahydro-2H-pyran-2-yl)-1H-pyrazolo[3,4-c]pyridin-3-yl)pyridin-2-yl)piperazine-1-carboxylate.

Step 2 tert-Butyl 4-(6-(5-(3-tert-butylureido)-1-(tetrahydro-2H-pyran-2-yl)-1H-pyrazolo[3,4-c]pyridin-3-yl)pyridin-2-yl)piperazine-1-carboxylate was deprotected by the procedure of Example 229 and purified via reverse phase HPLC using a gradient of MeOH in water with 0.1% NH$_4$OH to afford 17 mg (25%) of 224 over two steps. ESI MS m/z 339.1 (M+1). 1H NMR (400 MHz, DMSO): 13.71-13.30 (s, 1H), 8.93 (s, 1H), 8.74 (d, J=10.4 Hz, 2H), 7.52 (m, 1H), 7.41 (d, J=7.4 Hz, 1H), 6.76 (d, J=8.4 Hz, 1H), 6.34 (s, 2H), 3.57 (s, 2H), 2.87 (d, J=4.7 Hz, 2H)

Example 225

3-cyclopentenyl-5-(pyridin-3-yl)-1H-pyrazolo[3,4-c]pyridine 225

Step 1: 3-Cyclopentenyl-5-(pyridin-3-yl)-1-(tetrahydro-2H-pyran-2-yl)-1H-pyrazolo[3,4-c]pyridine

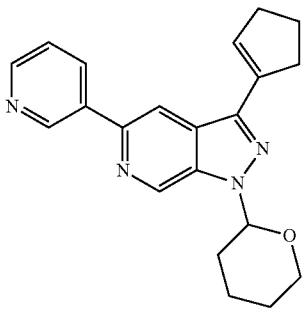 [SMILES: C1=C(c2nn(C3CCCCO3)c3cnc(-c4cccnc4)cc23)CCC1]

Following the Suzuki coupling procedure of Example 159, 5-bromo-3-iodo-1-(tetrahydro-2H-pyran-2-yl)-1H-pyrazolo[3,4-c]pyridine and 2-cyclopentenyl-4,4,5,5-tetramethyl-1,3,2-dioxaborolane were reacted. The product was reacted with 3-pyridineboronic acid pinacol ester by the Suzuki coupling procedure of Example 10 and the mixture was purified via silica gel chromatography using a gradient of ethyl acetate in heptane to afford 106 mg (61%) of 3-Cyclopentenyl-5-(pyridin-3-yl)-1-(tetrahydro-2H-pyran-2-yl)-1H-pyrazolo[3,4-c]pyridine over two steps. ESI MS m/z 347.3 (M+1).

Step 2

A mixture of 35 mg (0.10 mmol) of 3-cyclopentenyl-5-(pyridin-3-yl)-1-(tetrahydro-2H-pyran-2-yl)-1H-pyrazolo[3,4-c]pyridine in 4 ml of trifluoroacetic acid was stirred for 6 hours. The mixture was concentrated in vacuum, the residue partitioned between saturated aqueous solution of NaHCO3 and ethyl acetate. The organic extracts were washed with water, brine, dried over MgSO4 and concentrated. The residue was purified via reverse phase HPLC using a gradient of MeOH in water with 0.1% NH4OH to afford 10 mg (38%) of 225. ESI MS m/z 263.0 (M+1). 1H NMR (400 MHz, DMSO): 13.59 (s, 1H), 9.39 (s, 1H), 9.14 (s, 1H), 8.53-8.600 (m, 3H), 7.50 (dd, J=7.9, 4.8 Hz, 1H), 6.88 (s, 1H), 2.91 (t, J=6.6 Hz, 2H), 2.64 (s, 2H), 2.04-1.94 (m, 2H)

Example 226

1-(6-(5-(1-methyl-1H-pyrazol-4-yl)-1H-pyrazolo[3,4-c]pyridin-3-yl)pyridin-2-yl)azepan-3-amine 226

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl azepan-3-ylcarbamate were reacted. The product was deprotected to give 226 as a white solid (58.6% over two steps). 1H NMR (400 MHz, DMSO) δ 9.04 (s, 1H), 8.52 (s, 1H), 8.32 (s, 1H), 8.28 (s, 1H), 7.94 (s, 1H), 7.64 (t, J=7.9 Hz, 1H), 7.43 (d, J=7.4 Hz, 1H), 6.75 (d, J=8.5 Hz, 1H), 4.18 (d, J=12 Hz, 1H), 4.13-4.06 (m, 1H), 3.90 (s, 3H), 3.54 (m, 1H), 3.36 (d, J=8.8 Hz, 1H), 3.32 (s, 1H), 2.05-1.95 (m, 1H), 1.84-1.69 (m, 3H), 1.53-1.41 (m, 1H), 1.40-1.27 (m, 1H); 2 protons not seen. LC/MS: m/z 389.2 [M+1]

Example 227

(S)-1-(6-(5-(1-methyl-1H-pyrazol-4-yl)-1H-pyrazolo[3,4-c]pyridin-3-yl)pyridin-2-yl)azepan-4-amine 227

Step 1: benzyl (4S)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-ylcarbamate Following the procedure of Example 189, (S)-benzyl azepan-4-ylcarbamate and 3-(6-fluoropyridin-2-yl)-5-(1-methyl-1H-pyrazol-4-yl)-1-(tetrahydro-2H-pyran-2-yl)-1H-pyrazolo[3,4-c]pyridine were reacted to give benzyl (4S)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-ylcarbamate as a solid (73.4%). LC/MS: m/z 607.3 [M+1].

Step 2

To a solution of benzyl (4S)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-ylcarbamate (70.0 mg, 0.13 mmol) in DCM (5.0 mL) at −10° C. was added dropwise 1 M of boron tribromide in DCM (0.33 mL, 0.33 mmol), and the reaction mixture was slowly warmed to room temperature (RT) and stirred at RT under N2 for 16 h. The reaction mixture was diluted into ethyl acetate and water. The organic layer was washed with aqueous saturated sodium bicarbonate solution, water and brine, dried over Na2SO4, filtered, and concentrated under reduced pressure. The crude was redissolved in DMSO (1 mL) and was purified by reverse phase HPLC to give 227 as a white solid (4.3 mg, 8.3%). 1H NMR (400 MHz, DMSO) δ 9.03 (s, 1H), 8.55 (s, 1H), 8.11 (s, 1H), 7.83 (s, 1H), 7.60 (t. J=7.8 Hz, 1H), 7.37 (d, J=7.1 Hz, 1H), 6.61 (d, J=8.4 Hz, 1H), 3.91 (s, 3H), 3.85-3.75 (m, 1H), 3.74-3.58 (m, 2H), 3.33-3.40 (m, 1H), 2.95-2.85 (m, 1H), 2.12-1.93 (m, 2H), 1.86-1.58 (m, 3H), 1.56-1.33 (m, 2H); 2 protons not seen. LC/MS: m/z 389.4 [M+1]

Example 228

3-cyclopentyl-5-(pyridin-3-yl)-1H-pyrazolo[3,4-c]pyridine 228

Step 1: 3-Cyclopentyl-5-(pyridin-3-yl)-1-(tetrahydro-2H-pyran-2-yl)-1H-pyrazolo[3,4-c]pyridine

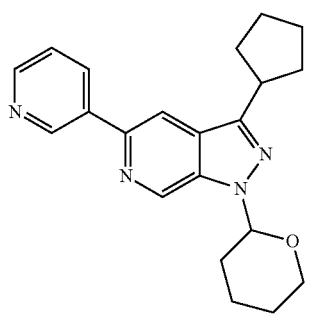 [SMILES: c1cncc(-c2cc3c(C4CCCC4)nn(C4CCCCO4)c3cn2)c1]

A mixture of 42 mg (0.12 mmol) of 3-cyclopentenyl-5-(pyridin-3-yl)-1-(tetrahydro-2H-pyran-2-yl)-1H-pyrazolo[3,4-c]pyridine, 2.0 ml (21 mmol) of 1,4-cyclohexadiene and 100 mg of 10% palladium on carbon in 10 ml of ethanol was heated to reflux for 48 hours, during which 1,4-cyclohexadiene was added incrementally. The mixture was filtered through celite, and the filtrate was concentrated to afford 31 mg (76%) of 3-Cyclopentyl-5-(pyridin-3-yl)-1-(tetrahydro-2H-pyran-2-yl)-1H-pyrazolo[3,4-c]pyridine. ESI MS m/z 349.2 (M+1).

Step 2

3-Cyclopentyl-5-(pyridin-3-yl)-1-(tetrahydro-2H-pyran-2-yl)-1H-pyrazolo[3,4-c]pyridine was deprotected by the procedure of Example 229 and purified by triturating with ethyl ether. The product was collected by filtration to afford 9 mg (30%) of 228. ESI MS m/z 265.0 (M+1). 1H NMR (400 MHz, DMSO): 13.24 (s, 1H), 9.33 (s, 1H), 9.08 (s, 1H), 8.56 (d, J=4.2 Hz, 1H), 8.48 (d, J=8.0 Hz, 1H), 8.40 (s, 1H), 7.50 (m, 1H), 3.54 (dd, J=16.4, 8.2 Hz, 1H), 2.16 (m, 2H), 2.00-1.63 (m, 6H)

Example 229

4-amino-1-(6-(5-(pyridin-3-yl)-1H-pyrazolo[3,4-c]pyridin-3-yl)pyridin-2-yl)piperidine-4-carboxamide 229

Step 1: Methyl 4-(tert-butoxycarbonylamino)-1-(6-(5-(pyridin-3-yl)-1-(tetrahydro-2H-pyran-2-yl)-1H-pyrazolo[3,4-c]pyridin-3-yl)pyridin-2-yl)piperidine-4-carboxylate

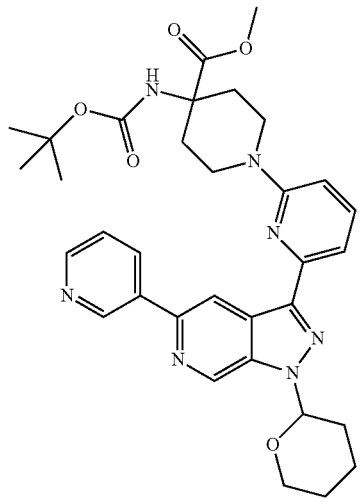 [SMILES: COC(=O)C1(NC(=O)OC(C)(C)C)CCN(c2cccc(-c3nn(C4CCCCO4)c4cnc(-c5cccnc5)cc34)n2)CC1]

Following the procedures of Example 144, and starting with 3-(6-Fluoropyridin-2-yl)-5-(pyridin-3-yl)-1-(tetrahydro-2H-pyran-2-yl)-1H-pyrazolo[3,4-c]pyridine and methyl 4-(tert-butoxycarbonylamino)piperidine-4-carboxylate were reacted and purified via silica gel chromatography using a gradient of EtOAc in heptane to afford 241 mg (67%) of Methyl 4-(tert-butoxycarbonylamino)-1-(6-(5-(pyridin-3- yl)-1-(tetrahydro-2H-pyran-2-yl)-1H-pyrazolo[3,4-c]pyridin-3-yl)pyridin-2-yl)piperidine-4-carboxylate. ESI MS m/z 614.2 (M+1).

Step 2: 4-(tert-Butoxycarbonylamino)-1-(6-(5-(pyridin-3-yl)-1-(tetrahydro-2H-pyran-2-yl)-1H-pyrazolo[3,4-c]pyridin-3-yl)pyridin-2-yl)piperidine-4-carboxylic acid

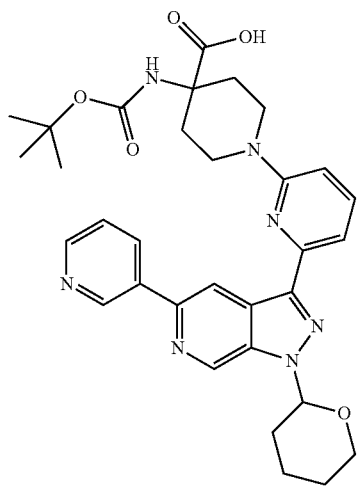 [SMILES: CC(C)(C)OC(=O)NC1(C(=O)O)CCN(c2cccc(-c3nn(C4CCCCO4)c4cnc(-c5cccnc5)cc34)n2)CC1]

A mixture of 240 mg (0.39 mmol) of methyl 4-(tert-butoxycarbonylamino)-1-(6-(5-(pyridin-3-yl)-1-(tetrahydro-2H-pyran-2-yl)-1H-pyrazolo[3,4-c]pyridin-3-yl)pyridin-2-yl)piperidine-4-carboxylate and 3 ml of 1 M aqueous solution of lithium hydroxide in 20 ml of methanol and 10 ml of tetrahydrofuran was stirred for 18 hours at room temperature and 2 hours at 60° C. The mixture was concentrated in vacuum, neutralized to pH 5 by careful addition of 1 N aqueous HCl and extracted with ethyl acetate. The organic extracts were washed with water, brine, dried over MgSO4 and concentrated to afford 150 mg (43%) of 4-(tert-Butoxycarbonylamino)-1-(6-(5-(pyridin-3-yl)-1-(tetrahydro-2H-pyran-2-yl)-1H-pyrazolo[3,4-c]pyridin-3-yl)pyridin-2-yl)piperidine-4-carboxylic acid over two steps. ESI MS m/z 600.2 (M+1).

Step 3: tert-Butyl 4-carbamoyl-1-(6-(5-(pyridin-3-yl)-1-(tetrahydro-2H-pyran-2-yl)-1H-pyrazolo[3,4-c]pyridin-3-yl)pyridin-2-yl)piperidin-4-ylcarbamate

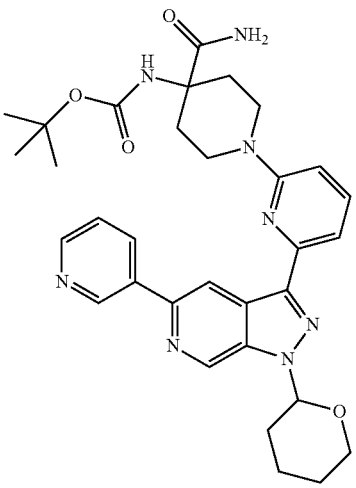 [SMILES: CC(C)(C)OC(=O)NC1(C(N)=O)CCN(c2cccc(-c3nn(C4CCCCO4)c4cnc(-c5cccnc5)cc34)n2)CC1]

N,N,N',N'-tetramethyl-O-(7-azabenzotriazol-1-yl)uronium hexafluorophosphate 45.6 mg, 0.120 mmol) was added to a mixture of 4-(tert-butoxycarbonylamino)-1-(6-(5-(pyridin-3-yl)-1-(tetrahydro-2H-pyran-2-yl)-1H-pyrazolo[3,4-c]pyridin-3-yl)pyridin-2-yl)piperidine-4-carboxylic acid (60.0 mg, 0.100 mmol), ammonium chloride 21 mg (0.40 mmol) and N,N-Diisopropylethylamine (0.087 ml, 0.50 mmol) in 2 ml of N,N-dimethylformamide. The mixture was stirred for 18 hours and concentrated. The residue was partitioned between ethyl acetate and 1% of aqueous citric acid. The organic extracts were washed with water, 5% aqueous solution of NaHCO3, brine, dried over MgSO4 and concentrated to give tert-Butyl 4-carbamoyl-1-(6-(5-(pyridin-3-yl)-1-(tetrahydro-2H-pyran-2-yl)-1H-pyrazolo[3,4-c]pyridin-3-yl)pyridin-2-yl)piperidin-4-ylcarbamate. Yield 47 mg (78%). ESI MS m/z 599.2 (M+1).

Step 4

A mixture of 45 mg (0.08 mmol) of tert-butyl 4-carbamoyl-1-(6-(5-(pyridin-3-yl)-1-(tetrahydro-2H-pyran-2-yl)-1H-pyrazolo[3,4-c]pyridin-3-yl)pyridin-2-yl)piperidin-4-ylcarbamate in 3 ml of methanol and 12 ml of 4 N solution of HCl in dioxane was stirred for 18 hours. The mixture was concentrated in vacuum, the residue purified via reverse phase HPLC using a gradient of MeCN in water with 0.1% HCOOH to afford 20 mg (43%) of 229. ESI MS m/z 415.2 (M+1). 1H NMR (400 MHz, DMSO): 9.22 (d, J=5.7 Hz, 2H), 8.94 (s, 1H), 8.60 (d, J=4.6 Hz, 1H), 8.40-8.32 (m, 4H), 7.67 (t, J=7.9 Hz, 1H), 7.54 (dd, J=8.0, 4.8 Hz, 1H), 7.46 (d, J=7.4 Hz, 1H), 6.95 (s, 1H), 6.90 (d, J=8.5 Hz, 1H), 4.20 (d, J=13.2 Hz, 1H), 3.50 (t, J=11.4 Hz, 1H), 2.06 (td, J=13.0, 4.2 Hz, 1H), 1.48 (d, J=13.2 Hz, 1H).

Example 232

3-(1-methyl-1H-pyrazol-3-yl)-5-(pyridin-3-yl)-1H-pyrazolo[3,4-c]pyridine 232

Step 1: 3-(1-methyl-1H-pyrazol-3-yl)-5-(pyridin-3-yl)-1-((2-(trimethylsilyl)ethoxy)methyl)-1H-pyrazolo[3,4-c]pyridine

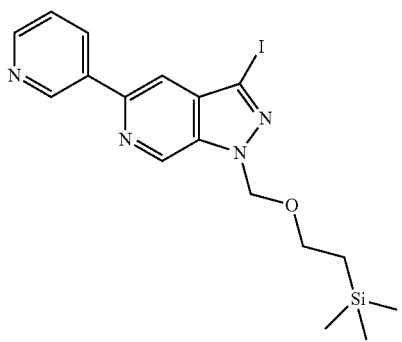 [SMILES: C[Si](C)(C)CCOCn1nc(I)c2cc(-c3cccnc3)ncc21]

In a microwave reaction vials was charged with 3-iodo-5-(pyridin-3-yl)-1-((2-(trimethylsilyl)ethoxy)methyl)-1H-pyrazolo[3,4-c]pyridine (49.10 mg, 0.11 mmol), 1-methyl-3-(4,4,5,5-tetramethyl-1,3,2-dioxaborolan-2-yl)-1H-pyrazole (33.19 mg, 0.16 mmol), 1,1'-Bis(diphenylphosphino)ferrocenepalladium (II) chloride (8.68 mg, 0.011 mmol), 1.00 M of Potassium acetate in Water (0.16 mL, 0.16 mmol), 1.00 M of Sodium carbonate in Water (0.16 mL, 0.16 mmol), and Acetonitrile (3 mL). The reaction mixture was heated under microwave at 150° C. for 5 minutes. The mixture was concentrated to afford 3-(1-methyl-1H-pyrazol-3-yl)-5-(pyridin-3-yl)-1-((2-(trimethylsilyl)ethoxy)methyl)-1H-pyrazolo[3,4-c]pyridine, which was used without purification.

Step 2

A solution of 3-(1-methyl-1H-pyrazol-3-yl)-5-(pyridin-3-yl)-1-((2-(trimethylsilyl)ethoxy)methyl)-1H-pyrazolo[3,4-c]pyridine (43.22 mg, 0.1063 mmol) in Dioxane (5 mL) was treated with 4.0 M of Hydrogen chloride in 1,4-Dioxane (5 mL) overnight at room temperature. The reaction mixture was concentrated, and the residue was purified by reverse phase HPLC to afford 232 as an off-white solid (23.7 mg, 81%). 1H NMR (400 MHz, DMSO) δ 13.74 (s, 1H), 9.33 (s, 1H), 9.19 (s, 1H), 8.67 (d, J=11.2 Hz, 2H), 8.56 (d, J=7.9 Hz, 1H), 7.85 (s, 1H), 7.63 (s, 1H), 6.82 (s, 1H), 4.01 (s, 3H). ESI MS m/z=277.0 (M+1)

Example 234

5-(1-methyl-1H-pyrazol-4-yl)-3-(6-(piperazin-1-yl)pyridin-2-yl)-1H-pyrazolo[3,4-c]pyridine 234

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl 1-piperazinecarboxylate were reacted. The product was deprotected to give 234 as a white solid (61% over two steps). 1H NMR (400 MHz, DMSO) δ 9.03 (s, 1H), 8.53 (s, 1H), 8.11 (s, 1H), 7.82 (s, 1H), 7.65 (t, J=7.9 Hz, 1H), 7.45 (d, J=7.2 Hz, 1H), 6.83 (d, J=8.5 Hz, 1H), 3.91 (s, 3H), 3.63 (s, 4H), 2.94 (s, 4H); two protons not seen. LC/MS: m/z 361.1 [M+1]

Example 235

2-(3-(6-(piperazin-1-yl)pyridin-2-yl)-1H-pyrazolo[3,4-c]pyridin-5-yl)acetonitrile 235

Step 1: tert-Butyl 4-(6-(5-(cyanomethyl)-1-(tetrahydro-2H-pyran-2-yl)-1H-pyrazolo[3,4-c]pyridin-3-yl)pyridin-2-yl)piperazine-1-carboxylate

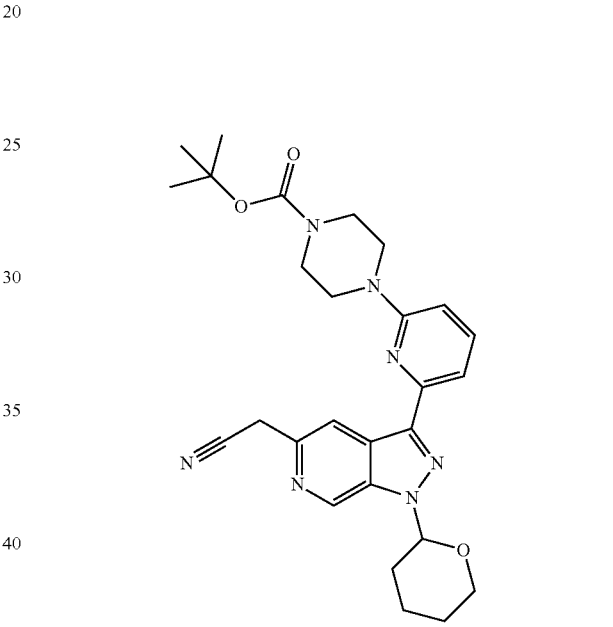

A solution of 0.940 mL of 1.6 M of n-Butyllithium in hexane was added dropwise to a solution of 0.102 mL, (1.95 mmol) of acetonitrile in tetrahydrofuran at −78° C. The mixture was stirred for 30 min and a solution of 272 mg (0.500 mmol) of 4-{6-[5-bromo-1-(tetrahydro-pyran-2-yl)-1H-pyrazolo[3,4-c]pyridin-3-yl]-pyridin-2-yl}-piperazine-1-carboxylic acid tert-butyl ester was added. The brown mixture was stirred for 30 min at −50° C. and 2 ml of saturated aqueous NH4Cl was added. The mixture was allowed to warm to room temperature and extracted with ethyl acetate. The organic extracts were washed with water, brine, dried over MgSO4 and concentrated. The residue was purified via silica gel chromatography using a gradient of ethyl acetate in heptane to afford 44 mg (17%) of tert-Butyl 4-(6-(5-(cyanomethyl)-1-(tetrahydro-2H-pyran-2-yl)-1H-pyrazolo[3,4-c]pyridin-3-yl)pyridin-2-yl)piperazine-1-carboxylate. ESI MS m/z 504.2 (M+1).

Step 2: tert-Butyl 4-(6-(5-(cyanomethyl)-1-(tetrahydro-2H-pyran-2-yl)-1H-pyrazolo[3,4-c]pyridin-3-yl)pyridin-2-yl)piperazine-1-carboxylate was deprotected following the procedure of Example 225 and purified via reverse phase HPLC using a gradient of MeOH in water with 0.1% NH$_4$OH to afford 10.4 mg (6.5%) of 235 over two steps. ESI MS m/z 320.1 (M+1). $^1$H NMR (400 MHz, DMSO) δ 13.34 (s, 1H), 7.62 (dd, J=8.4, 4.1 Hz, 1H), 7.04 (d, J=7.2 Hz, 1H), 6.98 (d, J=9.1 Hz, 1H), 6.79 (d, J=8.6 Hz, 1H), 5.98 (s, 1H), 3.63 (s, 2H), 2.92 (s, 2H)

Example 236

4-amino-N-methyl-1-(6-(5-(pyridin-3-yl)-1H-pyrazolo[3,4-c]pyridin-3-yl)pyridin-2-yl)piperidine-4-carboxamide 236

Following the procedures of Example 229, and starting with 4-(tert-butoxycarbonylamino)-1-(6-(5-(pyridin-3-yl)-1-(tetrahydro-2H-pyran-2-yl)-1H-pyrazolo[3,4-c]pyridin-3-yl)pyridin-2-yl)piperidine-4-carboxylic acid and methylamine, were reacted and purified via reverse phase HPLC using a gradient of MeCN in water with 0.1% HCOOH to afford 19 mg (24%) of 236 over two steps. ESI MS m/z 429.2 (M+1). 1H NMR (400 MHz, DMSO): 13.95 (s, 1H), 9.22 (d, J=8.4 Hz, 2H), 8.92 (s, 1H), 8.61 (s, 1H), 8.41 (d, J=7.6 Hz, 1H), 8.28 (s, 1H), 8.13 (s, 1H), 7.72 (t, J=7.9 Hz, 1H), 7.52 (d, J=7.6 Hz, 2H), 6.96 (d, J=8.3 Hz, 1H), 6.49 (s, 1H), 4.27 (d, J=13.0 Hz, 2H), 3.53 (t, J=12.5 Hz, 2H), 2.67 (s, 3H), 2.29 (m, 2H), 1.87-1.73 (m, 2H).

Example 237

(R)-2-(1-(6-(5-(pyridin-3-yl)-1H-pyrazolo[3,4-c]pyridin-3-yl)pyridin-2-yl)piperidin-3-yl)ethanamine 237 and Example 242 (S)-2-(1-(6-(5-(pyridin-3-yl)-1H-pyrazolo[3,4-c]pyridin-3-yl)pyridin-2-yl)piperidin-3-yl)ethanamine 242

Following the procedures of Example 149, and starting with 3-(6-fluoropyridin-2-yl)-5-(pyridin-3-yl)-1-(tetrahydro-2H-pyran-2-yl)-1H-pyrazolo[3,4-c]pyridine and racemic tert-butyl 2-(piperidin-3-yl)ethylcarbamate, 237 and 242 were obtained and purified via reverse phase HPLC using a gradient of MeOH in water with 0.1% NH$_4$OH followed by SFC separation of the enantiomers to afford 27 mg (14%) and 23 mg (12%).

ESI MS m/z 400.2 (M+1). 1H NMR (400 MHz, DMSO): 9.24 (d, J=8.8 Hz, 2H), 8.96 (s, 1H), 8.61 (s, 1H), 8.42 (d, J=8.2 Hz, 1H), 7.67 (t, J=7.9 Hz, 1H), 7.60-7.52 (m, 1H), 7.47 (d, J=7.1 Hz, 1H), 6.90 (d, J=8.5 Hz, 1H), 4.34 (t, J=11.3 Hz, 2H), 3.00 (m, 2H), 2.83-2.76 (m, 2H), 1.91-1.19 (m, 5H).

ESI MS m/z 400.2 (M+1). 1H NMR (400 MHz, DMSO): 9.23 (d, J=9.3 Hz, 2H), 8.95 (s, 1H), 8.60 (s, 1H), 8.41 (d, J=7.9 Hz, 1H), 7.66 (t, J=7.6 Hz, 1H), 7.56 (s, 1H), 7.46 (d, J=6.3 Hz, 1H), 6.88 (d, J=7.9 Hz, 1H), 4.30 (t, J=10.7 Hz, 2H), 3.02 (m, 2H), 2.75-2.68 (m, 2H), 1.88-1.17 (m, 5H)

Example 238

3-(3-(6-(piperazin-1-yl)pyridin-2-yl)-1H-pyrazolo[3,4-c]pyridin-5-yl)pyridin-2-amine 238

Step 1: tert-Butyl 4-(6-(5-bromo-1-(tetrahydro-2H-pyran-2-yl)-1H-pyrazolo[3,4-c]pyridin-3-yl)pyridin-2-yl)piperazine-1-carboxylate

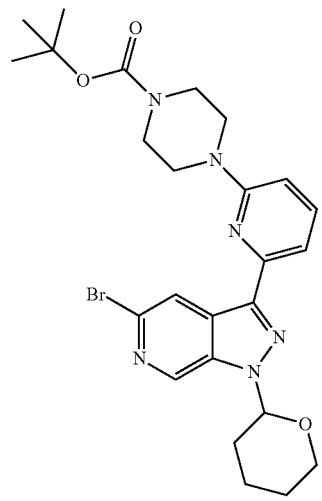 [SMILES: CC(C)(C)OC(=O)N1CCN(c2cccc(-c3nn(C4CCCCO4)c4cnc(Br)cc34)n2)CC1]

Following the procedures of Example 144, 5-bromo-3-(6-fluoropyridin-2-yl)-1-(tetrahydro-2H-pyran-2-yl)-1H-pyrazolo[3,4-c]pyridine and tert-butyl piperazine-1-carboxylate were reacted, triturated with ethyl ether, and collected by filtration to afford 910 mg (80%) of tert-Butyl 4-(6-(5-bromo-1-(tetrahydro-2H-pyran-2-yl)-1H-pyrazolo[3,4-c]pyridin-3-yl)pyridin-2-yl)piperazine-1-carboxylate. ESI MS m/z 543.2 (M+1).

Step 2

Following the Suzuki coupling procedure of Example 10, 5-bromo-3-(6-fluoropyridin-2-yl)-1-(tetrahydro-2H-pyran-2-yl)-1H-pyrazolo[3,4-c]pyridine and 3-(4,4,5,5-tetramethyl-1,3,2-dioxaborolan-2-yl)pyridin-2-amine were reacted and the deprotected by the procedure of Example 229. The crude compound was triturated with ethyl ether and collected by filtration to afford 117 mg (81%) of 238. ESI MS m/z 373.1 (M+1). 1H NMR (400 MHz, DMSO): 14.25 (s, 1H), 9.39 (s, 2H), 9.25 (s, 1H), 8.85 (s, 1H), 8.77 (s, 2H), 8.45 (d, J=7.4 Hz, 1H), 8.13 (d, J=5.4 Hz, 1H), 7.79 (t, J=7.9 Hz, 1H), 7.60 (d, J=7.2 Hz, 1H), 7.11 (t, 1H), 7.01 (d, J=8.3 Hz, 1H), 3.91 (s, 2H), 3.28 (s, 2H)

Example 239

(1S,3R)—N1-(6-(5-(pyridin-3-yl)-1H-pyrazolo[3,4-c]pyridin-3-yl)pyridin-2-yl)cyclohexane-1,3-diamine 239 and Example 245 (1S,3S)—N1-(6-(5-(pyridin-3-yl)-1H-pyrazolo[3,4-c]pyridin-3-yl)pyridin-2-yl)cyclohexane-1,3-diamine 245

Following the procedures of Example 143, and starting with 3-(6-Fluoropyridin-2-yl)-5-(pyridin-3-yl)-1-(tetrahydro-2H-pyran-2-yl)-1H-pyrazolo[3,4-c]pyridine and a mixture of cis- and trans-cyclohexanediamine, 239 and 245 were obtained and purified via reverse phase HPLC using a gradient of MeOH in water with 0.1% NH₄OH followed by SFC separation of the enantiomers to afford 35 mg (29%) ESI MS m/z 386.1 (M+1), and 10 mg (8%). ESI MS m/z 386.1 (M+1).

Example 240

3-(piperazin-1-yl)-5-(5-(pyridin-3-yl)-1H-pyrazolo[3,4-c]pyridin-3-yl)benzonitrile 240

Following the Suzuki coupling procedure of Example 159, 5-bromo-3-iodo-1-(tetrahydro-2H-pyran-2-yl)-1H-pyrazolo[3,4-c]pyridine and tert-butyl 4-(3-cyano-5-(4,4,5,5-tetramethyl-1,3,2-dioxaborolan-2-yl)phenyl)piperazine-1-carboxylate were reacted. The product was coupled with 3-pyridineboronic acid pinacol ester by the Suzuki coupling procedure of Example 10 and deprotected by the procedure of Example 225. The mixture was purified via reverse phase HPLC using a gradient of MeOH in water with 0.1% NH₄OH to afford 37 mg (19%) of 240 over three steps. ESI MS m/z 382.2 (M+1). 1H NMR (400 MHz, DMSO): 9.41 (s, 1H), 9.23 (s, 1H), 8.68-8.59 (m, 2H), 8.55 (d, J=7.8 Hz, 1H), 7.87 (s, 1H), 7.80 (s, 1H), 7.56-7.50 (m, 1H), 7.43 (s, 1H), 3.26-3.23 (m, 4H), 2.87-2.81 (m, 4H)

Example 241

1-(3-chloro-6-(5-(pyridin-3-yl)-1H-pyrazolo[3,4-c]pyridin-3-yl)pyridin-2-yl)piperidin-4-amine 241

Step 1: 5-(pyridin-3-yl)-1-((2-(trimethylsilyl)ethoxy)methyl)-3-(trimethylstannyl)-1H-pyrazolo[3,4-c]pyridine

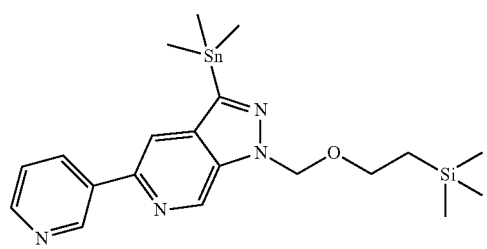 [SMILES: C[Si](C)(C)CCOCn1n[c]([Sn]([CH3])([CH3])[CH3])c2cc(-c3cccnc3)ncc21]

To a mixture of 3-iodo-5-(pyridin-3-yl)-1-((2-(trimethylsilyl)ethoxy)methyl)-1H-pyrazolo[3,4-c]pyridine (3.3435 g, 7.3912 mmol) in Tetrahydrofuran (50 mL, 600 mmol) under Argon was added trans-dichlorobis(triphenylphosphine) palladium (II) (259.39 mg, 0.36956 mmol), Hexamethylditin (1.6859 mL, 8.1303 mmol) and Lithium chloride (1.8800 g, 44.347 mmol). The resulting mixture was refluxed at 65° C. for 2 hours. The mixture was cooled to room temperature, filtered through Celite® and washed with Ethyl acetate. The filtrated was concentrated, and the residue was purified on silica eluted with 0 to 6% Methanol in dichloromethane to afford 5-(pyridin-3-yl)-1-((2-(trimethylsilyl)ethoxy)methyl)-3-(trimethylstannyl)-1H-pyrazolo[3,4-c]pyridine as a yellow oil (2.2541 g, 62.33%).

Step 2: 3-(5-chloro-6-fluoropyridin-2-yl)-5-(pyridin-3-yl)-1-((2-(trimethylsilyl)ethoxy)methyl)-1H-pyrazolo[3,4-c]pyridine

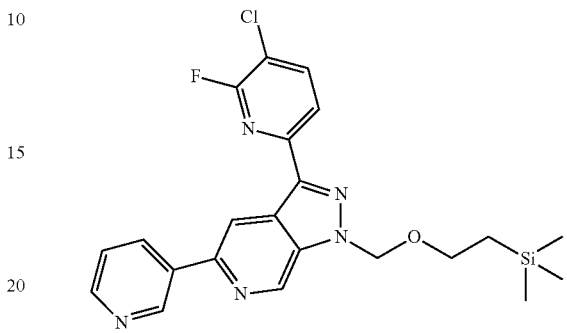

To a solution of 5-(pyridin-3-yl)-1-((2-(trimethylsilyl)ethoxy)methyl)-3-(trimethylstannyl)-1H-pyrazolo[3,4-c]pyridine (1.3490 g, 2.7571 mmol) and 6-bromo-3-chloro-2-fluoropyridine (696.23 mg, 3.3086 mmol) in tetrahydrofuran (10 mL, 100 mmol) under Argon in a pressure tube was added Cesium fluoride (837.64 mg, 5.5143 mmol), Palladium(II) Chloride (24.446 mg, 0.13786 mmol), Copper(I) iodide (52.510 mg, 0.27571 mmol), and 1.000 M of Tri-tert-butylphosphine in Toluene (275.71 uL) at room temperature. The tube was sealed and the mixture was heated at 45° C. overnight. The mixture was cooled to room temperature, and filtered through Celite®. The filter cake was washed with ethyl acetate; the combined organic layer was washed with brine, dried with MgSO4, and then concentrated. The residue was purified on silica eluted with 0 to 100% EtOAc in Heptane to afford 3-(5-chloro-6-fluoropyridin-2-yl)-5-(pyridin-3-yl)-1-((2-(trimethylsilyl)ethoxy)methyl)-1H-pyrazolo[3,4-c]pyridine as a yellow oil, which solidified upon standing.

Step 3

In a pressure tube was charged with 3-(5-chloro-6-fluoropyridin-2-yl)-5-(pyridin-3-yl)-1-((2-(trimethylsilyl)ethoxy)methyl)-1H-pyrazolo[3,4-c]pyridine (103.4 mg, 0.2268 mmol), 4-(N-Boc-amino)-piperidine (136.24 mg, 0.6803 mmol), 4-Methylmorpholine (249.30 uL, 10 mmol), and N-Methylpyrrolidinone (3 mL). The mixture was heated at 120° C. overnight. The reaction mixture was cooled to room temperature, diluted with EtOAc, washed 3 times with water. The organic layer was dried with MgSO4, and then concentrated. The residue was purified on silica eluted with 0 to 100% EtOAc in DCM to afford tert-butyl 1-(3-chloro-6-(5-(pyridin-3-yl)-1-((2-(trimethylsilyl)ethoxy)methyl)-1H-pyrazolo[3,4-c]pyridin-3-yl)pyridin-2-yl)piperidin-4-ylcarbamate. It was dissolved in 1,4-Dioxane (5 mL) and treated with 4.0 M of Hydrogen chloride in 1,4-Dioxane (5 mL) overnight. The mixture was concentrated, and the residue was purified by reverse phase HPLC to afford 241 as an off-white solid (8.7 mg, 19%). 1H NMR (400 MHz, DMSO) δ 9.24 (d, J=10.3 Hz, 2H), 8.99 (s, 1H), 8.61 (s, 1H), 8.42 (d, J=7.5 Hz, 1H), 7.89 (d, J=8.1 Hz, 1H), 7.77 (d, J=8.1 Hz, 1H), 7.56 (d, J=4.4 Hz, 1H), 3.99 (d, J=12.0 Hz, 2H), 3.09 (d, J=12.4 Hz, 3H), 1.94 (d, J=11.6 Hz, 2H), 1.56 (d, J=11.1 Hz, 2H). ESI MS m/z=406.1 (M+1)

Example 243

1-(3-methyl-6-(5-(pyridin-3-yl)-1H-pyrazolo[3,4-c]pyridin-3-yl)pyridin-2-yl)piperidin-4-amine 243

In a microwave reaction vial was charged with tert-butyl 1-(3-chloro-6-(5-(pyridin-3-yl)-1-((2-(trimethylsilyl)ethoxy)methyl)-1H-pyrazolo[3,4-c]pyridin-3-yl)pyridin-2-yl)piperidin-4-ylcarbamate from Example 241 (72.1 mg, 0.113 mmol), Methyl boronic acid (34.0 mg, 0.567 mmol), 1,1'-Bis(diphenylphosphino)ferrocenepalladium (II) chloride (9.25 mg, 0.0113 mmol), 1.00 M of Potassium acetate in Water (0.17 mL, 0.17 mmol), 1.00 M of Sodium carbonate in Water (0.17 mL, 0.17 mmol), and Acetonitrile (3 mL). The reaction mixture was heated under microwave at 150° C. for 3 minutes. Another 5 equivalents of Methyl boronic acid was added and continue heated under microwave at 150° C. for 3 minutes. The same procedure was repeated 2 more times. The mixture was concentrated to afford crude tert-butyl 1-(3-methyl-6-(5-(pyridin-3-yl)-1-((2-(trimethylsilyl)ethoxy)methyl)-1H-pyrazolo[3,4-c]pyridin-3-yl)pyridin-2-yl)piperidin-4-ylcarbamate, which was dissolved in 1,4-Dioxane (5 mL) and treated with 4.0 M of Hydrogen chloride in 1,4-Dioxane (5 mL) overnight at room temperature. The mixture was then concentrated, and the residue was purified by reverse phase HPLC to afford 243 as an off-white solid (14.0 mg, 32%). 1H NMR (400 MHz, DMSO) δ 9.24 (d, J=17.9 Hz, 2H), 9.07 (s, 1H), 8.61 (s, 1H), 8.43 (d, J=7.8 Hz, 1H), 8.38 (s, 1H), 7.76 (d, J=7.6 Hz, 1H), 7.65 (d, J=7.6 Hz, 1H), 7.56 (d, J=4.6 Hz, 1H), 3.73 (d, J=11.9 Hz, 2H), 3.13 (s, 1H), 3.01 (d, J=11.6 Hz, 2H), 2.32 (s, 3H), 2.02 (d, J=12.0 Hz, 2H), 1.68 (d, J=11.1 Hz, 2H). ESI MS m/z=386.2 (M+1)

Example 246

(R)-1-(6-(5-(1-methyl-1H-pyrazol-4-yl)-1H-pyrazolo[3,4-c]pyridin-3-yl)pyridin-2-yl)azepan-4-amine 246

Step 1: benzyl (4R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-ylcarbamate

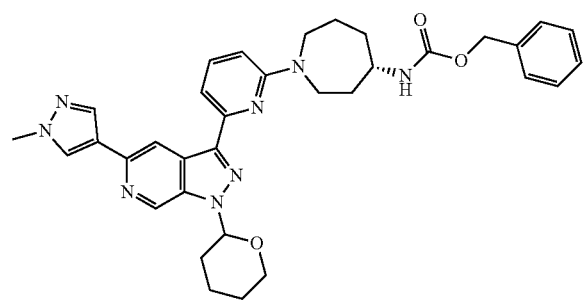 [SMILES: Cn1cc(-c2cc3c(-c4cccc(N5CCC[C@H](NC(=O)OCc6ccccc6)CC5)n4)nn(C4CCCCO4)c3cn2)cn1]

Following the procedure of Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and (R)-benzyl azepan-4-ylcarbamate were reacted to give benzyl (4R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-ylcarbamate as a solid (90.5%). LC/MS: m/z 607.3 [M+1].

Step 2: (4R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-amine In a 5-mL high-pressure vial was placed benzyl (4R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-ylcarbamate (110.0 mg, 0.18 mmol), 1,4-cyclohexadiene (102 μL, 1.09 mmol) in ethanol (8.3). 10% Pd on C (11.0 mg) was added, and the reaction mixture was vacuum purged with N₂ 3×. The vial was sealed and the reaction mixture was stirred at 100° C. After 2 h additional 10% Pd on C (11.0 mg) and 1,4-cyclohexadiene (102 μL) were added. The vial was resealed and the reaction mixture was stirred at 100° C. for 14 h. The cooled reaction was filtered reaction through a pad of Celite®, and the pad was rinsed with EtOAc (3×5 mL), MeOH (3×5 mL), DCM (3×5 mL), and a final rinse of EtOAc (3×5 mL). The filtrate was concentrated under reduced pressure, and the crude product was purified using flash chromatography (Si-PPC gradient elution, solvent: 0-80% MeOH in EtOAc+1% Et₃N) to give (4R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-amine as a solid (61.1 mg, 71.3%). LC/MS: m/z 473.3 [M+1].

Step 3

Following the procedure of Example 189, (4R)-1-(6-(5-(1-methyl-1H-pyrazol-4-yl)-1-(tetrahydro-2H-pyran-2-yl)-1H-pyrazolo[3,4-c]pyridin-3-yl)pyridin-2-yl)azepan-4-amine was deprotected to give 246 as a white solid (52.1%). 1H NMR (400 MHz, DMSO) δ 9.03 (d, J=1.1 Hz, 1H), 8.55 (d, J=1.1 Hz, 1H), 8.11 (s, 1H), 7.84 (s, 1H), 7.66-7.56 (m, 1H), 7.38 (d, J=7.3 Hz, 1H), 6.62 (d, J=8.5 Hz, 1H), 3.97 (m, 1H), 3.91 (s, 3H), 3.86-3.76 (m, 1H), 3.76-3.58 (m, 3H), 2.93 (t, 1H), 2.14-1.95 (m, 2H), 1.86-1.60 (m, 3H), 1.42 (m, 1H); 2 protons not seen. LC/MS: m/z 389.2 [M+1]

Example 247

5-(1-methyl-1H-pyrazol-4-yl)-3-(6-(piperidin-4-yl)pyridin-2-yl)-1H-pyrazolo[3,4-c]pyridine 247

Step 1: tert-butyl 4-(6-(5-(1-methyl-1H-pyrazol-4-yl)-1-(tetrahydro-2H-pyran-2-yl)-1H-pyrazolo[3,4-c]pyridin-3-yl)pyridin-2-yl)-5,6-dihydropyridine-1(2H)-carboxylate

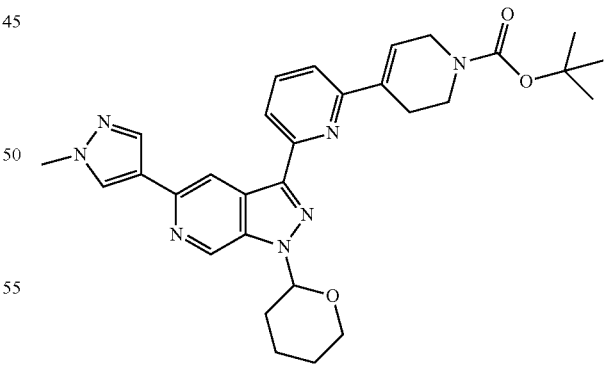

In a high-pressure vial was placed 3-(6-chloropyridin-2-yl)-5-(1-methyl-1H-pyrazol-4-yl)-1-(tetrahydro-2H-pyran-2-yl)-1H-pyrazolo[3,4-c]pyridine ((84.1 mg, 0.21 mmol), tert-butyl 4-(4,4,5,5-tetramethyl-1,3,2-dioxaborolan-2-yl)-5,6-dihydropyridine-1(2H)-carboxylate (197.5 mg, 0.64 mmol), cesium carbonate (346.979 mg, 1.06494 mmol;), and [1,1'-bis(diphenylphosphino)ferrocene]dichloropalladium (II), complex with dichloro-methane (1:1) (17.4 mg, 0.021 mmol), and N,N-Dimethylformamide (2.5 mL). Nitrogen was passed through the mixture for 15 minutes and the vessel was sealed. The reaction mixture was stirred at 90° C. under N₂ for 4 days, cooled to RT, and diluted with EtOAc. The reaction mixture was filtered through a pad of Celite®. The organic layer was washed with water and brine, dried over Na₂SO₄, filtered, and evaporated in vacuo. The crude product was purified using both flash chromatography (Si-PPC gradient elution, solvent: 0-20% methanol in ethyl acetate) and reverse phase HPLC purification to give tert-butyl 4-(6-(5-(1-methyl-1H-pyrazol-4-yl)-1-(tetrahydro-2H-pyran-2-yl)-1H-pyrazolo[3,4-c]pyridin-3-yl)pyridin-2-yl)-5,6-dihydropyridine-1(2H)-carboxylate as an oil (40.4 mg, 35.0%). ¹H NMR (400 MHz, CDCl₃) δ 9.12 (s, 1H), 8.72 (s, 1H), 8.08 (d, J=7.8 Hz, 1H), 7.98 (s, 1H), 7.93 (s, 1H), 7.75 (t, J=7.8 Hz, 1H), 7.39 (d, J=7.7 Hz, 1H), 6.79 (s, 1H), 5.87 (dd, J=8.5, 2.0 Hz, 1H), 4.23 (d, J=2.6 Hz, 2H), 4.07-3.96 (m, 1H), 3.98 (s, 3H), 3.85-3.72 (m, 3H), 2.87 (s, 2H), 2.66-2.52 (m, 1H), 2.17 (d, J=9.2 Hz, 2H), 1.90-1.67 (m, 3H), 1.52 (s, 9H). LC/MS: m/z 542.4 [M+1].

Step 2: tert-butyl 4-(6-(5-(1-methyl-1H-pyrazol-4-yl)-1-(tetrahydro-2H-pyran-2-yl)-1H-pyrazolo[3,4-c]pyridin-3-yl)pyridin-2-yl)piperidine-1-carboxylate

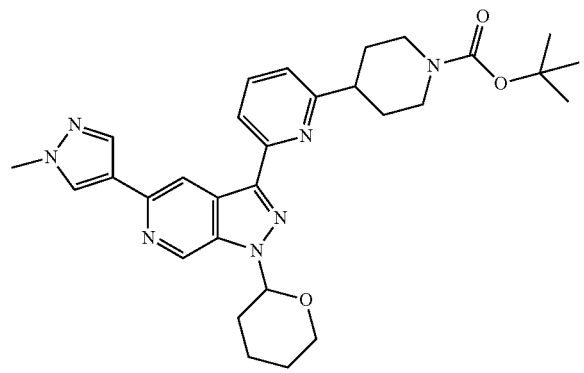 [SMILES: Cn1cc(-c2cc3c(-c4cccc(C5CCN(C(=O)OC(C)(C)C)CC5)n4)nn(C4CCCCO4)c3cn2)cn1]

In a microwave vial was placed tert-butyl 4-(6-(5-(1-methyl-1H-pyrazol-4-yl)-1-(tetrahydro-2H-pyran-2-yl)-1H-pyrazolo[3,4-c]pyridin-3-yl)pyridin-2-yl)-5,6-dihydropyridine-1(2H)-carboxylate (40.0 mg, 0.074 mmol), 1,4-cyclohexadiene (69 µL, 0.74 mmol), and ethanol (3.000 mL). Palladium (4.0 mg, 0.04 mmol; 10% Pd on C) was added and the reaction mixture was vacuum purged with N₂ 3×, ending with N₂. The vial was capped and the reaction mixture was subjected to microwave irradiation at 120° C. for 60 min. Additional 10% palladium on C (4.0 mg) and cyclohexadiene (69 µL) were added, and the reaction mixture was resubjected to microwave irradiation 120° C. for 60 minutes. This process was repeated (2×) until no starting material was detected by LC/MS. The reaction mixture was filtered through a pad of Celite®. The pad was rinsed with ethyl acetate (3×5 mL), MeOH (3×5 mL), DCM (3×5 mL), and a final EtOAc rinse (3×5 mL). The combined filtrates were concentrated under reduced pressure and pumped dry on high-vac to give tert-butyl 4-(6-(5-(1-methyl-1H-pyrazol-4-yl)-1-(tetrahydro-2H-pyran-2-yl)-1H-pyrazolo[3,4-c]pyridin-3-yl)pyridin-2-yl)-5,6-dihydropyridine-1(2H)-carboxylate (27.7 mg, 69.0%). LC/MS: m/z 544.4 [M+1].

Step 3

Following the procedure as in Example 189, tert-butyl 4-(6-(5-(1-methyl-1H-pyrazol-4-yl)-1-(tetrahydro-2H-pyran-2-yl)-1H-pyrazolo[3,4-c]pyridin-3-yl)pyridin-2-yl)piperidine-1-carboxylate was deprotected to give 247 as a solid (45.3%). ¹H NMR (400 MHz, DMSO) δ 9.06 (d, J=1.2 Hz, 1H), 8.65 (s, 1H), 8.37 (s, 2H), 8.22 (s, 1H), 8.02 (d, J=7.8 Hz, 1H), 7.96 (s, 1H), 7.87 (t, J=7.8 Hz, 1H), 7.31 (d, J=7.6 Hz, 1H), 3.92 (s, 3H), 3.36 (broad s, 1H), 3.33 (broad s, 1H), 3.10 (t, 1H), 2.97 (t, 2H), 2.11 (d, 2H), 2.03 (m, 2H). LC/MS: m/z 360.1 [M+1]

Example 248

(S)-1-(6-(5-(pyridin-3-yl)-1H-pyrazolo[3,4-c]pyridin-3-yl)pyridin-2-yl)azepan-4-amine 248

To benzyl (4S)-1-(6-(5-(pyridin-3-yl)-1-(tetrahydro-2H-pyran-2-yl)-1H-pyrazolo[3,4-c]pyridin-3-yl)pyridin-2-yl)azepan-4-ylcarbamate (0.100 g, 0.166 mmol) was added 2.0 M Hydrogen chloride in Water (10.0 mL). The reaction was stirred for 18 h at 100° C. The reaction was concentrated then submitted to HPLC purification to give 248 (6.9 mg, 11% yield). ESI MS m/z=386.1 (M+1). ¹H NMR (500 MHz, DMSO) δ 9.22 (s, 1H), 9.19 (s, 1H), 8.95 (s, 1H), 8.59 (d, J=4.3 Hz, 1H), 8.38 (d, J=7.6 Hz, 1H), 7.61 (t, J=7.7 Hz, 1H), 7.57-7.51 (m, 1H), 7.42 (d, J=7.3 Hz, 1H), 6.61 (d, J=8.3 Hz, 1H), 3.80-3.70 (m, 2H), 3.60-3.55 (m, 2H), 2.95-2.85 (m, 1H), 2.10-1.96 (m, 2H), 1.86-1.56 (m, 3H), 1.40 (m, 1H)

Example 249

(R)-1-(6-(5-(pyridin-3-yl)-1H-pyrazolo[3,4-c]pyridin-3-yl)pyridin-2-yl)azepan-4-amine 249

A solution containing 3-(6-fluoropyridin-2-yl)-5-(pyridin-3-yl)-1-(tetrahydro-2H-pyran-2-yl)-1H-pyrazolo[3,4-c]pyridine (0.075 g, 0.20 mmol) and (R)-benzyl azepan-4-ylcarbamate (0.298 g, 1.20 mmol) in Dimethyl sulfoxide (1.20 mL) was heated at 95° C. for 18 h. The reaction was quenched with water and then extracted with EtOAc 2×. The combined organic layer was dried with Na2SO4, filtered and concentrated. The crude product was dried under high vacuum overnight to give benzyl (4R)-1-(6-(5-(pyridin-3-yl)-1-(tetrahydro-2H-pyran-2-yl)-1H-pyrazolo[3,4-c]pyridin-3-yl)pyridin-2-yl)azepan-4-ylcarbamate which was dissolved in Methylene chloride (2.56 mL) at −10° C. and treated with slowly with 1.00 M of Boron tribromide in Methylene chloride (0.600 mL). The reaction was stirred at RT for 7 h. The mixture was concentrated. The crude product was diluted in water and washed with EtOAc. The aqueous layer was basified to pH 11 then extracted with EtOAc. The combined organic layers was dried Na2SO4, filtered, and concentrated. The crude product was submitted for rHPLC to give 249 (21 mg, 27% yield). ESI MS m/z=386.1 (M+1). ¹H NMR (500 MHz, DMSO) δ 9.21 (d, J=12.7 Hz, 2H), 8.96 (s, 1H), 8.59 (d, J=3.8 Hz, 1H), 8.38 (d, J=7.6 Hz, 1H), 7.61 (t, J=7.6 Hz, 1H), 7.58-7.51 (m, 1H), 7.42 (d, J=7.3 Hz, 1H), 6.62 (d, J=8.2 Hz, 1H), 4.00-3.78 (m, 2H), 3.76-3.57 (m, 2H), 2.89 (s, 1H), 2.00 (d, J=30.7 Hz, 2H), 1.85-1.55 (m, 3H), 1.44-1.31 (m, 1H)

Example 250

2-methyl-1-(4-(5-(1-methyl-1H-pyrazol-4-yl)-1H-pyrazolo[3,4-c]pyridin-3-yl)-1H-pyrazol-1-yl)propan-2-ol 250

Following the procedures in Example 172, 2-methyl-1-(4-(4,4,5,5-tetramethyl-1,3,2-dioxaborolan-2-yl)-1H-pyrazol-1-yl)propan-2-ol and 3-chloro-5-(1-methyl-1H-pyrazol-4-yl)-1-(tetrahydro-2H-pyran-2-yl)-1H-pyrazolo[3,4-c]pyridine were reacted and deprotected to give 250 as a white solid (40.7% over two steps). ¹H NMR (500 MHz, DMSO) δ 13.39 (s, 1H), 8.97 (s, 1H), 8.39 (s, 1H), 8.30 (s, 1H), 8.16 (d, J=10.2 Hz, 1H), 8.10 (s, 1H), 4.78 (s, 1H), 4.13 (s, 2H), 3.90 (s, 3H), 1.13 (s, 6H). LC/MS: m/z 338.1 [M+1]

Example 251

(1s,4s)-N1-(6-(5-(1-methyl-1H-pyrazol-4-yl)-1H-pyrazolo[3,4-c]pyridin-3-yl)pyridin-2-yl)cyclohexane-1,4-diamine 251

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl (1s,4s)-4-aminocyclohexylcarbamate were reacted. The product was deprotected and purified to give 251 as a white solid (41.4% over two steps). $^1$H NMR (500 MHz, DMSO) δ 9.01 (s, 1H), 8.59 (s, 1H), 8.13 (s, 1H), 7.87 (s, 1H), 7.46 (t, J=7.5 Hz, 1H), 7.29 (d, J=7.0 Hz, 1H), 6.55 (dd, J=14.4, 7.8 Hz, 2H), 4.12 (s, 1H), 3.90 (s, 3H), 3.42 (s, 1H), 2.87 (s, 1H), 1.99-1.39 (m, 9H); 1 proton not seen. LC/MS: m/z 389.2 [M+1]

Example 252

5-(pyridin-3-yl)-3-(pyrrolidin-1-yl)-1H-pyrazolo[3,4-c]pyridine 252

To a solution of 5-(pyridin-3-yl)-3-(pyrrolidin-1-yl)-1-trityl-1H-pyrazolo[3,4-c]pyridine (0.120 g, 0.236 mmol) in Methylene chloride (3.030 mL, 47.28 mmol) was added Triethylsilane (0.151 mL, 0.946 mmol) and Trifluoroacetic Acid (3.642 mL, 47.28 mmol). The mixture was stirred at RT for 3 h. The reaction was concentrated. The crude was submitted for HPLC purification in DMF to give 252 (22.4 mg, 35.7% yield). ESI MS m/z=266.1 (M+1). $^1$H NMR (400 MHz, DMSO) δ 12.34 (s, 1H), 9.30 (d, J=1.8 Hz, 1H), 8.90 (d, J=0.9 Hz, 1H), 8.53 (dd, J=4.7, 1.5 Hz, 1H), 8.50-8.42 (m, 1H), 8.32 (s, 1H), 7.47 (dd, J=7.9, 4.7 Hz, 1H), 3.63 (t, J=6.5 Hz, 4H), 1.99 (t, J=6.5 Hz, 4H)

Example 253

2-(3-(6-(piperazin-1-yl)pyridin-2-yl)-1H-pyrazolo[3,4-c]pyridin-5-yl)acetamide 253

Step 1: Diethyl 2-(3-(6-(4-(tert-butoxycarbonyl)piperazin-1-yl)pyridin-2-yl)-1-(tetrahydro-2H-pyran-2-yl)-1H-pyrazolo[3,4-c]pyridin-5-yl)malonate

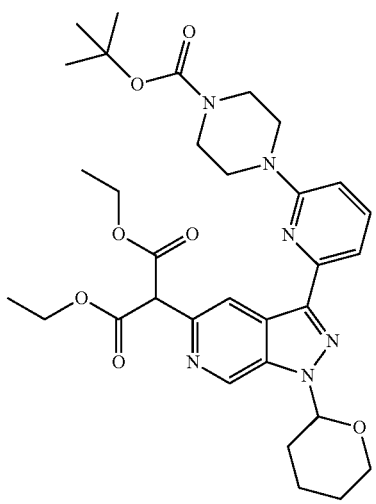 [SMILES: CCOC(=O)C(C(=O)OCC)c1cc2c(-c3cccc(N4CCN(C(=O)OC(C)(C)C)CC4)n3)nn(C3CCCCO3)c2cn1]

A mixture of 218 mg (0.40 mmol) of 4-{6-[5-Bromo-1-(tetrahydro-pyran-2-yl)-1H-pyrazolo[3,4-c]pyridin-3-yl]-pyridin-2-yl}-piperazine-1-carboxylic acid tert-butyl ester, 1.22 mL (8.02 mmol) of Ethyl malonate, 76 mg (0.40 mmol) of copper(I) iodide, 654 mg (2.006 mmol) of cesium carbonate and 99 mg (0.80 mmol) of picolinic acid in 4.0 ml of 1,4-dioxane was degassed and then heated for 24 hours at 100° C. The mixture was filtered and the filtrate concentrated in vacuum. The residue was partitioned between ethyl acetate and water, the organic extracts were washed consequently with saturated aqueous NaHCO3, 5% aqueous citric acid, water, brine, dried over MgSO4 and concentrated. The residue was purified via silica gel chromatography using a gradient of ethyl acetate in heptane to afford 117 mg (47%) of Diethyl 2-(3-(6-(4-(tert-butoxycarbonyl)piperazin-1-yl)pyridin-2-yl)-1-(tetrahydro-2H-pyran-2-yl)-1H-pyrazolo[3,4-c]pyridin-5-yl)malonate. ESI MS m/z 623.3 (M+1).

Step 2: 2-(3-(6-(4-(tertButoxycarbonyl)piperazin-1-yl)pyridin-2-yl)-1-(tetrahydro-2H-pyran-2-yl)-1H-pyrazolo[3,4-c]pyridin-5-yl)acetic acid

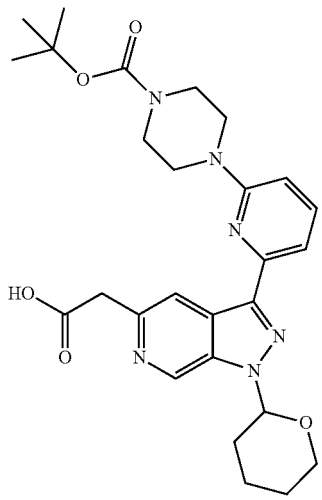 [SMILES: CC(C)(C)OC(=O)N1CCN(c2cccc(-c3nn(C4CCCCO4)c4cnc(CC(=O)O)cc34)n2)CC1]

A mixture of diethyl 2-(3-(6-(4-(tert-butoxycarbonyl)piperazin-1-yl)pyridin-2-yl)-1-(tetrahydro-2H-pyran-2-yl)-1H-pyrazolo[3,4-c]pyridin-5-yl)malonate (117 mg (0.188 mmol) and 0.5 ml of 1 M aqueous solution of LiOH in 6 ml of methanol/THF mixture (2:1) was heated at 60° C. for 1 hour. The mixture was acidified with 1 N aqueous HCl to pH<1 and stirred for 20 min. The mixture was concentrated, the residue partitioned between ethyl acetate and water. The pH of the mixture was adjusted to 4 by careful addition of saturated aqueous sodium bicarbonate. The organic extracts were washed with brine, dried over MgSO4 and concentrated to afford 2-(3-(6-(4-(tertButoxycarbonyl)piperazin-1-yl)pyridin-2-yl)-1-(tetrahydro-2H-pyran-2-yl)-1H-pyrazolo[3,4-c]pyridin-5-yl)acetic acid (68 mg, 32% over two steps. ESI MS m/z 523.4 (M+1).

Step 3

Following the procedure of Example 229, 2-(3-(6-(4-(tert-butoxycarbonyl)piperazin-1-yl)pyridin-2-yl)-1-(tetrahydro-2H-pyran-2-yl)-1H-pyrazolo[3,4-c]pyridin-5-yl)acetic acid was converted into amide which was deprotected by Example 225. The mixture was purified via reverse phase HPLC using a gradient of MeOH in water with 0.1% NH₄OH to afford 7.3 mg (5.4%%) of 253 over four steps. ESI MS m/z 338.1 (M+1). 1H NMR (500 MHz, DMSO): 13.70 (s, 1H), 8.97 (s, 1H), 8.33 (s, 1H), 7.64 (t, J=7.8 Hz, 1H), 7.52 (s, 1H), 7.44 (d, J=7.2 Hz, 1H), 6.96 (s, 1H), 6.80 (d, J=8.3 Hz, 1H), 3.70 (s, 2H), 3.54 (s, 4H), 2.87 (s, 4H)

Example 254

1-methyl-3-(5-(pyridin-3-yl)-1H-pyrazolo[3,4-c]pyridin-3-yl)imidazolidin-2-one 254

A solution of 1-methyl-3-(5-(pyridin-3-yl)-1-(tetrahydro-2H-pyran-2-yl)-1H-pyrazolo[3,4-c]pyridin-3-yl)imidazolidin-2-one (0.140 g, 0.371 mmol) in 4.00 M of Hydrogen chloride in 1,4-Dioxane (3.00 mL) and 1,4-Dioxane (3.00 mL, 38.4 mmol) was stirred at RT for 18 h. The reaction was concentrated. The crude product was submitted HPLC to give 254 (16.9 mg, 15.4% yield). ESI MS m/z=295.1 (M+1). ¹H NMR (400 MHz, DMSO) δ 9.18 (s, 1H), 9.04 (s, 1H), 8.82 (s, 1H), 8.56 (d, J=4.3 Hz, 1H), 8.32 (d, J=8.0 Hz, 1H), 7.50 (dd, J=7.9, 4.7 Hz, 1H), 4.01-3.93 (m, 2H), 3.64-3.53 (m, 2H), 2.86 (s, 3H)

Example 255

3-(5-chloro-6-(4-methylpiperazin-1-yl)pyridin-2-yl)-5-(pyridin-3-yl)-1H-pyrazolo[3,4-c]pyridine 255

Following the procedures as described in Example 241 and starting with 1-methylpiperazine, 255 was obtained as an off-white solid (11.0 mg, 29%) over two steps. 1H NMR (400 MHz, DMSO) δ 9.30-9.20 (m, 2H), 8.97 (s, 1H), 8.61 (d, J=4.7 Hz, 1H), 8.41 (d, J=8.0 Hz, 1H), 7.91 (d, J=8.1 Hz, 1H), 7.79 (d, J=8.1 Hz, 1H), 7.56 (dd, J=8.0, 4.7 Hz, 1H), 3.54 (s, 4H), 2.58 (s, 4H), 2.29 (s, 3H); ESI MS m/z=406.1 (M+1)

Example 256

3,5-di(pyridin-2-yl)-1H-pyrazolo[3,4-c]pyridine 256

3-(Pyridin-2-yl)-5-(pyridin-3-yl)-1-(tetrahydro-2H-pyran-2-yl)-1H-pyrazolo[3,4-c]pyridine (67.6 mg, 0.189 mmol) in 4.0 M of Hydrogen chloride in 1,4-Dioxane (5 mL) and Methanol (5 mL, 100 mmol) was stirred overnight at room temperature. The mixture was then concentrated, and the residue was purified by reverse phase HPLC to afford 256 as an off-white solid (20.8 mg, 40%). 1H NMR (400 MHz, DMSO) δ 14.04 (s, 1H), 9.50 (s, 1H), 9.19 (d, J=0.9 Hz, 1H), 8.84 (d, J=4.4 Hz, 1H), 8.72 (d, J=4.0 Hz, 1H), 8.45 (d, J=8.0 Hz, 1H), 8.23 (d, J=8.0 Hz, 1H), 7.95 (qd, J=7.6, 1.7 Hz, 2H), 7.46-7.38 (m, 2H); ESI MS m/z=274.1 (M+1)

Example 257

3-(5-methyl-6-(4-methylpiperazin-1-yl)pyridin-2-yl)-5-(pyridin-3-yl)-1H-pyrazolo[3,4-c]pyridine 257

Following the procedures as described in Example 241 and starting with 1-methylpiperazine, 257 was obtained as an off-white solid (6.8 mg, 19%) over two steps. 1H NMR (400 MHz, DMSO) δ 9.25 (s, 1H), 9.21 (s, 1H), 9.07 (s, 1H), 8.61 (d, J=4.6 Hz, 1H), 8.41 (d, J=8.0 Hz, 1H), 8.16 (s, 1H), 7.76 (d, J=7.6 Hz, 1H), 7.65 (d, J=7.7 Hz, 1H), 7.56 (dd, J=7.9, 4.8 Hz, 1H), 2.60 (s, 4H), 2.31 (d, J=3.7 Hz, 6H); ESI MS m/z=386.2 (M+1)

Example 258

1-(5-(pyridin-3-yl)-1H-pyrazolo[3,4-c]pyridin-3-yl)pyrrolidin-2-one 258

Following the procedures of Example 254, 1-(5-(pyridin-3-yl)-1-(tetrahydro-2H-pyran-2-yl)-1H-pyrazolo[3,4-c]pyridin-3-yl)pyrrolidin-2-one was converted to 258. ESI MS m/z=280.1 (M+1). ¹H NMR (400 MHz, DMSO) δ 9.20 (d, J=1.9 Hz, 1H), 9.09 (d, J=1.0 Hz, 1H), 8.66 (d, J=1.0 Hz, 1H), 8.57 (dd, J=4.7, 1.5 Hz, 1H), 8.37-8.31 (m, 1H), 7.51 (dd, J=7.9, 4.8 Hz, 1H), 4.02 (t, J=7.1 Hz, 2H), 2.60 (t, J=8.0 Hz, 2H), 2.27-2.15 (m, 2H)

Example 259

1-methyl-4-(3-phenyl-1H-pyrazolo[3,4-c]pyridin-5-yl)-1H-pyrrol-2(5H)-one 259

Step 1: 4-(3-phenyl-1-(tetrahydro-2H-pyran-2-yl)-1H-pyrazolo[3,4-c]pyridin-5-yl)furan-2(5H)-one

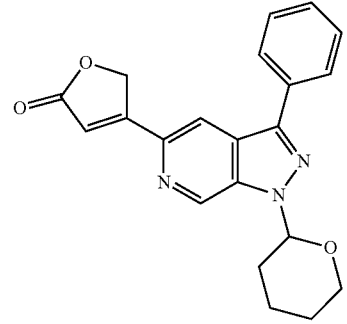 [SMILES: O=C1C=C(c2cc3c(-c4ccccc4)nn(C4CCCCO4)c3cn2)CO1]

A high-pressure reaction vessel was charged with 5-bromo-3-phenyl-1-(tetrahydro-2H-pyran-2-yl)-1H-pyrazolo[3,4-c]pyridine (400.0 mg, 1.12 mmol), bis(triphenylphosphine)palladium(II) chloride (79.0 mg, 0.11 mmol), and anhydrous toluene (8.0 mL). Tributylstannanyl-5H-furan-2-one (437.5 mg, 1.17 mmol) was added, and the reaction mixture was vacuum-purged and back filled with nitrogen (3×). The vessel was sealed, and the reaction mixture was stirred at 110° C. for 3 days. The reaction was cooled to RT and slowly poured into saturated aqueous sodium bicarbonate solution (30 mL). The resultant mixture was extracted with ethyl acetate (3×75 mL). The combined organic layers were dried over Na₂SO₄, filtered, and concentrated under reduced pressure. The crude product was purified using flash column chromatography (Si-PPC gradient elution, solvent: 0-100% ethyl acetate in heptanes) to give 4-(3-phenyl-1-(tetrahydro- 2H-pyran-2-yl)-1H-pyrazolo[3,4-c]pyridin-5-yl)furan-2 (5H)-one as white solid (130.0 mg, 32.2%). LC/MS: m/z 362.3 [M+1].

Step 2: 1-methyl-5-(methylamino)-4-(3-phenyl-1-(tetrahydro-2H-pyran-2-yl)-1H-pyrazolo[3,4-c]pyridin-5-yl)pyrrolidin-2-one

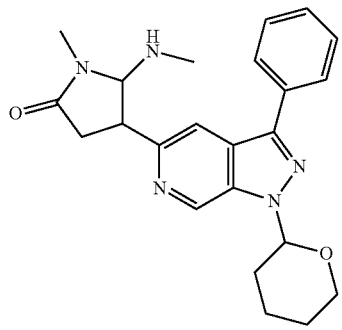 [SMILES: CNC1C(c2cc3c(-c4ccccc4)nn(C4CCCCO4)c3cn2)CC(=O)N1C]

A high-pressure reaction vessel was charged with 4-(3-phenyl-1-(tetrahydro-2H-pyran-2-yl)-1H-pyrazolo[3,4-c]pyridin-5-yl)furan-2(5H)-one (120.0 mg, 0.33 mmol) and 2M methylamine in methanol (10 mL). The vessel was sealed and the heterogeneous reaction mixture was stirred at 90° C. for 17 h. The resultant reaction mixture was cooled to RT. Volatile solvent was evaporated in vacuo to afford an oil. The oil was taken up in 1:1 v/v DCM-ether (~10 mL). Heptane was slowly added until an orange solid precipitated out and the precipitate was filtered off. The filtrate was evaporated in vacuo and dried on high-vacuum pump to give 1-methyl-5-(methylamino)-4-(3-phenyl-1-(tetrahydro-2H-pyran-2-yl)-1H-pyrazolo[3,4-c]pyridin-5-yl)pyrrolidin-2-one (104.8 mg, 77.8%) as a foam. ¹H NMR 1H NMR (400 MHz, CDCl₃) δ 9.16 (d, J=8.2 Hz, 1H), 7.94 (d, J=7.6 Hz, 2H), 7.75 (s, 1H), 7.52 (t, J=7.5 Hz, 2H), 7.43 (t, J=7.3 Hz, 1H), 5.90-5.83 (m, 1H), 4.66 (dd, J=5.4, 2.0 Hz, 1H), 4.09-4.01 (m, 1H), 3.87-3.76 (m, 1H), 3.59-3.52 (m, 1H), 2.88 (s, 3H), 2.64-2.52 (m, 1H), 2.40 (s, 3H), 2.20 (d, J=14.8 Hz, 2H), 1.91-1.68 (m, 6H). LC/MS: m/z 406.3 [M+1].

Step 3

A mixture of 1-methyl-5-(methylamino)-4-(3-phenyl-1-(tetrahydro-2H-pyran-2-yl)-1H-pyrazolo[3,4-c]pyridin-5-yl)pyrrolidin-2-one (34.3 mg, 0.084 mmol) and trifluoroacetic acid (3 mL) in a sealed high-pressure tube was stirred at 105° C. for 3 days. The reaction was cooled to RT and trifluoroacetic acid was removed via rotary evaporator. The resultant oil was diluted with ethyl acetate (30 mL). The organic layer was washed with aqueous saturated sodium bicarbonate solution (2×), water and brine, dried over Na₂SO₄, filtered, and evaporated in vacuo. The crude product was purified by reverse phase HPLC to give 259 as white solid (4.0 mg, 16.3%). ¹H NMR (400 MHz, DMSO) δ 9.13 (s, 1H), 8.43 (s, 1H), 8.11 (d, J=7.5 Hz, 2H), 7.56 (t, J=7.6 Hz, 2H), 7.47 (d, J=7.3 Hz, 1H), 6.82 (s, 1H), 6.68 (s, 1H), 4.61 (s, 2H), 2.99 (s, 3H). LC/MS: m/z 291.0 [M+1]

Example 260

1-(5-(pyridin-3-yl)-1H-pyrazolo[3,4-c]pyridin-3-yl)piperidin-2-one 260

Following the procedures of Example 254, 1-(5-(pyridin-3-yl)-1-(tetrahydro-2H-pyran-2-yl)-1H-pyrazolo[3,4-c]pyridin-3-yl)piperidin-2-one was converted to 260. ESI MS m/z=294.1 (M+1)

Example 261

3-(6-(piperidin-1-yl)pyridin-2-yl)-5-(pyridin-3-yl)-1H-pyrazolo[3,4-c]pyridine 261

Following the procedures of Example 271, and starting with 3-(6-fluoropyridin-2-yl)-5-(pyridin-3-yl)-1-((2-(trimethylsilyl)ethoxy)methyl)-1H-pyrazolo[3,4-c]pyridine from Example 279, 261 was obtained as a yellow solid (20 mg, 32%) over two steps. ¹H NMR (400 MHz, DMSO) δ 9.22 (s, 2H), 8.97 (s, 1H), 8.60 (s, 1H), 8.38 (d, 1H, J=6, 4 Hz), 7.67-7.64 (t, 1H, J=6, 4 Hz), 7.57-7.54 (m, 1H), 7.45 (d, 1H, J=6, 4 Hz), 6.87 (d, 1H, J=6, 8 Hz), 3.73 (s, 4H), 1.69 (s, 6H). ESI MS m/z=356.4 (M+1)

Example 262

1-(6-(5-(1-methyl-1H-pyrazol-4-yl)-1H-pyrazolo[3,4-c]pyridin-3-yl)pyridin-2-yl)piperidin-3-ol 262

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and piperidin-3-ol were reacted. The product was deprotected and purified to give 262 as a white solid (62.8% over two steps). ¹H NMR δ 13.68 (broad s, 1H), 9.03 (s, 1H), 8.60 (s, 1H), 8.24 (s, 1H), 7.96 (s, 1H), 7.67-7.58 (m, 1H), 7.42 (d, J=7.4 Hz, 1H), 6.83 (d, J=8.5 Hz, 1H), 5.04 (d, J=5.1 Hz, 1H), 4.59-4.49 (m, 1H), 4.08 (d, J=13.1 Hz, 1H), 3.89 (s, 3H), 3.65 (dt, J=14.0, 4.8 Hz, 1H), 3.05 (dd, J=17.1, 6.8 Hz, 1H), 2.91 (dd, J=12.4, 9.4 Hz, 1H), 2.07-1.97 (m, 1H), 1.91-1.78 (m, 1H), 1.65-1.42 (m, 2H). LC/MS: m/z 376.1 [M+1]

Example 263

1-methyl-4-(3-phenyl-1H-pyrazolo[3,4-c]pyridin-5-yl)pyrrolidin-2-one 263

In a high-pressure vessel was placed 1-methyl-5-(methylamino)-4-(3-phenyl-1-(tetrahydro-2H-pyran-2-yl)-1H-pyrazolo[3,4-c]pyridin-5-yl)pyrrolidin-2-one 259 (70.0 mg, 0.17 mmol) and trifluoroacetic acid (5 mL). The vessel was sealed and the reaction mixture was stirred at 105° C. for 20 h. The reaction mixture was cooled to RT, and triethylsilane (0.50 mL) was added. The vessel was resealed, and the reaction mixture was stirred at 75° C. After 2 h, more triethylsilane (0.5 mL) was added at RT, and the reaction mixture was stirred in a sealed vessel at 95° C. for 17 h. Volatile solvent was evaporated in vacuo. The resultant crude oil was dissolved in DMF (2 mL). Black insoluble material was filtered and rinsed well with methanol (2×2 mL). The combined filtrates were evaporated in vacuo and the crude product was purified by reverse phase HPLC to give 263 as a white solid (12.7 mg, 25.2%). ¹H NMR (400 MHz, DMSO) δ 13.37 (broad s, 1H), 9.08 (s, 1H), 8.04 (d, J=7.4 Hz, 2H), 7.98 (s, 1H), 7.54 (t, J=7.6 Hz, 2H), 7.44 (d, J=7.4 Hz, 1H), 3.98-3.85

(m, 1H), 3.75 (t, J=9.0 Hz, 1H), 3.53 (dd, J=9.3, 7.2 Hz, 1H), 2.78 (s, 3H), 2.66 (dd, J=8.8, 2.9 Hz, 2H). LC/MS: m/z 293.1 [M+1]

Example 264

(R)-5-(1-methyl-1H-pyrazol-4-yl)-3-(6-(piperidin-3-yloxy)pyridin-2-yl)-1H-pyrazolo[3,4-c]pyridine 264

Step 1: (3R)-tert-butyl 3-(6-(5-(1-methyl-1H-pyrazol-4-yl)-1-(tetrahydro-2H-pyran-2-yl)-1H-pyrazolo[3,4-c]pyridin-3-yl)pyridin-2-yloxy)piperidine-1-carboxylate

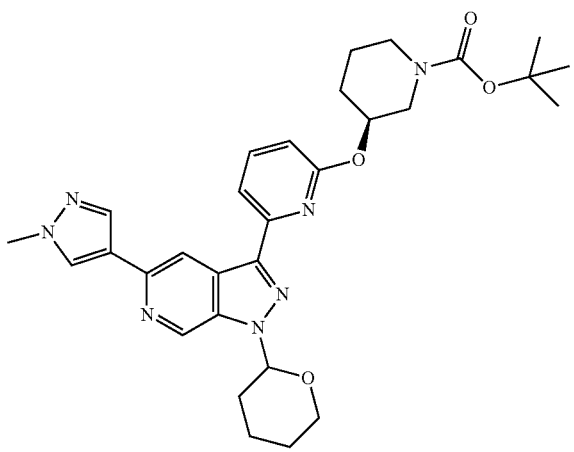 [SMILES: Cn1cc(-c2cc3c(-c4cccc(O[C@H]5CCCN(C(=O)OC(C)(C)C)C5)n4)nn(C4CCCCO4)c3cn2)cn1]

To (R)-tert-butyl 3-hydroxypiperidine-1-carboxylate (61.2 mg, 0.30 mmol) in anhydrous DMF (3 mL) was added sodium hydride (40.5 mg, 1.01 mmol, 60% in mineral oil), and the reaction mixture was stirred at 60° C. under $N_2$ for 1 h. A solution of 3-(6-chloropyridin-2-yl)-5-(1-methyl-1H-pyrazol-4-yl)-1-(tetrahydro-2H-pyran-2-yl)-1H-pyrazolo[3,4-c]pyridine (40.0 mg, 0.10 mmol) in anhydrous DMF (~1.0 mL) was then added, and the reaction mixture was stirred at 90° C. under $N_2$ for 16 h. The reaction mixture was quenched with aqueous saturated $NH_4Cl$ solution and was extracted with ethyl acetate (3×). The combined organic layers were dried over $Na_2SO_4$, filtered, and evaporated in vacuo. The crude product was purified using flash chromatography (Si-PPC gradient elution, solvent: 0-60% MeOH/EA) to give (3R)-tert-butyl 3-(6-(5-(1-methyl-1H-pyrazol-4-yl)-1-(tetrahydro-2H-pyran-2-yl)-1H-pyrazolo[3,4-c]pyridin-3-yl)pyridin-2-yloxy)piperidine-1-carboxylate as a foam (15.8 mg, 27.9%). LC/MS: m/z 560.4 [M+1].

Step 2

Following the procedure as in Example 189, (3R)-tert-butyl 3-(6-(5-(1-methyl-1H-pyrazol-4-yl)-1-(tetrahydro-2H-pyran-2-yl)-1H-pyra-zolo[3,4-c]pyridin-3-yl)pyridin-2-yloxy)piperidine-1-carboxylate was deprotected to give 264 as a solid (19.1%). $^1$H NMR (400 MHz, MeOD) δ 8.98 (s, 1H), 8.55 (s, 1H), 8.50 (s, 1H), 8.12 (s, 1H), 7.98 (s, 1H), 7.90-7.80 (m, 2H), 6.90 (d, J=7.6 Hz, 1H), 5.68 (s, 1H), 3.99 (s, 3H), 3.54 (dd, J=13.0, 3.9 Hz, 1H), 3.48-3.42 (m, 1H), 3.29-3.22 (m, 1H), 3.20-3.09 (m, 1H), 2.33-2.23 (m, 1H), 2.19-2.06 (m, 2H), 1.89-1.77 (m, 1H); 1 proton not seen. LC/MS: m/z 376.1 [M+1]

Example 265

(S)-1-(3-chloro-6-(5-(pyridin-3-yl)-1H-pyrazolo[3,4-c]pyridin-3-yl)pyridin-2-yl)piperidin-3-amine 265

Following the procedures as described in Example 241 and starting with (S)-tert-butyl piperidin-3-ylcarbamate, 265 was obtained as an off-white solid (8.4 mg, 25%) over two steps. 1H NMR (400 MHz, DMSO) δ 9.31 (s, 1H), 9.23 (s, 1H), 9.03 (s, 1H), 8.60 (d, J=4.4 Hz, 1H), 8.49-8.42 (m, 1H), 7.90 (d, J=8.1 Hz, 1H), 7.78 (d, J=8.1 Hz, 1H), 7.53 (dd, J=7.9, 4.8 Hz, 1H), 6.62 (s, 1H), 3.90 (dd, J=33.6, 11.5 Hz, 2H), 2.91 (dd, J=13.2, 7.5 Hz, 2H), 2.85-2.75 (m, 1H), 1.96 (d, J=12.4 Hz, 1H), 1.83 (s, 1H), 1.74 (d, J=9.8 Hz, 2H), 1.36-1.24 (m, 1H); ESI MS m/z=406.2 (M+1)

Example 266

(R)-1-(3-chloro-6-(5-(pyridin-3-yl)-1H-pyrazolo[3,4-c]pyridin-3-yl)pyridin-2-yl)piperidin-3-amine 266

Following the procedures as described in Example 241 and starting with (R)-tert-butyl piperidin-3-ylcarbamate, 266 was obtained as an off-white solid (55.1 mg, 58%) over two steps. 1H NMR (400 MHz, DMSO) δ 9.31 (d, J=2.1 Hz, 1H), 9.22 (s, 1H), 9.03 (s, 1H), 8.59 (dd, J=4.7, 1.4 Hz, 1H), 8.48-8.43 (m, 1H), 7.89 (d, J=8.1 Hz, 1H), 7.77 (d, J=8.1 Hz, 1H), 7.52 (dd, J=8.0, 4.8 Hz, 1H), 3.94 (d, J=9.1 Hz, 1H), 3.87 (d, J=12.1 Hz, 1H), 2.88 (dd, J=17.0, 6.1 Hz, 2H), 2.82-2.73 (m, 1H), 1.95 (d, J=12.7 Hz, 1H), 1.89-1.72 (m, 2H), 1.31-1.22 (m, 1H); ESI MS m/z=406.2 (M+1)

Example 267

4-(6-(5-(pyridin-3-yl)-1H-pyrazolo[3,4-c]pyridin-3-yl)pyridin-2-yl)morpholine 267

Following the procedures of Example 271, and starting with 3-(6-fluoropyridin-2-yl)-5-(pyridin-3-yl)-1-((2-(trimethylsilyl)ethoxy)methyl)-1H-pyrazolo[3,4-c]pyridine, 267 was obtained as a yellow solid (20 mg, 32%) over two steps. $^1$H NMR (400 MHz, DMSO) δ 9.25 (s, 1H), 9.22 (s, 1H), 8.93 (s, 1H), 8.60-9.59 (m, 1H), 8.39-8.37 (m, 1H), 7.74-7.71 (t, 1H), 7.57-7.54 (m, 2H), 6.91 (d, 1H, J=6, 8 Hz), 3.83-3.80 (m, 4H), 3.67-3.65 (m, 4H). ESI MS m/z=358.4 (M+1)

Example 268

(S)-1-(6-(5-(pyridin-3-yl)-1H-pyrazolo[3,4-c]pyridin-3-yl)pyridin-2-yl)pyrrolidin-3-amine 268

Following the procedures of Example 271, and starting with 3-(6-fluoropyridin-2-yl)-5-(pyridin-3-yl)-1-((2-(trimethylsilyl)ethoxy)methyl)-1H-pyrazolo[3,4-c]pyridine, 268 was obtained as a yellow solid (58 mg, 46%) over two steps. $^1$H NMR (400 MHz, DMSO) δ 9.29 (s, 1H), 9.23 (s, 1H), 9.06 (s, 1H), 8.62 (s, 1H), 8.44 (d, J=6.0, 1H), 7.69 (t, J=6.4, 1 H), 7.59-7.57 (m, 1H), 7.49 (d, J=5.6, 1H), 6.54 (d, J=6.4, 1H), 3.98 (s, 1H), 3.88-3.68 (m, 4H), 2.40-2.35 (m, 1H), 2.17-2.13 (m, 1H). ESI MS m/z=358.1 (M+1)

Example 269

(S)-(1-(6-(5-(pyridin-3-yl)-1H-pyrazolo[3,4-c]pyridin-3-yl)pyridin-2-yl)pyrrolidin-3-yl)methanamine 269

Following the procedures of Example 271, and starting with (S)-pyrrolidin-3-ylmethanamine, 269 was obtained as a yellow solid (30 mg, 35%) over three steps. ¹H NMR (400 MHz, DMSO) δ 9.27 (s, 1H), 9.20 (s, 1H), 9.13 (s, 1H), 8.59 (s, 1H), 8.43-8.41 (m, 1H), 7.64-7.61 (s, 1H), 7.54-7.52 (m, 1H), 7.42-7.40 (m, 1H), 6.46-6.45 (dj=6.4, 1H), 3.81-3.80 (m, 2H), 3.65-3.64 (m, 2H), 3.14-3.13 (m, 2H), 2.18-2.13 (m, 2H), 1.83-1.81 (m, 2H), 1.22 (s, 1H). ESI MS m/z=374 (M+1)

Example 270

(R)-(1-(6-(5-(pyridin-3-yl)-1H-pyrazolo[3,4-c]pyridin-3-yl)pyridin-2-yl)pyrrolidin-3-yl)methanamine 270

Following the procedures of Example 271, and starting with (R)-pyrrolidin-3-ylmethanamine, 270 was obtained as a yellow solid (34 mg, 36%) over three steps. ¹H NMR (400 MHz, DMSO) δ 9.28 (s, 1H), 9.21 (s, 1H), 9.15 (s, 1H), 8.60 (s, 1H), 8.42-8.41 (m, 1H), 7.63-7.60 (s, 1H), 7.54-7.52 (m, 1H), 7.42-7.40 (m, 1H), 6.46-6.45 (d, j=6.4, 1H), 3.81-3.80 (m, 2H), 3.65-3.64 (m, 2H), 3.14-3.13 (m, 2H), 2.19-2.17 (m, 2H), 1.82-1.78 (m, 2H), 1.24 (s, 1H). ESI MS m/z=374 (M+1)

Example 271

(R)-1-(6-(5-(pyridin-3-yl)-1H-pyrazolo[3,4-c]pyridin-3-yl)pyridin-2-yl)piperidin-3-ol 271

Step 1: 3-(6-fluoropyridin-2-yl)-5-(pyridin-3-yl)-1-((2-(trimethylsilyl)ethoxy)methyl)-1H-pyrazolo[3,4-c]pyridine

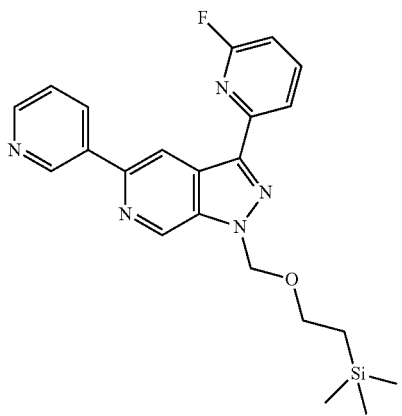 [SMILES: C[Si](C)(C)CCOCn1nc(-c2cccc(F)n2)c2cc(-c3cccnc3)ncc21]

To a mixture of 3-iodo-5-(pyridin-3-yl)-1-((2-(trimethylsilyl)ethoxy)methyl)-1H-pyrazolo[3,4-c]pyridine (GCP-P3-205-1) (200 mg, 0.44 mmol) and 2-fluoro-6-(tributylstannyl)pyridine (206 mg, 0.53 mmol) in 3 mL DMF, was added TEA 1 mL, LiCl (56 mg, 1.32 mmol) and CuI (84 mg, 0.44 mmol), and Pd(PPh₃)₄ (254 mg, 0.22 mmol). The reaction mixture was heated at 120° C. under microwave irradiation for 1 h, and the reaction was monitored by LCMS. Upon completion, the reaction mixture was extracted with 100 mL EtOAc, washed with 50 mL brine, and dried. The solvent was distilled off and the crude material was purified via flash chromatography, eluting with 5% to 30% ethyl acetate in heptane to afford 3-(6-fluoropyridin-2-yl)-5-(pyridin-3-yl)-1-((2-(trim-ethylsilyl)ethoxy)methyl)-1H-pyrazolo[3,4-c]pyridine as a yellow solid (148 mg, 80%). ESI MS m/z=421.1 (M+1).

Step 2: (R)-1-(6-(5-(pyridin-3-yl)-1-((2-(trimethylsilyl)ethoxy)methyl)-1H-pyrazolo[3,4-c]pyridin-3-yl)pyridin-2-yl)piperidin-3-ol

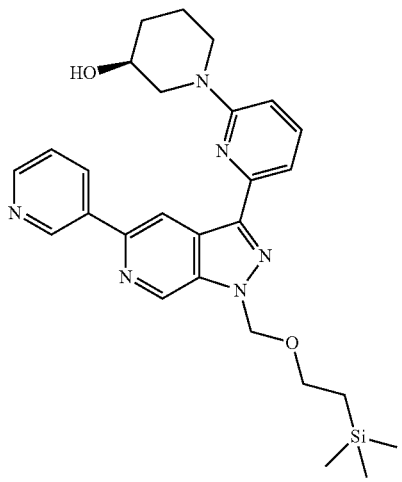 [SMILES: C[Si](C)(C)CCOCn1nc(-c2cccc(N3CCC[C@H](O)C3)n2)c2cc(-c3cccnc3)ncc21]

To a mixture of 3-(6-fluoropyridin-2-yl)-5-(pyridin-3-yl)-1-((2-(trimethylsilyl)ethoxy)methyl)-1H-pyrazolo[3,4-c]pyridine (200 mg, 0.5 mmol) and (R)-piperidin-3-ol (100 mg, 1.0 mmol) in EtOH 5 mL, was added DIPEA 5 mL. The reaction mixture was heated at 120° C. for 15 h, and the reaction was monitored by LCMS. Upon completion of the reaction, the solvent was distilled off and the crude material was purified via flash chromatography, eluting with 5% to 30% heptane/ethyl acetate to afford (R)-1-(6-(5-(pyridin-3-yl)-1-((2-(trimethylsilyl)ethoxy)methyl)-1H-pyrazolo[3,4-c]pyridin-3-yl)pyridin-2-yl)piperidin-3-ol as a yellow oil, (163 mg, 65%). ESI MS m/z=502.2 (M+1).

Step 3

To a solution of (R)-1-(6-(5-(pyridin-3-yl)-1-((2-(trimethylsilyl)ethoxy)methyl)-1H-pyrazolo[3,4-c]pyridin-3-yl)pyridin-2-yl)piperidin-3-ol (60 mg, 0.12 mmol) in dioxane 5 mL, was added 10% HCl (1 mL). The reaction mixture was heated at 70° C. for 2 h, and the reaction was monitored by LCMS. Upon completion of the reaction, the solvent was distilled off and the crude material was purified via reverse phase prep-HPLC eluting with 40% to 80% MeOH in aqueous 0.1% NH₄OH to afford 271 as a yellow solid (20 mg, 45%). ¹H NMR (400 MHz, DMSO) δ 9.34-9.28 (m, 1H), 9.21 (s, 1H), 8.62-8.58 (m, 1H), 8.45 (d, J=6, 1H), 7.67-7.64 (m, 1H), 7.54-7.50 (m, 1H), 7.45-7.44 (m, 1H), 6.87-6.85 (m, 1H), 4.96 (s, 1H), 4.36-4.34 (m, 1H), 4.15-4.12 (m, 1H), 3.63 (s, 1H), 3.16-3.12 (m, 1H), 3.01-2.97 (m, 1H), 1.99-1.97 (m, 1H), 1.85-1.83 (m, 1H), 1.60-1.56 (m, 1H), 1.52-1.45 (m, 1H). ESI MS m/z=373.7 (M+1)

Example 272

1-(6-(5-(pyridin-3-yl)-1H-pyrazolo[3,4-c]pyridin-3-yl)pyridin-2-yl)piperidin-4-ol 272

Following the procedures of Example 271, and starting with 3-(6-fluoropyridin-2-yl)-5-(pyridin-3-yl)-1-((2-(trimethylsilyl)ethoxy)methyl)-1H-pyrazolo[3,4-c]pyridine, 272 was obtained as a yellow solid (20 mg, 30%) over two steps. 1H NMR (400 MHz, DMSO) δ 9.22-9.20 (m, 2H), 8.94 (s, 1H), 8.60-8.59 (m, 1H), 8.39-8.38 (m, 1H), 7.67-7.64 (m, 1H), 7.56-7.53 (m, 1H), 7.47-7.44 (m, 1H), 6.90-6.89 (m, 1H), 4.77-4.76 (m, 1H), 4.22-4.19 (m, 2H), 3.80-3.79 (m, 1H), 3.42-3.39 (m, 1H), 1.91-1.89 (m, 2H), 1.51-1.49 (m, 2H). ESI MS m/z=373.7 (M+1)

Example 273

3-(6-(4,4'-bipiperidin-1-yl)pyridin-2-yl)-5-(pyridin-3-yl)-1H-pyrazolo[3,4-c]pyridine 273

Following the procedures of Example 143, and starting with 3-(6-Fluoropyridin-2-yl)-5-(pyridin-3-yl)-1-(tetrahydro-2H-pyran-2-yl)-1H-pyrazolo[3,4-c]pyridine and 4,4'-bipiperidine, 273 was obtained and purified via reverse phase HPLC using a gradient of MeCN in water with 0.1% HCOOH to afford 25 mg (20%) over two steps. ESI MS m/z 440.2 (M+1). 1H NMR (400 MHz, DMSO): 9.23 (s, 1H), 8.97 (s, 1H), 8.61 (s, 1H), 8.39 (s, 1H), 7.67 (t, J=7.9 Hz, 1H), 7.55 (s, 1H), 7.46 (d, J=7.3 Hz, 1H), 6.89 (d, J=8.2 Hz, 1H), 4.54 (d, J=11.1 Hz, 2H), 2.97 (s, 2H), 2.66 (s, 2H), 1.88-1.71 (m, 4H), 1.46 (s, 1H), 1.31 (s, 5H)

Example 274

3-(6-fluoro-5-methylpyridin-2-yl)-5-(pyridin-3-yl)-1H-pyrazolo[3,4-c]pyridine 274

A microwave reaction vial was charged with 3-(5-chloro-6-fluoropyridin-2-yl)-5-(pyridin-3-yl)-1-((2-(trimethylsilyl)ethoxy)methyl)-1H-pyrazolo[3,4-c]pyridine (387.1 mg, 0.8489 mmol), methyl boronic acid (254.1 mg, 4.245 mmol), 1,1'-Bis(diphenylphosphino)ferrocenepalladium (II) chloride (69.3 mg, 0.085 mmol), 1.00 M of Potassium acetate in Water (1.27 mL, 1.27 mmol), 1.00 M of Sodium carbonate in Water (1.27 mL, 1.27 mmol), and Acetonitrile (10 mL). The reaction mixture was heated under microwave at 150° C. for 5 minutes. Added another 5 equivalences of Methyl boronic acid and continue heated under microwave at 150° C. for 3 minutes. The same procedure was repeated one more times. The mixture was concentrated, and the residue was purified on silica eluted with 0 to 100% EtOAc in Heptane to afford 3-(6-fluoro-5-methylpyridin-2-yl)-5-(pyridin-3-yl)-1-((2-(trimethylsilyl)ethoxy)methyl)-1H-pyrazolo[3,4-c]pyridine (311.7 mg, 84%).

3-(6-Fluoro-5-methylpyridin-2-yl)-5-(pyridin-3-yl)-1-((2-(trimethylsilyl)ethoxy)methyl)-1H-pyrazolo[3,4-c]pyridine was dissolved in trifluoroacetic acid (5 mL) and methylene chloride (5 mL). To the solution was added trifluoromethanesulfonic acid (104.2 uL, 1.18 mmol) and triethylsilane (18.1 uL, 1.18 mmol). The resulting mixture was stirred overnight at room temperature. The mixture was then concentrated, and the residue was purified by reverse phase HPLC to afford 274 as an off-white solid (7.8 mg, 11%). 1H NMR (400 MHz, DMSO) δ 9.29-9.21 (m, 2H), 8.81 (s, 1H), 8.62 (dd, J=4.7, 1.4 Hz, 1H), 8.42 (dt, J=8.0, 1.9 Hz, 1H), 8.06 (dd, J=7.6, 1.6 Hz, 1H), 8.01-7.95 (m, 1H), 7.55 (dd, J=8.0, 4.8 Hz, 1H), 2.34 (s, 3H); ESI MS m/z=306.1 (M+1)

Example 275

3-(5-methylpyridin-2-yl)-5-(pyridin-3-yl)-1H-pyrazolo[3,4-c]pyridine 275

Step 1: 5-(pyridin-3-yl)-1-((2-(trimethylsilyl)ethoxy)methyl)-3-(trimethylstannyl)-1H-pyrazolo[3,4-c]pyridine

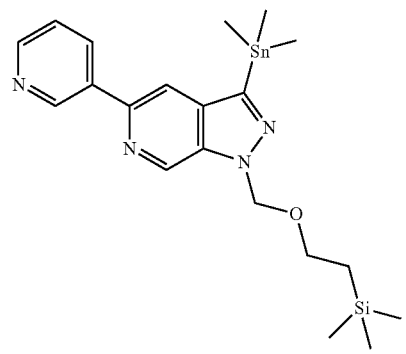 [SMILES: C[Si](C)(C)CCOCn1n[c]([Sn]([CH3])([CH3])[CH3])c2cc(-c3cccnc3)ncc21]

To a mixture of 3-iodo-5-(pyridin-3-yl)-1-((2-(trimethylsilyl)ethoxy)methyl)-1H-pyrazolo[3,4-c]pyridine (200 mg, 0.44 mmol) and 1,1,1,2,2,2-hexamethyldistannane (159 mg, 0.48 mmol) in 10 mL THF, was added LiCl (112 mg, 2.64 mmol) and Pd(PPh$_3$)Cl$_2$ (16 mg, 0.02 mmol). The reaction mixture was heated at 80° C. under argon for 1 h, and the reaction was monitored by LCMS. Upon completion of the reaction, the mixture was evaporated to dryness. The residue was purified via flash chromatography eluting with CH$_2$Cl$_2$/CH$_3$OH (9:1) to afford 5-(pyridin-3-yl)-1-((2-(trimethylsilyl)ethoxy)methyl)-3-(trimethylstannyl)-1H-pyrazolo[3,4-c]pyridine as a clear oil (188 mg, 87%). ESI MS m/z=490.1 (M+1).

Step 2: 3-(5-methylpyridin-2-yl)-5-(pyridin-3-yl)-1-((2-(trimethylsilyl)ethoxy)methyl)-1H-pyrazolo[3,4-c]pyridine

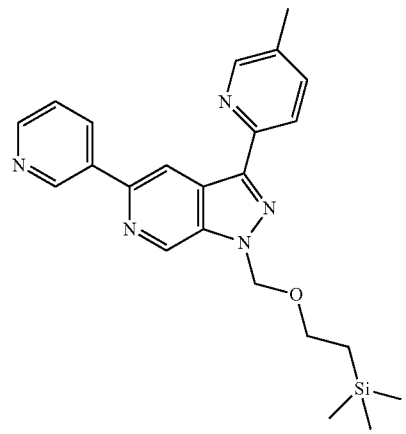 [SMILES: Cc1ccc(-c2nn(COCC[Si](C)(C)C)c3cnc(-c4cccnc4)cc23)nc1]

To a mixture of 5-(pyridin-3-yl)-1-((2-(trimethylsilyl)ethoxy)methyl)-3-(trimethylstannyl)-1H-pyrazolo[3,4-c]pyridine (250 mg, 0.51 mmol) and 2-bromo-5-methylpyridine (87 mg, 0.51 mmol) in DMF 10 mL, was added TEA (10 mL), LiCl (64 mg, 1.53 mmol), CuI (97 mg, 0.51 mmol), and Pd(PPh$_3$)$_4$ (294 mg, 0.25 mmol). The reaction mixture was heated at 120° C. under microwave irradiation for 1 h, and the reaction was monitored by LCMS. Upon completion of the reaction, the mixture was extracted with 100 mL EtOAc, washed with 50 mL brine, and dried. The solvent was distilled off and the crude material was purified via flash chromatography, eluting with 33% to 66% ethyl acetate in heptane to afford 3-(5-methylpyridin-2-yl)-5-(pyridin-3-yl)-1-((2-(trimethylsilyl)ethoxy)methyl)-1H-pyrazolo[3,4-c]pyridine as an clear oil (115 mg, 54%). ESI MS m/z=417.2 (M+1).

Step 3

To a solution of 3-(5-methylpyridin-2-yl)-5-(pyridin-3-yl)-1H-pyrazolo[3,4-c]pyridine (110 mg, 0.26 mmol) in dioxane (5 mL), was added 10% HCl (2 mL). The reaction mixture was heated at 80° C. for 2 h, and the reaction was monitored by LCMS. Upon completion of the reaction, the solvent was distilled off and the crude material was purified via reverse phase prep-HPLC eluting with 40% to 80% CH$_3$CN in aqueous 0.1% NH$_4$OH solution to afford 275 as a pink solid (32 mg, 42%). $^1$H NMR (400 MHz, DMSO) δ 9.28 (s, 1H), 9.23 (s, 1H), 9.21 (s, 1H), 8.93 (s, 1H), 8.65-8.60 (m, 2H), 8.44-8.43 (m, 1H), 8.11 (d, 1H, J=6, 4 Hz), 7.77 (d, 1H, J=6, 8 Hz), 7.55-7.53 (m, 1H), 3.32 (s, 3H). ESI MS m/z=287.3 (M+1)

Example 276

(R)-1-(6-(5-(pyridin-3-yl)-1H-pyrazolo[3,4-c]pyridin-3-yl)pyridin-2-yl)pyrrolidin-3-amine 276

Following the procedures in Example 271, 3-(6-fluoropyridin-2-yl)-5-(pyridin-3-yl)-1-((2-(trimethylsilyl)ethoxy)methyl)-1H-pyrazolo[3,4-c]pyridine was converted to 276 as a yellow solid (24 mg, 25%) over two steps. $^1$H NMR (400 MHz, DMSO&H$_2$O) δ 9.13 (d, J=8.0, 1H), 9.01 (s, 1H), 8.55 (s, 1H), 8.36 (d, J=6.0, 1H), 7.60-7.54 (m, 2H), 7.35 (d, J=5.6, 1H), 6.42 (d, J=6.8, 1H), 3.72-3.53 (m, 4H), 3.27 (s, 1H), 2.19 (s, 1H), 1.83 (s, 1H). ESI MS m/z=358.1 (M+1)

Example 277

(S)-1-(6-(5-(pyridin-3-yl)-1H-pyrazolo[3,4-c]pyridin-3-yl)pyridin-2-yl)piperidin-3-ol 277

Following the procedures in Example 271, and starting with 3-(6-fluoropyridin-2-yl)-5-(pyridin-3-yl)-1-((2-(trimethylsilyl)ethoxy)methyl)-1H-pyrazolo[3,4-c]pyridine (GCP-P3-205-3), 277 was obtained as a yellow solid (20 mg, 25%) over two steps. $^1$H NMR (400 MHz, DMSO) δ 9.34-9.28 (m, 1H), 9.21 (s, 1H), 8.62-8.58 (m, 1H), 8.45 (d, J=6, 1H), 7.67-7.64 (m, 1H), 7.54-7.50 (m, 1H), 7.45-7.44 (m, 1H), 6.87-6.85 (m, 1H), 4.96 (s, 1H), 4.36-4.34 (m, 1H), 4.15-4.12 (m, 1H), 3.63 (s, 1H), 3.16-3.12 (m, 1H), 3.01-2.97 (m, 1H), 1.99-1.97 (m, 1H), 1.85-1.83 (m, 1H), 1.60-1.56 (m, 1H), 1.52-1.45 (m, 1H). ESI MS m/z=373.7 (M+1)

Example 278

(1-(6-(5-(pyridin-3-yl)-1H-pyrazolo[3,4-c]pyridin-3-yl)pyridin-2-yl)piperidin-4-yl)methanamine 278

Step 1: tert-butyl (1-(6-(5-(pyridin-3-yl)-1-((2-(trimethylsilyl)ethoxy)methyl)-1H-pyrazolo[3,4-c]pyridin-3-yl)pyridin-2-yl)piperidin-4-yl)methylcarbamate

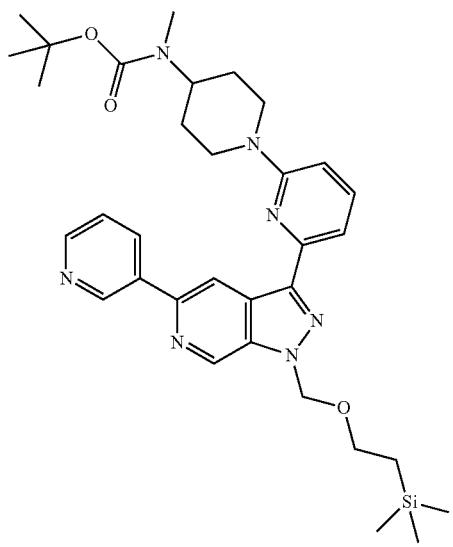 [SMILES: CN(C(=O)OC(C)(C)C)C1CCN(c2cccc(-c3nn(COCC[Si](C)(C)C)c4cnc(-c5cccnc5)cc34)n2)CC1]

To a mixture of 3-(6-fluoropyridin-2-yl)-5-(pyridin-3-yl)-1-((2-(trimethylsilyl)ethoxy)methyl)-1H-pyrazolo[3,4-c]pyridine from Example 271 (211 mg, 0.5 mmol) and tert-butyl methyl(piperidin-4-yl)carbamate (213 mg, 1.0 mmol) in DMF (5 mL), was added potassium carbonate (138 mg, 1.0 mmol). The reaction mixture was heated at 120° C. for 15 h, and the reaction was monitored by LCMS. Upon completion of the reaction, the solvent was distilled off and the crude material was purified via flash chromatography, eluting with 5% to 30% ethyl acetate in heptane to afford tert-butyl (1-(6-(5-(pyridin-3-yl)-1-((2-(trimethylsilyl)ethoxy)methyl)-1H-pyrazolo[3,4-c]pyridin-3-yl)pyridin-2-yl)piperidin-4-yl)methylcarbamate as a yellow oil (193 mg, 63%). ESI MS m/z=615.34 (M+1).

Step 2

To a solution of tert-butyl (1-(6-(5-(pyridin-3-yl)-1-((2-(trimethylsilyl)ethoxy)methyl)-1H-pyrazolo[3,4-c]pyridin-3-yl)pyridin-2-yl)piperidin-4-yl)methylcarbamate (190 mg, 0.31 mmol) in dioxane (5 mL), was added 10% HCl (1 mL). The reaction mixture was heated at 70° C. for 2 h, and the reaction was monitored by LCMS. Upon completion of the reaction, the solvent was distilled off and the crude material was purified via reverse phase prep-HPLC eluting with 40% to 80% MeOH in aqueous 0.1% NH$_4$OH solution to afford 278 as a yellow solid (60 mg, 50%). $^1$H NMR (400 MHz, DMSO) 9.23 (s, 2H), 8.95 (s, 1H), 8.61-8.60 (d, J=2.8, 1H), 8.40-8.38 (m, 1H), 7.68-7.65 (m, 1H), 7.58-7.55 (m, 1H), 7.48-7.46 (m, 1H), 4.96 (s, 1H), 4.53-4.50 (d, J=10.4, 1H), 3.38-3.36 (m, 3H), 2.69-2.68 (d, J=4, 2H), 188-1.86 (d, J=8.3H), 1.32-1.30 (m, 3H). ESI MS m/z=385.2 (M+1)

Example 279

4-(6-(5-(pyridin-3-yl)-1H-pyrazolo[3,4-c]pyridin-3-yl)pyridin-2-yl)piperazin-2-one 279

Step 1: 4-(6-(5-(pyridin-3-yl)-1-((2-(trimethylsilyl)ethoxy)methyl)-1H-pyrazolo[3,4-c]pyridin-3-yl)pyridin-2-yl)piperazin-2-one

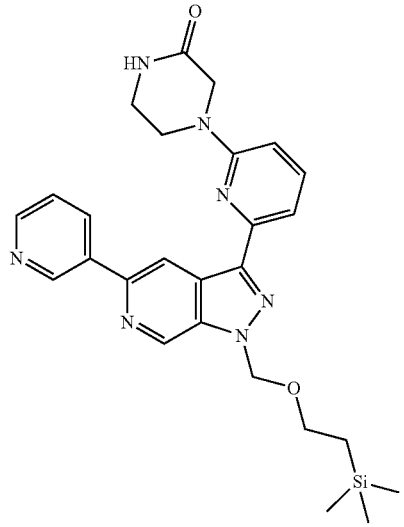 [SMILES: C[Si](C)(C)CCOCn1nc(-c2cccc(N3CCNC(=O)C3)n2)c2cc(-c3cccnc3)ncc21]

The mixture of 3-(6-fluoropyridin-2-yl)-5-(pyridin-3-yl)-1-((2-(trimethylsilyl)ethoxy)methyl)-1H-pyrazolo[3,4-c]pyridine from Example 271 (211 mg, 0.5 mmol) and piperazin-2-one (100 mg, 1.0 mmol) in pyridine (5 mL) was heated at 130° C. for 16 h, and the reaction was monitored by LCMS. Upon completion of the reaction, the solvent was distilled off and the crude material was purified via flash chromatography, eluting with 5% to 30% acetate in heptane to afford 4-(6-(5-(pyridin-3-yl)-1-((2-(trimethylsilyl)ethoxy)methyl)-1H-pyrazolo[3,4-c]pyridin-3-yl)pyridin-2-yl)piperazin-2-one as a yellow oil (76 mg, 30%). ESI MS m/z=501.23 (M+1).

Step 2

To a solution of 4-(6-(5-(pyridin-3-yl)-1-((2-(trimethylsilyl)ethoxy)methyl)-1H-pyrazolo[3,4-c]pyridin-3-yl)pyridin-2-yl)piperazin-2-one (70 mg, 0.14 mmol) in dioxane (5 mL), was added 10% HCl 1 mL. The reaction mixture was stirred at 25° C. for 16 h, and the reaction was monitored by LCMS. Upon completion of the reaction, the solvent was distilled off and the crude material was purified via reverse phase prep-HPLC eluting with 40% to 80% MeOH in aqueous 0.1% NH$_4$OH solution to afford 279 as a yellow solid (13 mg, 25%). $^1$H NMR (400 MHz, DMSO) δ 9.28 (s, 1H), 9.13 (s, 1H), 9.02 (s, 1H), 8.58-8.53 (m, 2H), 7.76-7.73 (t, 1H), 7.64-7.60 (m, 2H), 6.88-6.87 (d, J=6.4, 1H), 4.39 (s, 2H), 3.99-3.98 (t, J=4, 2H). ESI MS m/z=371.15 (M+1)

Example 280

N1-(6-(5-(pyridin-3-yl)-1H-pyrazolo[3,4-c]pyridin-3-yl)pyridin-2-yl)propane-1,3-diamine 280

Following the procedures in Example 271, 3-(6-fluoropyridin-2-yl)-5-(pyridin-3-yl)-1-((2-(trimethylsilyl)ethoxy)methyl)-1H-pyrazolo[3,4-c]pyridine and propane-1,3-diamine were reacted and the product was deprotected to give 280 as a yellow solid (20 mg, 31%) over two steps. $^1$H NMR (400 MHz, DMSO) δ 9.30 (s, 1H), 9.22 (s, 1H), 9.03 (s, 1H), 8.60 (s, 1H) 8.43-8.44 (m, 1H), 7.53-7.57 (m, 2H), 7.38-7.40 (m, 1H), 7.03 (s, 1H), 6.53 (d, J=6.4 Hz, 1H), 4.01 (t, J=1.2 Hz, 2H), 2.92 (m, 2H), 2.50 (t, J=1.2 Hz, 2). ESI MS m/z=346 (M+1)

Example 281

3-(3,4-dihydro-2H-pyran-5-yl)-5-(pyridin-3-yl)-1H-pyrazolo[3,4-c]pyridine 281

In a microwave tube was added 3-iodo-5-(pyridin-3-yl)-1H-pyrazolo[3,4-c]pyridine from Example 4 (0.32 g, 1 mmol), 2-(5,6-dihydro-4H-pyran-3-yl)-4,4,5,5-tetramethyl-1,3,2-dioxaborolane (0.31 g, 1.5 mmol), 2 M Na$_2$CO$_3$ (2 mmol, 1 mL), PdCl$_2$(dppf) (87 mg, 0.1 mmol) and dioxane (8 mL). The suspension was purged with N$_2$ and heated under microwave radiation at 130° C. for 1 hour. It was then cooled to room temperature. Solvent was removed under reduced pressure. The residue was purified by SGC (Petrol/EtOAc:5/1 to 1/1) to give 281 as a yellow solid (97 mg, 35%). $^1$H NMR (400 MHz, DMSO) δ 9.19 (d, J=1.2 Hz, 1H), 9.07 (d, J=0.8 Hz, 1H), 8.53-856 (m, 2H), 8.45 (d, J=0.8 Hz, 1H), 7.71 (s, 1H), 7.47-7.49 (m, 1H), 4.08-4.10 (m, 2H), 2.59-2.61 (m, 2H), 1.98-2.0 (m, 2H). ESI MS m/z=279 (M+1)

Example 282

2-(4-(6-(5-(pyridin-3-yl)-1H-pyrazolo[3,4-c]pyridin-3-yl)pyridin-2-yl)piperazin-1-yl)ethanol 282

Following the procedures in Example 271, 3-(6-fluoropyridin-2-yl)-5-(pyridin-3-yl)-1-((2-(trimethylsilyl)ethoxy)methyl)-1H-pyrazolo[3,4-c]pyridine and piperazin-1-yl)ethanol were reacted and the product was deprotected to give 282 as a yellow solid (20 mg, 32%) over two steps. $^1$H NMR (400 MHz, DMSO) δ 9.22 (s, 1H), 8.94 (s, 1H), 8.61 (s, 1H), 8.40-8.38 (m, 1H), 7.70-7.67 (m, 1H), 7.57-7.55 (m, 1H), 7.51-7.49 (m, 1H), 6.90-6.88 (m, 1H), 4.50 (s, 1H), 3.69 (s, 4H), 3.60-3.57 (m, 2H), 2.62 (s, 1H), 2.51-2.48 (m, 2H). ESI MS m/z=402.7 (M+1)

Example 283

N1-(6-(5-(pyridin-3-yl)-1H-pyrazolo[3,4-c]pyridin-3-yl)pyridin-2-yl)butane-1,4-diamine 283

Following the procedures Example 271, 3-(6-fluoropyridin-2-yl)-5-(pyridin-3-yl)-1-((2-(trimethylsilyl)ethoxy)methyl)-1H-pyrazolo[3,4-c]pyridine and butane-1,4-diamine were reacted and the product was deprotected to give 283 as a yellow solid (20 mg, 28%) over two steps. $^1$H NMR (400 MHz, DMSO) δ 9.19-9.21 (m, 1H), 9.12-9.13 (m, 2H), 8.53-8.60 (m, 2H), 7.60-7.63 (m, 1H) 7.51-7.54 (m, 1H), 7.44-7.46 (m, 1H), 6.53 (d, J=6.4 Hz, 1H), 3.65 (t, J=1.2 Hz, 2H), 2.93 (t, J=1.2 Hz, 2H), 1.80-1.85 (m, 4H). ESI MS m/z=360 (M+1)

Example 284

3-(4,5-dihydrofuran-3-yl)-5-(pyridin-3-yl)-1H-pyrazolo[3,4-c]pyridine 284

Following the procedures Example 281, 3-iodo-5-(pyridin-3-yl)-1H-pyrazolo[3,4-c]pyridine from Example 4 and 2-(4,5-dihydrofuran-3-yl)-4,4,5,5-tetramethyl-1,3,2-dioxaborolane were reacted to give 284 as a white solid (0.1 g, 40%). 1H NMR (400 MHz, DMSO): δ 9.42 (s, 1H), 9.09 (s, 1H), 8.56-8.57 (m, 2H), 8.51 (s, 1H), 7.86 (s, 1H), 7.47-7.49 (m, 1H), 4.46-4.50 (m, 2H), 3.12-3.14 (m, 2H). ESI MS m/z=265 (M+1)

Example 285

(R)-1-(6-(5-(1-ethyl-1H-pyrazol-4-yl)-1H-pyrazolo[3,4-c]pyridin-3-yl)pyridin-2-yl)piperidin-3-amine 285

Following the procedures as described in Example 189, 3-(6-fluoropyridin-2-yl)-5-(1-ethyl-1H-pyrazol-4-yl)-1-(tetrahydro-2H-pyran-2-yl)-1H-pyrazolo[3,4-c]pyridine and (R)-tert-butyl piperidin-3-ylcarbamate were reacted. The product was deprotected and purified to give 285 as a white solid (41.6% over two steps). ¹H NMR (400 MHz, DMSO) δ 9.02 (s, 1H), 8.60 (s, 1H), 8.34 (s, 1H), 7.97 (s, 1H), 7.62 (t, J=8.0 Hz, 1H), 7.42 (d, J=7.4 Hz, 1H), 6.83 (d, J=8.5 Hz, 1H), 4.45 (d, J=8.7 Hz, 1H), 4.28-4.12 (m, 3H), 2.98 (t, J=10.9 Hz, 1H), 2.82-2.72 (m, 2H), 2.03-1.93 (m, 1H), 1.86-1.77 (m, 1H), 1.67-1.51 (m, 1H), 1.42 (t, J=7.3 Hz, 3H), 1.38-1.26 (m, 1H); 3 protons not seen. LC/MS: m/z 389.2 [M+1]

Example 286

1-(6-(5-(1-methyl-1H-pyrazol-4-yl)-1H-pyrazolo[3,4-c]pyridin-3-yl)pyridin-2-yl)-3-(trifluoromethyl)pyrrolidin-3-amine 286

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and tert-butyl 3-(trifluoromethyl)pyrrolidin-3-ylcarbamate were reacted. The product was deprotected and purified to give 286 as a white solid (47.3% over two steps). ¹H NMR (400 MHz, DMSO) δ 9.02 (s, 1H), 8.65 (s, 1H), 8.09 (s, 1H), 7.86 (s, 1H), 7.65 (t, J=7.9 Hz, 1H), 7.44 (d, J=7.4 Hz, 1H), 6.51 (d, J=8.3 Hz, 1H), 3.91-3.86 (m, 4H), 3.84-3.65 (m, 3H), 2.47 (s, 2H), 2.38-2.27 (m, 1H), 2.05 (dd, J=12.3, 6.1 Hz, 1H); 1 proton not seen. LC/MS: m/z 429.2 [M+1]

Example 287

(R)-1-(3-bromo-6-(5-(pyridin-3-yl)-1H-pyrazolo[3,4-c]pyridin-3-yl)pyridin-2-yl)pyrrolidin-3-amine 287

Step 1: 3-bromo-2-fluoro-6-iodopyridine

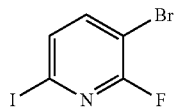

To a solution of 2-fluoropyridin-3-amine (5.00 g, 44.60 mmol) in DMF (100 mL) was added N-iodosuccinimide (11.04 g, 49.06 mmol). The resulting mixture was stirred overnight. The reaction mixture was partitioned between EtOAc and water. The organic layer was dried with MgSO4 and concentrated. The residue was purified on silica eluted 0 to 50% EtOAc in Heptane. 2-fluoro-6-iodopyridin-3-amine was obtained as a dark tan solid (8.8674 g, 83%). To an ice cooled mixture of tert-Butyl nitrite (356.8 uL, 3.000 mmol) and Copper(II) bromide (536.0 mg, 2.400 mmol) in Acetonitrile (5 mL) was added 2-fluoro-6-iodopyridin-3-amine was obtained as a dark tan solid (476.0 mg, 2.000 mmol). The resulting mixture was stirred overnight allowing warming to room temperature. The mixture was filtered through Celite. The filtrated was concentrated. The residue was partitioned between Et2O and saturated NH4Cl. The organic layer was dried with MgSO4, and then concentrated. The residue was purified on silica eluted with 0 to 20% EtOAc in Heptane. 3-Bromo-2-fluoro-6-iodopyridine was obtained as a yellow solid (407.1 mg, 57%)

Step 2: 3-(5-bromo-6-fluoropyridin-2-yl)-5-(pyridin-3-yl)-1-((2-(trimethylsilyl)ethoxy)methyl)-1H-pyrazolo[3,4-c]pyridine

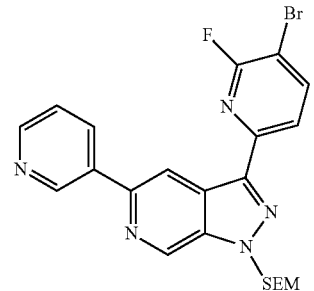 [SMILES: C[Si](C)(C)CCOCn1nc(-c2ccc(Br)c(F)n2)c2cc(-c3cccnc3)ncc21]

To an argon protected mixture of 5-(pyridin-3-yl)-1-((2-(trimethylsilyl)ethoxy)methyl)-3-(trimethylstannyl)-1H-pyrazolo[3,4-c]pyridine (239 mg, 0.489 mmol) and 3-bromo-2-fluoro-6-iodopyridine (162.3 mg, 0.538 mmol) in N,N-Dimethylformamide (5 mL, 60 mmol) was added Cesium fluoride (148 mg, 0.98 mmol). Tetrakis(triphenylphosphine)palladium(0) (56.482 mg, 0.048878 mmol) and Copper(I) iodide (18.618 mg, 0.097757 mmol) were then added and the resulting mixture was stirred at 40° C. for 2 hours. The mixture was cooled to room temperature, filtered through Celite®. The filter cake was washed with EtOAc. The organic layer was washed with brine, dried with MgSO4, and then concentrated. The residue was purified on silica eluted with 0 to 100% EtOAc in Heptane to afford 3-(5-bromo-6-fluoropyridin-2-yl)-5-(pyridin-3-yl)-1-((2-(trimethylsilyl)ethoxy)methyl)-1H-pyrazolo[3,4-c]pyridine as a light yellow oil, which solidified upon standing (208.1 mg, 85%).

Step 3

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-tert-butyl pyrrolidin-3-ylcarbamate, 287 was obtained as an off-white solid (12.2 mg, 34%) over two steps. 1H NMR (400 MHz, DMSO) δ 9.27 (s, 1H), 9.22 (s, 1H), 9.02 (s, 1H), 8.60 (d, J=4.6 Hz, 1H), 8.41 (d, J=8.0 Hz, 1H), 7.92 (d, J=8.0 Hz, 1H), 7.62 (dd, J=11.8, 7.2 Hz, 3H), 7.58-7.49 (m, 3H), 7.45 (d, J=8.0 Hz, 1H), 4.01-3.92 (m, 2H), 3.64-3.51 (m, 3H), 2.10 (dt, J=12.0, 5.9 Hz, 1H), 1.82-1.72 (m, 1H); ESI MS m/z=358.2 (M+1)

Example 288

1-(3-methyl-6-(5-(pyridin-3-yl)-1H-pyrazolo[3,4-c]pyridin-3-yl)pyridin-2-yl)piperidin-4-ol 288

Following the procedures as described in Examples 241, 243, and 287 and starting with 3-(5-bromo-6-fluoropyridin- 2-yl)-5-(pyridin-3-yl)-1-((2-(trimethylsilyl)ethoxy)methyl)-1H-pyrazolo[3,4-c]pyridine and piperidin-4-ol, 288 was obtained as an off-white solid (20.4 mg, 29%) over three steps. 1H NMR (400 MHz, DMSO) δ 13.85 (s, 1H), 9.25 (d, J=1.5 Hz, 1H), 9.20 (s, 1H), 9.09 (s, 1H), 8.61 (d, J=3.7 Hz, 1H), 8.41 (d, J=8.0 Hz, 1H), 7.74 (d, J=7.6 Hz, 1H), 7.63 (d, J=7.7 Hz, 1H), 7.55 (dd, J=7.9, 4.8 Hz, 1H), 4.73 (d, J=4.0 Hz, 1H), 3.74 (dd, J=8.7, 4.3 Hz, 1H), 3.61 (d, J=12.7 Hz, 2H), 3.06 (t, J=10.3 Hz, 2H), 2.31 (s, 3H), 1.95 (d, J=10.4 Hz, 2H), 1.65 (q, J=9.2 Hz, 2H); ESI MS m/z=387.2 (M+1)

Example 289

(S)-1-(3-bromo-6-(5-(pyridin-3-yl)-1H-pyrazolo[3,4-c]pyridin-3-yl)pyridin-2-yl)piperidin-3-amine 289

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (S)-tert-butyl piperidin-3-ylcarbamate, 289 was obtained as an off-white solid (17.8 mg, 22.32%) over two steps. 1H NMR (400 MHz, DMSO) δ 9.31 (d, J=1.8 Hz, 1H), 9.23 (s, 1H), 9.03 (s, 1H), 8.60 (d, J=4.7 Hz, 1H), 8.46 (d, J=7.9 Hz, 1H), 8.06 (d, J=8.1 Hz, 1H), 7.71 (d, J=8.1 Hz, 1H), 7.62 (dd, J=11.8, 7.1 Hz, 1H), 7.52 (dd, J=8.0, 4.8 Hz, 1H), 3.92 (d, J=10.0 Hz, 1H), 3.84 (d, J=11.7 Hz, 1H), 2.89 (dt, J=16.9, 10.7 Hz, 2H), 2.82-2.75 (m, 1H), 1.96 (d, J=12.6 Hz, 1H), 1.90-1.71 (m, 2H), 1.27 (dd, J=20.9, 9.6 Hz, 1H); ESI MS m/z=450.1 (M+1)

Example 290

(R)-1-(3-bromo-6-(5-(pyridin-3-yl)-1H-pyrazolo[3,4-c]pyridin-3-yl)pyridin-2-yl)piperidin-3-amine 290

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-tert-butyl piperidin-3-ylcarbamate, 290 was obtained as an off-white solid (19.7 mg, 35.9%) over two steps. 1H NMR (400 MHz, DMSO) δ 9.31 (s, 1H), 9.22 (s, 1H), 9.03 (s, 1H), 8.59 (d, J=4.7 Hz, 1H), 8.46 (d, J=8.0 Hz, 1H), 8.05 (d, J=8.1 Hz, 1H), 7.70 (d, J=8.1 Hz, 1H), 7.62 (dd, J=11.8, 7.1 Hz, 1H), 7.54 (ddd, J=12.7, 7.2, 4.0 Hz, 2H), 3.92 (d, J=9.3 Hz, 1H), 3.84 (d, J=12.1 Hz, 1H), 2.88 (d, J=12.9 Hz, 2H), 2.81-2.69 (m, 1H), 1.95 (d, J=12.6 Hz, 1H), 1.90-1.69 (m, 2H), 1.26 (dd, J=22.3, 7.8 Hz, 1H); ESI MS m/z=450.1 (M+1)

Example 291

(R)-1-(3-bromo-6-(5-(pyridin-3-yl)-1H-pyrazolo[3,4-c]pyridin-3-yl)pyridin-2-yl)piperidin-3-ol 291

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-piperidin-3-ol hydrochloride, 291 was obtained as an off-white solid (11.0 mg, 29.9%) over two steps. 1H NMR (400 MHz, DMSO) δ 9.31 (d, J=1.8 Hz, 1H), 9.24 (s, 1H), 9.01 (s, 1H), 8.60 (d, J=4.0 Hz, 1H), 8.44 (d, J=8.1 Hz, 1H), 8.06 (d, J=8.1 Hz, 1H), 7.70 (d, J=8.1 Hz, 1H), 7.51 (dd, J=8.0, 4.8 Hz, 1H), 4.93 (d, J=4.4 Hz, 1H), 3.97 (d, J=11.6 Hz, 1H), 3.83 (d, J=12.2 Hz, 1H), 3.74 (dd, J=9.2, 4.8 Hz, 1H), 2.99-2.81 (m, 2H), 2.02 (d, J=9.1 Hz, 1H), 1.88 (d, J=13.3 Hz, 1H), 1.72 (dd, J=22.7, 10.5 Hz, 1H), 1.39 (dd, J=22.0, 8.0 Hz, 1H); ESI MS m/z=451.1 (M+1)

Example 292

1-(3-bromo-6-(5-(pyridin-3-yl)-1H-pyrazolo[3,4-c]pyridin-3-yl)pyridin-2-yl)piperidin-4-ol 292

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and piperidin-4-ol, 292 was obtained as an off-white solid (9.50 mg, 26.8%) over two steps. 1H NMR (400 MHz, DMSO) δ 9.26-9.20 (m, 2H), 8.99 (s, 1H), 8.61 (d, J=3.7 Hz, 1H), 8.41 (d, J=7.9 Hz, 1H), 8.06 (d, J=8.1 Hz, 1H), 7.70 (d, J=8.1 Hz, 1H), 7.55 (dd, J=8.0, 4.8 Hz, 1H), 4.75 (d, J=3.7 Hz, 1H), 3.91-3.71 (m, 3H), 3.18 (d, J=10.1 Hz, 2H), 1.96 (d, J=11.1 Hz, 2H), 1.65 (dd, J=18.8, 9.2 Hz, 2H); ESI MS m/z=451.2 (M+1)

Example 293

(R)-1-(3-bromo-6-(5-(pyridin-3-yl)-1H-pyrazolo[3,4-c]pyridin-3-yl)pyridin-2-yl)pyrrolidin-3-ol 293

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-pyrrolidin-3-ol hydrochloride, 293 was obtained as an off-white solid (3.50 mg, 9.60%) over two steps. ESI MS m/z=437.1 (M+1)

Example 294

1-(6-(5-(1-methyl-1H-pyrazol-4-yl)-1H-pyrazolo[3,4-c]pyridin-3-yl)pyridin-2-yl)piperidin-4-ol 294

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and piperidin-4-ol were reacted. The product was deprotected and purified to give 294 as a white solid (56.1% over two steps). $^1$H NMR (400 MHz, DMSO) δ 13.69 (broad s, 1H), 9.03 (s, 1H), 8.53 (s, 1H), 8.11 (s, 1H), 7.82 (s, 1H), 7.64 (t, J=7.9 Hz, 1H), 7.42 (d, J=7.4 Hz, 1H), 6.87 (d, J=8.5 Hz, 1H), 4.73 (d, J=3.2 Hz, 1H), 4.24-4.15 (m, 2H), 3.91 (s, 3H), 3.6-3.76 (m, 1H), 3.37-3.29 (m, 2H), 1.97-1.86 (m, 2H), 1.58-1.44 (m, 2H). LC/MS: m/z 376.2 [M+1]

Example 295

2-(5-(pyridin-3-yl)-1H-pyrazolo[3,4-c]pyridin-3-yl)-2,8-diazaspiro[4.5]decan-1-one 295

Step 1: benzyl 1-oxo-2-(5-(pyridin-3-yl)-1-((2-(trimethylsilyl)ethoxy)methyl)-1H-pyrazolo[3,4-c]pyridin-3-yl)-2,8-diazaspiro[4.5]decane-8-carboxylate

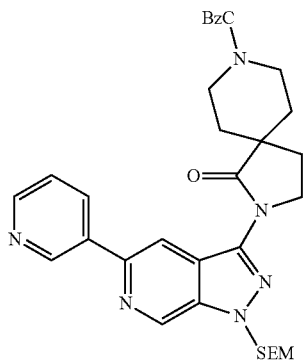

A solution containing 3-iodo-5-(pyridin-3-yl)-1-((2-(trimethylsilyl)ethoxy)methyl)-1H-pyrazolo[3,4-c]pyridine (0.196 g, 0.434 mmol), benzyl 1-oxo-2,8-diazaspiro[4.5]decane-8-carboxylate (0.250 g, 0.867 mmol), N,N'-Dimethylethylenediamine (0.103 mL, 0.954 mmol), Copper(I) iodide (0.0908 g, 0.477 mmol) and Cesium Carbonate (0.311 g, 0.954 mmol) in 1,4-Dioxane (7.08 mL, 90.7 mmol) was stirred at 75° C. for 2 h. The reaction was filtered thru celite and concentrated. The crude product purified by Isco column (EtOAc/Hep eluted at 50% EtOAc) to give benzyl 1-oxo-2-(5-(pyridin-3-yl)-1-((2-(trimethylsilyl)ethoxy)methyl)-1H-pyrazolo[3,4-c]pyridin-3-yl)-2,8-diazaspiro[4.5]decane-8-carboxylate (140 mg, 52.7% yield). ESI MS m/z=613.1 (M+1).

Step 2

A solution of benzyl 1-oxo-2-(5-(pyridin-3-yl)-1-((2-(trimethylsilyl)ethoxy)methyl)-1H-pyrazolo[3,4-c]pyridin-3-yl)-2,8-diazaspiro[4.5]decane-8-carboxylate (0.140 g, 0.229 mmol) in 2.00 M of Hydrogen chloride in Water (16.2 mL) was stirred at 100° C. for 18 h. The reaction was concentrated then submitted for rHPLC to give 295 (21.2 mg, 26.5% yield). ESI MS m/z=349.2 (M+1). $^1$H NMR (400 MHz, DMSO) δ 9.19 (d, J=1.8 Hz, 1H), 9.07 (s, 1H), 8.67 (s, 1H), 8.57 (d, J=4.6 Hz, 1H), 8.33 (d, J=8.0 Hz, 1H), 7.51 (dd, J=7.9, 4.7 Hz, 1H), 3.97 (t, J=7.0 Hz, 2H), 2.92 (d, J=12.6 Hz, 2H), 2.63 (dd, J=21.4, 9.3 Hz, 2H), 2.20 (t, J=7.0 Hz, 2H), 1.74 (td, J=12.5, 4.1 Hz, 2H), 1.48 (d, J=13.0 Hz, 2H)

Example 296

1-(piperidin-4-ylmethyl)-3-(5-(pyridin-3-yl)-1H-pyrazolo[3,4-c]pyridin-3-yl)imidazolidin-2-one 296

Step 1: 1-acetyl-3-(5-bromo-1-(tetrahydro-2H-pyran-2-yl)-1H-pyrazolo[3,4-c]pyridin-3-yl)imidazolidin-2-one

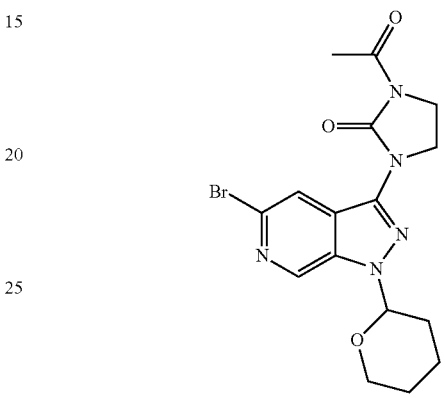

A solution containing 5-bromo-3-iodo-1-(tetrahydro-2H-pyran-2-yl)-1H-pyrazolo[3,4-c]pyridine (1.00 g, 2.45 mmol), 1-acetylimidazolidin-2-one (0.3768 g, 2.941 mmol), N,N'-Dimethylethylenediamine (0.528 mL, 4.90 mmol), Copper(I) iodide (0.467 g, 2.45 mmol) and Potassium carbonate (0.4064 g, 2.941 mmol) in 1,4-Dioxane (40.0 mL, 512 mmol) was stirred at 75° C. for 2 h. The reaction was filtered thru celite and concentrated. The crude product purified by Isco column (1% MeOH/EtOAc/Hep eluted at 55% EtOAc) to give 1-acetyl-3-(5-bromo-1-(tetrahydro-2H-pyran-2-yl)-1H-pyrazolo[3,4-c]pyridin-3-yl)imidazolidin-2-one (620 mg, 62% yield). ESI MS m/z=408.1 (M+1).

Step 2: 1-(5-(pyridin-3-yl)-1-(tetrahydro-2H-pyran-2-yl)-1H-pyrazolo[3,4-c]pyridin-3-yl)imidazolidin-2-one

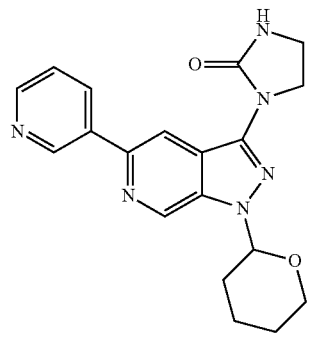 [SMILES: O=C1NCCN1c1nn(C2CCCCO2)c2cnc(-c3cccnc3)cc12]

To a solution containing 1-acetyl-3-(5-bromo-1-(tetrahydro-2H-pyran-2-yl)-1H-pyrazolo[3,4-c]pyridin-3-yl)imidazolidin-2-one (0.295 g, 0.722 mmol), 3-pyridineboronic acd pinacol ester (0.444 g, 2.17 mmol), 1,1'-Bis(diphenylphosphino)ferrocenepalladium (II) chloride (0.0472 g, 0.0578 mmol) in Acetonitrile (5.47 mL, 105 mmol) was added 1.00 M of Potassium acetate in Water (1.44 mL) and 1.00 M of Sodium carbonate in Water (1.44 mL). The reaction was stirred at 100° C. for 3 h. The reaction is filtered thru celite. The crude product was diluted in EtOAc then washed with water and sat. NaCl. The organic layer was dried Na2SO4, filtered, and concentrated to give 1-(5-(pyridin-3-yl)-1-(tetrahydro-2H-pyran-2-yl)-1H-pyrazolo[3,4-c]pyridin-3-yl)imidazolidin-2-one. ESI MS m/z=365.2 (M+1).

Step 3

To a solution of 1-(5-(pyridin-3-yl)-1-(tetrahydro-2H-pyran-2-yl)-1H-pyrazolo[3,4-c]pyridin-3-yl)imidazolidin-2-one (0.120 g, 0.329 mmol) dissolved in N,N-Dimethylformamide (3.43 mL) and cooled to 0° C. was added NaH in Oil (6:4, Sodium hydride:Mineral Oil, 26.3 mg). The reaction mixture was stirred at RT for 30 mins then cooled to 0° C. 4-bromomethyl-piperidine-1-carboxylic acid tert-butyl ester (0.183 g, 0.659 mmol) was added. The reaction was stirred at RT for 18 hr. The mixture was quenched with H2O then extracted with EtOAc. The organic layers was dried, filtered, and concentrated to give tert-butyl 4-((2-oxo-3-(5-(pyridin-3-yl)-1-(tetrahydro-2H-pyran-2-yl)-1H-pyrazolo[3,4-c]pyridin-3-yl)imidazolidin-1-yl)methyl)piperidine-1-carboxylate which was dissolved in 4.0 M of Hydrogen chloride in 1,4-Dioxane (6.00 mL) and 1,4-Dioxane (3.00 mL, 38.4 mmol;) was stirred at RT 18 h. The reaction was concentrated and submitted for rHPLC purification to give 296 (11.6 mg, 9.3% yield). ESI MS m/z=378.2 (M+1). $^1$H NMR (400 MHz, DMSO) δ 9.17 (s, 1H), 9.03 (s, 1H), 8.78 (s, 1H), 8.55 (d, J=4.7 Hz, 1H), 8.30 (d, J=8.0 Hz, 1H), 7.50 (dd, J=8.0, 4.7 Hz, 1H), 4.03-3.93 (m, 2H), 3.65-3.56 (m, 2H), 3.11 (d, J=7.2 Hz, 2H), 2.92 (d, J=12.0 Hz, 2H), 2.42 (d, J=10.9 Hz, 1H), 1.79-1.67 (m, 1H), 1.59 (d, J=11.8 Hz, 2H), 1.05 (dd, J=21.5, 9.9 Hz, 2H)

Example 297

2-methyl-1-(6-(5-(1-methyl-1H-pyrazol-4-yl)-1H-pyrazolo[3,4-c]pyridin-3-yl)pyridin-2-ylamino)propan-2-ol 297

Following the procedures as described in Example 189, 3-(6-fluoropyridin-2-yl)-5-(1-methyl-1H-pyrazol-4-yl)-1-(tetrahydro-2H-pyran-2-yl)-1H-pyrazolo[3,4-c]pyridine and 1-amino-2-methyl-propan-2-ol were reacted. The product was deprotected and purified to give 297 as a white solid (87% over two steps). $^1$H NMR (400 MHz, DMSO) δ 13.62 (broad s, 1H), 9.01 (s, 1H), 8.72 (s, 1H), 8.25 (s, 1H), 7.98 (s, 1H), 7.47 (t, J=7.8 Hz, 1H), 7.31 (d, J=7.3 Hz, 1H), 6.63-6.56 (m, 2H), 4.73 (s, 1H), 3.89 (s, 3H), 3.56 (d, J=5.8 Hz, 2H), 1.25 (s, 6H). LC/MS: m/z 364.2 [M+1]

Example 298

(S)-1-(3-(6-(3-aminopiperidin-1-yl)pyridin-2-yl)-1H-pyrazolo[3,4-c]pyridin-5-yl)urea 298

Following the Buchwald-Hartwig procedure of Example 224, tert-butyl (3S)-1-(6-(5-bromo-1-(tetrahydro-2H-pyran-2-yl)-1H-pyrazolo[3,4-c]pyridin-3-yl)pyridin-2-yl)piperidin-3-ylcarbamate and (1,1-dimethylethyl)urea were reacted and deprotected by the procedure of Example 229. The mixture was purified via reverse phase HPLC using a gradient of MeOH in water with 0.1% NH4OH to afford 20 mg (23%) of 298 over three steps. ESI MS m/z 353.2 (M+1). 1H NMR (400 MHz, DMSO): 9.14 (s, 1H), 8.96 (s, 1H), 8.75 (s, 1H), 8.40 (s, 2H), 7.63 (t, J=8.0 Hz, 1H), 7.45 (d, J=7.4 Hz, 1H), 6.80 (d, J=8.5 Hz, 1H), 6.48 (s, 2H), 4.92 (d, J=11.4 Hz, 1H), 4.05 (d, J=12.9 Hz, 1H), 3.09 (m, 1H), 2.94-2.77 (m, 2H), 2.54 (s, 2H), 2.05 (d, J=9.7 Hz, 1H), 1.84 (d, J=13.1, Hz, 1H), 1.64-1.42 (m, 2H)

Example 299

(1S,3R)-3-(6-(5-(pyridin-3-yl)-1H-pyrazolo[3,4-c]pyridin-3-yl)pyridin-2-yloxy)cyclohexanamine 299

Step 1: tert-Butyl (1S,3S)-3-hydroxycyclohexylcarbamate

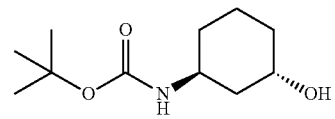

A solution of 0.5238 g (2.4 mmol) of di-tert-butyldicarbonate in 5 ml of THF and 0.6 ml of 4.0 M of sodium hydroxide in water were added dropwise to a solution of 230.3 mg (2.0 mmol) of (1S,3S)-3-aminocyclohexanol in 6 ml of tetrahydrofuran and 4 ml of water at 0° C. The mixture was stirred for 18 hours, diluted with water and extracted with ethyl acetate. The organic extracts were washed with water, brine, dried over MgSO4 and concentrated to afford 434 mg (100%) of tert-Butyl (1S,3S)-3-hydroxycyclohexylcarbamate as a crystalline residue.

Step 2: tert-Butyl (1S,3R)-3-(6-bromopyridin-2-yloxy)cyclohexylcarbamate

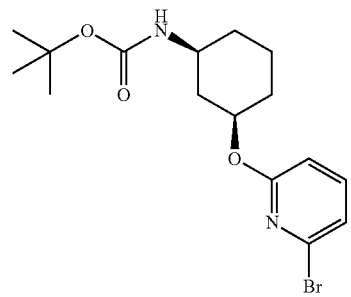 [SMILES: CC(C)(C)OC(=O)N[C@H]1CCC[C@@H](Oc2cccc(Br)n2)C1]

A solution of 0.473 mL (2.4 mmol) of diisopropylazodicarboxylate in 2 ml of tetrahydrofuran was added dropwise to a mixture of 454 mg (2.0 mmol) of tert-butyl (1S,3S)-3-hydroxycyclohexylcarbamate, 418 mg (2.40 mmol) of 2-bromo-6-hydroxypyridine and 629.5 mg (2.4 mmol) of triphenylphosphine in 5 ml of tetrahydrofuran at 0-5° C. The mixture was stirred for 18 hours. The mixture was concentrated, the residue purified via silica gel chromatography using a gradient of ethyl acetate in heptane to afford 222 mg (30%) of tert-Butyl (1S,3R)-3-(6-bromopyridin-2-yloxy)cyclohexylcarbamate. ESI MS m/z 370.9 (M+1).

Step 3: tert-Butyl (1S,3R)-3-(6-(5-(pyridin-3-yl)-1-((2-(trimethylsilyl)ethoxy)methyl)-1H-pyrazolo[3,4-c]pyridin-3-yl)pyridin-2-yloxy)cyclohexylcarbamate

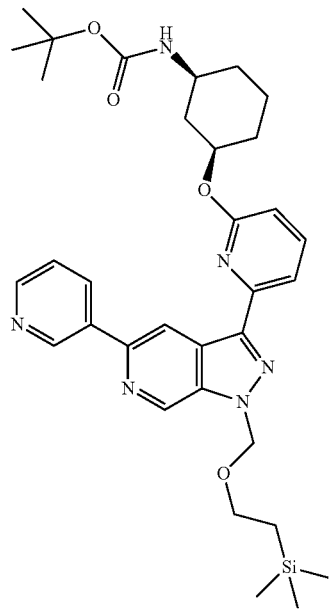 [SMILES: CC(C)(C)OC(=O)N[C@H]1CCC[C@@H](Oc2cccc(-c3nn(COCC[Si](C)(C)C)c4cnc(-c5cccnc5)cc34)n2)C1]

A mixture of 147 mg (0.3 mmol) of 5-(pyridin-3-yl)-1-((2-(trimethylsilyl)ethoxy)methyl)-3-(trimethylstannyl)-1H-pyrazolo[3,4-c]pyridine, 123 mg, 0.33 mmol) of tert-butyl (1S,3R)-3-(6-bromopyridin-2-yloxy)cyclohexylcarbamate, 109 mg (0.72 mmol) of Cesium fluoride, 35 mg (0.03 mmol) of tetrakis(triphenylphosphine)palladium(0) and 11.4 mg (0.06 mmol) of copper(I) iodide in 2 ml of N,N-dimethylformamide was heated at 50° C. for 2 hours in a Stille coupling. The mixture was diluted with water and extracted with ethyl acetate. The organic extracts were washed with water, brine, dried over MgSO4 and concentrated. The residue was purified via silica gel chromatography using a gradient of ethyl acetate in heptane to afford 98 mg (53%) of tert-Butyl (1S,3R)-3-(6-(5-(pyridin-3-yl)-1-((2-(trimethylsilyl)ethoxy)methyl)-1H-pyrazolo[3,4-c]pyridin-3-yl)pyridin-2-yloxy)cyclohexylcarbamate. ESI MS m/z 617.5 (M+1).

Step 4 tert-Butyl (1S,3R)-3-(6-(5-(pyridin-3-yl)-1-((2-(trimethylsilyl)ethoxy)methyl)-1H-pyrazolo[3,4-c]pyridin-3-yl)pyridin-2-yloxy)cyclohexylcarbamate was deprotected by the procedure of Example 225 and purified via reverse phase HPLC using a gradient of MeOH in water with 0.1% NH4OH to afford 32 mg (61%) of 299. ESI MS m/z 387.2 (M+1). 1H NMR (400 MHz, DMSO): 9.26 (d, J=1.7 Hz, 1H), 9.23 (s, 1H), 8.86 (s, 1H), 8.61 (d, J=4.7 Hz, 1H), 8.42 (d, J=8.0 Hz, 1H), 7.86-7.78 (m, 2H), 7.52 (dd, J=7.9, 4.8 Hz, 1H), 6.81-6.73 (m, 1H), 5.35 (m, 1H), 2.79-2.69 (m, 1H), 2.33 (m, 1H), 2.22 (s, 1H), 1.71 (m, 2H), 1.36-1.19 (m, 3H), 1.06-0.93 (m, 1H)

Example 300

(R)-1-(4-(5-(pyridin-3-yl)-1H-pyrazolo[3,4-c]pyridin-3-yl)pyrimidin-2-yl)piperidin-3-amine 300

Step 1: 3-(2-Chloropyrimidin-4-yl)-5-(pyridin-3-yl)-1-((2-(trimethylsilyl)ethoxy)methyl)-1H-pyrazolo[3,4-c]pyridine

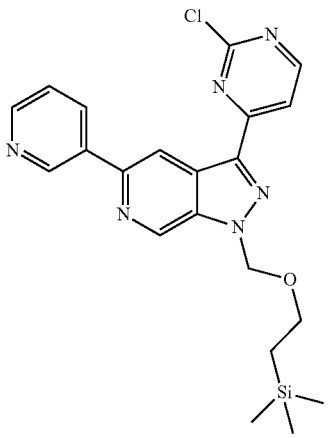 [SMILES: C[Si](C)(C)CCOCn1nc(-c2ccnc(Cl)n2)c2cc(-c3cccnc3)ncc21]

Following the Stille coupling procedure of Example 299, 5-(pyridin-3-yl)-1-((2-(trimethylsilyl)ethoxy)methyl)-3-(trimethylstannyl)-1H-pyrazolo[3,4-c]pyridine and 2,4-dichloropyrimidine were reacted. The product was purified via silica gel chromatography using a gradient of ethyl acetate in heptane to afford 60 mg (50%) of 3-(2-Chloropyrimidin-4-yl)-5-(pyridin-3-yl)-1-((2-(trimethylsilyl)ethoxy)methyl)-1H-pyrazolo[3,4-c]pyridine. ESI MS m/z 439.2 (M+1).

Step 2

Following the procedure of Example 144, 3-(2-chloropyrimidin-4-yl)-5-(pyridin-3-yl)-1-((2-(trimethylsilyl)ethoxy)methyl)-1H-pyrazolo[3,4-c]pyridine and (R)-tert-butyl piperidin-3-ylcarbamate were reacted. The product was deprotected by the procedure of Example 225 and purified via reverse phase HPLC using a gradient of MeOH in water with 0.1% NH4OH to afford 32 mg (63%) of 300. ESI MS m/z 373.2 (M+1). 1H NMR (400 MHz, DMSO): 9.30 (s, 1H), 9.25 (s, 1H), 8.91 (s, 1H), 8.59 (dd, J=4.7, 1.2 Hz, 1H), 8.45 (t, J=8.1 Hz, 2H), 7.53 (dd, J=7.9, 4.7 Hz, 1H), 7.32 (d, J=5.0 Hz, 1H), 4.71 (d, J=10.8 Hz, 1H), 4.61 (d, J=12.5 Hz, 1H), 3.15-3.06 (m, 1H), 2.91-2.83 (m, 1H), 2.82-2.73 (m, 1H), 1.96 (d, J=11. Hz, 1H), 1.81 (d, J=13.4 Hz, 1H), 1.55 (d, J=12.1 Hz, 1H), 1.36 (td, J=12.2, 3.8 Hz, 1H)

Example 301

1-(6-(5-(pyridin-3-yl)-1H-pyrazolo[3,4-c]pyridin-3-yl)pyridin-2-yl)piperazin-2-one 301

Step 1: 3-(6-Bromopyridin-2-yl)-5-(pyridin-3-yl)-1-((2-(trimethylsilyl)ethoxy)methyl)-1H-pyrazolo[3,4-c]pyridine

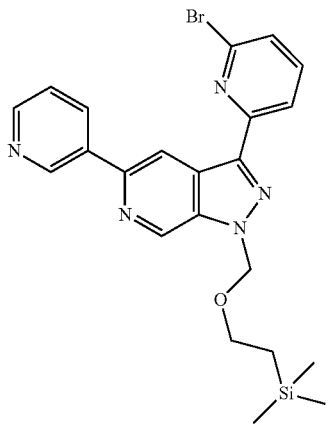 [SMILES: C[Si](C)(C)CCOCn1nc(-c2cccc(Br)n2)c2cc(-c3cccnc3)ncc21]

Following the Stille coupling procedure of Example 299, 5-(pyridin-3-yl)-1-((2-(trimethylsilyl)ethoxy)methyl)-3-(trimethylstannyl)-1H-pyrazolo[3,4-c]pyridine and 2,6-dibromopyridine were reacted. The mixture was purified via silica gel chromatography using a gradient of ethyl acetate in heptane to afford 81 mg (67%) of 3-(6-Bromopyridin-2-yl)-5-(pyridin-3-yl)-1-((2-(trimethylsilyl)ethoxy)methyl)-1H-pyrazolo[3,4-c]pyridine. ESI MS m/z 482.2 (M+1).

Step 2

Following the procedure of Example 224, 3-(6-bromopyridin-2-yl)-5-(pyridin-3-yl)-1-((2-(trimethylsilyl)ethoxy)methyl)-1H-pyrazolo[3,4-c]pyridine and tert-butyl 3-oxopiperazine-1-carboxylate were reacted. The product was deprotected by the procedure of Example 225 and purified via reverse phase HPLC using a gradient of MeOH in water with 0.1% NH$_4$OH to afford 8.0 mg (20%) of 301 over two steps. ESI MS m/z 372.1 (M+1). 1H NMR (400 MHz, DMSO); 14.08 (s, 1H), 9.29 (d, J=2.0 Hz, 1H), 9.25 (s, 1H), 8.94 (s, 1H), 8.61 (dd, J=4.7, 1.3 Hz, 1H), 8.47-8.40 (m, 1H), 8.07-7.92 (m, 3H), 7.56 (dd, J=7.9, 4.8 Hz, 1H), 6.48 (s, 1H), 4.22 (t, J=5.4 Hz, 2H), 3.56 (s, 2H), 3.18 (t, J=5.4 Hz, 2H). m/z 372.1 (M+1)

Example 302

2-(5-(pyridin-3-yl)-1H-pyrazolo[3,4-c]pyridin-3-yl)isonicotinamide 302

Following the Stille coupling procedure of Example 299, 5-(pyridin-3-yl)-1-((2-(trimethylsilyl)ethoxy)methyl)-3-(trimethylstannyl)-1H-pyrazolo[3,4-c]pyridine and 2-bromoisonicotinamide were reacted. The product was deprotected by the procedure of Example 225 and purified via silica gel chromatography using a gradient of methanol in dichloromethane to afford 10 mg (21%) of 302 over two steps. ESI MS m/z 317.1 (M+1). 1H NMR (400 MHz, DMSO): 14.16 (s, 1H), 9.28 (d, J=12.0 Hz, 2H), 8.96 (s, 1H), 8.94 (d, J=5.1 Hz, 1H), 8.62 (d, J=5.3 Hz, 2H), 8.45 (d, J=8.0 Hz, 1H), 8.40 (s, 1H), 7.80 (d, J=5.1 Hz, 1H), 7.76 (s, 1H), 7.55 (dd, J=8.0, 4.7 Hz, 1H)

Example 303

1-(5-(pyridin-3-yl)-1H-pyrazolo[3,4-c]pyridin-3-yl)-3-(pyrrolidin-3-ylmethyl)imidazolidin-2-one 303

Following the procedures in Example 296, 1-(5-(pyridin-3-yl)-1-(tetrahydro-2H-pyran-2-yl)-1H-pyrazolo[3,4-c]pyridin-3-yl)imidazolidin-2-one was converted to 303. ESI MS m/z=364.2 (M+1). $^1$H NMR (400 MHz, DMSO) δ 9.17 (d, J=2.1 Hz, 1H), 9.05 (s, 1H), 8.81 (s, 1H), 8.57 (dd, J=4.7, 1.3 Hz, 1H), 8.31 (d, J=8.0 Hz, 1H), 7.51 (dd, J=8.0, 4.7 Hz, 1H), 4.06-3.96 (m, 2H), 3.69-3.60 (m, 2H), 3.30 (dd, J=7.4, 3.5 Hz, 2H), 3.22-3.07 (m, 2H), 3.00 (dd, J=17.3, 9.1 Hz, 1H), 2.77 (dd, J=11.0, 7.1 Hz, 1H), 1.98 (dt, J=12.7, 7.6 Hz, 1H), 1.57 (dt, J=20.3, 7.6 Hz, 1H)

Example 305

(S)-1-(3-methyl-6-(5-(pyridin-3-yl)-1H-pyrazolo[3,4-c]pyridin-3-yl)pyridin-2-yl)pyrrolidin-3-ol 305

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (S)-pyrrolidin-3-ol, 305 was obtained as an off-white solid (17 mg, 20%) over three steps. 1H NMR (400 MHz, DMSO) δ 9.25 (s, 1H), 9.18 (s, 1H), 9.09 (s, 1H), 8.59 (d, J=4.6 Hz, 1H), 8.40 (d, J=8.0 Hz, 1H), 7.53 (dd, J=7.9, 4.7 Hz, 1H), 7.47 (q, J=7.6 Hz, 2H), 4.96 (s, 1H), 4.43 (s, 1H), 4.00-3.87 (m, 2H), 3.75 (td, J=8.8, 3.9 Hz, 1H), 3.51 (d, J=11.0 Hz, 1H), 2.37 (s, 3H), 2.12-2.04 (m, 1H), 1.97-1.88 (m, 1H); ESI MS m/z=373.2 (M+1)

Example 306

(R)-1-(3-methyl-6-(5-(pyridin-3-yl)-1H-pyrazolo[3,4-c]pyridin-3-yl)pyridin-2-yl)pyrrolidin-3-ol 306

Following the procedures as described in Examples 241, 243, 287, and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-pyrrolidin-3-ol hydrochloride, 306 was obtained as an off-white solid (25.5 mg, 35%) over three steps. 1H NMR (400 MHz, DMSO) δ 9.25 (s, 1H), 9.18 (s, 1H), 9.09 (s, 1H), 8.60 (d, J=4.6 Hz, 1H), 8.40 (d, J=7.9 Hz, 1H), 7.54 (dd, J=7.9, 4.8 Hz, 1H), 7.51-7.44 (m, 2H), 4.96 (s, 1H), 4.43 (s, 1H), 4.00-3.88 (m, 2H), 3.80-3.70 (m, 1H), 3.51 (d, J=10.2 Hz, 1H), 2.38 (s, 3H), 2.10-2.03 (m, 1H), 1.93 (s, 1H); ESI MS m/z=373.2 (M+1)

Example 307

(S)-1-(6-(5-(pyridin-3-yl)-1H-pyrazolo[3,4-c]pyridin-3-yl)-3-vinylpyridin-2-yl)piperidin-3-amine 307

A microwave reaction vial was charged with (S)-tert-butyl 1-(3-bromo-6-(5-(pyridin-3-yl)-1-((2-(trimethylsilyl)ethoxy)methyl)-1H-pyrazolo[3,4-c]pyridin-3-yl)pyridin-2-yl)piperidin-3-ylcarbamate (128.3 mg, 0.189 mmol), 4,4,5,5-tetramethyl-2-vinyl-1,3,2-dioxaborolane (320 uL, 1.9 mmol), 1,1'-Bis(diphenylphosphino)ferrocenepalladium (II) chloride (15.4 mg, 0.0189 mmol), 1.00 M of Potassium acetate in Water (0.28 mL, 0.28 mmol), 1.00 M of Sodium carbonate in Water (0.28 mL, 0.28 mmol), and Acetonitrile (10 mL). The reaction mixture was heated under microwave at 150° C. for 5 minutes. The mixture was concentrated, and the residue was purified on silica eluted with 0 to 100% EtOAc in Heptane to afford (S)-tert-butyl 1-(6-(5-(pyridin-3-yl)-1-((2-(trimethylsilyl)ethoxy)methyl)-1H-pyrazolo[3,4-c]pyridin-3-yl)-3-vinylpyridin-2-yl)piperidin-3-ylcarbamate (107 mg, 91%).

The above (S)-tert-butyl 1-(6-(5-(pyridin-3-yl)-1-((2-(trimethylsilyl)ethoxy)methyl)-1H-pyrazolo[3,4-c]pyridin-3-yl)-3-vinylpyridin-2-yl)piperidin-3-ylcarbamate (23.7 mg, 0.038 mmol) was dissolved in Trifluoroacetic Acid (2 mL) and Methylene chloride (2 mL). To the solution was add Trifluoromethanesulfonic acid (50 uL, 0.6 mmol) and Triethylsilane (30 uL, 0.19 mmol). The resulting mixture was stirred overnight at room temperature. The mixture was then concentrated, and the residue was purified by reverse phase HPLC to afford 307 as an off-white solid (5.1 mg, 34%). 1H NMR (400 MHz, DMSO) δ 9.32 (d, J=1.9 Hz, 1H), 9.20 (s, 1H), 9.11 (s, 1H), 8.59 (d, J=3.8 Hz, 1H), 8.46 (d, J=8.0 Hz, 1H), 7.96 (d, J=7.9 Hz, 1H), 7.82 (d, J=7.9 Hz, 1H), 7.52 (dd, J=8.0, 4.7 Hz, 1H), 6.80 (dd, J=17.7, 11.0 Hz, 1H), 5.88 (d, J=17.6 Hz, 1H), 5.38 (d, J=11.3 Hz, 1H), 3.77 (d, J=9.7 Hz, 1H), 3.58 (d, J=12.1 Hz, 1H), 2.92-2.82 (m, 2H), 2.82-2.72 (m, 1H), 1.95 (d, J=12.7 Hz, 1H), 1.87-1.71 (m, 2H), 1.25 (dd, J=19.0, 10.7 Hz, 1H); ESI MS m/z=398.2 (M+1)

Example 308

(S)-1-(3-(prop-1-en-2-yl)-6-(5-(pyridin-3-yl)-1H-pyrazolo[3,4-c]pyridin-3-yl)pyridin-2-yl)piperidin-3-amine 308

Following the procedures as described in Example 307 and staring with 4,4,5,5-tetramethyl-2-(prop-1-en-2-yl)-1,3,2-dioxaborolane, 308 was obtained as an off-white solid (6.7 mg, 43%) over two steps. 1H NMR (400 MHz, DMSO) δ 9.33 (d, J=1.8 Hz, 1H), 9.21 (s, 1H), 9.11 (s, 1H), 8.59 (d, J=3.6 Hz, 1H), 8.48 (d, J=8.0 Hz, 1H), 7.73 (d, J=7.7 Hz, 1H), 7.58 (d, J=7.7 Hz, 1H), 7.51 (dd, J=8.0, 4.7 Hz, 1H), 5.23 (d, J=27.4 Hz, 2H), 4.00 (d, J=10.2 Hz, 1H), 3.83 (d, J=12.2 Hz, 1H), 2.76 (ddd, J=30.9, 18.3, 10.1 Hz, 3H), 2.13 (s, 3H), 1.93 (d, J=8.9 Hz, 1H), 1.82-1.62 (m, 2H), 1.22 (dd, J=22.4, 7.9 Hz, 1H); ESI MS m/z=412.2 (M+1)

Example 309

(R)-1-(3-methyl-6-(5-(pyridin-3-yl)-1H-pyrazolo[3,4-c]pyridin-3-yl)pyridin-2-yl)piperidin-3-ol 309

Following the procedures as described in Examples 241, 243, 287, and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-piperidin-3-ol hydrochloride, 309 was obtained as an off-white solid (18 mg, 34%) over three steps. 1H NMR (400 MHz, DMSO) δ 13.87 (s, 1H), 9.31 (d, J=1.7 Hz, 1H), 9.21 (s, 1H), 9.11 (s, 1H), 8.60 (d, J=3.6 Hz, 1H), 8.45 (d, J=8.0 Hz, 1H), 7.74 (d, J=7.6 Hz, 1H), 7.63 (d, J=7.7 Hz, 1H), 7.51 (dd, J=8.0, 4.7 Hz, 1H), 4.88 (d, J=4.4 Hz, 1H), 3.80-3.65 (m, 2H), 3.53 (d, J=12.2 Hz, 1H), 2.84 (dt, J=20.1, 9.9 Hz, 2H), 2.31 (s, 3H), 2.00 (d, J=11.7 Hz, 1H), 1.86 (d, J=13.5 Hz, 1H), 1.77-1.63 (m, 1H), 1.39 (dd, J=21.1, 8.2 Hz, 1H); ESI MS m/z=387.2 (M+1)

Example 310

(R)-1-(3-methyl-6-(5-(pyridin-3-yl)-1H-pyrazolo[3,4-c]pyridin-3-yl)pyridin-2-yl)piperidin-3-amine 310

Following the procedures as described in Examples 241, 243, 287, and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-tert-butyl piperidin-3-ylcarbamate, 310 was obtained as an off-white solid (46 mg, 42%) over three steps. 1H NMR (400 MHz, DMSO) δ 9.30 (s, 1H), 9.22 (s, 1H), 9.08 (s, 1H), 8.61 (d, J=4.6 Hz, 1H), 8.45 (d, J=7.9 Hz, 1H), 8.32 (s, 2H), 7.77 (d, J=7.7 Hz, 1H), 7.66 (d, J=7.7 Hz, 1H), 7.54 (dd, J=7.9, 4.7 Hz, 1H), 3.70 (s, 2H), 2.90 (s, 2H), 1.98 (s, 1H), 1.88 (s, 1H), 1.77 (s, 1H), 1.43 (s, 1H); ESI MS m/z=386.3 (M+1)

Example 311

(R)-1-(3-methyl-6-(5-(pyridin-3-yl)-1H-pyrazolo[3,4-c]pyridin-3-yl)pyridin-2-yl)azepan-4-amine 311

Following the procedures as described in Examples 241, 243, 287, 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-benzyl azepan-4-ylcarbamate hydrochloride were reacted to give (R)-benzyl 1-(3-methyl-6-(5-(pyridin-3-yl)-1-((2-(trimethylsilyl)ethoxy)methyl)-1H-pyrazolo[3,4-c]pyridin-3-yl)pyridin-2-yl)azepan-4-ylcarbamate, which was dissolved in Trifluoroacetic Acid (5 mL) and Methylene chloride (5 mL), and treated with Trifluoromethanesulfonic acid (5 eq.) and Triethylsilane (5 eq.). The resulting mixture was stirred at room temperature for 2 days. The mixture was then concentrated, and the residue was purified by reverse phase HPLC to afford 311 as an off-white solid (31 mg, 28%) over three steps. 1H NMR (400 MHz, DMSO) δ 9.23 (d, J=14.6 Hz, 2H), 8.99 (s, 1H), 8.61 (d, J=4.6 Hz, 1H), 8.42 (d, J=8.0 Hz, 1H), 8.29 (s, 1H), 7.59 (ddd, J=14.0, 12.7, 6.2 Hz, 3H), 3.82 (dd, J=10.5, 5.8 Hz, 1H), 3.72 (t, J=9.3 Hz, 1H), 3.66-3.61 (m, 1H), 3.55-3.50 (m, 2H), 2.34 (s, 3H), 2.17 (d, J=9.2 Hz, 1H), 2.06-1.80 (m, 4H), 1.72 (q, J=10.4 Hz, 1H); ESI MS m/z=400.2 (M+1)

Example 312

(S)-1-(3-bromo-6-(5-(pyridin-3-yl)-1H-pyrazolo[3,4-c]pyridin-3-yl)pyridin-2-yl)azepan-4-amine 312

Following the procedures of Examples 241 and 287, 3-(5-bromo-6-fluoropyridin-2-yl)-5-(pyridin-3-yl)-1-(2-(trimethylsilyl)ethoxy)methyl)-1H-pyrazolo[3,4-c]pyridine and (S)-benzyl azepan-4-ylcarbamate were reacted to give (S)-benzyl 1-(3-bromo-6-(5-(pyridin-3-yl)-1-((2-(trimethylsilyl)ethoxy)methyl)-1H-pyrazolo[3,4-c]pyridin-3-yl)pyridin-2-yl)azepan-4-ylcarbamate, which was dissolved in Trifluoroacetic Acid (5 mL) and Methylene chloride (5 mL), and treated with Trifluoromethanesulfonic acid (5 eq.) and Triethylsilane (5 eq.). The resulting mixture was stirred at room temperature for 2 days. The mixture was then concentrated, and the residue was purified by reverse phase HPLC to afford 312 as an off-white solid (21 mg, 37%) over two steps. 1H NMR (400 MHz, DMSO) δ 9.25 (s, 2H), 8.91 (s, 1H), 8.62 (d, J=3.7 Hz, 1H), 8.42 (d, J=8.0 Hz, 1H), 8.04 (d, J=8.1 Hz, 1H), 7.60 (d, J=8.0 Hz, 1H), 7.56 (dd, J=7.8, 4.7 Hz, 1H), 4.02 (d, J=15.1 Hz, 1H), 3.91-3.83 (m, 1H), 3.78 (dd, J=11.6, 6.8 Hz, 1H), 3.69-3.58 (m, 1H), 2.19 (s, 1H), 1.99 (d, J=38.8 Hz, 4H), 1.71 (dd, J=21.2, 10.1 Hz, 1H); ESI MS m/z=464.01 (M+1)

Example 313

(R)-1-(3-bromo-6-(5-(pyridin-3-yl)-1H-pyrazolo[3,4-c]pyridin-3-yl)pyridin-2-yl)azepan-4-amine 313

Following the procedures of Examples 241 and 287, 3-(5-bromo-6-fluoropyridin-2-yl)-5-(pyridin-3-yl)-1-((2-(trimethylsilyl)ethoxy)methyl)-1H-pyrazolo[3,4-c]pyridine and (R)-benzyl azepan-4-ylcarbamate hydrochloride were reacted to give (R)-benzyl 1-(3-bromo-6-(5-(pyridin-3-yl)-1-((2-(trimethylsilyl)ethoxy)methyl)-1H-pyrazolo[3,4-c]pyridin-3-yl)pyridin-2-yl)azepan-4-ylcarbamate, which was dissolved in Trifluoroacetic Acid (5 mL) and Methylene chloride (5 mL), and treated with Trifluoromethanesulfonic acid (5 eq.) and Triethylsilane (5 eq.). The resulting mixture was stirred at room temperature for 2 days. The mixture was then concentrated, and the residue was purified by reverse phase HPLC to afford 313 as an off-white solid (14.2 mg, 25.5%) over two steps. 1H NMR (400 MHz, DMSO) δ 9.24 (s, 2H), 8.91 (s, 1H), 8.61 (d, J=3.6 Hz, 1H), 8.42 (d, J=8.0 Hz, 1H), 8.35 (s, 1H), 8.03 (d, J=8.0 Hz, 1H), 7.62-7.51 (m, 2H), 4.00 (d, J=14.6 Hz, 2H), 3.90-3.81 (m, 2H), 3.77 (dd, J=11.4, 6.7 Hz, 2H), 3.67-3.59 (m, 3H), 2.18 (s, 1H), 1.98 (dd, J=31.3, 18.3 Hz, 4H), 1.75-1.59 (m, 1H); ESI MS m/z=464.01 (M+1)

Example 314

(S)-1-(3-methyl-6-(5-(pyridin-3-yl)-1H-pyrazolo[3,4-c]pyridin-3-yl)pyridin-2-yl)azepan-4-amine 314

Following the procedures of Example 241, 3-(5-bromo-6-fluoropyridin-2-yl)-5-(pyridin-3-yl)-1-((2-(trimethylsilyl)ethoxy)methyl)-1H-pyrazolo[3,4-c]pyridine and (S)-benzyl azepan-4-ylcarbamate were reacted to give (S)-benzyl 1-(3-methyl-6-(5-(pyridin-3-yl)-1-((2-(trimethylsilyl)ethoxy)methyl)-1H-pyrazolo[3,4-c]pyridin-3-yl)pyridin-2-yl)azepan-4-ylcarbamate, which was dissolved in Trifluoroacetic Acid (5 mL) and Methylene chloride (5 mL), and treated with Trifluoromethanesulfonic acid (5 eq.) and Triethylsilane (5 eq.). The resulting mixture was stirred at room temperature for 2 days. The mixture was then concentrated, and the residue was purified by reverse phase HPLC to afford 314 as an off-white solid (34.1 mg, 30.5%) over three steps. 1H NMR (400 MHz, DMSO) δ 9.25 (d, J=1.9 Hz, 1H), 9.21 (s, 1H), 8.99 (s, 1H), 8.61 (d, J=4.7 Hz, 1H), 8.41 (d, J=7.9 Hz, 1H), 8.34 (s, 1H), 7.63 (t, J=10.2 Hz, 1H), 7.59-7.53 (m, 1H), 2.34 (s, 3H), 2.15 (s, 1H), 1.95 (dd, J=29.7, 7.9 Hz, 4H), 1.77-1.64 (m, 1H); ESI MS m/z=400.12 (M+1)

Example 315

(S)-1-(3-methyl-6-(5-(pyridin-3-yl)-1H-pyrazolo[3,4-c]pyridin-3-yl)pyridin-2-yl)piperidin-3-amine 315

Following the procedures of Examples 241, 243, 287, and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (S)-tert-butyl piperidin-3-ylcarbamate, 315 was obtained as an off-white solid (37 mg, 29%) over three steps. 1H NMR (400 MHz, DMSO) δ 9.31 (d, J=2.0 Hz, 1H), 9.20 (s, 1H), 9.13 (s, 1H), 8.59 (dd, J=4.7, 1.3 Hz, 1H), 8.46 (d, J=8.0 Hz, 1H), 7.74 (d, J=7.6 Hz, 1H), 7.62 (d, J=7.7 Hz, 1H), 7.52 (dd, J=8.0, 4.7 Hz, 1H), 3.67 (d, J=9.6 Hz, 1H), 3.53 (d, J=11.9 Hz, 1H), 2.89 (dd, J=11.6, 7.5 Hz, 1H), 2.81 (t, J=10.3 Hz, 1H), 2.75-2.65 (m, 1H), 2.31 (s, 3H), 1.95 (d, J=12.4 Hz, 1H), 1.84 (d, J=13.4 Hz, 1H), 1.75 (t, J=11.7 Hz, 1H), 1.24 (dt, J=12.0, 6.0 Hz, 1H); ESI MS m/z=386.1 (M+1)

Example 316

(R)-1-(3-methyl-6-(5-(pyridin-3-yl)-1H-pyrazolo[3,4-c]pyridin-3-yl)pyridin-2-yl)pyrrolidin-3-amine 316

A microwave reaction vial was charged with (R)-tert-butyl 1-(3-bromo-6-(5-(pyridin-3-yl)-1-((2-(trimethylsilyl)ethoxy)methyl)-1H-pyrazolo[3,4-c]pyridin-3-yl)pyridin-2-yl)pyrrolidin-3-ylcarbamate (124.5 mg, 0.1867 mmol), Methyl boronic acid (111.76 mg, 1.867 mmol), 1,1'-Bis(diphenylphosphino)ferrocenepalladium (II) chloride (15.2 mg, 0.01876 mmol), 1.00 M of Potassium acetate in Water (0.28 mL, 0.28 mmol), 1.00 M of Sodium carbonate in Water (0.28 mL, 0.28 mmol), and Acetonitrile (10 mL). The reaction mixture was heated under microwave at 150° C. for 5 minutes. The mixture was concentrated, and the residue was purified on silica eluted with 0 to 100% EtOAc in Heptane to afford (R)-tert-butyl 1-(3-methyl-6-(5-(pyridin-3-yl)-1-((2-(trimethylsilyl)ethoxy)methyl)-1H-pyrazolo[3,4-c]pyridin-3-yl)pyridin-2-yl)pyrrolidin-3-ylcarbamate (43.8 mg, 39%).

To (R)-tert-butyl 1-(3-methyl-6-(5-(pyridin-3-yl)-1-((2-(trimethylsilyl)ethoxy)methyl)-1H-pyrazolo[3,4-c]pyridin-3-yl)pyridin-2-yl)pyrrolidin-3-ylcarbamate in MeOH (4 mL) was added 4.0 M of Hydrogen chloride in 1,4-Dioxane (6 mL). The resulting mixture was stirred overnight at room temperature. The mixture was then concentrated, and the residue was purified by reverse phase HPLC to afford 316 as an off-white solid (15.4 mg, 56.9%). 1H NMR (400 MHz, DMSO) δ 9.27 (d, J=1.7 Hz, 1H), 9.19 (s, 1H), 9.12 (s, 1H), 8.59 (d, J=3.8 Hz, 1H), 8.41 (d, J=8.0 Hz, 1H), 7.53 (dd, J=7.9, 4.8 Hz, 1H), 7.51-7.43 (m, 2H), 3.85 (dd, J=9.5, 5.6 Hz, 2H), 3.77 (dd, J=16.6, 7.1 Hz, 1H), 3.63-3.57 (m, 1H), 3.43 (dd, J=9.6, 5.6 Hz, 1H), 2.37 (s, 3H), 2.11 (td, J=12.2, 5.9 Hz, 1H), 1.74 (dq, J=13.8, 7.1 Hz, 1H); ESI MS m/z=372.2 (M+1)

Example 317

(S)-1-(3-methyl-6-(5-(pyridin-3-yl)-1H-pyrazolo[3,4-c]pyridin-3-yl)pyridin-2-yl)pyrrolidin-3-amine 317

Following the procedures as described in Examples 241, 243, 287, and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (S)-tert-butyl piperidin-3-ylcarbamate, 317 was obtained as an off-white solid (11 mg, 38%) over three steps. 1H NMR (400 MHz, DMSO) δ 9.27 (d, J=2.1 Hz, 1H), 9.18 (s, 1H), 9.12 (s, 1H), 8.59 (dd, J=4.7, 1.3 Hz, 1H), 8.41 (d, J=8.0 Hz, 1H), 7.53 (dd, J=7.9, 4.7 Hz, 1H), 7.49-7.43 (m, 2H), 3.89-3.81 (m, 2H), 3.81-3.73 (m, 1H), 3.63-3.55 (m, 1H), 3.45-3.41 (m, 1H), 2.37 (s, 3H), 2.10 (td, J=12.3, 5.9 Hz, 1H), 1.74 (dq, J=14.0, 7.1 Hz, 1H); ESI MS m/z=372.2 (M+1)

Example 318

(S)-1-(3-bromo-6-(5-(pyridin-3-yl)-1H-pyrazolo[3,4-c]pyridin-3-yl)pyridin-2-yl)pyrrolidin-3-ol 318

Following the procedures as described in Example 241 and starting with 3-(5-bromo-6-fluoropyridin-2-yl)-5-(pyridin-3-yl)-1-((2-(trimethylsilyl)ethoxy)methyl)-1H-pyrazolo[3,4-c]pyridine and (S)-pyrrolidin-3-ol, 318 was obtained as an off-white solid (1.8 mg, 3.0%) over two steps. 1H NMR (400 MHz, DMSO) δ 9.29-9.18 (m, 2H), 9.00 (s, 1H), 8.60 (d, J=4.6 Hz, 1H), 8.40 (d, J=8.0 Hz, 1H), 7.93 (d, J=8.0 Hz, 1H), 7.54 (dd, J=8.0, 4.7 Hz, 1H), 7.46 (d, J=8.0 Hz, 1H), 5.75 (s, 1H), 5.01 (d, J=3.5 Hz, 1H), 4.45 (s, 1H), 4.11-4.00 (m, 2H), 3.90-3.81 (m, 1H), 3.63 (d, J=10.7 Hz, 1H), 2.06 (dd, J=8.4, 4.2 Hz, 1H), 1.95 (s, 1H); ESI MS m/z=437.1 (M+1)

Example 327

(S)-1-(3-ethyl-6-(5-(pyridin-3-yl)-1H-pyrazolo[3,4-c]pyridin-3-yl)pyridin-2-yl)piperidin-3-amine 327

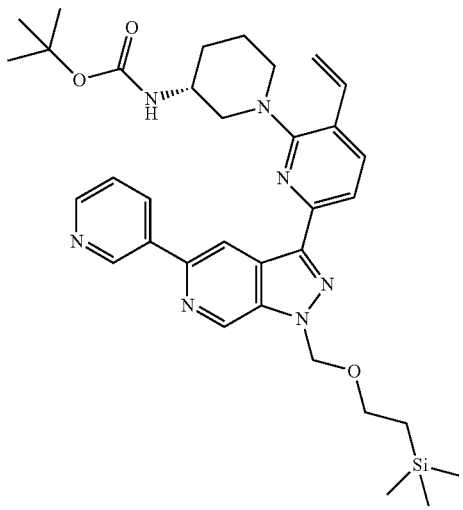 [SMILES: C=Cc1ccc(-c2nn(COCC[Si](C)(C)C)c3cnc(-c4cccnc4)cc23)nc1N1CCC[C@@H](NC(=O)OC(C)(C)C)C1]

(S)-tert-butyl 1-(6-(5-(pyridin-3-yl)-1-((2-(trimethylsilyl)ethoxy)methyl)-1H-pyrazolo[3,4-c]pyridin-3-yl)-3-vinylpyridin-2-yl)piperidin-3-ylcarbamate (59.18 mg, 0.09426 mmol) and palladium hydroxide on carbon 20% (0.2:0.8, Palladium hydroxide:carbon black, 6.619 mg) in Ethanol (30 mL) in a round bottom flask was vacuumed and connected to a Hydrogen balloon. The mixture was stirred at room temperature over the weekend. The reaction mixture was filtered through Celite. The filtrate was concentrated to afford (S)-tert-butyl 1-(3-ethyl-6-(5-(pyridin-3-yl)-1-((2-(trimethylsilyl)ethoxy)methyl)-1H-pyrazolo[3,4-c]pyridin-3-yl)pyridin-2-yl)piperidin-3-ylcarbamate, which was dissolved in Trifluoroacetic Acid (3 mL) and Methylene chloride (3 mL), and treated with Trifluoromethanesulfonic acid (83.4 uL, 0.943 mmol) and Triethylsilane (150.6 uL, 0.943 mmol). The resulting mixture was stirred at room temperature overnight. The mixture was then concentrated, and the residue was purified by reverse phase HPLC to afford 327 as an off-white solid (5.8 mg, 15%) over two steps. 1H NMR (400 MHz, DMSO) δ 9.31 (s, 1H), 9.20 (s, 1H), 9.13 (s, 1H), 8.59 (d, J=4.5 Hz, 1H), 8.46 (d, J=8.0 Hz, 1H), 7.81 (d, J=7.8 Hz, 1H), 7.71 (d, J=7.8 Hz, 1H), 7.53 (dd, J=8.0, 4.8 Hz, 1H), 3.60 (d, J=11.4 Hz, 2H), 2.86 (dt, J=20.8, 9.5 Hz, 2H), 2.70 (dd, J=18.0, 10.0 Hz, 2H), 1.95 (d, J=12.5 Hz, 1H), 1.84 (d, J=13.1 Hz, 1H), 1.80-1.69 (m, 1H), 1.26 (t, J=7.5 Hz, 3H); ESI MS m/z=400.2 (M+1)

Example 328

(S)-1-(3-isopropyl-6-(5-(pyridin-3-yl)-1H-pyrazolo[3,4-c]pyridin-3-yl)pyridin-2-yl)piperidin-3-amine 328

(S)-tert-butyl 1-(3-(prop-1-en-2-yl)-6-(5-(pyridin-3-yl)-1-((2-(trimethylsilyl)ethoxy)methyl)-1H-pyrazolo[3,4-c]pyridin-3-yl)pyridin-2-yl)piperidin-3-ylcarbamate (60.50 mg, 0.09426 mmol) and palladium hydroxide on carbon 20% (0.2:0.8, Palladium hydroxide:carbon black, 6.619 mg) in Ethanol (30 mL) in a round bottom flask was vacuumed and connected to a Hydrogen balloon. The mixture was stirred at room temperature over the weekend. The reaction mixture was filtered through Celite. The filtrate was concentrated to afford (S)-tert-butyl 1-(3-isopropyl-6-(5-(pyridin-3-yl)-1-((2-(trimethylsilyl)ethoxy)methyl)-1H-pyrazolo[3,4-c]pyridin-3-yl)pyridin-2-yl)piperidin-3-ylcarbamate, which was dissolved in Trifluoroacetic Acid (3 mL) and Methylene chloride (3 mL), and treated with Trifluoromethanesulfonic acid (83.4 uL, 0.943 mmol) and Triethylsilane (150.6 uL, 0.943). The resulting mixture was stirred at room temperature overnight. The mixture was then concentrated, and the residue was purified by reverse phase HPLC to afford 328 as an off-white solid (8.2 mg, 21%) over two steps. 1H NMR (400 MHz, DMSO) δ 9.31 (d, J=2.1 Hz, 1H), 9.22 (s, 1H), 9.06 (s, 1H), 8.61 (dd, J=4.7, 1.3 Hz, 1H), 8.45 (d, J=8.0 Hz, 1H), 8.32 (s, 1H), 7.88 (d, J=7.9 Hz, 1H), 7.82 (d, J=7.9 Hz, 1H), 7.54 (dd, J=8.0, 4.8 Hz, 1H), 2.90 (d, J=9.1 Hz, 2H), 2.00 (d, J=12.6 Hz, 1H), 1.90 (d, J=13.4 Hz, 1H), 1.76 (dd, J=24.1, 11.0 Hz, 1H), 1.46-1.34 (m, 1H), 1.25 (t, J=6.9 Hz, 6H); ESI MS m/z=414.2 (M+1)

Example 901

Pim Kinase Binding Activity

PIM-1, PIM-2, and PIM-3 enzymes were generated as fusion proteins expressed in bacteria and purified by IMAC column chromatography (Sun, X., Chiu, J. F., and He, Q. Y. (2005) Expert Rev. Proteomics, 2:649-657). A fluorescent-labeled Pim-specific peptide substrate, was custom synthesized by American Peptide Company (Sunnyvale, Calif.). Reaction Buffer contained 10 mM HEPES, pH 7.2, 10 mM MgCl$_2$, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 μL per well in a 384-well plate. A standard enzymatic reaction, initiated by the addition of 5 μL 2×ATP and test compound to 5 μL of 2× enzyme and FAM-peptide, contained 20 pM PIM-1, 50 pM PIM-2, or 55 pM PIM-3, 1 μM FAM-peptide, and 10 μM ATP, in Reaction Buffer. After 90 minutes of incubation at room temperature, the phosphorylation reaction was stopped by the addition of 10 μL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electropherogram using HTS Well Analyzer software (Caliper Life Sciences, Hopkinton, Mass.). Ki values for the test compound were calculated.

Example 902

In Vitro Cell Proliferation Potency Assays

BaF3 parental line was obtained from the DSMZ repository. BaF3 lines transfected with PIM-1 or PIM-2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 µg/mL. Media for MM1.S (multiple myeloma cells) line contained RPMI, 10% FBS, 2 mM L-Glutamine.

BaF3, a murine interleukin-3 dependent pro-B cell line, parental cells, BaF3 PIM1 cells, BaF3 PIM-2 cells, and MM1.S (multiple myeloma) cells were seeded at 2 k/well, 5 k/well, 5 k/well, and 10 k/well respectively, in a 384-well plate, at 45 µL/well. Test compound was added at 5 µL/well. BaF3 cells (parental and transfected) were incubated overnight, while MM1.S cells were incubated for 72 hours at 37° C., 5% $CO_2$. Cell Titer Glo Reagent (Promega) was added at 50 µL/well, the plates were incubated for 30 minutes, and their luminescence read on an HT Analyst. $IC_{50}/EC_{50}$ values for the test compound were calculated.

Representative compounds of the present invention were tested as described above and found to exhibit a $Ki/IC_{50}/EC_{50}$ in the in vitro cell proliferation potency assays, as shown below.

| No. | Prolif. BaF3 IL3 (IC50) µM | Prolif. BaF3 PIM-1 (IC50) µM | Prolif. MM1S ATP (EC50) µM |
|---|---|---|---|
| 116 | 13.7 | 21.3 | |
| 117 | 12.9 | 18.8 | |
| 129 | 5.6 | 5.2 | |
| 144 | 3.3 | 0.13 | 2.2 |
| 147 | 3.9 | 0.368 | 0.0604 |
| 149 | 1.5 | 0.261 | 0.166 |
| 152 | 2.7 | 0.0471 | 0.631 |
| 153 | 2.5 | 0.028 | 0.436 |
| 161 | 1.4 | 0.731 | 0.281 |
| 173 | 5.7 | 0.251 | 0.376 |
| 190 | 1.8 | 0.159 | 0.0672 |
| 241 | 1.3 | 0.584 | 0.0573 |
| 248 | 1.6 | 0.336 | 0.201 |
| 249 | 2.5 | 0.518 | 0.191 |
| 270 | 13.1 | 0.478 | 0.707 |
| 307 | 1.4 | 0.0671 | 0.141 |
| 316 | 1.0 | 0.0628 | 0.114 |
| 349 | 3.4 | 0.681 | 0.393 |
| 350 | 3.6 | 0.188 | 0.287 |
| 356 | 5.4 | 0.0766 | 0.638 |
| 357 | 4.9 | 0.709 | 0.244 |
| 376 | 4.1 | 0.0309 | 0.356 |
| 377 | 5.3 | 0.0637 | 0.23 |
| 381 | 2.2 | 0.129 | 0.228 |
| 382 | 17 | 0.274 | 3.2 |
| 383 | 1.3 | 0.11 | 0.17 |
| 390 | 5.7 | 0.0585 | 0.13 |
| 505 | 2.3 | 0.0402 | 0.0979 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A compound selected from Formula I:

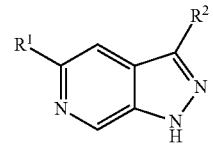

and stereoisomers, geometric isomers, tautomers, or pharmaceutically acceptable salts thereof, wherein:
$R^1$ is selected from $C_2$-$C_{20}$ heterocyclyl, $C_1$-$C_{20}$ heteroaryl, —($C_1$-$C_{20}$ heteroaryl)-($C_1$-$C_{20}$ heteroaryl), —($C_1$-$C_{20}$ heteroaryl)-($C_2$-$C_{20}$ heterocyclyl), —($C_1$-$C_{20}$ heteroaryl)-O—($C_2$-$C_{20}$ heterocyclyl), —($C_1$-$C_{20}$ heteroaryl)-O—($C_1$-$C_{12}$ alkylene)-($C_2$-$C_{20}$ heterocyclyl), —($C_1$-$C_{20}$ heteroaryl)-$NR^3$—($C_2$-$C_{20}$ heterocyclyl), and —($C_1$-$C_{20}$ heteroaryl)-$NR^3$—($C_1$-$C_{12}$ alkylene)-($C_2$-$C_{20}$ heterocyclyl);
$R^2$ is selected from $C_2$-$C_{20}$ heterocyclyl, $C_1$-$C_{20}$ heteroaryl, $C_6$-$C_{20}$ aryl, —($C_6$-$C_{20}$ aryl)-($C_2$-$C_{20}$ heterocyclyl), —($C_1$-$C_{20}$ heteroaryl)-($C_1$-$C_{20}$ heteroaryl), —($C_1$-$C_{20}$ heteroaryl)-($C_2$-$C_{20}$ heterocyclyl), —($C_1$-$C_{20}$ heteroaryl)-($C_2$-$C_{20}$ heterocyclyl)-($C_2$-$C_{20}$ heterocyclyl), —($C_1$-$C_{20}$ heteroaryl)-$NR^3$—($C_2$-$C_{20}$ heterocyclyl), —($C_1$-$C_{20}$ heteroaryl)-($C_1$-$C_{12}$ alkylene)-($C_2$-$C_{20}$ heterocyclyl), —($C_1$-$C_{20}$ heteroaryl)-$NR^3$—($C_1$-$C_{12}$ alkylene)-($C_2$-$C_{20}$ heterocyclyl), and —($C_1$-$C_{20}$ heteroaryl)-$NR^3$—($C_1$-$C_{12}$ alkylene)-($C_1$-$C_{20}$ heteroaryl);
$R^3$ is independently selected from H and $C_1$-$C_{12}$ alkyl optionally substituted with F, Cl, CN, —$CO_2H$, —$COCH_3$, —$CO_2CH_3$, —$CO_2C(CH_3)_3$, —COCH(OH)$CH_3$, —$CONH_2$, —$CONHCH_3$, —$CON(CH_3)_2$, —$NO_2$, —$NH_2$, —$NHCH_3$, —$N(CH_3)_2$, —$NHCOCH_3$, —$N(CH_3)COCH_3$, —$NHS(O)_2CH_3$, —$NHCH_2CH_2NH_2$, —$NHCH_2CH_2CH_2NH_2$, —$NHCH_2CH_2CH_2CH_2NH_2$, —$N(CH_3)C(CH_3)_2CONH_2$, —$N(CH_3)CH_2CH_2S(O)_2CH_3$, =O, —OH, —$OCH_3$, —$OCH_2CH_2OCH_3$, —$OCH_2CH_2NH_2$, —$S(O)_2N(CH_3)_2$, —$SCH_3$, and —$S(O)_2CH_3$;
where alkyl, alkylene, heterocyclyl, aryl, and heteroaryl are optionally substituted with one or more groups independently selected from F, Cl, Br, I, —$CH_3$, —$CH_2CH_3$, —$CH(CH_3)_2$, —$CH_2CH(CH_3)_2$, —$CH_2NH_2$, —$CH_2NHCH_3$, —$CH_2N(CH_3)_2$, —$CH_2CH_2NH_2$, —$CH_2CHCH_2NH_2$, —$CH_2CHCH_2CH_2NH_2$, —$CH_2CH(CH_3)NH_2$, —$CH_2CONH_2$, —$CH_2OH$, —$CH_2CH_2OH$, —$C(CH_3)_2OH$, —$CH(OH)CH(CH_3)_2$, —$C(CH_3)_2CH_2OH$, —$CH_2C(CH_3)_2OH$, —$CH_2CH_2SO_2CH_3$, —CN, —$CF_3$, —$CO_2H$, —$COCH_3$, —$CO_2CH_3$, —$CO_2C(CH_3)_3$, —COCH(OH)$CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$NHCH_2CH_2NH_2$, —$NHCH_2CH_2CH_2NH_2$, —$NHCH_2CH_2CH_2CH_2NH_2$, —$N(CH_3)C(CH_3)_2CONH_2$, —$N(CH_3)CH_2CH_2S(O)_2CH_3$, =O, —OH, —$OCH_3$, —$OCH_2CH_2OCH_3$, —$OCH_2CH_2NH_2$, —$S(O)_2N(CH_3)_2$, —$SCH_3$, —$CH_2OCH_3$, —$S(O)_2CH_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino.

2. The compound of claim 1 wherein $R^1$ is $C_1$-$C_{20}$ heteroaryl.

3. The compound of claim 1 wherein $R^1$ is selected from the structures:

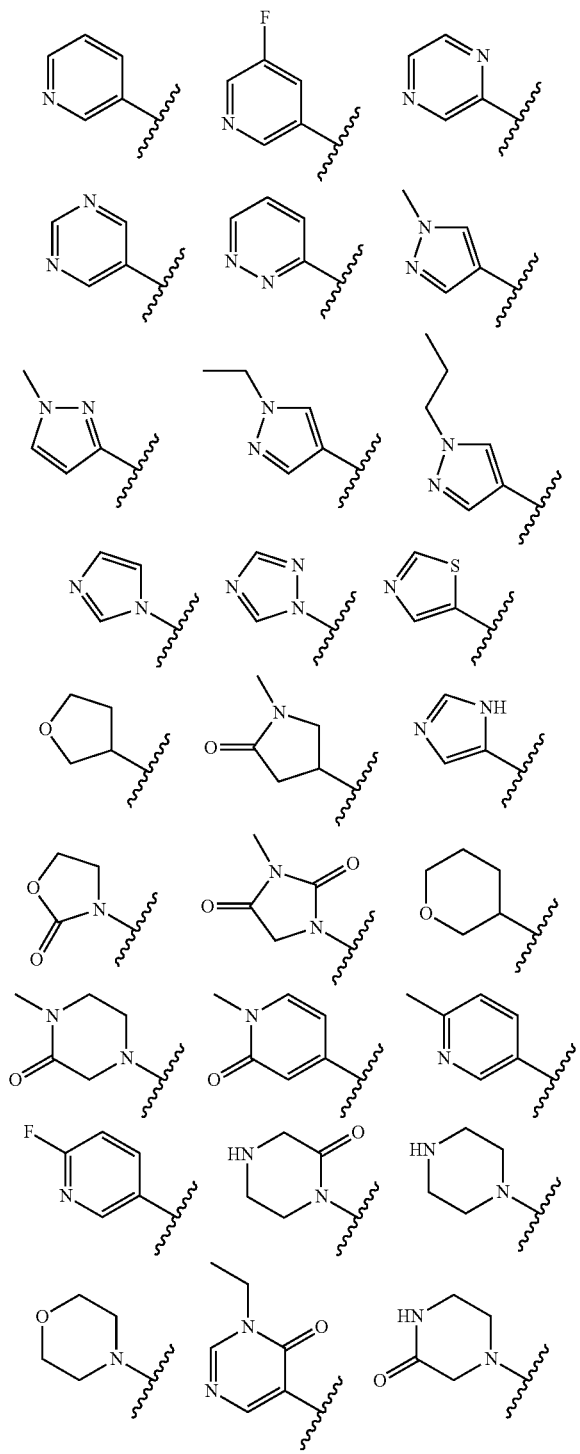

where the wavy line indicates the site of attachment.

4. The compound of claim 1 wherein $R^2$ is $C_1$-$C_{20}$ heteroaryl.

5. The compound of claim 1 wherein $R^2$ is —($C_1$-$C_{20}$ heteroaryl)-($C_2$-$C_{20}$ heterocyclyl).

6. The compound of claim 1 wherein $R^2$ is selected from the structures:

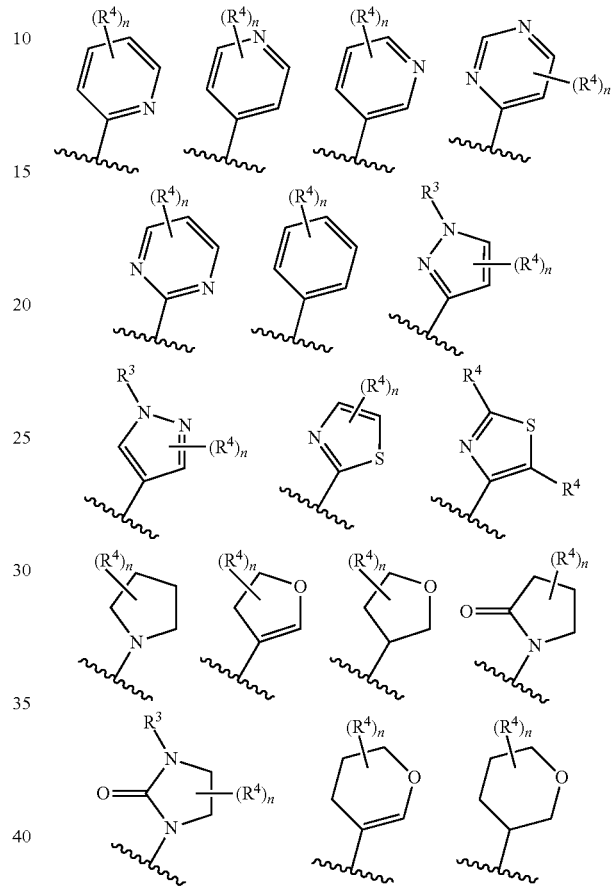

where the wavy line indicates the site of attachment; and $R^4$ is selected from F, Cl, Br, I, —$CH_3$, —$CH_2CH_3$, —$CH(CH_3)_2$, —$CH_2CH(CH_3)_2$, —$CH_2NH_2$, —$CH_2NHCH_3$, —$CH_2N(CH_3)_2$, —$CH_2CH_2NH_2$, —$CH_2CHCH_2NH_2$, —$CH_2CHCH_2CH_2NH_2$, —$CH_2CH(CH_3)NH_2$, —$CH_2CONH_2$, —$CH_2OH$, —$CH_2CH_2OH$, —$C(CH_3)_2OH$, —$CH(OH)CH(CH_3)_2$, —$C(CH_3)_2CH_2OH$, —$CH_2C(CH_3)_2OH$, —$CH_2CH_2SO_2CH_3$, —CN, —$CF_3$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$NHCH_2CH_2NH_2$, —$NHCH_2CH_2CH_2NH_2$, —$NHCH_2CH_2CH_2CH_2NH_2$, —$N(CH_3)C(CH_3)_2CONH_2$, —$N(CH_3)CH_2CH_2S(O)_2CH_3$, =O, —OH, —$OCH_3$, —$OCH_2CH_2OCH_3$, —$OCH_2CH_2NH_2$, —$S(O)_2N(CH_3)_2$, —$SCH_3$, —$CH_2OCH_3$, —$S(O)_2CH_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, or 2.

7. The compound of claim 1 having the structure of Formula Ia:

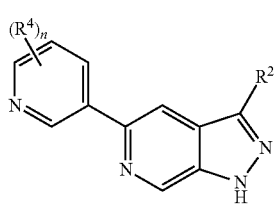

where $R^4$ is selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$NHCH$_3$, —CH$_2$N(CH$_3$)$_2$, —CH$_2$CH$_2$NH$_2$, —CH$_2$CHCH$_2$NH$_2$, —CH$_2$CHCH$_2$CH$_2$NH$_2$, —CH$_2$CH(CH$_3$)NH$_2$, —CH$_2$CONH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$C(CH$_3$)$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, or 2.

8. The compound of claim 1 having the structure of Formula Ib:

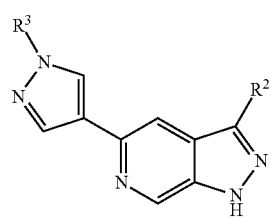

where $R^3$ is selected from H, and C$_1$-C$_{12}$ alkyl where alkyl is optionally substituted with F, Cl, CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, and —S(O)$_2$CH$_3$.

9. The compound of claim 1 having the structure of Formula Ic:

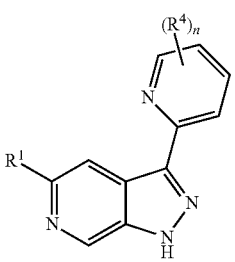

where $R^4$ is selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$NHCH$_3$, —CH$_2$N(CH$_3$)$_2$, —CH$_2$CH$_2$NH$_2$, —CH$_2$CHCH$_2$NH$_2$, —CH$_2$CHCH$_2$CH$_2$NH$_2$, —CH$_2$CH(CH$_3$)NH$_2$, —CH$_2$CONH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$C(CH$_3$)$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —NHCH$_2$CH$_2$NH$_2$, —NHCH$_2$CH$_2$CH$_2$NH$_2$, —NHCH$_2$CH$_2$CH$_2$CH$_2$NH$_2$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_2$OCH$_3$, —OCH$_2$CH$_2$NH$_2$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, or 2.

10. The compound of claim 1 selected from
3-phenyl-5-(pyridin-3-yl)-1H-pyrazolo[3,4-c]pyridine;
3-(2-fluorophenyl)-5-(pyridin-3-yl)-1H-pyrazolo[3,4-c]pyridine;
(S)-1-(3-(3-(2-fluorophenyl)-1H-pyrazolo[3,4-c]pyridin-5-yl)pyridin-4-yl)piperidin-3-amine;
3-(5-(pyridin-3-yl)-1H-pyrazolo[3,4-c]pyridin-3-yl)benzamide;
5-(pyridin-3-yl)-3-(3-(trifluoromethyl)phenyl)-1H-pyrazolo[3,4-c]pyridine;
1-(3-(3-(2-fluorophenyl)-1H-pyrazolo[3,4-c]pyridin-5-yl)pyridin-4-yl)piperidin-4-amine;
3-(2-fluorophenyl)-5-(1-methyl-1H-pyrazol-4-yl)-1H-pyrazolo[3,4-c]pyridine;
(S)-(1-(3-(3-(2-fluorophenyl)-1H-pyrazolo[3,4-c]pyridin-5-yl)pyridin-4-yl)pyrrolidin-3-yl)methanamine;
3-(6-fluoropyridin-2-yl)-5-(pyridin-3-yl)-1H-pyrazolo[3,4-c]pyridine;
6-(5-(pyridin-3-yl)-1H-pyrazolo[3,4-c]pyridin-3-yl)pyridin-2(1H)-one;
5-(1-methyl-1H-pyrazol-4-yl)-3-phenyl-1H-pyrazolo[3,4-c]pyridine;
3-(2-fluorophenyl)-5-(1H-pyrazol-4-yl)-1H-pyrazolo[3,4-c]pyridine;
3-phenyl-5-(1H-pyrazol-4-yl)-1H-pyrazolo[3,4-c]pyridine;
3-(2-fluorophenyl)-5-(pyrimidin-5-yl)-1H-pyrazolo[3,4-c]pyridine;

1-(3-(3-(2-fluorophenyl)-1H-pyrazolo[3,4-c]pyridin-5-yl)pyridin-4-yl)azepan-4-amine;
(S)-(1-(3-(3-(2-fluorophenyl)-1H-pyrazolo[3,4-c]pyridin-5-yl)pyridin-4-yl)piperidin-3-yl)methanamine;
(R)-1-(3-(3-(2-fluorophenyl)-1H-pyrazolo[3,4-c]pyridin-5-yl)pyridin-4-yl)piperidin-3-amine;
3-phenyl-5-(1H-1,2,4-triazol-1-yl)-1H-pyrazolo[3,4-c]pyridine;
N1-(6-(5-(pyridin-3-yl)-1H-pyrazolo[3,4-c]pyridin-3-yl)pyridin-2-yl)ethane-1,2-diamine;
1-(6-(5-(pyridin-3-yl)-1H-pyrazolo[3,4-c]pyridin-3-yl)pyridin-2-yl)piperidin-4-amine;
5-(1H-imidazol-1-yl)-3-phenyl-1H-pyrazolo[3,4-c]pyridine;
1-(6-(3-(2-fluorophenyl)-1H-pyrazolo[3,4-c]pyridin-5-yl)pyrazin-2-yl)piperidin-4-amine;
(S)-3-(2-fluorophenyl)-5-(4-(piperidin-3-yloxy)pyridin-3-yl)-1H-pyrazolo[3,4-c]pyridine;
(R)-1-(6-(5-(pyridin-3-yl)-1H-pyrazolo[3,4-c]pyridin-3-yl)pyridin-2-yl)piperidin-3-amine;
3-phenyl-5-(pyrimidin-5-yl)-1H-pyrazolo[3,4-c]pyridine;
(S)-1-(6-(3-(2-fluorophenyl)-1H-pyrazolo[3,4-c]pyridin-5-yl)pyrazin-2-yl)pyrrolidin-3-amine;
(S)-1-(6-(3-(2-fluorophenyl)-1H-pyrazolo[3,4-c]pyridin-5-yl)pyrazin-2-yl)piperidin-3-amine;
(R)-1-(6-(3-(2-fluorophenyl)-1H-pyrazolo[3,4-c]pyridin-5-yl)pyrazin-2-yl)piperidin-3-amine;
(R)-1-(6-(3-(2-fluorophenyl)-1H-pyrazolo[3,4-c]pyridin-5-yl)pyrazin-2-yl)pyrrolidin-3-amine;
3-(2-fluorophenyl)-5-(4-(piperidin-4-ylmethoxy)pyridin-3-yl)-1H-pyrazolo[3,4-c]pyridine;
3-(1H-pyrazol-4-yl)-5-(pyridin-3-yl)-1H-pyrazolo[3,4-c]pyridine;
1-(5-(3-(2-fluorophenyl)-1H-pyrazolo[3,4-c]pyridin-5-yl)pyridin-3-yl)piperidin-4-amine;
1-(5-(5-(pyridin-3-yl)-1H-pyrazolo[3,4-c]pyridin-3-yl)pyridin-3-yl)piperidin-4-amine;
N1-(4-(5-(pyridin-3-yl)-1H-pyrazolo[3,4-c]pyridin-3-yl)pyridin-2-yl)ethane-1,2-diamine;
1-(4-(5-(pyridin-3-yl)-1H-pyrazolo[3,4-c]pyridin-3-yl)pyridin-2-yl)piperidin-4-amine;
(S)-1-(6-(5-(pyridin-3-yl)-1H-pyrazolo[3,4-c]pyridin-3-yl)pyridin-2-yl)piperidin-3-amine;
3-(6-(piperazin-1-yl)pyridin-2-yl)-5-(pyridin-3-yl)-1H-pyrazolo[3,4-c]pyridine;
3,5-bis(1-methyl-1H-pyrazol-4-yl)-1H-pyrazolo[3,4-c]pyridine;
(R)-(1-(5-(3-(2-fluorophenyl)-1H-pyrazolo[3,4-c]pyridin-5-yl)pyridin-3-yl)pyrrolidin-3-yl)methanamine;
(1-(5-(5-(pyridin-3-yl)-1H-pyrazolo[3,4-c]pyridin-3-yl)pyridin-3-yl)piperidin-4-yl)methanamine;
1-(5-(3-(2-fluorophenyl)-1H-pyrazolo[3,4-c]pyridin-5-yl)pyridin-3-yl)azepan-4-amine;
(1-(5-(3-(2-fluorophenyl)-1H-pyrazolo[3,4-c]pyridin-5-yl)pyridin-3-yl)piperidin-4-yl)methanamine;
(R)-(1-(5-(5-(pyridin-3-yl)-1H-pyrazolo[3,4-c]pyridin-3-yl)pyridin-3-yl)pyrrolidin-3-yl)methanamine;
1-(5-(5-(pyridin-3-yl)-1H-pyrazolo[3,4-c]pyridin-3-yl)pyridin-3-yl)azepan-4-amine;
N-(piperidin-4-yl)-5-(5-(pyridin-3-yl)-1H-pyrazolo[3,4-c]pyridin-3-yl)pyridin-3-amine;
5-(3-(2-fluorophenyl)-1H-pyrazolo[3,4-c]pyridin-5-yl)-N-(piperidin-4-yl)pyridin-3-amine;
3-(2-fluoro-5-methoxyphenyl)-5-(1-methyl-1H-pyrazol-4-yl)-1H-pyrazolo[3,4-c]pyridine;
(S)-1-(6-(5-(1-methyl-1H-pyrazol-4-yl)-1H-pyrazolo[3,4-c]pyridin-3-yl)pyridin-2-yl)piperidin-3-amine;
1-(6-(5-(1-methyl-1H-pyrazol-4-yl)-1H-pyrazolo[3,4-c]pyridin-3-yl)pyridin-2-yl)piperidin-4-amine;
3-(1-(piperidin-4-yl)-1H-pyrazol-4-yl)-5-(pyridin-3-yl)-1H-pyrazolo[3,4-c]pyridine;
3,5-di(pyridin-3-yl)-1H-pyrazolo[3,4-c]pyridine;
(R)-1-(6-(5-(1-methyl-1H-pyrazol-4-yl)-1H-pyrazolo[3,4-c]pyridin-3-yl)pyridin-2-yl)piperidin-3-amine;
2-(4-(3-(6-fluoropyridin-2-yl)-1H-pyrazolo[3,4-c]pyridin-5-yl)-1H-pyrazol-1-yl)acetamide;
(S)-1-(6-(3-(2-fluorophenyl)-1H-pyrazolo[3,4-c]pyridin-5-yl)pyrazin-2-yl)azepan-4-amine;
(S)-1-(5-(3-(2-fluorophenyl)-1H-pyrazolo[3,4-c]pyridin-5-yl)pyridin-3-yl)piperidin-3-amine;
3-(6-(piperazin-1-yl)pyridin-2-yl)-5-(tetrahydro-2H-pyran-3-yl)-1H-pyrazolo[3,4-c]pyridine;
(1-(6-(5-(1-methyl-1H-pyrazol-4-yl)-1H-pyrazolo[3,4-c]pyridin-3-yl)pyridin-2-yl)piperidin-4-yl)methanamine;
6-(5-(1-methyl-1H-pyrazol-4-yl)-1H-pyrazolo[3,4-c]pyridin-3-yl)-N-(piperidin-4-ylmethyl)pyridin-2-amine;
5-(1-methyl-1H-pyrazol-4-yl)-3-(6-(1-methyl-1H-pyrazol-4-yl)pyridin-2-yl)-1H-pyrazolo[3,4-c]pyridine;
5-(furan-3-yl)-3-phenyl-1H-pyrazolo[3,4-c]pyridine;
3-(1-(piperidin-4-ylmethyl)-1H-pyrazol-4-yl)-5-(pyridin-3-yl)-1H-pyrazolo[3,4-c]pyridine;
3-(6-(1,4-diazepan-1-yl)pyridin-2-yl)-5-(pyridin-3-yl)-1H-pyrazolo[3,4-c]pyridine;
1-(6-(5-(1-methyl-1H-pyrazol-4-yl)-1H-pyrazolo[3,4-c]pyridin-3-yl)pyridin-2-yl)azepan-4-amine;
(R)-1-(6-(5-(1-methyl-1H-pyrazol-4-yl)-1H-pyrazolo[3,4-c]pyridin-3-yl)pyridin-2-yl)pyrrolidin-3-amine;
(S)-1-(5-(3-(2-fluorophenyl)-1H-pyrazolo[3,4-c]pyridin-5-yl)pyridin-3-yl)pyrrolidin-3-amine;
(R)-1-(5-(5-(pyridin-3-yl)-1H-pyrazolo[3,4-c]pyridin-3-yl)pyridin-2-yl)piperidin-3-amine;
(R)-1-(5-(3-(2-fluorophenyl)-1H-pyrazolo[3,4-c]pyridin-5-yl)pyridin-3-yl)pyrrolidin-3-amine;
3-(1H-pyrazol-3-yl)-5-(pyridin-3-yl)-1H-pyrazolo[3,4-c]pyridine;
5-(pyridin-3-yl)-3-(pyridin-4-yl)-1H-pyrazolo[3,4-c]pyridine;
3-(2-fluorophenyl)-5-(4-(piperidin-4-yloxy)pyridin-3-yl)-1H-pyrazolo[3,4-c]pyridine;
(S)-1-(5-(5-(pyridin-3-yl)-1H-pyrazolo[3,4-c]pyridin-3-yl)pyridin-2-yl)piperidin-3-amine;
1-(6-(5-(pyridin-3-yl)-1H-pyrazolo[3,4-c]pyridin-3-yl)pyridin-2-yl)azepan-4-amine;
5-(4-(azetidin-3-yloxy)pyridin-3-yl)-3-(2-fluorophenyl)-1H-pyrazolo[3,4-c]pyridine;
(R)-3-(2-fluorophenyl)-5-(4-(piperidin-3-ylmethoxy)pyridin-3-yl)-1H-pyrazolo[3,4-c]pyridine;
6-(5-(1-methyl-1H-pyrazol-4-yl)-1H-pyrazolo[3,4-c]pyridin-3-yl)-N-(piperidin-4-ylmethyl)pyridin-2-amine;
(S)-3-(2-fluorophenyl)-5-(4-(piperidin-3-ylmethoxy)pyridin-3-yl)-1H-pyrazolo[3,4-c]pyridine;
(S)-1-(5-(5-(pyridin-3-yl)-1H-pyrazolo[3,4-c]pyridin-3-yl)pyridin-2-yl)pyrrolidin-3-amine;
(R)-1-(5-(5-(pyridin-3-yl)-1H-pyrazolo[3,4-c]pyridin-3-yl)pyridin-2-yl)pyrrolidin-3-amine;
3-(pyridin-2-yl)-5-(pyridin-3-yl)-1H-pyrazolo[3,4-c]pyridine;
3-(2-fluoro-5-methylphenyl)-5-(1-methyl-1H-pyrazol-4-yl)-1H-pyrazolo[3,4-c]pyridine;
(S)-1-(6-(5-(5-fluoropyridin-3-yl)-1H-pyrazolo[3,4-c]pyridin-3-yl)pyridin-2-yl)piperidin-3-amine;
3-(3-(2-fluorophenyl)-1H-pyrazolo[3,4-c]pyridin-5-yl)-N-(piperidin-4-ylmethyl)pyridin-4-amine;

5-(5-fluoropyridin-3-yl)-3-(6-(piperazin-1-yl)pyridin-2-yl)-1H-pyrazolo[3,4-c]pyridine;
(R)-3-(2-fluorophenyl)-5-(4-(pyrrolidin-3-ylmethoxy)pyridin-3-yl)-1H-pyrazolo[3,4-c]pyridine;
(R)-1-(6-(5-(5-fluoropyridin-3-yl)-1H-pyrazolo[3,4-c]pyridin-3-yl)pyridin-2-yl)piperidin-3-amine;
(S)-3-(2-fluorophenyl)-5-(4-(pyrrolidin-3-ylmethoxy)pyridin-3-yl)-1H-pyrazolo[3,4-c]pyridine;
3-(6-(piperazin-1-yl)pyridin-2-yl)-5-(tetrahydrofuran-3-yl)-1H-pyrazolo[3,4-c]pyridine;
5-(1H-imidazol-5-yl)-3-phenyl-1H-pyrazolo[3,4-c]pyridine;
3-phenyl-5-(pyrazin-2-yl)-1H-pyrazolo[3,4-c]pyridine;
3-(1-(piperidin-4-yl)-1H-pyrazol-3-yl)-5-(pyridin-3-yl)-1H-pyrazolo[3,4-c]pyridine;
3-(6-(((1S,4S)-2,5-diazabicyclo[2.2.1]heptan-2-yl)pyridin-2-yl)-5-(1-methyl-1H-pyrazol-4-yl)-1H-pyrazolo[3,4-c]pyridine;
N-(2-(1H-imidazol-4-yl)ethyl)-6-(5-(1-methyl-1H-pyrazol-4-yl)-1H-pyrazolo[3,4-c]pyridin-3-yl)pyridin-2-amine;
3-(2-fluorophenyl)-5-(1H-imidazol-5-yl)-1H-pyrazolo[3,4-c]pyridine;
3-(2-fluorophenyl)-5-(pyrazin-2-yl)-1H-pyrazolo[3,4-c]pyridine;
3-(2-fluorophenyl)-5-(4-(2-(piperidin-4-yl)ethoxy)pyridin-3-yl)-1H-pyrazolo[3,4-c]pyridine;
1-(6-(3-(1-methyl-1H-pyrazol-4-yl)-1H-pyrazolo[3,4-c]pyridin-5-yl)pyrazin-2-yl)piperidin-4-amine;
(R)-1-(3-(5-(1-methyl-1H-pyrazol-4-yl)-1H-pyrazolo[3,4-c]pyridin-3-yl)phenyl)piperidin-3-amine;
1-methyl-4-(3-(6-(piperazin-1-yl)pyridin-2-yl)-1H-pyrazolo[3,4-c]pyridin-5-yl)piperazin-2-one;
1-(3-(6-(piperazin-1-yl)pyridin-2-yl)-1H-pyrazolo[3,4-c]pyridin-5-yl)urea;
1-(6-(5-(1-methyl-1H-pyrazol-4-yl)-1H-pyrazolo[3,4-c]pyridin-3-yl)pyridin-2-yl)azepan-3-amine;
(S)-1-(6-(5-(1-methyl-1H-pyrazol-4-yl)-1H-pyrazolo[3,4-c]pyridin-3-yl)pyridin-2-yl)azepan-4-amine;
4-amino-1-(6-(5-(pyridin-3-yl)-1H-pyrazolo[3,4-c]pyridin-3-yl)pyridin-2-yl)piperidine-4-carboxamide;
1-(6-(3-(2,6-difluorophenyl)-1H-pyrazolo[3,4-c]pyridin-5-yl)pyrazin-2-yl)piperidin-4-amine;
1-(6-(3-phenyl-1H-pyrazolo[3,4-c]pyridin-5-yl)pyrazin-2-yl)piperidin-4-amine;
3-(1-methyl-1H-pyrazol-3-yl)-5-(pyridin-3-yl)-1H-pyrazolo[3,4-c]pyridine;
1-(6-(3-(1-methyl-1H-pyrazol-3-yl)-1H-pyrazolo[3,4-c]pyridin-5-yl)pyrazin-2-yl)piperidin-4-amine;
5-(1-methyl-1H-pyrazol-4-yl)-3-(6-(piperazin-1-yl)pyridin-2-yl)-1H-pyrazolo[3,4-c]pyridine;
4-amino-N-methyl-1-(6-(5-(pyridin-3-yl)-1H-pyrazolo[3,4-c]pyridin-3-yl)pyridin-2-yl)piperidine-4-carboxamide;
(R)-2-(1-(6-(5-(pyridin-3-yl)-1H-pyrazolo[3,4-c]pyridin-3-yl)pyridin-2-yl)piperidin-3-yl)ethanamine;
3-(3-(6-(piperazin-1-yl)pyridin-2-yl)-1H-pyrazolo[3,4-c]pyridin-5-yl)pyridin-2-amine;
3-(piperazin-1-yl)-5-(5-(pyridin-3-yl)-1H-pyrazolo[3,4-c]pyridin-3-yl)benzo nitrile;
1-(3-chloro-6-(5-(pyridin-3-yl)-1H-pyrazolo[3,4-c]pyridin-3-yl)pyridin-2-yl)piperidin-4-amine;
(S)-2-(1-(6-(5-(pyridin-3-yl)-1H-pyrazolo[3,4-c]pyridin-3-yl)pyridin-2-yl)piperidin-3-yl)ethanamine;
1-(3-methyl-6-(5-(pyridin-3-yl)-1H-pyrazolo[3,4-c]pyridin-3-yl)pyridin-2-yl)piperidin-4-amine;
(R)-1-(6-(3-(2-fluorophenyl)-1H-pyrazolo[3,4-c]pyridin-5-yl)pyrazin-2-yl)azepan-4-amine;
(R)-1-(6-(5-(1-methyl-1H-pyrazol-4-yl)-1H-pyrazolo[3,4-c]pyridin-3-yl)pyridin-2-yl)azepan-4-amine;
5-(1-methyl-1H-pyrazol-4-yl)-3-(6-(piperidin-4-yl)pyridin-2-yl)-1H-pyrazolo[3,4-c]pyridine;
(S)-1-(6-(5-(pyridin-3-yl)-1H-pyrazolo[3,4-c]pyridin-3-yl)pyridin-2-yl)azepan-4-amine;
(R)-1-(6-(5-(pyridin-3-yl)-1H-pyrazolo[3,4-c]pyridin-3-yl)pyridin-2-yl)azepan-4-amine;
2-methyl-1-(4-(5-(1-methyl-1H-pyrazol-4-yl)-1H-pyrazolo[3,4-c]pyridin-3-yl)-1H-pyrazol-1-yl)propan-2-ol;
5-(pyridin-3-yl)-3-(pyrrolidin-1-yl)-1H-pyrazolo[3,4-c]pyridine;
1-methyl-3-(5-(pyridin-3-yl)-1H-pyrazolo[3,4-c]pyridin-3-yl)imidazolidin-2-one;
3-(5-chloro-6-(4-methylpiperazin-1-yl)pyridin-2-yl)-5-(pyridin-3-yl)-1H-pyrazolo[3,4-c]pyridine;
3,5-di(pyridin-2-yl)-1H-pyrazolo[3,4-c]pyridine;
3-(5-methyl-6-(4-methylpiperazin-1-yl)pyridin-2-yl)-5-(pyridin-3-yl)-1H-pyrazolo[3,4-c]pyridine;
1-(5-(pyridin-3-yl)-1H-pyrazolo[3,4-c]pyridin-3-yl)pyrrolidin-2-one;
1-methyl-4-(3-phenyl-1H-pyrazolo[3,4-c]pyridin-5-yl)-1H-pyrrol-2(5H)-one;
1-(5-(pyridin-3-yl)-1H-pyrazolo[3,4-c]pyridin-3-yl)piperidin-2-one;
3-(6-(piperidin-1-yl)pyridin-2-yl)-5-(pyridin-3-yl)-1H-pyrazolo[3,4-c]pyridine;
1-(6-(5-(1-methyl-1H-pyrazol-4-yl)-1H-pyrazolo[3,4-c]pyridin-3-yl)pyridin-2-yl)piperidin-3-ol;
1-methyl-4-(3-phenyl-1H-pyrazolo[3,4-c]pyridin-5-yl)pyrrolidin-2-one;
(R)-5-(1-methyl-1H-pyrazol-4-yl)-3-(6-(piperidin-3-yloxy)pyridin-2-yl)-1H-pyrazolo[3,4-c]pyridine;
(S)-1-(3-chloro-6-(5-(pyridin-3-yl)-1H-pyrazolo[3,4-c]pyridin-3-yl)pyridin-2-yl)piperidin-3-amine;
(R)-1-(3-chloro-6-(5-(pyridin-3-yl)-1H-pyrazolo[3,4-c]pyridin-3-yl)pyridin-2-yl)piperidin-3-amine;
4-(6-(5-(pyridin-3-yl)-1H-pyrazolo[3,4-c]pyridin-3-yl)pyridin-2-yl)morpholine;
(S)-1-(6-(5-(pyridin-3-yl)-1H-pyrazolo[3,4-c]pyridin-3-yl)pyridin-2-yl)pyrrolidin-3-amine;
(S)-(1-(6-(5-(pyridin-3-yl)-1H-pyrazolo[3,4-c]pyridin-3-yl)pyridin-2-yl)pyrrolidin-3-yl)methanamine;
(R)-(1-(6-(5-(pyridin-3-yl)-1H-pyrazolo[3,4-c]pyridin-3-yl)pyridin-2-yl)pyrrolidin-3-yl)methanamine;
(R)-1-(6-(5-(pyridin-3-yl)-1H-pyrazolo[3,4-c]pyridin-3-yl)pyridin-2-yl)piperidin-3-ol;
1-(6-(5-(pyridin-3-yl)-1H-pyrazolo[3,4-c]pyridin-3-yl)pyridin-2-yl)piperidin-4-ol;
3-(6-(4,4'-bipiperidin-1-yl)pyridin-2-yl)-5-(pyridin-3-yl)-1H-pyrazolo[3,4-c]pyridine;
3-(6-fluoro-5-methylpyridin-2-yl)-5-(pyridin-3-yl)-1H-pyrazolo[3,4-c]pyridine;
3-(5-methylpyridin-2-yl)-5-(pyridin-3-yl)-1H-pyrazolo[3,4-c]pyridine;
(R)-1-(6-(5-(pyridin-3-yl)-1H-pyrazolo[3,4-c]pyridin-3-yl)pyridin-2-yl)pyrrolidin-3-amine;
(S)-1-(6-(5-(pyridin-3-yl)-1H-pyrazolo[3,4-c]pyridin-3-yl)pyridin-2-yl)piperidin-3-ol;
(1-(6-(5-(pyridin-3-yl)-1H-pyrazolo[3,4-c]pyridin-3-yl)pyridin-2-yl)piperidin-4-yl)methanamine;
4-(6-(5-(pyridin-3-yl)-1H-pyrazolo[3,4-c]pyridin-3-yl)pyridin-2-yl)piperazin-2-one;
N1-(6-(5-(pyridin-3-yl)-1H-pyrazolo[3,4-c]pyridin-3-yl)pyridin-2-yl)propane-1,3-diamine;

3-(3,4-dihydro-2H-pyran-5-yl)-5-(pyridin-3-yl)-1H-pyrazolo[3,4-c]pyridine;
2-(4-(6-(5-(pyridin-3-yl)-1H-pyrazolo[3,4-c]pyridin-3-yl)pyridin-2-yl)piperazin-1-yl)ethanol;
N1-(6-(5-(pyridin-3-yl)-1H-pyrazolo[3,4-c]pyridin-3-yl)pyridin-2-yl)butane-1,4-diamine;
3-(4,5-dihydrofuran-3-yl)-5-(pyridin-3-yl)-1H-pyrazolo[3,4-c]pyridine;
(R)-1-(6-(5-(1-ethyl-1H-pyrazol-4-yl)-1H-pyrazolo[3,4-c]pyridin-3-yl)pyridin-2-yl)piperidin-3-amine;
1-(6-(5-(1-methyl-1H-pyrazol-4-yl)-1H-pyrazolo[3,4-c]pyridin-3-yl)pyridin-2-yl)-3-(trifluoromethyl)pyrrolidin-3-amine;
(R)-1-(3-bromo-6-(5-(pyridin-3-yl)-1H-pyrazolo[3,4-c]pyridin-3-yl)pyridin-2-yl)pyrrolidin-3-amine;
1-(3-methyl-6-(5-(pyridin-3-yl)-1H-pyrazolo[3,4-c]pyridin-3-yl)pyridin-2-yl)piperidin-4-ol;
(S)-1-(3-bromo-6-(5-(pyridin-3-yl)-1H-pyrazolo[3,4-c]pyridin-3-yl)pyridin-2-yl)piperidin-3-amine;
(R)-1-(3-bromo-6-(5-(pyridin-3-yl)-1H-pyrazolo[3,4-c]pyridin-3-yl)pyridin-2-yl)piperidin-3-amine;
(R)-1-(3-bromo-6-(5-(pyridin-3-yl)-1H-pyrazolo[3,4-c]pyridin-3-yl)pyridin-2-yl)piperidin-3-ol;
1-(3-bromo-6-(5-(pyridin-3-yl)-1H-pyrazolo[3,4-c]pyridin-3-yl)pyridin-2-yl)piperidin-4-ol;
(R)-1-(3-bromo-6-(5-(pyridin-3-yl)-1H-pyrazolo[3,4-c]pyridin-3-yl)pyridin-2-yl)pyrrolidin-3-ol;
1-(6-(5-(1-methyl-1H-pyrazol-4-yl)-1H-pyrazolo[3,4-c]pyridin-3-yl)pyridin-2-yl)piperidin-4-ol;
2-(5-(pyridin-3-yl)-1H-pyrazolo[3,4-c]pyridin-3-yl)-2,8-diazaspiro[4.5]decan-1-one;
1-(piperidin-4-ylmethyl)-3-(5-(pyridin-3-yl)-1H-pyrazolo[3,4-c]pyridin-3-yl)imidazolidin-2-one;
2-methyl-1-(6-(5-(1-methyl-1H-pyrazol-4-yl)-1H-pyrazolo[3,4-c]pyridin-3-yl)pyridin-2-ylamino)propan-2-ol;
(R)-1-(4-(5-(pyridin-3-yl)-1H-pyrazolo[3,4-c]pyridin-3-yl)pyrimidin-2-yl)piperidin-3-amine;
1-(6-(5-(pyridin-3-yl)-1H-pyrazolo[3,4-c]pyridin-3-yl)pyridin-2-yl)piperazin-2-one;
2-(5-(pyridin-3-yl)-1H-pyrazolo[3,4-c]pyridin-3-yl)isonicotinamide;
1-(5-(pyridin-3-yl)-1H-pyrazolo[3,4-c]pyridin-3-yl)-3-(pyrrolidin-3-ylmethyl)imidazolidin-2-one;
(S)-3-amino-1-(6-(5-(pyridin-3-yl)-1H-pyrazolo[3,4-c]pyridin-3-yl)pyridin-2-yl)pyrrolidin-2-one;
(S)-1-(3-methyl-6-(5-(pyridin-3-yl)-1H-pyrazolo[3,4-c]pyridin-3-yl)pyridin-2-yl)pyrrolidin-3-ol;
(R)-1-(3-methyl-6-(5-(pyridin-3-yl)-1H-pyrazolo[3,4-c]pyridin-3-yl)pyridin-2-yl)pyrrolidin-3-ol;
(S)-1-(6-(5-(pyridin-3-yl)-1H-pyrazolo[3,4-c]pyridin-3-yl)-3-vinylpyridin-2-yl)piperidin-3-amine;
(S)-1-(3-(prop-1-en-2-yl)-6-(5-(pyridin-3-yl)-1H-pyrazolo[3,4-c]pyridin-3-yl)pyridin-2-yl)piperidin-3-amine;
(R)-1-(3-methyl-6-(5-(pyridin-3-yl)-1H-pyrazolo[3,4-c]pyridin-3-yl)pyridin-2-yl)piperidin-3-ol;
(R)-1-(3-methyl-6-(5-(pyridin-3-yl)-1H-pyrazolo[3,4-c]pyridin-3-yl)pyridin-2-yl)piperidin-3-amine;
(R)-1-(3-methyl-6-(5-(pyridin-3-yl)-1H-pyrazolo[3,4-c]pyridin-3-yl)pyridin-2-yl)azepan-4-amine;
(S)-1-(3-bromo-6-(5-(pyridin-3-yl)-1H-pyrazolo[3,4-c]pyridin-3-yl)pyridin-2-yl)azepan-4-amine;
(R)-1-(3-bromo-6-(5-(pyridin-3-yl)-1H-pyrazolo[3,4-c]pyridin-3-yl)pyridin-2-yl)azepan-4-amine;
(S)-1-(3-methyl-6-(5-(pyridin-3-yl)-1H-pyrazolo[3,4-c]pyridin-3-yl)pyridin-2-yl)azepan-4-amine;
(S)-1-(3-methyl-6-(5-(pyridin-3-yl)-1H-pyrazolo[3,4-c]pyridin-3-yl)pyridin-2-yl)piperidin-3-amine;
(R)-1-(3-methyl-6-(5-(pyridin-3-yl)-1H-pyrazolo[3,4-c]pyridin-3-yl)pyridin-2-yl)pyrrolidin-3-amine;
(S)-1-(3-methyl-6-(5-(pyridin-3-yl)-1H-pyrazolo[3,4-c]pyridin-3-yl)pyridin-2-yl)pyrrolidin-3-amine;
(S)-1-(3-bromo-6-(5-(pyridin-3-yl)-1H-pyrazolo[3,4-c]pyridin-3-yl)pyridin-2-yl)pyrrolidin-3-ol;
(1-(6-(5-(pyridin-3-yl)-1H-pyrazolo[3,4-c]pyridin-3-yl)pyridin-2-yl)piperidin-3-yl)methanamine;
3-(3-(piperazin-1-yl)pyrrolidin-1-yl)-5-(pyridin-3-yl)-1H-pyrazolo[3,4-c]pyridine;
(3S,5R)-5-fluoro-1-(6-(5-(pyridin-3-yl)-1H-pyrazolo[3,4-c]pyridin-3-yl)pyridin-2-yl)piperidin-3-amine;
4-(6-(5-(pyridin-3-yl)-1H-pyrazolo[3,4-c]pyridin-3-yl)pyridin-2-yl)-1,4-diazepan-2-one;
5-(3-phenyl-1H-pyrazolo[3,4-c]pyridin-5-yl)thiazole;
(1-(6-(5-(pyridin-3-yl)-1H-pyrazolo[3,4-c]pyridin-3-yl)pyridin-2-yl)piperidin-2-yl)methanamine;
3-(4-aminopiperidine-1-carbonyl)-1-(5-(pyridin-3-yl)-1H-pyrazolo[3,4-c]pyridin-3-yl)pyrrolidin-2-one;
N-(2-aminoethyl)-6-(5-(pyridin-3-yl)-1H-pyrazolo[3,4-c]pyridin-3-yl)picolinamide;
(S)-1-(3-ethyl-6-(5-(pyridin-3-yl)-1H-pyrazolo[3,4-c]pyridin-3-yl)pyridin-2-yl)piperidin-3-amine;
(S)-1-(3-isopropyl-6-(5-(pyridin-3-yl)-1H-pyrazolo[3,4-c]pyridin-3-yl)pyridin-2-yl)piperidin-3-amine;
N-(azetidin-3-yl)-6-(5-(pyridin-3-yl)-1H-pyrazolo[3,4-c]pyridin-3-yl)picolinamide;
1-methyl-4-(3-phenyl-1H-pyrazolo[3,4-c]pyridin-5-yl)piperazin-2-one;
1-methyl-4-(3-(1-methyl-1H-pyrazol-4-yl)-1H-pyrazolo[3,4-c]pyridin-5-yl)piperazin-2-one;
5-(1-methyl-1H-pyrazol-4-yl)-3-(pyridin-2-yl)-1H-pyrazolo[3,4-c]pyridine;
2-(1-(6-(5-(pyridin-3-yl)-1H-pyrazolo[3,4-c]pyridin-3-yl)pyridin-2-yl)pyrrolidin-3-yl)ethanamine;
(S)-3-amino-1-(6-(5-(pyridin-3-yl)-1H-pyrazolo[3,4-c]pyridin-3-yl)pyridin-3-yl)pyrrolidin-2-one;
4-(3-(6-(piperazin-1-yl)pyridin-2-yl)-1H-pyrazolo[3,4-c]pyridin-5-yl)piperazin-2-one;
(4-aminopiperidin-1-yl) (6-(5-(pyridin-3-yl)-1H-pyrazolo[3,4-c]pyridin-3-yl)pyridin-2-yl)methanone;
N-(piperidin-4-yl)-6-(5-(pyridin-3-yl)-1H-pyrazolo[3,4-c]pyridin-3-yl)picolinamide;
5-(3-(pyridin-2-yl)-1H-pyrazolo[3,4-c]pyridin-5-yl)thiazole;
4-(3-(2-fluorophenyl)-1H-pyrazolo[3,4-c]pyridin-5-yl)-1-methylpiperazin-2-one;
(S)-1-(3-ethynyl-6-(5-(pyridin-3-yl)-1H-pyrazolo[3,4-c]pyridin-3-yl)pyridin-2-yl)piperidin-3-amine;
(S)-3-methyl-1-(6-(5-(pyridin-3-yl)-1H-pyrazolo[3,4-c]pyridin-3-yl)pyridin-2-yl)piperidin-3-amine;
(S)-1-(6-(5-(pyridin-3-yl)-1H-pyrazolo[3,4-c]pyridin-3-yl)pyridin-3-yl)pyrrolidine-2-carboxamide;
(S)-4-(3-(6-(3-aminopiperidin-1-yl)pyridin-2-yl)-1H-pyrazolo[3,4-c]pyridin-5-yl)piperazin-2-one;
1-(3-(6-(piperazin-1-yl)pyridin-2-yl)-1H-pyrazolo[3,4-c]pyridin-5-yl)piperazin-2-one;
(R)-3-methyl-1-(6-(5-(pyridin-3-yl)-1H-pyrazolo[3,4-c]pyridin-3-yl)pyridin-2-yl)piperidin-3-amine;
5-(3-(2-fluorophenyl)-1H-pyrazolo[3,4-c]pyridin-5-yl)thiazole;
(S)-1-(6-(5-(thiazol-5-yl)-1H-pyrazolo[3,4-c]pyridin-3-yl)pyridin-2-yl)piperidin-3-amine;
(R)-1-(6-(5-(thiazol-5-yl)-1H-pyrazolo[3,4-c]pyridin-3-yl)pyridin-2-yl)piperidin-3-amine;

1-methyl-4-(3-(pyridin-2-yl)-1H-pyrazolo[3,4-c]pyridin-5-yl)piperazin-2-one;
2-(5-(pyridin-3-yl)-1H-pyrazolo[3,4-c]pyridin-3-yl)-5-(trifluoromethyl)pyridine 1-oxide;
3-methyl-1-(3-phenyl-1H-pyrazolo[3,4-c]pyridin-5-yl)imidazolidine-2,4-dione;
5-(1-ethyl-1H-pyrazol-4-yl)-3-(6-(piperazin-1-yl)pyridin-2-yl)-1H-pyrazolo[3,4-c]pyridine;
2-(4-(6-(5-(pyridin-3-yl)-1H-pyrazolo[3,4-c]pyridin-3-yl)pyridin-2-yl)-1,4-diazepan-1-yl)ethanol;
5-(3-(6-(piperidin-1-yl)pyridin-2-yl)-1H-pyrazolo[3,4-c]pyridin-5-yl)thiazole;
5-(3-(6-(piperazin-1-yl)pyridin-2-yl)-1H-pyrazolo[3,4-c]pyridin-5-yl)thiazole;
5-(1-methyl-1H-pyrazol-4-yl)-3-(2-(piperidin-1-yl)pyrimidin-4-yl)-1H-pyrazolo[3,4-c]pyridine;
5-(1-methyl-1H-pyrazol-4-yl)-3-(2-(piperazin-1-yl)pyrimidin-4-yl)-1H-pyrazolo[3,4-c]pyridine;
(S)-1-(3-butyl-6-(5-(pyridin-3-yl)-1H-pyrazolo[3,4-c]pyridin-3-yl)pyridin-2-yl)piperidin-3-amine;
5-(1H-imidazol-1-yl)-3-(6-(piperidin-1-yl)pyridin-2-yl)-1H-pyrazolo[3,4-c]pyridine;
(R)-1-(4-(5-(1-methyl-1H-pyrazol-4-yl)-1H-pyrazolo[3,4-c]pyridin-3-yl)pyrimidin-2-yl)piperidin-3-amine;
(S)-1-(4-(5-(1-methyl-1H-pyrazol-4-yl)-1H-pyrazolo[3,4-c]pyridin-3-yl)pyrimidin-2-yl)piperidin-3-amine;
1-methyl-4-(3-(6-(piperazin-1-yl)pyridin-2-yl)-1H-pyrazolo[3,4-c]pyridin-5-yl)pyridin-2(1H)-one;
5-(6-methylpyridin-3-yl)-3-(6-(piperazin-1-yl)pyridin-2-yl)-1H-pyrazolo[3,4-c]pyridine;
5-(1H-imidazol-1-yl)-3-(6-(piperazin-1-yl)pyridin-2-yl)-1H-pyrazolo[3,4-c]pyridine;
(R)-1-(6-(5-(1H-imidazol-1-yl)-1H-pyrazolo[3,4-c]pyridin-3-yl)pyridin-2-yl)piperidin-3-amine;
(R)-3-(3-(6-(3-aminopiperidin-1-yl)pyridin-2-yl)-1H-pyrazolo[3,4-c]pyridin-5-yl)oxazolidin-2-one;
3-methyl-1-(3-(6-(piperazin-1-yl)pyridin-2-yl)-1H-pyrazolo[3,4-c]pyridin-5-yl)imidazolidine-2,4-dione;
5-(1-ethyl-1H-pyrazol-4-yl)-3-(6-(4-methylpiperazin-1-yl)pyridin-2-yl)-1H-pyrazolo[3,4-c]pyridine;
3-(3-(6-(piperidin-1-yl)pyridin-2-yl)-1H-pyrazolo[3,4-c]pyridin-5-yl)oxazolidin-2-one;
(S)-3-(3-(6-(3-aminopiperidin-1-yl)pyridin-2-yl)-1H-pyrazolo[3,4-c]pyridin-5-yl)oxazolidin-2-one;
3-(6-(piperazin-1-yl)pyridin-2-yl)-5-(1-propyl-1H-pyrazol-4-yl)-1H-pyrazolo[3,4-c]pyridine;
(S)-1-(3-bromo-6-(5-(1-methyl-1H-pyrazol-4-yl)-1H-pyrazolo[3,4-c]pyridin-3-yl)pyridin-2-yl)piperidin-3-amine;
(S)-1-(6-(5-(1-ethyl-1H-pyrazol-4-yl)-1H-pyrazolo[3,4-c]pyridin-3-yl)pyridin-2-yl)-N-methylpiperidin-3-amine;
5-(6-fluoropyridin-3-yl)-3-(6-(piperazin-1-yl)pyridin-2-yl)-1H-pyrazolo[3,4-c]pyridine;
1-(3-amino-2,2-dimethylpropyl)-5-(5-(pyridin-3-yl)-1H-pyrazolo[3,4-c]pyridin-3-yl)pyridin-2(1H)-one;
(S)-1-(6-(5-(1H-imidazol-1-yl)-1H-pyrazolo[3,4-c]pyridin-3-yl)pyridin-2-yl)piperidin-3-amine;
5-(1-isobutyl-1H-pyrazol-4-yl)-3-(6-(piperazin-1-yl)pyridin-2-yl)-1H-pyrazolo[3,4-c]pyridine;
5-(1-(2-methoxyethyl)-1H-pyrazol-4-yl)-3-(6-(piperazin-1-yl)pyridin-2-yl)-1H-pyrazolo[3,4-c]pyridine;
3-methyl-1-(6-(5-(1-methyl-1H-pyrazol-4-yl)-1H-pyrazolo[3,4-c]pyridin-3-yl)pyridin-2-yl)piperidin-3-ol;
5-(5-methylpyridin-3-yl)-3-(6-(piperazin-1-yl)pyridin-2-yl)-1H-pyrazolo[3,4-c]pyridine;
(3S,5R)-1-(6-(5-(1-ethyl-1H-pyrazol-4-yl)-1H-pyrazolo[3,4-c]pyridin-3-yl)pyridin-2-yl)-5-fluoropiperidin-3-amine;
(S)-1-(6-(5-(pyridin-3-yl)-1H-pyrazolo[3,4-c]pyridin-3-yl)-3-(trifluoromethyl)pyridin-2-yl)piperidin-3-amine;
4-(1-(3-bromo-6-(5-(1-methyl-1H-pyrazol-4-yl)-1H-pyrazolo[3,4-c]pyridin-3-yl)pyridin-2-yl)azetidin-3-yl)-1,1-dioxothiomorpholine;
2-methyl-1-(4-(3-(6-(piperazin-1-yl)pyridin-2-yl)-1H-pyrazolo[3,4-c]pyridin-5-yl)-1H-pyrazol-1-yl)propan-2-ol;
5-(1-isopropyl-1H-pyrazol-4-yl)-3-(6-(piperazin-1-yl)pyridin-2-yl)-1H-pyrazolo[3,4-c]pyridine;
5-(1-cyclobutyl-1H-pyrazol-4-yl)-3-(6-(piperazin-1-yl)pyridin-2-yl)-1H-pyrazolo[3,4-c]pyridine;
5-(1-(2-fluoroethyl)-1H-pyrazol-4-yl)-3-(6-(piperazin-1-yl)pyridin-2-yl)-1H-pyrazolo[3,4-c]pyridine;
1-(3-bromo-6-(5-(1-methyl-1H-pyrazol-4-yl)-1H-pyrazolo[3,4-c]pyridin-3-yl)pyridin-2-yl)piperidin-4-amine;
(S)-1-(3-bromo-6-(5-(1-methyl-1H-pyrazol-4-yl)-1H-pyrazolo[3,4-c]pyridin-3-yl)pyridin-2-yl)piperidin-3-ol;
(R)-1-(3-bromo-6-(5-(1-methyl-1H-pyrazol-4-yl)-1H-pyrazolo[3,4-c]pyridin-3-yl)pyridin-2-yl)piperidin-3-ol;
5-(1-ethyl-1H-pyrazol-4-yl)-3-(6-((3aR,6aS)-hexahydropyrrolo[3,4-c]pyrrol-2(1H)-yl)pyridin-2-yl)-1H-pyrazolo[3,4-c]pyridine;
(S)-5-(1-ethyl-1H-pyrazol-4-yl)-3-(6-(3-methylpiperazin-1-yl)pyridin-2-yl)-1H-pyrazolo[3,4-c]pyridine;
(R)-5-(1-ethyl-1H-pyrazol-4-yl)-3-(6-(3-methylpiperazin-1-yl)pyridin-2-yl)-1H-pyrazolo[3,4-c]pyridine;
4-(3-(6-(piperazin-1-yl)pyridin-2-yl)-1H-pyrazolo[3,4-c]pyridin-5-yl)morpholine;
3-(5-bromo-6-(4-methylpiperazin-1-yl)pyridin-2-yl)-5-(1-methyl-1H-pyrazol-4-yl)-1H-pyrazolo[3,4-c]pyridine;
(S)-1-(3-bromo-6-(5-(1-ethyl-1H-pyrazol-4-yl)-1H-pyrazolo[3,4-c]pyridin-3-yl)pyridin-2-yl)piperidin-3-amine;
3-bromo-6-(piperazin-1-yl)pyridin-2-yl)-5-(1-ethyl-1H-pyrazol-4-yl)-1H-pyrazolo[3,4-c]pyridine;
4-(1-(3-bromo-6-(5-(1-methyl-1H-pyrazol-4-yl)-1H-pyrazolo[3,4-c]pyridin-3-yl)pyridin-2-yl)azetidin-3-yl)piperazin-2-one;
3-(5-bromo-6-(3,3-dimethyl-4-(2-(methylsulfonyl)ethyl)piperazin-1-yl)pyridin-2-yl)-5-(1-methyl-1H-pyrazol-4-yl)-1H-pyrazolo[3,4-c]pyridine;
(R)-1-(3-bromo-6-(5-(1-ethyl-1H-pyrazol-4-yl)-1H-pyrazolo[3,4-c]pyridin-3-yl)pyridin-2-yl)piperidin-3-amine;
4-(1-(3-bromo-6-(5-(pyridin-3-yl)-1H-pyrazolo[3,4-c]pyridin-3-yl)pyridin-2-yl)azetidin-3-yl)piperazin-2-one;
3-(6-(1,4-diazepan-1-yl)pyridin-2-yl)-5-(1-ethyl-1H-pyrazol-4-yl)-1H-pyrazolo[3,4-c]pyridine;
(S)-1-(6-(5-(1-ethyl-1H-pyrazol-4-yl)-1H-pyrazolo[3,4-c]pyridin-3-yl)pyridin-2-yl)-1,4-diazepan-6-ol;
(R)-1-(6-(5-(1-ethyl-1H-pyrazol-4-yl)-1H-pyrazolo[3,4-c]pyridin-3-yl)pyridin-2-yl)-1,4-diazepan-6-ol;
(S)-1-(6-(5-(1-methyl-1H-pyrazol-4-yl)-1H-pyrazolo[3,4-c]pyridin-3-yl)-3-vinylpyridin-2-yl)piperidin-3-amine;
4-(1-(3-methyl-6-(5-(1-methyl-1H-pyrazol-4-yl)-1H-pyrazolo[3,4-c]pyridin-3-yl)pyridin-2-yl)azetidin-3-yl)-1,1-dioxo thiomorpholine;

(S)-1-(6-(5-(1-methyl-1H-pyrazol-4-yl)-1H-pyrazolo[3,4-c]pyridin-3-yl)-3-(prop-1-en-2-yl)pyridin-2-yl)piperidin-3-amine;
3-(3-(6-(piperazin-1-yl)pyridin-2-yl)-1H-pyrazolo[3,4-c]pyridin-5-yl)oxazolidin-2-one;
5-(1-(oxetan-3-ylmethyl)-1H-pyrazol-4-yl)-3-(6-(piperazin-1-yl)pyridin-2-yl)-1H-pyrazolo[3,4-c]pyridine;
1-(3-methyl-6-(5-(1-methyl-1H-pyrazol-4-yl)-1H-pyrazolo[3,4-c]pyridin-3-yl)pyridin-2-yl)piperidin-4-amine;
(R)-1-(3-methyl-6-(5-(1-methyl-1H-pyrazol-4-yl)-1H-pyrazolo[3,4-c]pyridin-3-yl)pyridin-2-yl)piperidin-3-ol;
4-(3-methyl-6-(5-(1-methyl-1H-pyrazol-4-yl)-1H-pyrazolo[3,4-c]pyridin-3-yl)pyridin-2-yl)morpholine;
4-(6-(5-(1-methyl-1H-pyrazol-4-yl)-1H-pyrazolo[3,4-c]pyridin-3-yl)pyridin-2-yl)morpholine;
3-(6-(4-fluoropiperidin-4-yl)pyridin-2-yl)-5-(pyridin-3-yl)-1H-pyrazolo[3,4-c]pyridine;
4-(6-(5-(pyridin-3-yl)-1H-pyrazolo[3,4-c]pyridin-3-yl)pyridin-2-yl)piperidin-4-ol;
(S)-3-methyl-1-(6-(5-(1-methyl-1H-pyrazol-4-yl)-1H-pyrazolo[3,4-c]pyridin-3-yl)pyridin-2-yl)piperidin-3-ol;
(R)-3-methyl-1-(6-(5-(1-methyl-1H-pyrazol-4-yl)-1H-pyrazolo[3,4-c]pyridin-3-yl)pyridin-2-yl)piperidin-3-ol;
4-(1-(3-methyl-6-(5-(1-methyl-1H-pyrazol-4-yl)-1H-pyrazolo[3,4-c]pyridin-3-yl)pyridin-2-yl)azetidin-3-yl)piperazin-2-one;
4-(1-(3-methyl-6-(5-(pyridin-3-yl)-1H-pyrazolo[3,4-c]pyridin-3-yl)pyridin-2-yl)azetidin-3-yl)piperazin-2-one;
(S)-1-(6-(5-(1-ethyl-1H-pyrazol-4-yl)-1H-pyrazolo[3,4-c]pyridin-3-yl)-3-(prop-1-en-2-yl)pyridin-2-yl)piperidin-3-amine;
3-(6-(3,3-dimethyl-4-(2-(methylsulfonyl)ethyl)piperazin-1-yl)-5-methylpyridin-2-yl)-5-(1-methyl-1H-pyrazol-4-yl)-1H-pyrazolo[3,4-c]pyridine;
(S)-1-(3-ethyl-6-(5-(1-methyl-1H-pyrazol-4-yl)-1H-pyrazolo[3,4-c]pyridin-3-yl)pyridin-2-yl)piperidin-3-amine;
(S)-1-(6-(5-(1-ethyl-1H-pyrazol-4-yl)-1H-pyrazolo[3,4-c]pyridin-3-yl)-3-methylpyridin-2-yl)piperidin-3-amine;
(S)-1-(6-(5-(1-ethyl-1H-pyrazol-4-yl)-1H-pyrazolo[3,4-c]pyridin-3-yl)-3-vinylpyridin-2-yl)piperidin-3-amine;
5-(1-ethyl-1H-pyrazol-4-yl)-3-(5-methyl-6-(piperazin-1-yl)pyridin-2-yl)-1H-pyrazolo[3,4-c]pyridine;
(S)-1-(3-methyl-6-(5-(1-methyl-1H-pyrazol-4-yl)-1H-pyrazolo[3,4-c]pyridin-3-yl)pyridin-2-yl)piperidin-3-amine;
(S)-1-(3-isopropyl-6-(5-(1-methyl-1H-pyrazol-4-yl)-1H-pyrazolo[3,4-c]pyridin-3-yl)pyridin-2-yl)piperidin-3-amine;
4-fluoro-1-(6-(5-(pyridin-3-yl)-1H-pyrazolo[3,4-c]pyridin-3-yl)pyridin-2-yl)piperidin-3-ol;
5-(5-methoxypyridin-3-yl)-3-(6-(piperazin-1-yl)pyridin-2-yl)-1H-pyrazolo[3,4-c]pyridine;
N-methyl-6-(5-(pyridin-3-yl)-1H-pyrazolo[3,4-c]pyridin-3-yl)pyridin-2-amine;
5-(5-ethylpyridin-3-yl)-3-(6-(piperazin-1-yl)pyridin-2-yl)-1H-pyrazolo[3,4-c]pyridine;
5-(1-methyl-1H-pyrazol-4-yl)-3-(2-(piperidin-4-yl)pyrimidin-4-yl)-1H-pyrazolo[3,4-c]pyridine;
5-(1-methyl-1H-pyrazol-4-yl)-3-(5-methyl-6-(4-methylpiperazin-1-yl)pyridin-2-yl)-1H-pyrazolo[3,4-c]pyridine;
(S)-1-(3-methyl-6-(5-(1-methyl-1H-pyrazol-4-yl)-1H-pyrazolo[3,4-c]pyridin-3-yl)pyridin-2-yl)piperidin-3-ol;
(S)-1-(6-(5-(1-methyl-1H-pyrazol-4-yl)-1H-pyrazolo[3,4-c]pyridin-3-yl)pyridin-2-yl)piperidin-3-ol;
(R)-1-(6-(5-(1-ethyl-1H-pyrazol-4-yl)-1H-pyrazolo[3,4-c]pyridin-3-yl)-3-methylpyridin-2-yl)piperidin-3-amine;
3-(6-((3S,5R)-3,5-dimethylpiperazin-1-yl)pyridin-2-yl)-5-(1-ethyl-1H-pyrazol-4-yl)-1H-pyrazolo[3,4-c]pyridine;
(S)-1-(6-(5-(1-ethyl-1H-pyrazol-4-yl)-1H-pyrazolo[3,4-c]pyridin-3-yl)pyridin-2-yl)piperidin-3-amine;
3-(6-(3,3-dimethylpiperazin-1-yl)pyridin-2-yl)-5-(1-ethyl-1H-pyrazol-4-yl)-1H-pyrazolo[3,4-c]pyridine;
3-(6-(6,6-difluoro-1,4-diazepan-1-yl)pyridin-2-yl)-5-(1-ethyl-1H-pyrazol-4-yl)-1H-pyrazolo[3,4-c]pyridine;
5-(1-tert-butyl-1H-pyrazol-4-yl)-3-(6-(piperazin-1-yl)pyridin-2-yl)-1H-pyrazolo[3,4-c]pyridine;
4-(3-bromo-6-(5-(1-methyl-1H-pyrazol-4-yl)-1H-pyrazolo[3,4-c]pyridin-3-yl)pyridin-2-yl)morpholine;
4-(6-(5-(1-ethyl-1H-pyrazol-4-yl)-1H-pyrazolo[3,4-c]pyridin-3-yl)pyridin-2-yl)morpholine;
(R)-1-(6-(5-(1-methyl-1H-pyrazol-4-yl)-1H-pyrazolo[3,4-c]pyridin-3-yl)pyridin-2-yl)piperidin-3-ol;
cis-4-fluoro-1-(6-(5-(pyridin-3-yl)-1H-pyrazolo[3,4-c]pyridin-3-yl)pyridin-2-yl)piperidin-3-amine;
trans-4-fluoro-1-(6-(5-(pyridin-3-yl)-1H-pyrazolo[3,4-c]pyridin-3-yl)pyridin-2-yl)piperidin-3-amine;
(3S,5R)-1-(3-bromo-6-(5-(1-ethyl-1H-pyrazol-4-yl)-1H-pyrazolo[3,4-c]pyridin-3-yl)pyridin-2-yl)-5-fluoropiperidin-3-amine;
(3R,5R)-1-(3-bromo-6-(5-(1-ethyl-1H-pyrazol-4-yl)-1H-pyrazolo[3,4-c]pyridin-3-yl)pyridin-2-yl)-5-fluoropiperidin-3-amine;
(3S,5R)-1-(3-bromo-6-(5-(1-methyl-1H-pyrazol-4-yl)-1H-pyrazolo[3,4-c]pyridin-3-yl)pyridin-2-yl)-5-fluoropiperidin-3-amine;
3-(6-(1,4-diazepan-1-yl)-4-methylpyridin-2-yl)-5-(1-ethyl-1H-pyrazol-4-yl)-1H-pyrazolo[3,4-c]pyridine;
(R)-1-(6-(5-(1-ethyl-1H-pyrazol-4-yl)-1H-pyrazolo[3,4-c]pyridin-3-yl)pyridin-2-yl)-3-methylpiperidin-3-ol;
N1-(6-(5-(1-ethyl-1H-pyrazol-4-yl)-1H-pyrazolo[3,4-c]pyridin-3-yl)pyridin-2-yl)cyclohexane-1,3-diamine;
trans-1-(6-(5-(1-ethyl-1H-pyrazol-4-yl)-1H-pyrazolo[3,4-c]pyridin-3-yl)pyridin-2-yl)-4-fluoropiperidin-3-amine;
(4-(6-(5-(1-ethyl-1H-pyrazol-4-yl)-1H-pyrazolo[3,4-c]pyridin-3-yl)pyridin-2-yl)piperazin-2-yl)methanol;
(S)-1-(6-(5-(1-ethyl-1H-pyrazol-4-yl)-1H-pyrazolo[3,4-c]pyridin-3-yl)pyridine-2-yl)-3-methylpiperidin-3-ol;
cis-1-(6-(5-(1-ethyl-1H-pyrazol-4-yl)-1H-pyrazolo[3,4-c]pyridin-3-yl)pyridin-2-yl)-4-fluoropiperidin-3-amine;
(S)-1-(5-chloro-6-(5-(1-ethyl-1H-pyrazol-4-yl)-1H-pyrazolo[3,4-c]pyridin-3-yl)pyridin-2-yl)piperidin-3-amine;
3-(6-(piperazin-1-yl)pyridin-2-yl)-5-(5-(trifluoromethyl)pyridin-3-yl)-1H-pyrazolo[3,4-c]pyridine;
5-(1-ethyl-1H-pyrazol-4-yl)-3-(6-(3-(trifluoromethyl)piperazin-1-yl)pyridin-2-yl)-1H-pyrazolo[3,4-c]pyridine;
5-(1-ethyl-1H-pyrazol-4-yl)-3-(4-(trifluoromethyl)pyridin-2-yl)-1H-pyrazolo[3,4-c]pyridine;

5-(5-(methylsulfonyl)pyridin-3-yl)-3-(6-(piperazin-1-yl)pyridin-2-yl)-1H-pyrazolo[3,4-c]pyridine;
(R)-1-(6-(5-(1-ethyl-1H-pyrazol-4-yl)-1H-pyrazolo[3,4-c]pyridin-3-yl)pyridin-2-yl)azepan-4-amine;
1-(4-(6-(5-(1-ethyl-1H-pyrazol-4-yl)-1H-pyrazolo[3,4-c]pyridin-3-yl)pyridin-2-yl)piperazin-1-yl)ethanone;
2-(4-(3-(6-(piperazin-1-yl)pyridin-2-yl)-1H-pyrazolo[3,4-c]pyridin-5-yl)-1H-pyrazol-1-yl)acetonitrile;
5-(1-ethyl-1H-pyrazol-4-yl)-3-(4-methoxypyridin-2-yl)-1H-pyrazolo[3,4-c]pyridine;
(S)-1-(3-ethyl-6-(5-(1-ethyl-1H-pyrazol-4-yl)-1H-pyrazolo[3,4-c]pyridin-3-yl)pyridin-2-yl)piperidin-3-amine;
(S)-1-(6-(5-(1-ethyl-1H-pyrazol-4-yl)-1H-pyrazolo[3,4-c]pyridin-3-yl)-3-isopropylpyridin-2-yl)piperidin-3-amine;
5-(1-ethyl-1H-pyrazol-4-yl)-3-(6-(piperazin-1-yl)pyrazin-2-yl)-1H-pyrazolo[3,4-c]pyridine;
5-(1-ethyl-1H-pyrazol-4-yl)-3-(6-(4-(oxetan-3-yl)piperazin-1-yl)pyridin-2-yl)-1H-pyrazolo[3,4-c]pyridine;
(S)-1-(6-(5-(1-ethyl-1H-pyrazol-4-yl)-1H-pyrazolo[3,4-c]pyridin-3-yl)pyridin-2-yl)azepan-4-amine;
(R)-1-(6-(5-(1-ethyl-1H-pyrazol-4-yl)-1H-pyrazolo[3,4-c]pyridin-3-yl)pyridin-2-yl)-N-methylpiperidin-3-amine;
1-(5-(3-(6-(piperazin-1-yl)pyridin-2-yl)-1H-pyrazolo[3,4-c]pyridin-5-yl)pyridin-3-yl)ethanol;
3-(4-cyclopropylpyridin-2-yl)-5-(1-ethyl-1H-pyrazol-4-yl)-1H-pyrazolo[3,4-c]pyridine;
(S)-1-(3-cyclopropyl-6-(5-(pyridin-3-yl)-1H-pyrazolo[3,4-c]pyridin-3-yl)pyridin-2-yl)piperidin-3-amine;
(S)-1-(3-cyclopropyl-6-(5-(1-methyl-1H-pyrazol-4-yl)-1H-pyrazolo[3,4-c]pyridin-3-yl)pyridin-2-yl)piperidin-3-amine;
5-(1-cyclopropyl-1H-pyrazol-4-yl)-3-(6-(piperazin-1-yl)pyridin-2-yl)-1H-pyrazolo[3,4-c]pyridine;
3-(6-(piperazin-1-yl)pyridin-2-yl)-5-(1-(2,2,2-trifluoroethyl)-1H-pyrazol-4-yl)-1H-pyrazolo[3,4-c]pyridine;
3-(6-(1,4-diazepan-1-yl)pyridin-2-yl)-5-(1-(2-fluoroethyl)-1H-pyrazol-4-yl)-1H-pyrazolo[3,4-c]pyridine;
2-(1,4-diazepan-1-yl)-6-(5-(1-ethyl-1H-pyrazol-4-yl)-1H-pyrazolo[3,4-c]pyridin-3-yl)isonicotinonitrile;
5-(1-ethyl-1H-pyrazol-4-yl)-3-(6-(5-(trifluoromethyl)-1,4-diazepan-1-yl)pyridin-2-yl)-1H-pyrazolo[3,4-c]pyridine;
5-(1-ethyl-1H-pyrazol-4-yl)-3-(4-methylpyridin-2-yl)-1H-pyrazolo[3,4-c]pyridine;
5-(1-ethyl-1H-pyrazol-4-yl)-3-(4-ethylpyridin-2-yl)-1H-pyrazolo[3,4-c]pyridine;
1-(6-(5-(1-ethyl-1H-pyrazol-4-yl)-1H-pyrazolo[3,4-c]pyridin-3-yl)pyridin-2-yl)azepan-3-ol;
(3S,5R)-5-fluoro-1-(6-(5-(1-methyl-1H-pyrazol-4-yl)-1H-pyrazolo[3,4-c]pyridin-3-yl)pyridin-2-yl)piperidin-3-amine;
2-(4-(3-(6-(piperazin-1-yl)pyridin-2-yl)-1H-pyrazolo[3,4-c]pyridin-5-yl)-1H-pyrazol-1-yl)ethanol;
5-(1-(cyclopropylmethyl)-1H-pyrazol-4-yl)-3-(6-(piperazin-1-yl)pyridin-2-yl)-1H-pyrazolo[3,4-c]pyridine;
(2-(5-(1-ethyl-1H-pyrazol-4-yl)-1H-pyrazolo[3,4-c]pyridin-3-yl)pyridin-4-yl)methanol;
1-(6-(5-(1-ethyl-1H-pyrazol-4-yl)-1H-pyrazolo[3,4-c]pyridin-3-yl)pyridin-2-yl)-1,4-diazepane-6-carbonitrile;
5-(1-ethyl-1H-pyrazol-4-yl)-3-(4-(prop-1-en-2-yl)pyridin-2-yl)-1H-pyrazolo[3,4-c]pyridine;
(S)-1-(6-(5-(1-ethyl-1H-pyrazol-4-yl)-1H-pyrazolo[3,4-c]pyridin-3-yl)pyridin-2-yl)azepan-3-ol;
(R)-1-(6-(5-(1-ethyl-1H-pyrazol-4-yl)-1H-pyrazolo[3,4-c]pyridin-3-yl)pyridin-2-yl)azepan-3-ol;
(S)-5-(1-(2-fluoroethyl)-1H-pyrazol-4-yl)-3-(6-(3-methylpiperazin-1-yl)pyridin-2-yl)-1H-pyrazolo[3,4-c]pyridine;
5-(1-ethyl-1H-pyrazol-4-yl)-3-(6-(6-fluoro-1,4-diazepan-1-yl)pyridin-2-yl)-1H-pyrazolo[3,4-c]pyridine;
5-(6-methylpyrazin-2-yl)-3-(6-(piperazin-1-yl)pyridin-2-yl)-1H-pyrazolo[3,4-c]pyridine;
(S)-1-(3-cyclopropyl-6-(5-(1-ethyl-1H-pyrazol-4-yl)-1H-pyrazolo[3,4-c]pyridin-3-yl)pyridin-2-yl)piperidin-3-amine;
5-(1-ethyl-1H-pyrazol-4-yl)-3-(4-isopropylpyridin-2-yl)-1H-pyrazolo[3,4-c]pyridine;
5-(1-ethyl-1H-pyrazol-4-yl)-3-(pyridin-2-yl)-1H-pyrazolo[3,4-c]pyridine;
(3S,5R)-5-fluoro-1-(3-methyl-6-(5-(1-methyl-1H-pyrazol-4-yl)-1H-pyrazolo[3,4-c]pyridin-3-yl)pyridin-2-yl)piperidin-3-amine;
(3S,5R)-1-(6-(5-(1-ethyl-1H-pyrazol-4-yl)-1H-pyrazolo[3,4-c]pyridin-3-yl)-3-methylpyridin-2-yl)-5-fluoropiperidin-3-amine;
(1-(6-(5-(1-ethyl-1H-pyrazol-4-yl)-1H-pyrazolo[3,4-c]pyridin-3-yl)pyridin-2-yl)-1,4-diazepan-6-yl)methanol;
(1-(6-(5-(1-ethyl-1H-pyrazol-4-yl)-1H-pyrazolo[3,4-c]pyridin-3-yl)pyridin-2-yl)-1,4-diazepan-6-yl)methanol;
N-(6-(5-(1-ethyl-1H-pyrazol-4-yl)-1H-pyrazolo[3,4-c]pyridin-3-yl)pyridin-2-yl)azepan-3-amine;
1-(6-(5-(1-(2-fluoroethyl)-1H-pyrazol-4-yl)-1H-pyrazolo[3,4-c]pyridin-3-yl)pyridin-2-yl)azepan-3-amine;
3-ethyl-5-(3-(6-(piperazin-1-yl)pyridin-2-yl)-1H-pyrazolo[3,4-c]pyridin-5-yl)pyrimidin-4(3H)-one;
5-(1-(2-fluoroethyl)-1H-pyrazol-4-yl)-3-(6-(3-methylpiperazin-1-yl)pyridin-2-yl)-1H-pyrazolo[3,4-c]pyridine;
(3R,5R)-5-fluoro-1-(6-(5-(1-methyl-1H-pyrazol-4-yl)-1H-pyrazolo[3,4-c]pyridin-3-yl)pyridin-2-yl)piperidin-3-amine;
1-(6-(5-(1-ethyl-1H-pyrazol-4-yl)-1H-pyrazolo[3,4-c]pyridin-3-yl)pyridin-2-yl)azepan-3-amine;
(S)-1-(6-(5-(1-(2-fluoroethyl)-1H-pyrazol-4-yl)-1H-pyrazolo[3,4-c]pyridin-3-yl)pyridin-2-yl)azepan-3-amine;
(R)-1-(6-(5-(1-(2-fluoroethyl)-1H-pyrazol-4-yl)-1H-pyrazolo[3,4-c]pyridin-3-yl)pyridin-2-yl)azepan-3-amine; and
(R)-5-(1-(2-fluoroethyl)-1H-pyrazol-4-yl)-3-(6-(3-methylpiperazin-1-yl)pyridin-2-yl)-1H-pyrazolo[3,4-c]pyridine.

11. A pharmaceutical composition comprised of a compound of claim 1 and a pharmaceutically acceptable carrier, glidant, diluent, or excipient.

12. The pharmaceutical composition according to claim 11, further comprising a second chemotherapeutic agent.

13. A kit for treating a condition mediated by Pim kinase, comprising:
   a) a first pharmaceutical composition comprising a compound of claim 1; and
   b) instructions for use.

14. The compound of claim 1 selected from
3-(6-(1,4-diazepan-1-yl)pyridin-2-yl)-5-(6-methylpyrazin-2-yl)-1H-pyrazolo[3,4-c]pyridine;
3-(2,5-difluorophenyl)-5-(1H-pyrazol-4-yl)-1H-pyrazolo[3,4-c]pyridine;
4-(3-(2-fluorophenyl)-1H-pyrazolo[3,4-c]pyridin-5-yl)-1H-pyrazol-3-amine;

3-(2-fluorophenyl)-5-(3-(trifluoromethyl)-1H-pyrazol-4-yl)-1H-pyrazolo[3,4-c]pyridine;
3-(2-fluorophenyl)-5-(5-methyl-1H-pyrazol-4-yl)-1H-pyrazolo[3,4-c]pyridine; and
2-(5-(1H-pyrazol-4-yl)-1H-pyrazolo[3,4-c]pyridin-3-yl)-3-fluoroaniline.

* * * * *